US010066009B2

(12) United States Patent
Kovacevich et al.

(10) Patent No.: US 10,066,009 B2
(45) Date of Patent: Sep. 4, 2018

(54) ANTI-CGRP COMPOSITIONS AND USE THEREOF

(71) Applicant: ALDERBIO HOLDINGS LLC, Las Vegas, NV (US)

(72) Inventors: Brian Robert Kovacevich, Snohomish, WA (US); Leon F. Garcia-Martinez, Woodinville, WA (US); Katie Olson Anderson, Kirkland, WA (US); Benjamin H. Dutzar, Seattle, WA (US); Jens J. Billgren, Seattle, WA (US); John A. Latham, Seattle, WA (US); Danielle M. Mitchell, Seattle, WA (US); Patricia Dianne McNeill, Federal Way, WA (US); Nicole M. Janson, Seattle, WA (US); Maria-Cristina Loomis, Bothell, WA (US)

(73) Assignee: ALDERBIO HOLDINGS LLC, Las Vegas, NV (US)

( * ) Notice: Subject to any disclaimer, the term of this patent is extended or adjusted under 35 U.S.C. 154(b) by 0 days.

(21) Appl. No.: 15/257,562

(22) Filed: Sep. 6, 2016

(65) Prior Publication Data
US 2017/0174754 A1 Jun. 22, 2017

Related U.S. Application Data

(62) Division of application No. 13/476,465, filed on May 21, 2012, now Pat. No. 9,745,373.

(60) Provisional application No. 61/488,660, filed on May 20, 2011.

(51) Int. Cl.
| *A61K 31/485* | (2006.01) |
| *C07K 16/18* | (2006.01) |
| *A61K 39/395* | (2006.01) |
| *A61K 49/00* | (2006.01) |
| *A61K 39/00* | (2006.01) |

(52) U.S. Cl.
CPC ............ *C07K 16/18* (2013.01); *A61K 31/485* (2013.01); *A61K 39/3955* (2013.01); *A61K 49/00* (2013.01); *A61K 2039/505* (2013.01); *C07K 2317/24* (2013.01); *C07K 2317/52* (2013.01); *C07K 2317/56* (2013.01); *C07K 2317/565* (2013.01); *C07K 2317/567* (2013.01)

(58) Field of Classification Search
None
See application file for complete search history.

(56) References Cited

U.S. PATENT DOCUMENTS

| 5,116,964 A | 5/1992 | Capon et al. |
| 5,266,561 A | 11/1993 | Cooper et al. |
| 5,364,841 A | 11/1994 | Cooper et al. |
| 5,585,089 A | 12/1996 | Queen et al. |
| 5,624,821 A | 4/1997 | Winter et al. |
| 5,648,260 A | 7/1997 | Winter et al. |
| 5,942,227 A | 8/1999 | Cooper et al. |
| 6,180,370 B1 | 1/2001 | Queen et al. |
| 6,313,097 B1 | 11/2001 | Eberlein et al. |
| 6,509,014 B1 | 1/2003 | De Lacharriere et al. |
| 6,521,609 B1 | 2/2003 | Doods et al. |
| 6,737,056 B1 | 5/2004 | Presta |
| 6,956,107 B2 | 10/2005 | Fung et al. |
| 7,279,471 B2 | 10/2007 | Mueller et al. |
| 7,479,488 B2 | 1/2009 | Mueller et al. |
| 7,696,209 B2 | 4/2010 | Mueller et al. |
| 7,700,735 B2 | 4/2010 | Young et al. |
| 7,879,991 B2 | 2/2011 | Vater et al. |
| 7,927,863 B2 | 4/2011 | Cregg et al. |
| 7,935,340 B2 | 5/2011 | Garcia-Martinez et al. |

(Continued)

FOREIGN PATENT DOCUMENTS

| AU | 2006313434 | 5/2007 |
| CA | 2611433 | 12/2006 |

(Continued)

OTHER PUBLICATIONS

Edvinsson et al., Inhibitory effect of BIBN4096BS, CGRP8-37, a CGRP antibody and an RNA-Spiegelmer on CGRP induced vasodilatation in the perfused and non-perfused rat middle cerebral artery, 2007, British Journal of Pharmocology 150:633-640.*
"Cluster Headache," Wolff's Headache 1974, p. 348.
"Highlights of Prescribing Information" BLA STN 103000/5215—FDA Approved Labeling Text, Botox Package Insert, Oct. 2010, 25 pages.
"Teva to Acquire Labrys Biologics, Inc.: Novel Migraine Prophylaxis Treatment Adds Significant New Dimension to Teva's Growing Pain Care Franchise" "Business Wire Jun. 3, 2014." 4 pages.
"TMJ Disorders," National Institute of Dental and Craniofacial Research, NIH Publication No. 15-3487, Apr. 2015.
Abdiche YN, et al. "Probing the binding mechanism and affinity of tanezumab, a recombinant humanized anti-NGF monoclonal antibody, using a repertoire of biosensors," Protein Sci. Aug. 2008;17(8):1326-35.

(Continued)

*Primary Examiner* — John D Ulm
(74) *Attorney, Agent, or Firm* — Robin L. Teskin; LeClairRyan PLLC

(57) ABSTRACT

The present invention is directed to antibodies and fragments thereof having binding specificity for CGRP. Another embodiment of this invention relates to the antibodies described herein, and binding fragments thereof, comprising the sequences of the $V_H$, $V_L$ and CDR polypeptides described herein, and the polynucleotides encoding them. The invention also contemplates conjugates of anti-CGRP antibodies and binding fragments thereof conjugated to one or more functional or detectable moieties. The invention also contemplates methods of making said anti-CGRP antibodies and binding fragments thereof. Embodiments of the invention also pertain to the use of anti-CGRP antibodies, and binding fragments thereof, for the diagnosis, assessment and treatment of diseases and disorders associated with CGRP.

30 Claims, 74 Drawing Sheets

Specification includes a Sequence Listing.

(56) References Cited

U.S. PATENT DOCUMENTS

| | | |
|---|---|---|
| 8,007,794 B2 | 8/2011 | Zeller et al. |
| 8,293,239 B2 | 10/2012 | Poulsen et al. |
| 8,298,536 B2 | 10/2012 | Poulsen et al. |
| 8,586,045 B2 | 11/2013 | Zeller et al. |
| 8,597,649 B2 | 12/2013 | Zeller et al. |
| 8,623,366 B2 | 1/2014 | Pios et al. |
| 8,734,802 B1 | 5/2014 | Zeller et al. |
| 9,073,991 B2 | 7/2015 | Allan et al. |
| 9,708,393 B2 | 7/2017 | Russo et al. |
| 9,745,373 B2 | 8/2017 | Kovacevich et al. |
| 9,855,332 B2 | 1/2018 | Russo et al. |
| 2001/0036647 A1 | 11/2001 | Choudary et al. |
| 2002/0162125 A1 | 10/2002 | Salmon et al. |
| 2002/0164707 A1 | 11/2002 | Adamou et al. |
| 2003/0027213 A1 | 2/2003 | Zhu et al. |
| 2003/0181462 A1 | 9/2003 | Doods et al. |
| 2003/0194404 A1 | 10/2003 | Greenfeder et al. |
| 2004/0110170 A1 | 6/2004 | Pisegna et al. |
| 2004/0132824 A1 | 7/2004 | Gil et al. |
| 2005/0234054 A1 | 10/2005 | Mueller et al. |
| 2006/0183700 A1 | 8/2006 | Vater et al. |
| 2006/0270045 A1 | 11/2006 | Cregg et al. |
| 2009/0023644 A1 | 1/2009 | Southard et al. |
| 2009/0028784 A1 | 1/2009 | Garcia-Martinez et al. |
| 2009/0220489 A1 | 9/2009 | Zeller et al. |
| 2010/0152171 A1 | 6/2010 | Rudolf et al. |
| 2011/0054150 A1 | 3/2011 | Poulsen et al. |
| 2011/0257371 A1 | 10/2011 | Poulsen et al. |
| 2011/0305711 A1 | 12/2011 | Allan et al. |
| 2012/0000192 A1 | 1/2012 | Zeller et al. |
| 2012/0225075 A1 | 9/2012 | Pios et al. |
| 2012/0294797 A1* | 11/2012 | Kovacevich ........... C07K 16/26 424/1.11 |
| 2012/0294802 A1 | 11/2012 | Russo et al. |
| 2012/0294822 A1 | 11/2012 | Russo et al. |
| 2013/0216535 A1 | 8/2013 | Zeller et al. |
| 2013/0295087 A1 | 11/2013 | Poulsen et al. |
| 2013/0295088 A1 | 11/2013 | Poulsen et al. |
| 2015/0050267 A1* | 2/2015 | Zeller ................. C07K 16/26 424/133.1 |

FOREIGN PATENT DOCUMENTS

| | | |
|---|---|---|
| CA | 2626120 | 12/2012 |
| CN | 101309704 | 11/2008 |
| CN | 101979650 | 2/2011 |
| CN | 103421114 | 12/2013 |
| EA | 015526 | 10/2008 |
| EP | 0212432 | 3/1987 |
| EP | 1031350 | 8/2000 |
| EP | 1770091 | 4/2007 |
| EP | 1556020 | 2/2009 |
| EP | 1957106 | 10/2013 |
| JP | Hei6-87890 | 3/1994 |
| JP | 08-268874 | 10/1996 |
| JP | 2007517911 | 7/2007 |
| JP | 2009-515942 | 4/2009 |
| JP | 2011046710 | 3/2011 |
| JP | 2011513386 | 4/2011 |
| JP | 2011513387 | 4/2011 |
| JP | 5123197 | 1/2013 |
| KR | 10-1250049 | 4/2013 |
| RU | 2329062 | 7/2008 |
| WO | WO 1996/0004928 | 2/1996 |
| WO | WO 97/09046 | 3/1997 |
| WO | WO 98/09630 | 3/1998 |
| WO | WO 98/11128 | 3/1998 |
| WO | WO 98/56779 | 12/1998 |
| WO | WO 00/18764 | 4/2000 |
| WO | WO 2001/022972 | 4/2001 |
| WO | WO 2003/093472 | 11/2003 |
| WO | WO 03/104236 | 12/2003 |
| WO | WO 2004/003019 | 1/2004 |
| WO | WO 2004/014351 | 2/2004 |
| WO | WO 2004/050683 | 6/2004 |
| WO | WO 2004058184 | 7/2004 |
| WO | WO 2004/082602 | 9/2004 |
| WO | WO 2004/082605 | 9/2004 |
| WO | WO 2004/082678 | 9/2004 |
| WO | WO 2004/083187 | 9/2004 |
| WO | WO 2004/087649 | 10/2004 |
| WO | WO 2004/091514 | 10/2004 |
| WO | WO 2004/092166 | 10/2004 |
| WO | WO 2004/092168 | 10/2004 |
| WO | WO 2004096122 | 11/2004 |
| WO | WO 2004097421 | 11/2004 |
| WO | WO 2005/009962 | 2/2005 |
| WO | WO 2005/040395 | 5/2005 |
| WO | WO 2005041757 | 5/2005 |
| WO | WO 2005070444 | 8/2005 |
| WO | WO 2005/100360 | 10/2005 |
| WO | WO 2006/077212 | 7/2006 |
| WO | WO 2007/025212 | 3/2007 |
| WO | WO 2007/048026 | 4/2007 |
| WO | WO 2007/054800 | 5/2007 |
| WO | WO 2007/054809 | 5/2007 |
| WO | WO 2007/061676 | 5/2007 |
| WO | WO 2007/076336 | 7/2007 |
| WO | WO 2007/141285 | 12/2007 |
| WO | WO 2008/011190 | 1/2008 |
| WO | WO 2009/109908 | 9/2009 |
| WO | WO 2009/109911 | 9/2009 |
| WO | WO 2010075238 | 7/2010 |
| WO | WO 2011/024113 | 3/2011 |
| WO | WO 2011/156324 | 12/2011 |

OTHER PUBLICATIONS

Adwanikar H, et al. Spinal CGRP1 receptors contribute to supraspinally organized pain behavior and pain-related sensitization of amygdala neurons. Pain. Nov. 2007;132(1-2):53-66. Epub Mar. 1, 2007.

Akerman S, et al. "Nitric oxide synthase inhibitors can antagonize neurogenic and calcitonin gene-related peptide induced dilation of dural meningeal vessels," Br J Pharmacol. Sep. 2002;137(1):62-8.

Akerman, S., et al. "Pearls and pitfalls in experimental in vivo models of migraine: dural trigeminovascular nociception," Cephalalgia. Jun. 2013;33(8):577-92.

Alder Biopharmaceuticals Inc., "Alder Presents Positive ALD403 Clinical Data at European Headache and Migraine Trust International Congress," Press Release, Sep. 15, 2016.

Alder Biopharmaceuticals Inc., "Alder Presents Positive Clinical Data for ALD403 at the 17th Congress of the International Headache Society" Press Release, May 15, 2015. (3 pages).

Alder Biopharmaceuticals Inc., "Alder Reports Phase 2b Trial of ALD403 Meets Primary and Secondary Endpoints Demonstrating Migraine Prevention in Patients with Chronic Migraine," Press Release, Mar. 28, 2016. (4 pages).

Alder Biopharmaceuticals Inc., "Alder Reports Positive Top-Line 24-Week Data Demonstrating Persistent Migraine Prevention in Phase 2b Study of ALD403 in Patients with Chronic Migraine" Press Release, Jul. 25, 2016. (3 pages).

Alder Biopharmaceuticals Inc., "Data From Proof-of-Concept Clinical Trial of ALD403, a Monoclonal Antibody Against CGRP for the Prevention of Migraine, to be Presented at 56th Annual Scientific Meeting of the American Headache Society," Press Release, Jun. 26, 2014.

Almagro JC et al. "Chapter 13 Antibody Engineering: Humanization, Affinity Maturation, and Selection Techniques." Therapeutic Monoclonal Antibodies: From Bench to Clinic (Zhiqiang An (Editor)) Oct. 2009: 311-34.

Amara SG, et al. "Expression in brain of a messenger RNA encoding a novel neuropeptide homologous to calcitonin gene-related peptide." Science. Sep. 13, 1985;229(4718):1094-7.

Ambalavanar R., et al. "Deep tissue inflammation upregulates neuropeptides and evokes nociceptive behaviors which are modulated by a neuropeptide antagonist." Pain. Jan. 2006;120(1-2):53-68. Epub Dec. 13, 2005.

Amrutkar DV. "Calcitonin gene-related peptide (CGRP) uptake and release in rat dura mater, trigeminal ganglion and trigeminal nucleus

(56) References Cited

OTHER PUBLICATIONS caudalis," PhD thesis, Faculty of Health and Medical Sciences University of Copenhagen, Academic advisor: Inger Jansen-Olesen and Jes Olesen, Submitted: Feb. 20, 2013.
An Z. "Therapeutic Monoclonal Antibodies: From Bench to Clinic." Wiley & Sons, Inc., 2009 Chapter 31, 711-62.
Andersen DC, et al. "Production technologies for monoclonal antibodies and their fragments," Curr Opin Biotechnol. Oct. 2004;15(5):456-62.
Andrew DP, et al. "Monoclonal antibodies distinguishing alpha and beta forms of calcitonin gene-related peptide." J Immunol Methods. Nov. 6, 1990;134(1):87-94.
Antibody Structure and Function, Chapter 4 of Elgert's Immunology: Understanding the Immune System, pp. 58-78. Wiley 1998.
Aoki KR. "Review of a proposed mechanism for the antinociceptive action of botulinum toxin type A," Neurotoxicology. Oct. 2005;26(5):785-93.
Aoki-Nagase T, et al. "Attenuation of antigen-induced airway hyperresponsiveness in CGRP-deficient mice," Am J Physiol Lung Cell Mol Physiol. Nov. 2002;283(5):L963-70.
Armour KL, et al. "Recombinant human IgG molecules lacking Fcgamma receptor I binding and monocyte triggering activities," Eur J Immunol. Aug. 1999;29(8):2613-24.
Arulmani U, et al. "Calcitonin gene-related peptide and its role in migraine pathophysiology." Eur J Pharmacol. Oct. 1, 2004;500(1-3):315-30.
Arulmani U, et al. "Experimental migraine models and their relevance in migraine therapy," Cephalalgia. Jun. 2006;26(6):642-59.
Arulmozhi DK, et al., "Migraine: current concepts and emerging therapies." Vascul Pharmacol. Sep. 2005;43(3):176-87.
Asghar, MS, et al. "Evidence for a vascular factor in migraine," Ann Neurol. Apr. 2011;69(4):635-45.
Ashina M, "Vascular changes have a primary role in migraine," Cephalalgia. Apr. 2012;32(5):428-30.
Ashina M, et al. "Evidence for increased plasma levels of calcitonin gene-related peptide in migraine outside of attacks." Pain. May 2000;86(1-2):133-8.
Ashina M, et al. "Pearls and pitfalls in human pharmacological models of migraine: 30 years' experience," Cephalalgia. Jun. 2013;33(8):540-53.
Ashina M, et al. "Plasma levels of calcitonin gene-related peptide in chronic tension-type headache," Neurology. Nov. 14, 2000;55(9):1335-40.
Ashina M. "Calcitonin gene-related peptide in tension-type headache," ScientificWorldJournal. Jun. 7, 2002;2:1527-31.
Aziz Q., "Visceral hypersensitivity: fact or fiction." Gastroenterology. Aug. 2006;131(2):661-4.
Bagdy, G, et al. "Headache-type adverse effects of NO donors: vasodilation and beyond," Br J Pharmacol. May 2010;160(1):20-35.
Balint RF, et al. "Antibody engineering by parsimonious mutagenesis." Gene. Dec. 27, 1993;137(1):109-18.
Barker JN, et al. "Progress in psoriasis. Psoriasis: from gene to clinic. London, UK, Dec. 5-7, 1996," Mol Med Today. May 1997;3(5):193-4.
Batra SK, et al. "Pharmacokinetics and biodistribution of genetically engineered antibodies," Curr Opin Biotechnol. Dec. 2002;13(6):603-8.
Baxter LT, et al. "Biodistribution of monoclonal antibodies: scale-up from mouse to human using a physiologically based pharmacokinetic model," Cancer Res. Oct. 15, 1995;55(20):4611-22.
Bell RD, et al. "Breaching the blood-brain barrier for drug delivery," Neuron. Jan. 8, 2014;81(1):1-3.
Benarroch EE. "CGRP: sensory neuropeptide with multiple neurologic implications," Neurology. Jul. 19, 2011;77(3):281-7.
Benemei S, et al. "CGRP receptors in the control of pain and inflammation," Curr Opin Pharmacol. Feb. 2009;9(1):9-14.
Benemei S, et al. "Migraine," Handb Exp Pharmacol. 2009;(194):75-89.

Benemei S, et al. "Pain pharmacology in migraine: focus on CGRP and CGRP receptors," Neurol Sci. May 2007;28 Suppl 2:S89-93.
Benincosa LJ, et al. "Pharmacokinetics and Pharmacodynamics of a Humanized Monoclonal Antibody to Factor IX in Cynomolgus Monkeys," J Pharmacol Exp Ther. Feb. 2000;292(2):810-6.
Bennett AD, et al. "Alleviation of mechanical and thermal allodynia by CGRP(8-37) in a rodent model of chronic central pain." Pain. May 2000;86(1-2):163-75.
Benschop U.S. Appl. No. 60/753,044, filed Dec. 22, 2005. File History. 48 pages.
Biacore 3000 Instrument Handbook, Mar. 1999. 201 pages.
Bigal and Krymchantowski, "Emerging drugs for migraine prophylaxis and treatment," Med. Gen. Med. 2006;8(2):31.
Bigal M. "Clinical Trials Update—2012: Year in Review—A Comment" Headache. Jun. 2013;53(6):1003-4.
Bigal ME, et al. "Emerging drugs for migraine prophylaxis and treatment," MedGenMed. May 4, 2006;8(2):31.
Bigal ME, et al. "Ergotamine and dihydroergotamine: a review," Curr Pain Headache Rep. Feb. 2003 ;7(1):55-62.
Bigal ME, et al. "Headache prevention outcome and body mass index," Cephalalgia. Apr. 2006;26(4):445-50.
Bigal ME, et al. "Migraine in the Triptan Era: Lessons From Epidemiology, Pathophysiology, and Clinical Science," Headache. Feb. 2009;49 Suppl 1:S21-33.
Bigal ME, et al. "Migraine in the triptan era: progresses achieved, lessons learned and future developments," Arq Neuropsiquiatr. Jun. 2009;67(2B):559-69.
Bigal ME, et al. "Modifiable risk factors for migraine progression," Headache. Oct. 2006;46(9):1334-43.
Bigal ME, et al. "Monoclonal Antibodies for Migraine: Preventing Calcitonin Gene-Related Peptide Activity," CNS Drugs. May 2014;28(5):389-99.
Bigal ME, et al. "New developments in migraine prophylaxis," Expert Opin Pharmacother. Apr. 2003;4(4):433-43.
Bigal ME, et al. "New migraine preventive options: an update with pathophysiological considerations," Rev Hosp Clin Fac Med Sao Paulo. Nov.-Dec. 2002;57(6):293-8.
Bigal ME, et al. "Obesity and migraine: a population study," Neurology. Feb. 28, 2006;66(4):545-50.
Bigal ME, et al. "Obesity is a risk factor for transformed migraine but not chronic tension-type headache," Neurology. Jul. 25, 2006;67(2):252-7.
Bigal ME, et al. "Prophylactic migraine therapy: emerging treatment options," Curr Pain Headache Rep. Jun. 2004;8(3):178-84.
Bigal ME, et al. "Safety and tolerability of LBR-101, a humanized monoclonal antibody that blocks the binding of CGRP to its receptor: Results of the Phase 1 program," Cephalalgia. Dec. 23, 2013;34(7):483-492.
Bigal ME, et al. "Safety, tolerability, and efficacy of TEV-48125 for preventive treatment of high-frequency episodic migraine: a multicentre, randomised, double-blind, placebo-controlled, phase 2b study," Lancet Neurol. Nov. 2015;14(11):1081-90.
Bigal ME, et al. "The preventive treatment of migraine," Neurologist. Jul. 2006;12(4):204-13.
Bigal ME, et al. "The triptans," Expert Rev Neurother. May 2009;9(5):649-59.
Bigal, ME "Glutamate Receptor Antagonists," Headache Currents, 1:20-21. Jul. 2004.
Birder L, et al. "Neural control of the lower urinary tract: peripheral and spinal mechanisms," Neurourol Urodyn. 2010;29(1):128-39.
Boeckh M, et al. "Phase 1 Evaluation of the Respiratory Syncytial Virus-Specific Monoclonal Antibody Palivizumab in Recipients of Hematopoietic Stem Cell Transplants," J Infect Dis. Aug. 1, 2001;184(3):350-4.
Bolay H, et al. "Intrinsic brain activity triggers trigeminal meningeal afferents in a migrane model," Nat Med. Feb. 2002;8(2):136-42.
Brain SD, et al. "CGRP receptors: a headache to study, but will antagonists prove therapeutic in migraine?" Trends Pharmacol Sci. Feb. 2002;23(2):51-3.
Brain SD, et al. "Vascular actions of calcitonin gene-related peptide and adrenomedullin." Physiol Rev. Jul. 2004;84(3):903-34.

(56) References Cited

OTHER PUBLICATIONS

Brekke OH, et al. "Therapeutic Antibodies for Human Diseases At the Dawn of the Twenty-First Century," Nat Rev Drug Discov. Jan. 2003;2(1):52-62.
Brorson K, et al. "Mutational analysis of avidity and fine specificity of anti-levan antibodies." J Immunol. Dec. 15, 1999;163(12):6694-701.
Brüggemann M, et al. "The Immunogenicity of Chimeric Antibodies," J Exp Med. Dec. 1, 1989;170(6):2153-7.
Brummell DA, et al. "Probing the combining site of an anti-carbohydrate antibody by saturation-mutagenesis: role of the heavy-chain CDR3 residues." Biochemistry. Feb. 2, 1993;32(4):1180-7.
Buckley TL, et al. "The partial inhibition of inflammatory responses induced by capsaicin using the Fab fragment of a selective calcitonin gene-related peptide antiserum in rabbit skin." Neuroscience. Jun. 1992;48(4):963-8.
Burks EA, "In vitro scanning saturation mutagenesis of an antibody binding pocket." Proc Natl Acad Sci U S A. Jan. 21, 1997;94(2):412-7.
Buzzi MG, et al. "The antimigraine drug, sumatriptan (GR43175), selectively blocks neurogenic plasma extravasation from blood vessels in dura mater," Br J Pharmacol. Jan. 1990;99(1):202-6.
Carter PJ. "Potent antibody therapeutics by design," Nat Rev Immunol. May 2006;6(5):343-57.
Casset F, et al. "A peptide mimetic of an anti-CD4 monoclonal antibody by rational design." Biochem Biophys Res Commun. Jul. 18, 2003;307(1):198-205.
Castaño, et al. "Headache in symptomatic intracranial hypertension secondary to leptospirosis: a case report," Cephalalgia. Apr. 2005;25(4):309-11.
Cernuda-Morollón E, et al. "CGRP and VIP levels as predictors of efficacy of Onabotulinumtoxin type A in chronic migraine," Headache. Jun. 2014;54(6):987-95.
Chancellor MB, et al. "Neurophysiology of stress urinary incontinence," Rev Urol. 2004;6 Suppl 3:S19-28.
Charbit, A et al. "Dopamine: what's new in migraine?" Curr Opin Neurol. Jun. 2010;23(3):275-81.
Charles A, "Migraine is not primarily a vascular disorder," Cephalalgia. Apr. 2012;32(5):431-2.
Chauhan M, et al. "Studies on the effects of the N-terminal domain antibodies of calcitonin receptor-like receptor and receptor activity-modifying protein 1 on calcitonin gene-related peptide-induced vasorelaxation in rat uterine artery," Biol Reprod. Jun. 2004;70(6):1658-63.
Chen JT, et al. "Menopausal flushes and calcitonin-gene-related peptide," Lancet. Jul. 3, 1993;342(8862):49.
Chen Y, et al. "Selection and analysis of an optimized anti-VEGF antibody: crystal structure of an affinity-matured Fab in complex with antigen." J Mol Biol. Nov. 5, 1999;293(4):865-81.
Cheung B et al. "Adrenomedullin: Its Role in the Cardiovascular System," Semin Vasc Med. May 2004;4(2):129-34.
Chowdhury PS, et al. "Tailor-made antibody therapeutics," Methods. May 2005;36(1):11-24.
Chuang YC, et al. "Intraprostatic botulinum toxin a injection inhibits cyclooxygenase-2 expression and suppresses prostatic pain on capsaicin induced prostatitis model in rat," J Urol. Aug. 2008;180(2):742-8.
Chuang YC, et al. "Urodynamic and immunohistochemical evaluation of intravesical botulinum toxin A delivery using liposomes," J Urol. Aug. 2009;182(2):786-92.
Cianchetti C. "The role of the neurovascular scalp structures in migraine," Cephalalgia. Jul. 2012;32(10):778-84.
Clinical Trial No. LY2951742, started Mar. 2015, https://clinicaltrials.gov/ct2/show/study/NCT02397473?term=LY2951742&rank=9, retrieved Sep. 3, 2016.
Colcher D, et al. "Pharmacokinetics and biodistribution of genetically-engineered antibodies," Q J Nucl Med. Dec. 1998;42(4):225-41.
Colgate.ru Website on Temporomandibular Joint Disorders, 2017; http://www.colgate.ru/ru/ru/oc/oral-health/conditions/temporomandibular-disorder.
Colman PM. "Effects of amino acid sequence changes on antibody-antigen interactions." Res Immunol. Jan. 1994;145(1):33-6.
Conner AC, et al. "Interaction of calcitonin-gene-related peptide with its receptors." Biochem Soc Trans. Aug. 2002;30(4):451-5.
Conner AC, et al. "Ligand binding and activation of the CGRP receptor," Biochem Soc Trans. Aug. 2007;35(Pt 4):729-32.
Connor K M et al: "Randomized, controlled trial of telcagepant for the acute treatment of migraine.", Neurology Sep. 22, 2009, vol. 73, No. 12, Sep. 22, 2009 (Sep. 22, 2009), pp. 970-977, XP002732737, ISSN: 1526-632X.
Correia IR. "Stability of IgG isotypes in serum," MAbs. May-Jun. 2010;2(3):221-32.
Cottrell GS, et al. "Localization of calcitonin receptor-like receptor (CLR) and receptor activity-modifying protein 1 (RAMP1) in human gastrointestinal tract," Peptides. Jun. 2012;35(2):202-11.
Covell DG, et al. "Pharmacokinetics of monoclonal immunoglobulin G1, F(ab')2, and Fab' in mice." Cancer Res. Aug. 1986;46(8):3969-78.
Cutrer F. "Pathophysiology of Migraine," Semin Neurol. Apr. 2006;26(2):171-80.
Cutrer F. "Pathophysiology of Migraine," Semin Neurol. Apr. 2010;30(2):120-30.
Dakhama A, et al. "Calcitonin gene-related peptide: role in airway homeostasis," Curr Opin Pharmacol. Jun. 2004;4(3):215-20.
Davies J, et al. "Affinity improvement of single antibody VH domains: residues in all three hypervariable regions affect antigen binding." Immunotechnology. Sep. 1996;2(3):169-79.
Davis CD et al. "The Tortuous Road to an Ideal CGRP Function Blocker for the Treatment of Migraine," Curr Top Med Chem. 2008;8(16):1468-79.
Davletov B, et al. "Beyond Botox: advantages and limitations of individual botulinum neurotoxins," Trends Neurosci. Aug. 2005;28(8):446-52.
De Pascalis R, et al. "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Delafoy L, et al. "Interactive involvement of brain derived neurotrophic factor, nerve growth factor, and calcitonin gene related peptide in colonic hypersensitivity in the rat." Gut. Jul. 2006;55(7):940-5. Epub Jan. 9, 2006.
Denekas T, et al. "Inhibition of stimulated meningeal blood flow by a calcitonin gene-related peptide binding mirror-image RNA oligonucleotide," Br J Pharmacol. Jun. 2006;148(4):536-43.
Deng R et al. "Projecting human pharmacokinetics of therapeutic antibodies from nonclinical data," MAbs. Jan.-Feb. 2011;3(1):61-6.
Derosa G, et al. "Optimizing combination treatment in the management of type 2 diabetes," Vasc Health Risk Manag. 2007;3(5):665-71.
Diamond S, et al. "Patterns of diagnosis and acute and preventive treatment for migraine in the United States: results from the American Migraine Prevalence and Prevention study," Headache. Mar. 2007;47(3):355-63.
Diener HC, et al. "Utility of topiramate for the treatment of patients with chronic migraine in the presence or absence of acute medication overuse," Cephalalgia. Oct. 2009;29(10):1021-7.
Dockray et al., "Immunoneutralization studies with calcitonin gene-related peptide," Ann. NY Acad Sci. 1992;657:258-67.
Dodick D, et al. "Cluster Headache: Diagnosis, Management and Treatment," Wolff's Headache 2001, p. 283.
Dodick DW, et al. "Safety and efficacy of ALD403, an antibody to calcitonin gene-related peptide, for the prevention of frequent episodic migraine: a randomised, double-blind, placebo-controlled, exploratory phase 2 trial," Lancet Neurol. Nov. 2014;13(11):1100-7.
Doggrell S. "Migraine and beyond: cardiovascular therapeutic potential for CGRP modulators," Expert Opin Investig Drugs. Jun. 2001;10(6):1131-8.
Dolgin E. "Antibody drugs set to revive flagging migraine target," Nat Rev Drug Discov. Apr. 2013;12(4):249-50.

(56) References Cited

OTHER PUBLICATIONS

Doods H, et al. "Pharmacological profile of BIBN4096BS, the first selective small molecule CGRP antagonist." BR J Pharmacol. Feb. 2000;129(3):420-3.

Doods, H et al. "CGRP antagonists: unravelling the role of CGRP in migraine," Trends Pharmacol Sci. Nov. 2007;28(11):580-7.

Dooley JS, et al. "Antibiotics in the treatment of biliary infection," Gut. Sep. 1984;25(9):988-98.

Drake AW, et al. "Characterizing high-affinity antigen/antibody complexes by kinetic- and equilibrium-based methods," Anal Biochem. May 1, 2004;328(1):35-43.

Dressler and Saberi, "Botulinum toxin: mechanisms of action," Eur. Neurol, 2005;53:3-9.

Dressler D, et al. "Botulinum toxin: mechanisms of action," Arq Neuropsiquiatr. Mar. 2005;63(1):180-5.

Dufner P, et al. "Harnessing phage and ribosome display for antibody optimisation." Trends Biotechnol. Nov. 2006;24(11):523-9. Epub Sep. 26, 2006.

Durham P. "CGRP-receptor antagonists—a fresh approach to migraine therapy?" N Engl J Med. Mar. 11, 2004;350(11):1073-5.

Durham Paul L et al: "Calcitonin Gene-Related Peptide (CGRP) Receptor Antagonists in the Treatment of Migraine", CNS Drugs, vol. 24, No. 7, 2010, pp. 539-548.

Durham PL et al. "New insights into the molecular actions of serotonergic antimigraine drugs," Pharmacol Ther. Apr.-May 2002;94(1-2):77-92.

Durham PL, et al. "Regulation of calcitonin gene-related peptide secretion from trigeminal nerve cells by botulinum toxin type A: implications for migraine therapy," Headache. Jan. 2004;44(1):35-42; discussion 42-3.

Durham PL. "Calcitonin Gene-Related Peptide (CGRP) and Migraine," Headache. Jan. 2006;46 Suppl 1:S3-8.

Durham PL. "Inhibition of calcitonin gene-related peptide function: a promising strategy for treating migraine," Headache. Sep. 2008;48(8):1269-75.

Edvinsson L et al. "Blockade of CGRP receptors in the intracranial vasculature: a new target in the treatment of headache," Cephalalgia. Aug. 2004;24(8):611-22.

Edvinsson L et al. "CGRP Receptor Antagonism and Migraine," Neurotherapeutics. Apr. 2010;7(2):164-75.

Edvinsson L et al. "Extracerebral manifestations in migraine. A peptidergic involvement?" J Intern Med. Oct. 1990;228(4):299-304.

Edvinsson L et al. "Neurobiology in primary headaches," Brain Res Brain Res Rev. Jun. 2005;48(3):438-56.

Edvinsson L et al. "Perivascular neuropeptides (NPY, VIP, CGRP and SP) in human brain vessels after subarachnoid haemorrhage," Acta Neurol Scand. Nov. 1994;90(5):324-30.

Edvinsson L et al. "The blood-brain barrier in migraine treatment," Cephalalgia. Dec. 2008;28(12):1245-58.

Edvinsson L et al: "New drugs in migraine treatment and prophylaxis: telcagepant and topiramate", The Lancet, The Lancet Publishing Group, GB, vol. 376, No. 9741, Aug. 21, 2010 (Aug. 21, 2010), pp. 645-655.

Edvinsson L, et al. "Calcitonin gene-related peptide and cerebral blood vessels: distribution and vasomotor effects," J Cereb Blood Flow Metab. Dec. 1987;7(6):720-8.

Edvinsson L, et al. "Inhibitory effect of BIBN4096BS, CGRP(8-37), a CGRP antibody and an RNA-Spiegelmer on CGRP induced vasodilatation in the perfused and non-perfused rat middle cerebral artery." Br J Pharmacol. Mar. 2007;150(5):633-40. Epub Jan. 22, 2007.

Edvinsson L, et al. "Innervation of the human middle meningeal artery: immunohistochemistry, ultrastructure, and role of endothelium for vasomotility," Peptides. 1998;19(7):1213-25.

Edvinsson L, et al. "Neuropeptides in migraine and cluster headache," Cephalalgia. Oct. 1994;14(5):320-7.

Edvinsson L. "Aspects on the Pathophysiology of Migraine and Cluster Headache," Pharmacol Toxicol. Aug. 2001;89(2):65-73.

Edvinsson L. "Calcitonin Gene-Related Peptide (CGRP) and the Pathophysiology of Headache Therapeutic Implications," CNS Drugs. 2001;15(10):745-53.

Edvinsson L. "CGRP blockers in migraine therapy: where do they act?" Br J Pharmacol. Dec. 2008;155(7):967-9.

Edvinsson L. "CGRP-receptor antagonism in migraine treatment," Lancet. Dec. 20, 2008;372(9656):2089-90.

Edvinsson L. "Clinical Data on the CGRP Antagonist BIBN4096BS for Treatment of Migraine Attacks," CNS Drug Rev. Spring 2005;11(1):69-76.

Edvinsson L. "Innervation and effects of dilatory neuropeptides on cerebral vessels. New aspects," Blood Vessels. 1991;28(1-3):35-45.

Edvinsson L. "Neuronal Signal Substances as Biomarkers of Migraine," Headache. Jul.-Aug. 2006;46(7):1088-94.

Edvinsson L. "New therapeutic target in primary headaches—blocking the CGRP receptor," Expert Opin Ther Targets. Jun. 2003;7(3):377-83.

Edvinsson L. "Novel migraine therapy with calcitonin gene-regulated peptide receptor antagonists," Expert Opin Ther Targets. Sep. 2007;11(9):1179-88.

Edvinsson L: "CGRP blockers in migraine therapy: where do they act?", British Journal of Pharmacology, vol. 155, No. 7, Dec. 2008 (Dec. 2008), pp. 967-969.

Edvinsson Lars: "CGRP-receptor antagonism in migraine treatment.", Lancet Dec. 20, 2008, vol. 372, No. 9656, Dec. 20, 2008 (Dec. 20, 2008), pp. 2089-2090.

Eftekhari S et al. "Differentiation of Nerve Fibers Storing CGRP and CGRP Receptors in the Peripheral Trigeminovascular System," J Pain. Nov. 2013;14(11):1289-303.

Elshourbagy NA, et al. "Molecular cloning and characterization of the porcine calcitonin gene-related peptide receptor." Endocrinology. Apr. 1998;139(4):1678-83.

Emerick GT. "Migraines in the Presence of Glaucoma, Recent advances in diagnosis and management," Glaucoma Today, Sep./Oct. 2008, 21-23.

Escott et al., "Effect of a calcitonin gene-related peptide antagonist (CGRP8-37) on skin vasodilatation and oedema induced by stimulation of the rat saphenous nerve," Br. J. Pharmacol. 1993;110:772-6.

Escott KJ, et al. "Trigeminal ganglion stimulation increases facial skin blood flow in the rat: a major role for calcitonin gene-related peptide." Brain Res. Jan. 9, 1995;669(1):93-9.

Esfandyari T. "The Role of Calcitonin Gene-Related Peptide (CGRP) in Colonic Inflammation, and Secretion in the Rat Distal Colon," Thesis, University of Calagary, Department of Neuroscience and Gastrointestinal Sciences. 1999. 145 pages.

Evans BN, et al. "CGRP-RCP, a novel protein required for signal transduction at calcitonin gene-related peptide and adrenomedullin receptors," J Biol Chem. Oct. 6, 2000;275(40):31438-43.

Evans RW, et al. "Target doses and titration schedules for migraine preventive medications," Headache. Jan. 2006;46(1):160-4.

Evans RW. "Exploding head syndrome followed by sleep paralysis: a rare migraine aura," Headache. Apr. 2006;46(4):682-3.

Everitt DE et al. "The Pharmacokinetics, Antigenicity, and Fusion-Inhibition Activity of RSHZ19, a Humanized Monoclonal Antibody to Respiratory Syncytial Virus, in Healthy Volunteers," J Infect Dis. Sep. 1996;174(3):463-9.

Faraci FM, et al. "Vascular responses of dura mater," Am J Physiol. Jul. 1989;257(1 Pt 2):H157-61.

Farinelli, I et al. "Future drugs for migraine," Intern Emerg Med. Oct. 2009;4(5):367-73.

Feuerstein G et al. "Clinical perspectives of calcitonin gene related peptide pharmacology," Can J Physiol Pharmacol. Jul. 1995;73(7):1070-4.

File History U.S. Appl. No. 60/736,623, filed Nov. 14, 2005, Zeller, et al. Antagonist Antibodies Directed Against Calcitonin Gene-Related Peptide and Methods Using Same. 110 pages.

Fischer MJ et al. "The Nonpeptide Calcitonin Gene-Related Peptide Receptor Antagonist BIBN4096BS Lowers the Activity of Neurons with Meningeal Input in the Rat Spinal Trigeminal Nucleus," J Neurosci. Jun. 22, 2005;25(25):5877-83.

Fischer MJ. "Calcitonin gene-related peptide receptor antagonists for migraine," Expert Opin Investig Drugs. Jul. 2010;19(7):815-23.

(56) References Cited

OTHER PUBLICATIONS

Forssman B, et al. "Atenolol for migraine prophylaxis," Headache. Jul. 1983;23(4):188-90.
Forster ER, et al. "The role of calcitonin gene-related peptide in gastric mucosal protection in the rat," Exp Physiol. Jul. 1991;76(4):623-6.
Friend PJ, et al. "Phase I study of an engineered aglycosylated humanized CD3 antibody in renal transplant rejection," Transplantation. Dec. 15, 1999;68(11):1632-7.
Frobert Y, et al. "A sensitive sandwich enzyme immunoassay for calcitonin gene-related peptide (CGRP): characterization and application." Peptides. 1999;20(2):275-84.
Galitsky BA, et al. "Predicting amino acid sequences of the antibody human VH chains from its first several residues," Proc Natl Acad Sci U S A. Apr. 28, 1998;95(9):5193-8.
Gallai V, et al. "Vasoactive peptide levels in the plasma of young migraine patients with and without aura assessed both interictally and ictally." Cephalalgia. Oct. 1995;15(5):384-90.
Gangula PR, et al. "Increased blood pressure in alpha-calcitonin gene-related peptide/calcitonin gene knockout mice," Hypertension. Jan. 2000;35(1 Pt 2):470-5.
Gearing D, et al. "A fully caninised anti-NGF monoclonal antibody for pain relief in dogs," BMC Vet Res. Nov. 9, 2013;9:226.
Geppetti P et al. "Antidromic vasodilatation and the migraine mechanism," J Headache Pain. Mar. 2012;13(2):103-11.
Geppetti P et al. "CGRP and migraine: neurogenic inflammation revisited," J Headache Pain. Apr. 2005;6(2):61-70.
Geppetti P et al. "Novel therapeutic targets," Neurol Sci. May 2006;27 Suppl 2:S111-4.
Giamberardino MA, et al. "Emerging drugs for migraine treatment," Expert Opin Emerg Drugs. Mar. 2015;20(1):137-47.
Gillies S et al. "Improving the efficacy of antibody-interleukin 2 fusion proteins by reducing their interaction with Fc receptors," Cancer Res. May 1, 1999;59(9):2159-66.
Giniatullin R et al. "Molecular Mechanisms of Sensitization of Pain-transducing P2X3 Receptors by the Migraine Mediators CGRP and NGF," Mol Neurobiol. Feb. 2008;37(1):83-90.
Glennie MJ, et al. "Clinical trials of antibody therapy," Immunol Today. Aug. 2000;21(8):403-10.
Glover V, et al. "Can the vascular and neurogenic theories of migraine finally be reconciled?" Trends Pharmacol Sci. Jan. 1989;10(1):1-3.
Goadsby PJ et al. "Release of vasoactive peptides in the extracerebral circulation of humans and the cat during activation of the trigeminovascular system," Ann Neurol. Feb. 1988;23(2):193-6.
Goadsby PJ, et al. "Migraine—current understanding and treatment." N Engl J Med. Jan. 24, 2002;346(4):257-70.
Goadsby PJ, et al. "Vasoactive peptide release in the extracerebral circulation of humans during migraine headache." Ann Neurol. Aug. 1990;28(2):183-7.
Goadsby PJ. "Advances in the understanding of headache," Br Med Bull. Oct. 5, 2005;73-74:83-92. Print 2005.
Goadsby PJ. "Calcitonin gene-related peptide antagonists as treatments of migraine and.other primary headaches," Drugs. 2005;65(18):2557-67.
Goadsby PJ. "Can we develop neurally acting drugs for the treatment of migraine?" Nat Rev Drug Discov. Sep. 2005;4(9):741-50.
Goadsby PJ. "Headache: a good year for research," Lancet Neurol. Jan. 2006;5(1):5-6.
Goadsby PJ. "Migraine Pathophysiology," Headache. Apr. 2005;45 Suppl 1:S14-24.
Goadsby PJ. "New targets in the acute treatment of headache," Curr Opin Neurol. Jun. 2005;18(3):283-8.
Goadsby PJ. "The vascular theory of migraine—a great story wrecked by the facts," Brain. Jan. 2009;132(Pt 1):6-7.
Goadsby, PJ, et al. "Randomized, double-blind, placebo-controlled trial of ALD403, an anti-CGRP antibody in the prevention of frequent episodic migraine." 56th Annual Scientific Meeting of the American Headache Society, Jun. 2014.

Gómez-Foix AM, et al., "Anti-insulin effects of amylin and calcitonin-gene-related peptide on hepatic glycogen metabolism," Biochem J. Jun. 15, 1991;276 ( Pt 3):607-10.
Green LL, et al. "Antigen-specific human monoclonal antibodies from mice engineered with human Ig heavy and light chain YACs," Nat Genet. May 1994;7(1):13-21.
Grunenberger F. "[Calcitonin gene-related peptide (CGRP): a vasodilator neuropeptide with many potential applications]" Pathol Biol (Paris). Dec. 1993;41(10):936-42.
Gupta S et al. "Evidence for CGRP re-uptake in rat dura mater encephali," Br J Pharmacol. Dec. 2010;161(8):1885-98.
Gupta S et al. "Intravital microscopy on a closed cranial window in mice: a model to study trigeminovascular mechanisms involved in migraine," Cephalalgia. Nov. 2006;26(11):1294-303.
Gupta S et al. "Potential role of female sex hormones in the pathophysiology of migraine," Pharmacol Ther. Feb. 2007;113(2):321-40.
Gupta S et al. "The relevance of preclinical research models for the development of antimigraine drugs: focus on 5-HT(1B/1D) and CGRP receptors," Pharmacol Ther. Oct. 2010;128(1):170-90.
Hakala JM, et al. "Modelling constrained calcitonin gene-related peptide analogues." Protein Eng. Feb. 1996;9(2):143-8.
Halimi S, et al. "Combination treatment in the management of type 2 diabetes: focus on vildagliptin and metformin as a single tablet," Vasc Health Risk Manag. 2008;4(3):481-92.
Hanes J et al. "Picomolar affinity antibodies from a fully synthetic naive library selected and evolved by ribosome display," Nat Biotechnol. Dec. 2000;18(12):1287-92.
Hansen JM, et al. "Calcitonin gene-related peptide triggers migraine-like attacks in patients with migraine with aura," Cephalalgia. Oct. 2010;30(10):1179-86.
Hargreaves R. "New Migraine and Pain Research," Headache. Apr. 2007;47 Suppl 1:S26-43.
Hatcher JP, et al. "Biologics: the next-generation therapeutics for analgesia?" Expert Rev Neurother. Nov. 2011;11(11):1653-8.
Hay D et al. "A comparison of the actions of BIBN4096BS and CGRP(8-37) on CGRP and adrenomedullin receptors expressed on SK-N-MC, L6, col. 29 and Rat 2 cells," Br J Pharmacol. Sep. 2002;137(1):80-6.
Hay D et al. "International Union of Pharmacology. LXIX. Status of the Calcitonin Gene-Related Peptide Subtype 2 Receptor," Pharmacol Rev. Jun. 2008;60(2):143-5.
Hay D et al. "The pharmacology of CGRP-responsive receptors in cultured and transfected cells," Peptides. Nov. 2004;25(11):2019-26.
Hay D et al. "The Preclinical Pharmacology of BIBN4096BS, a CGRP Antagonist," Cardiovasc Drug Rev. Spring 2005; 23(1):31-42.
Hay D. "What Makes a CGRP2 Receptor?" Clin Exp Pharmacol Physiol. Oct. 2007;34(10):963-71.
Hay DL, et al. "CL/RAMP2 and CL/RAMP3 produce pharmacologically distinct adrenomedullin receptors: a comparison of effects of adrenomedullin22-52, CGRP8-37 and BIBN4096BS," Br J Pharmacol. Oct. 2003;140(3):477-86. Epub Aug. 26, 2003.
Hershey JC, et al. "Investigation of the species selectivity of a nonpeptide CGRP receptor antagonist using a novel pharmacodynamic assay," Regul Pept. Apr. 15, 2005;127(1-3):71-7.
Hill RG et al. "Neuropeptide and Kinin Antagonists," Handb Exp Pharmacol. 2007;(177):181-216.
Hillmen P, et al. "Effect of eculizumab on hemolysis and transfusion requirements in patients with paroxysmal nocturnal hemoglobinuria," N Engl J Med. Feb. 5, 2004;350(6):552-9.
Hinton PR, et al. "Engineered human IgG antibodies with longer serum half-lives in primates," J Biol Chem. Feb. 20, 2004;279(8):6213-6.
Hirsch S et al. "The CGRP receptor antagonist BIBN4096BS peripherally alleviates inflammatory pain in rats," Pain. May 2013;154(5):700-7.
Ho TW et al. "CGRP and its receptors provide new insights into migraine pathophysiology," Nat Rev Neurol. Oct. 2010;6(10):573-82.

(56) References Cited

OTHER PUBLICATIONS

Ho TW, et al. "Impact of recent prior opioid use on rizatriptan efficacy. A post hoc pooled analysis," Headache. Mar. 2009;49(3):395-403.
Ho TW, et al. "Randomized controlled trial of the CGRP receptor antagonist telcagepant for migraine prevention," Neurology. Sep. 9, 2014;83(11):958-66.
Ho TW, et al. "Efficacy and tolerability of MK-0974 (telcagepant), a new oral antagonist of calcitonin gene-related peptide receptor, compared with zolmitriptan for acute migraine: a randomised, placebo-controlled, parallel-treatment trial," Lancet. Dec. 20, 2008;372(9656):2115-23.
Hoff AO et al. "Increased bone mass is an unexpected phenotype associated with deletion of the calcitonin gene," J Clin Invest. Dec. 2002;110(12):1849-57.
Hoffmann J, et al. "New Agents for Acute Treatment of Migraine: CGRP Receptor Antagonists, iNOS Inhibitors," Curr Treat Options Neurol. Feb. 2012;14(1):50-9.
Holland J et al. "Calcitonin Gene-Related Peptide Reduces Brain Injury in a Rat Model of Focal Cerebral Ischemia," Stroke. Oct. 1994;25(10):2055-8; discussion 2058-9.
Holliger P, et al. "Engineered antibody fragments and the rise of single domains," Nat Biotechnol. Sep. 2005;23(9):1126-36.
Holm P, et al. "Functional mapping and single chain construction of the anti-cytokeratin 8 monoclonal antibody TS1." Mol Immunol. Feb. 2007;44(6):1075-84. Epub Sep. 20, 2006.
Holman JJ, et al. "Human alpha- and beta-CGRP and rat alpha-CGRP are coronary vasodilators in the rat." Peptides. Mar.-Apr. 1986;7(2):231-5.
Holt LJ, et al. "Domain antibodies: proteins for therapy." Trends Biotechnol. Nov. 2003;21(11):484-90.
Holzer P et al. "Afferent Nerve-Mediated Protection Against Deep Mucosal Damage in the Rat Stomach," Gastroenterology. Apr. 1990;98(4):838-48.
Holzer P et al. "Sensory neurons mediate protective vasodilatation in rat gastric mucosa," Am J Physiol. Mar. 1991;260(3 Pt 1):G363-70.
Holzer P et al. "Stimulation of Afferent Nerve Endings by Intragastric Capsaicin Protects Against Ethanol-Induced Damage of Gastric Mucosa," Neuroscience. Dec. 1988;27(3):981-7.
Holzer P. "Implications of tachykinins and calcitonin gene-related peptide in inflammatory bowel disease," Digestion. Jul.-Aug. 1998;59(4):269-83.
Holzer P. "Capsaicin: Cellular Targets, Mechanisms of Action, and Selectivity for Thin Sensory Neurons," Pharmacol Rev. Jun. 1991;43(2):143-201.
Hong KW, et al. "Effect of omega-conotoxin GVIA and omega-agatoxin IVA on the capsaicin-sensitive calcitonin gene-related peptide release and autoregulatory vasodilation in rat pial arteries," J Cereb Blood Flow Metab. Jan. 1999;19(1):53-60.
Hong KW, et al. "Pharmacological coupling and functional role for CGRP receptors in the vasodilation of rat pial arterioles," Am J Physiol. Jan. 1996;270(1 Pt 2):H317-23.
Hong KW, et al. "Pharmacological evidence that calcitonin gene-related peptide is implicated in cerebral autoregulation," Am J Physiol. Jan. 1994;266(1 Pt 2):H11-6.
Hoogenboom HR, et al. "Multi-subunit proteins on the surface of filamentous phage: methodologies for displaying antibody (Fab) heavy and light chains," Nucleic Acids Res. Aug. 11, 1991;19(15):4133-7.
Hoogenboom HR. "Selecting and screening recombinant antibody libraries," Nat Biotechnol. Sep. 2005;23(9):1105-16.
Hopkins, CR. "ACS Chemical Neuroscience Molecule Spotlight on Telcagepant (MK-0974)," ACS Chem Neurosci. Jul. 20, 2011;2(7):334-5.
Hu H, et al. "Acute migraine treatment with rizatriptan in real world settings—focusing on treatment strategy, effectiveness, and behavior," Headache. Feb. 2009;49 Suppl 1:S34-42.
Hubbard JA, et al. "Identification of the epitopes of calcitonin gene-related peptide (CGRP) for two anti CGRP monoclonal antibodies by 2D NMR," Protein Sci. Sep. 1997;6(9):1945-52.
Hudson PJ, et al. "Engineered antibodies," Nat Med. Jan. 2003;9(1):129-34.
Hughes SR et al. "A calcitonin gene-related peptide (CGRP) antagonist (CGRP8-37) inhibits microvascular responses induced by CGRP and capsaicin in skin," Br J Pharmacol. Nov. 1991;104(3):738-42.
Hurley D. "CGRP Drug Improves Wellness on Headache-Free Days, Study Finds," Neurology Today, p. 31, Jul. 2016.
Hwang WY, et al. "Immunogenicity of engineered antibodies," Methods. May 2005;36(1):3-10.
Ibrahimi K, et al. "Development of an experimental model to study trigeminal nerve-mediated vasodilation on the human forehead," Cephalalgia. Jan. 3, 2014;34(7):514-522.
Idusogie EE, et al. "Mapping of the C1q Binding Site on Rituxan, a Chimeric Antibody with a Human IgG1 Fc," J Immunol. Apr. 15, 2000;164(8):4178-84.
Iovino M, et al. "Safety, tolerability and pharmacokinetics of BIBN 4096 BS, the first selective small molecule calcitonin gene-related peptide receptor antagonist, following single intravenous administration in healthy volunteers," Cephalalgia. Aug. 2004;24(8):645-56.
Janeway CA et al. "Immuno Biology: The Immune System in Health and Disease." Current Biology Ltd./Garland Publishing Inc. 1994 Glossary p. G:2.
Jang YJ, et al. "The structural basis for DNA binding by an anti-DNA autoantibody." Mol. Immunol. Dec. 1998;35(18):1207-17.
Jansen-Olesen I, et al. "In-depth characterization of CGRP receptors in human intracranial arteries," Eur J Pharmacol. Nov. 28, 2003;481(2-3):207-16.
Jones PT, et al. "Replacing the complementarity-determining regions in a human antibody with those from a mouse," Nature. May 29-Jun. 4, 1986;321(6069):522-5.
Juaneda C, et al. "The molecular pharmacology of CGRP and related peptide receptor subtypes," Trends Pharmacol Sci. Nov. 2000;21(11):432-8.
Juhasz G, et al. "NO-induced migraine attack: strong increase in plasma calcitonin gene-related peptide (CGRP) concentration and negative correlation with platelet serotonin release." Pain. Dec. 2003;106(3):461-70.
Juhl L, et al. "Effect of two novel CGRP-binding compounds in a closed cranial window rat model," Eur J Pharmacol. Jul. 12, 2007;567(1-2):117-24.
Julia V, et al. "Tachykininergic mediation of viscerosensitive responses to acute inflammation in rats: role of CGRP." Am J Physiol. Jan. 1997;272(1 Pt 1):G141-6.
Jung ST, et al. "Bypassing glycosylation: engineering aglycosylated full-length IgG antibodies for human therapy," Curr Opin Biotechnol. Dec. 2011;22(6):858-67.
Kaiser EA, et al. "CGRP and migraine: could PACAP play a role too?" Neuropeptides. Dec. 2013;47(6):451-61.
Kapoor K, et al. "Effects of BIBN4096BS on cardiac output distribution and on CGRP-induced carotid haemodynamic responses in the pig," Eur J Pharmacol. Aug. 15, 203;475(1-3):69-77.
Kapoor K, et al. "Effects of the CGRP receptor antagonist BIBN4096BS on capsaicin-induced carotid haemodynamic changes in anaesthetised pigs," Br J Pharmacol. Sep. 2003;140(2):329-38.
Kapoor, K. "Novel Potential Antimigraine Compounds: Carotid and Systemic Haemodynamic Effects in a Porcine Model of Migraine," Thesis, Erasmus University, Rotterdam. With summary in Dutch. 2003. 157 pages.
Karasek C., et al. "Characterization of the intrinsic binding features of three anti-CGRP therapeutic antibodies effective in preventing migraine: a comparative pre-clinical case study of ALD403, LY-2951742, TEV-48125." 5th European Headache and Migraine Trust International Congress, Sep. 2016.
Kato K, et al. "CGRP antagonists enhance gastric acid secretion in 2-h pylorus-ligated rats," Peptides. 1995;16(7):1257-62.

(56) References Cited

OTHER PUBLICATIONS

Kawamura M, et al. "Antinociceptive effect of intrathecally administered antiserum against calcitonin gene-related peptide on thermal and mechanical noxious stimuli in experimental hyperalgesic rats." Brain Res. Sep. 11, 1989;497(1):199-203.

Kaymakcalan Z, et al. "Comparisons of affinities, avidities, and complement activation of adalimumab, infliximab, and etanercept in binding to soluble andmembrane tumor necrosis factor," Clin Immunol. May 2009;131(2):308-16.

Keates AC, et al. "CGRP upregulation in dorsal root ganglia and ileal mucosa during Clostridium difficile toxin A-induced enteritis," Am J Physiol. Jan. 1998;274(1 Pt 1):G196-202.

Kennel SJ, et al. "Direct Binding of Radioiodinated Monoclonal Antibody to Tumor Cells: Significance of Antibody Purity and Affinity for Drug Targeting or Tumor Imaging," Hybridoma. 1983;2(3):297-310.

Kim SJ, et al. "Antibody Engineering for the Development of Therapeutic Antibodies," Mol Cells. Aug. 31, 2005;20(1):17-29.

Kipriyanov S, et al. "Generation and Production of Engineered Antibodies," Mol Biotechnol. Jan. 2004;26(1):39-60.

Kipriyanov S. "Generation of Antibody Molecules Through Antibody Engineering" from Methods in Molecular Biology, vol. 207: Recombinant Antibodies for Cancer Therapy Methods and Protocols, 2003 pp. 3-25.

Knotkova H, et al. "Imaging intracranial plasma extravasation in a migraine patient: a case report," Pain Med. May-Jun. 2007;8(4):383-7.

Kobayashi D, et al. "Calcitonin Gene-Related Peptide Mediated Neurogenic Vasorelaxation in the Isolated Canine Lingual Artery," Jpn J Pharmacol. Apr. 1995;67(4):329-39.

Kobayashi H, et al. "Tryptophan H33 plays an important role in pyrimidine (6-4) pyrimidone photoproduct binding by a high-affinity antibody." Protein Eng. Oct. 1999;12(10):879-84.

Krymchantowski AV, et al. "New and emerging prophylactic agents for migraine," CNS Drugs. 2002;16(9):611-34.

Krymchantowski AV, et al. "Rizatriptan in migraine," Expert Rev Neurother. Sep. 2005;5(5):597-603.

Krymchantowski AV, et al. "Rizatriptan vs. rizatriptan plus trimebutine for the acute treatment of migraine: a double-blind, randomized, cross-over, placebo-controlled study," Cephalalgia. Jul. 2006;26(7):871-4.

Krymchantowski AV, et al. "Topiramate plus nortriptyline in the preventive treatment of migraine: a controlled study for nonresponders," J Headache Pain. Jan. 2012;13(1):53-9.

Kumar S, et al. "Molecular cloning and expression of the Fabs of human autoantibodies in *Escherichia coli*. Determination of the heavy or light chain contribution to the anti-DNA/-cardiolipin activity of the Fab." J Biol Chem. Nov. 10, 2000;275(45):35129-36.

Kunkel RS, et al. "Surgical treatment of chronic migrainous neuralgia," Cleve Clin Q. Winter 1974;41(4):189-92.

Kuraishi Y, et al. "Antinociception induced in rats by intrathecal administration of antiserum against calcitonin gene-related peptide." Neurosci Lett. Oct. 17, 1988;92(3):325-9.

Kurosawa M, et al. "Increase of meningeal blood flow after electrical stimulation of rat dura mater encephali: mediation by calcitonin gene-related peptide," Br J Pharmacol. Apr. 1995;114(7):1397-402.

Kuus-Reichel K, et al. "Will Immunogenicity Limit the Use, Efficacy, and Future Development of Therapeutic Monoclonal Antibodies?" Clin Diagn Lab Immunol. Jul. 1994;1(4):365-72.

Lambrecht N, et al. "Role of calcitonin gene-related peptide and nitric oxide in the gastroprotective effect of capsaicin in the rat," Gastroenterology. May 1993;104(5):1371-80.

Lance J. "Migraine Pain Originates from Blood Vessels," Headache Pathogenesis: Monoamines, Neuropeptides, Purines, and Nitric Oxide, edited by J. Olesen and L. Edvinsson, Lippincott-Raven Publishers, Philadelphia, 1997. Chapter 1, pp. 3-9.

Lassen LH, et al. "CGRP may play a causative role in migraine." Cephalalgia. Feb. 2002;22(1):54-61.

Lassen LH, et al. "Involvement of calcitonin gene-related peptide in migraine: regional cerebral blood flow and blood flow velocity in migraine patients," J Headache Pain. Jun. 2008;9(3):151-7.

Lazzeria M, et al. "The Challenge of the Overactive Bladder: From Laboratory to New Drugs," European Association of Urology, vol. 5, Issue 6, Dec. 2007, pp. 250-258.

Lee CV, et al. "High-affinity human antibodies from phage-displayed synthetic Fab libraries with a single framework scaffold," J Mol Biol. Jul. 23, 2004;340(5):1073-93.

Leighton B, et al. "Pancreatic amylin and calcitonin gene-related peptide cause resistance to insulin in skeletal muscle in vitro," Nature. Oct. 13, 1988;335(6191):632-5.

Levêque D, et al. "Pharmacokinetics of therapeutic monoclonal antibodies used in oncology," Anticancer Res. May-Jun. 2005;25(3c):2327-43.

Levy D, et al. "A critical view on the role of migraine triggers in the genesis of migraine pain," Headache. Jun. 2009;49(6):953-7.

Levy D, et al. "Calcitonin gene-related peptide does not excite or sensitize meningeal nociceptors: implications for the pathophysiology of migraine," Ann Neurol. Nov. 2005;58(5):698-705.

Levy D, et al. "Migraine pain and nociceptor activation—where do we stand?" Headache. May 2010;50(5):909-16.

Levy D, et al. "The vascular theory of migraine: leave it or love it?" Ann Neurol. Apr. 2011;69(4):600-1.

Li DS, et al. "Role of calcitonin gene-related peptide in gastric hyperemic response to intragastric capsaicin," Am J Physiol. Oct. 1991;261(4 Pt 1):G657-61.

Lin HC, et al. "Immunoneutralization of Calcitonin Gene-Related Peptide (CGRP) During Inhibition of Intestinal Transit by Fat," Gastroenterology vol. 114, No. 4, 1998. 1 page. Abstract No. G3253.

Lin YS, et al. "Preclinical pharmacokinetics, interspecies scaling, and tissue distribution of a humanized monoclonal antibody against vascular endothelial growth factor," J Pharmacol Exp Ther. Jan. 1999;288(1):371-8.

Link AS, et al. "Treatment of migraine attacks based on the interaction with the trigemino-cerebrovascular system," J Headache Pain. Feb. 2008;9(1):5-12.

Lipton RB, et al. "CGRP antagonists in the acute treatment of migraine," Lancet Neurol. Jun. 2004;3(6):332.

Lipton RB, et al. "Headache: triumphs in translational research," Lancet Neurol. Jan. 2005;4(1):11-2.

Lipton RB, et al. "Moving forward—essential questions for the next 10 years," Headache. Feb. 2009;49 Suppl 1:S43-6.

Little M, et al. "Of mice and men: hybridoma and recombinant antibodies." Immunol Today. Aug. 2000;21(8):364-70.

Lonberg N, et al. "Antigen-specific human antibodies from mice comprising four distinct genetic modifications," Nature. Apr. 28, 1994;368(6474):856-9.

Lonberg N, et al. "Human antibodies from transgenic animals," Nat Biotechnol. Sep. 2005;23(9):1117-25.

Longoni M, et al. "Inflammation and excitotoxicity: role in migraine pathogenesis," Neurol Sci. May 2006;27 Suppl 2:S107-10.

Louis SM, et al. "Antibodies to calcitonin-gene related peptide reduce inflammation induced by topical mustard oil but not that due to carrageenin in the rat." Neurosci Lett. Jul. 31, 1989;102(2-3):257-60.

Louis SM, et al. "Immunization with calcitonin gene-related peptide reduces the inflammatory response to adjuvant arthritis in the rat," Neuroscience. 1990;39(3):727-31.

Louis SM, et al. "The role of substance P and calcitonin gene-related peptide in neurogenic plasma extravasation and vasodilatation in the rat." Neuroscience. 1989;32(3):581-6.

MacCallum RM, et al. "Antibody-antigen interactions: contact analysis and binding site topography." J Mol Biol. Oct. 11, 1996;262(5):732-45.

MacGregor EA. "Migraine in pregnancy and lactation: a clinical review," J Fam Plann Reprod Health Care. Apr. 2007;33(2):83-93.

Majima, M, et al. "Roles of calcitonin gene-related peptide in ehancement of angiogenesis," Inflammation and Regeneration vol. 31 No. 2 Mar. 2011, 146-150.

(56) References Cited

OTHER PUBLICATIONS

Mallee JJ, et al. "Receptor activity-modifying protein 1 determines the species selectivity of non-peptide CGRP receptor antagonists." J Biol Chem. Apr. 19, 2002;277(16):14294-8.
Marcelo E. Bigal et al: "Calcitonin Gene-Related Peptide (CGRP) and Migraine Current Understanding and State of Development", Headache, vol. 53, No. 8, Sep. 12, 2013 (Sep. 12, 2013), pp. 1230-1244.
Mareska M, et al. "Lambert-Eaton myasthenic syndrome," Semin Neurol. Jun. 2004;24(2):149-53.
Marquez de Prado B and Russo AF, "CGRP receptor antagonists: A new frontier of anti-migraine medications," Drug Discov Today Ther Strateg. Winter 2006;3(4):593-597.
Marshall I, et al. "Human and rat alpha-CGRP but not calcitonin cause mesenteric vasodilatation in rats." Eur J Pharmacol. Apr. 16, 1986;123(2):217-22.
Martínez-Sáenz A, et al. "Role of calcitonin gene-related peptide in inhibitory neurotransmission to the pig bladder neck," J Urol. Aug. 2011;186(2):728-35.
Maynard JA, et al. "Protection against anthrax toxin by recombinant antibody fragments correlates with antigen affinity," Nat Biotechnol. Jun. 2002;20(6):597-601.
McCafferty J, et al. "Phage antibodies: filamentous phage displaying antibody variable domains," Nature. Dec. 6, 1990;348(6301):552-4.
McCulloch J, et al. "Calcitonin gene-related peptide: functional role in cerebrovascular regulation," Proc Natl Acad Sci U S A. Aug. 1986;83(15):5731-5.
McLatchie LM, et al. "RAMPs regulate the transport and ligand specificity of the calcitonin-receptor-like receptor," Nature. May 28, 1998;393(6683):333-9.
Mehrotra S, et al. "Current and prospective pharmacological targets in relation to antimigraine action," Naunyn Schmiedebergs Arch Pharmacol. Oct. 2008;378(4):371-94.
Mense S. "Pathophysiology of low back pain and the transition to the chronic state—experimental data and new concepts." Schmerz. Dec. 2001;15(6):413-7.
Messlinger K, et al. "Neuropeptide effects in the trigeminal system: pathophysiology and clinical relevance in migraine," Keio J Med. 2011;60(3):82-9.
Messlinger K. "Migraine: where and how does the pain originate?" Exp Brain Res. Jun. 2009;196(1):179-93.
Messlinger, et al. "Inhibition of neurogenic blood flow increases in the rat cranial dura matter by a CGRP-binding Spiegelmer," Cephalalgia, No. F022 2004.
Middlemiss DN. "Direct evidence for an interaction of beta-adrenergic blockers with the 5-HT receptor," Nature. May 19, 1977;267(5608):289-90.
Middlemiss DN. "Stereoselective blockade at [3H]5-HT binding sites and at the 5-HT autoreceptor by propranolol," Eur J Pharmacol. Jun. 1, 1984;101(3-4):289-93.
Mirick GR, et al. "A review of human anti-globulin antibody (HAGA, HAMA, HACA, HAHA) responses to monoclonal antibodies. Not four letter words," Q J Nucl Med Mol Imaging. Dec. 2004;48(4):251-7.
Molina JM, et al. "Induction of insulin resistance in vivo by amylin and calcitonin gene-related peptide," Diabetes. Feb. 1990;39(2):260-5.
Moore CK, et al. "Urological Applications of Botulinum Toxin," Female Urology: A Practical Clinical Guide. 2007 Chapter 14:213-217.
Moore EL, et al. "Targeting a family B GPCR/RAMP receptor complex: CGRP receptor antagonists and migraine," Br J Pharmacol. May 2012;166(1):66-78.
Morara S, et al. "Monoclonal antibodies reveal expression of the CGRP receptor in Purkinje cells, interneurons and astrocytes of rat cerebellar cortex," Neuroreport. Nov. 16, 1998;9(16):3755-9.
Morell A, et al. "Metabolic properties of IgG subclasses in man." J Clin Invest. Apr. 1970;49(4):673-80.

Morrison SL, et al. "Chimeric human antibody molecules: mouse antigen-binding domains with human constant region domains," Proc Natl Acad Sci U S A. Nov. 1984;81(21):6851-5.
Moskowitz MA, "Neurogenic inflammation in the pathophysiology and treatment of migraine," Neurology. Jun. 1993;43(6 Suppl 3):S16-20.
Moskowitz MA, et al. "CGRP: blood flow and more?" Cephalalgia. Aug. 1996;16(5):287.
Moskowitz MA. "Pathophysiology of headache—past and present," Headache. Apr. 2007;47 Suppl 1:S58-63.
Mould DR, et al. "A population pharmacokinetic-pharmacodynamic analysis of single doses of clenoliximab in patients with rheumatoid arthritis," Clin Pharmacol Ther. Sep. 1999;66(3):246-57.
Mountain A, et al. "Engineering antibodies for therapy," Biotechnol Genet Eng Rev. 1992;10:1-142.
Muff R, et al. "Calcitonin, calcitonin gene-related peptide, adrenomedullin and amylin: homologous peptides, separate receptors and overlapping biological actions," Eur J Endocrinol. Jul. 1995;133(1):17-20.
Mulderry PK, et al. "Differential expression of alpha-CGRP and beta-CGRP by primary sensory neurons and enteric autonomic neurons of the rat." Neuroscience. Apr. 1988;25(1):195-205.
Mullins MW, et al. "Characterization of a calcitonin gene-related peptide (CGRP) receptor on mouse bone marrow cells." Regul Pept. Nov. 19, 1993;49(1):65-72.
Nakamura-Craig M, et al. "Effect of neurokinin A, substance P and calcitonin gene related peptide in peripheral hyperalgesia in the rat paw." Neurosci Lett. Mar. 11, 1991;124(1):49-51.
Naot D, et al. "The role of peptides and receptors of the calcitonin family in the regulation of bone metabolism," Bone. Nov. 2008;43(5):813-8.
Negro A, et al. "CGRP receptor antagonists: an expanding drug class for acute migraine?" Expert Opin Investig Drugs. Jun. 2012;21(6):807-18.
Newman R, et al. "Modification of the FC region of a primatized IgG antibody to human CD4 retains its ability to modulate CD4 receptors but does not deplete CD4(+) T cells in chimpanzees," Clin Immunol. Feb. 2001;98(2):164-74.
Ng-Mak DS, et al. "Migraine treatment with rizatriptan and almotriptan: a crossover study," Headache. May 2009;49(5):655-62.
Nippon Rinsho, "Recent Development of Calcitonin Gene-related Peptide (CGRP) receptor antagonist," 2005, vol. 63, Suppl.10, pp. 263-266 [Original With English Translation].
Nishimoto N, et al. "Anti-interleukin-6 receptor antibody therapy in rheumatic diseases," Endocr Metab Immune Disord Drug Targets. Dec. 2006;6(4):373-81.
Oates PJ, et al. "Studies on the mechanism of ethanol-induced gastric damage in rats," Gastroenterology. Jan. 1988;94(1):10-21.
Ober RJ, et al. "Visualizing the site and dynamics of IgG salvage by the MHC class I-related receptor, FcRn," J Immunol. Feb. 15, 2004;172(4):2021-9.
O'Connell JP, et al. "On the role of the C-terminus of alpha-calcitonin-gene-related peptide (alpha CGRP). The structure of des-phenylalaninamide37-alpha CGRP and its interaction with the CGRP receptor," Biochem J. Apr. 1, 1993;291 ( Pt 1):205-10.
Oh-hashi Y, et al. "Elevated sympathetic nervous activity in mice deficient in alphaCGRP," Circ Res. Nov. 23, 2001;89(11):983-90.
Olesen J, et al. "Calcitonin gene-related peptide receptor antagonist Bibn 4096 BS for the acute treatment of migraine." N Engl J Med. Mar. 11, 2004;350(11):1104-10.
Olesen J, et al. "Chapter 16: Calcitonin Gene-Related Peptide and Other Peptides." The Headaches Third Edition. Lippincott Williams & Wilkins 2006 159-164.
Olesen J, et al. "Chapter 31: CGRP Involvement in Mirgaines." The Headaches Third Edition Lippincott Williams & Wilkins 2006 289-99.
Olesen J, et al. "Emerging migraine treatments and drug targets," Trends Pharmacol Sci. Jun. 2011;32(6):352-9.
Olesen J, et al. "Finding new drug targets for the treatment of migraine attacks," Cephalalgia. Sep. 2009;29(9):909-20.
Olesen J, et al. "Migraine: a research field matured for the basic neurosciences," Trends Neurosci. Jan. 1991;14(1):3-5.

(56) References Cited

OTHER PUBLICATIONS

Olesen J, et al. "Origin of pain in migraine: evidence for peripheral sensitisation," Lancet Neurol. Jul. 2009;8(7):679-90.
Olesen J. "Migraine: A neural pathway for photophobia in migraine," Nat Rev Neurol. May 2010;6(5):241-2.
Ondo WG, et al. "Botulinum toxin A for chronic daily headache: a randomized, placebo-controlled, parallel design study," Cephalalgia. Jan. 2004;24(1):60-5.
O'Sullivan J, et al. "Migraine development, treatments, research advances, and anesthesia implications," AANA J. Feb. 2006;74(1):61-9.
Ottosson A, et al. "Release of histamine from dural mast cells by substance P and calcitonin gene-related peptide," Cephalalgia. May 1997;17(3):166-74.
Pabst MA, et al. "Ablation of capsaicin sensitive afferent nerves impairs defence but not rapid repair of rat gastric mucosa," Gut. Jul. 1993;34(7):897-903.
Panconesi A, et al. "Migraine pain: reflections against vasodilatation," J Headache Pain. Oct. 2009;10(5):317-25.
Panka DJ, et al. "Defining the structural correlates responsible for loss of arsonate affinity in an IDCR antibody isolated from an autoimmune mouse," Mol Immunol. Aug. 1993;30(11):1013-20.
Paone DV, et al. "Calcitonin gene-related peptide receptor antagonists for the treatment of migraine: a patent review," Expert Opin Ther Pat. Dec. 2009;19(12):1675-713.
Papadopoulos N, et al. "Binding and neutralization of vascular endothelial growth factor (VEGF) and related ligands by VEGF Trap, ranibizumab and bevacizumab." Angiogenesis. Jun. 2012;15(2):171-85.
Papp K, et al. "The treatment of moderate to severe psoriasis with a new anti-CD11a monoclonal antibody," J Am Acad Dermatol. Nov. 2001;45(5):665-74.
Pavlou AK, et al. "Recombinant protein therapeutics—success rates, market trends and values to 2010," Nat Biotechnol. Dec. 2004;22(12):1513-9.
Peroutka SJ, et al. "Neurogenic inflammation and migraine: implications for the therapeutics," Mol Interv. Oct. 2005;5(5):304-11.
Peskar BM, et al. "A monoclonal antibody to calcitonin gene-related peptide abolishes capsaicin-induced gastroprotection." Eur J Pharmacol. Nov. 30, 1993;250(1):201-3.
Petersen KA, et al. "BIBN4096BS antagonizes human alpha-calcitonin gene related peptide-induced headache and extracerebral artery dilatation." Clin Pharmacol Ther. Mar. 2005;77(3):202-13.
Petersen KA, et al. "Effect of hypotension and carbon dioxide changes in an improved genuine closed cranial window rat model," Cephalalgia. Jan. 2005;25(1):23-9.
Petersen KA, et al. "Inhibitory effect of BIBN4096BS on cephalic vasodilatation induced by CGRP or transcranial electrical stimulation in the rat." Br J Pharmacol. Nov. 2004;143(6):697-704.
Petersen KA, et al. "Presence and function of the calcitonin gene-related peptide receptor on rat pial arteries investigated in vitro and in vivo," Cephalalgia. Jun. 2005;25(6):424-32.
Petersen KA, et al. "The effect of nonpeptide CGRP-antagonist, BIBN4096BS on human-alphaCGRP induced headache and hemodynamics in healthy volunteers," Cephalalgia, vol. 23, extract from Abstracts of the XI Congress of the International Headache Society, p. 725, 2003.
Petkova SB, et al. "Enhanced half-life of genetically engineered human IgG1 antibodies in a humanized FcRn mouse model: potential application in humorally mediated autoimmune disease," Int Immunol. Dec. 2006;18(12):1759-69.
Pietrobon D, et al. "Pathophysiology of migraine," Annu Rev Physiol. 2013;75:365-91.
Plessas IN, et al. "Migraine-like episodic pain behavior in a dog: can dogs suffer from migraines?" J Vet Intern Med. Sep.-Oct. 2013;27(5):1034-40.
Plourde V, et al. "CGRP antagonists and capsaicin on celiac ganglia partly prevent postoperative gastric ileus." Peptides. Nov.-Dec. 1993;14(6):1225-9.

Poyner DR, et al. "International Union of Pharmacology. XXXII. The mammalian calcitonin gene-related peptides, adrenomedullin, amylin, and calcitonin receptors," Pharmacol Rev. Jun. 2002;54(2):233-46.
Presta L. "Antibody engineering for therapeutics," Curr Opin Struct Biol. Aug. 2003;13(4):519-25.
Presta LG, et al. "Engineering therapeutic antibodies for improved function," Biochem Soc Trans. Aug. 2002;30(4):487-90.
Prewett M, et al. "The biologic effects of C225, a chimeric monoclonal antibody to the EGFR, on human prostate carcinoma." J Immunother Emphasis Tumor Immunol. Nov. 1996;19(6):419-27.
Qing-Hui Niu, et al. "Expression of mast cell and calcition gene related peptides in the mucosa of irritable bowel syndrome," World Chinese Journal of Digestology, Jan. 18, 2009 p. 213-217; ISSN 1099-3079.
Raddant AC, et al. "Calcitonin gene-related peptide in migraine: intersection of peripheral inflammation and central modulation," Expert Rev Mol Med. Nov. 29, 2011;13:e36.
Ramadan NM, et al. "New and future migraine therapy," Pharmacol Ther. Oct. 2006;112(1):199-212.
Ramadan NM. "Acute treatments: future developments," Curr Med Res Opin. 2001;17 Suppl 1:s81-6.
Ramos ML, et al. "AMG 334 CGRP antibody for migraine: time to celebrate?" Lancet Neurol. Apr. 2016;15(4):347-9.
Rapoport AM, Bigal ME, et al. "Naratriptan in the preventive treatment of refractory chronic migraine." In Olsen J, Silberstein SD, Tfelt-Hansen P, eds. Preventive Pharmacotherapy of Headache Disorders. Copenhagen: Oxford University Press, 2004, Chapter 31.
Rapoport AM, et al. "Intranasal medications for the treatment of migraine and cluster headache," CNS Drugs. 2004;18(10):671-85.
Rapoport AM, et al. "Levetiracetam in the preventive treatmentof transformed migraine: A prospective, open-label, pilot study," Curr Ther Res Clin Exp. May 2005;66(3):212-21.
Rapoport AM, et al. "Migraine preventive therapy: current and emerging treatment options," Neurol Sci. May 2005;26 Suppl 2:s111-20.
Rapoport AM, et al. "Preventive migraine therapy: what is new," Neurol Sci. Oct. 2004;25 Suppl 3:S177-85.
Raybould HE, et al. "Selective ablation of spinal afferent neurons containing CGRP attenuates gastric hyperemic response to acid," Peptides. Mar.-Apr. 1992;13(2):249-54.
Reasbeck PG, et al. "Calcitonin gene-related peptide: enteric and cardiovascular effects in the dog," Gastroenterology. Oct. 1988;95(4):966-71.
Recober A, et al. "Calcitonin gene-related peptide: A molecular link between obesity and migraine?" Drug News Perspect. Mar. 2010;23(2):112-7.
Recober A, et al. "Calcitonin gene-related peptide: an update on the biology," Curr Opin Neurol. Jun. 2009;22(3):241-6.
Recober A, et al. "Olcegepant, a non-peptide CGRP1 antagonist for migraine treatment," IDrugs. Aug. 2007;10(8):566-74.
Recober A, et al., "Role of calcitonin gene-related peptide in light-aversive behavior: implications for migraine," J Neurosci. Jul. 8, 2009;29(27):8798-804.
Reddy MP, et al. "Elimination of Fc receptor-dependent effector functions of a modified IgG4 monoclonal antibody to human CD4," J Immunol. Feb. 15, 2000;164(4):1925-33.
Reff ME, et al. "A review of modifications to recombinant antibodies: attempt to increase efficacy in oncology applications," Crit Rev Oncol Hematol. Oct. 2001;40(1):25-35.
Reff ME, et al. "Depletion of B cells in vivo by a chimeric mouse human monoclonal antibody to CD20," Blood. Jan. 15, 1994;83(2):435-45.
Reichert JM, et al. "Monoclonal antibody successes in the clinic," Nat Biotechnol. Sep. 2005;23(9):1073-8.
Reinshagen M, et al. "Calcitonin gene-related peptide mediates the protective effect of sensory nerves in a model of colonic injury." J Pharmacol Exp Ther. Aug. 1998;286(2):657-61.
Reuter U, et al. "Experimental models of migraine," Funct Neurol. 2000;15 Suppl 3:9-18.
Reuter U. "Anti-CGRP antibodies: a new approach to migraine prevention," Lancet Neurol. Sep. 2014;13(9):857-9.

(56) References Cited

OTHER PUBLICATIONS

Rolston RK, et al., "Intravenous calcitonin gene-related peptide stimulates net water secretion in rat colon in vivo," Dig Dis Sci. Apr. 1989;34(4):612-6.

Roon KI, et al. "No acute antimigraine efficacy of CP-122,288, a highly potent inhibitor of neurogenic inflammation: results of two randomized, double-blind, placebo-controlled clinical trials," Ann Neurol. Feb. 2000;47(2):238-41.

Roopenian DC, et al. "FcRn: the neonatal Fc receptor comes of age," Nat Rev Immunol. Sep. 2007;7(9):715-25.

Roque AC, et al. "Antibodies and genetically engineered related molecules: production and purification," Biotechnol Prog. May-Jun. 2004;20(3):639-54.

Roskos LK, et al. "The Clinical Pharmacology of Therapeutic Monoclonal Antibodies," Drug Development Research 2004 61:108-120.

Rother RP, et al. "Discovery and development of the complement inhibitor eculizumab for the treatment of paroxysmal nocturnal hemoglobinuria," Nat Biotechnol. Nov. 2007;25(11):1256-64.

Rovero P, et al. "CGRP antagonist activity of short C-terminal fragments of human alpha CGRP, CGRP(23-37) and CGRP(19-37)." Peptides. Sep.-Oct. 1992;13(5):1025-7.

Rudikoff S, et al. "Single amino acid substitution altering antigen-binding specificity." Proc Natl Acad Sci U S A. Mar. 1982;79(6):1979-83.

Ruiz-Gayo M, et al. "Vasodilatory effects of cholecystokinin: new role for an old peptide?" Regul Pept. Dec. 10, 2006;137(3):179-84.

Russo AF, et al., "A Potential Preclinical Migraine Model: CGRP-Sensitized Mice," Mol Cell Pharmacol. 2009;1(5):264-270.

Russo AF. "Calcitonin gene-related peptide (CGRP): a new target for migraine," Annu Rev Pharmacol Toxicol. 2015;55:533-52.

Russo. "CGRP Meeting Abstract Book," The 4th International Meeting on CGRP, Copenhagen, Sep. 2001, 71 pages.

Russo. "CGRP Meeting Abstract Book," Joint International Symposium on Calictonin Gene-Related Peptide, Amylin and Calcitonin; 4th Symposium on Adrenomedullin and Proadrenomedullin N-20 Peptide, Zurich, Switzerland, Mar. 2004. 38 pages.

Ryan AM, et al. "Preclinical safety evaluation of rhuMAbVEGF, an antiangiogenic humanized monoclonal antibody," Toxicol Pathol. Jan.-Feb. 1999;27(1):78-86.

Ryan S. "Medicines for migraine," Arch Dis Child Educ Pract Ed. Apr. 2007;92(2):ep50-5.

Saleh MN, et al. "Phase I trial of the chimeric anti-GD2 monoclonal antibody ch14.18 in patients with malignant melanoma." Hum Antibodies Hybridomas. Jan. 1992;3(1):19-24.

Salonen R, et al. "Triptans: do they differ?" Curr Pain Headache Rep. Apr. 2002;6(2):133-9.

Salvatore CA, et al. "Pharmacological characterization of MK-0974 [N-[3R,6S)-6-(2,3-difluorophenyl)-2-oxo-1-(2,2,2-trifluoroethyl)azepan-3-yl]-4-(2-oxo-2,3-dihydro-1H-imidazo[4,5-B]pyridin-1-yl)piperidine-1-carboxamide], a potent and orally active calcitonin gene-related peptide receptor antagonist for the treatment of migraine," J Pharmacol Exp Ther. Feb. 2008;324(2):416-21.

Sams-Nielsen A, et al. "Pharmacological evidence for CGRP uptake into perivascular capsaicin sensitive nerve terminals," Br J Pharmacol. Mar. 2001;132(5):1145-53.

Saphire EO, et al. "Crystal structure of a neutralizing human IGG against HIV-1: a template for vaccine design," Science. Aug. 10, 2001;293(5532):1155-9.

Schaible HG, et al. "Mechanisms of pain in arthritis." Ann N Y Acad Sci. Jun. 2002;966:343-54.

Schelstraete C, et al. "CGRP antagonists: hope for a new era in acute migraine treatment," Acta Neurol Belg. Dec. 2009;109(4):252-61.

Schier R, et al. "Isolation of high-affinity monomeric human anti-c-erbB-2 single chain Fv using affinity-driven selection," J Mol Biol. Jan. 12, 1996;255(1):28-43.

Schier R, et al. "Isolation of picomolar affinity anti-c-erbB-2 single-chain Fv by molecular evolution of the complementarity determining regions in the center of the antibody binding site," J Mol Biol. Nov. 8, 1996;263(4):551-67.

Schifter S. "Circulating concentrations of calcitonin gene-related peptide (CGRP) in normal man determined with a new, highly sensitive radioimmunoassay," Peptides. Mar.-Apr. 1991;12(2):365-9.

Schindler M, et al. "Binding properties of the novel, non-peptide CGRP receptor antagonist radioligand, [(3)H]BIBN4096BS," Eur J Pharmacol. May 10, 2002;442(3):187-93.

Schoenen J, et al. "Almotriptan and its combination with aceclofenac for migraine attacks: a study of efficacy and the influence of auto-evaluated brush allodynia," Cephalalgia. Oct. 2008;28(10):1095-105.

Schreiber CP. "The pathophysiology of migraine," Dis Mon. Oct. 2006;52(10):385-401.

Schwenger N, et al. "Interaction of calcitonin gene-related peptide, nitric oxide and histamine release in neurogenic blood flow and afferent activation in the rat cranial dura mater,".Cephalalgia. Jun. 2007;27(6):481-91.

Schytz HW, et al. "What have we learnt from triggering migraine?" Curr Opin Neurol. Jun. 2010;23(3):259-65.

Seike M, et al. "Increased synthesis of calcitonin gene-related peptide stimulates keratinocyte proliferation in murine UVB-irradiated skin," J Dermatol Sci. Feb. 2002;28(2):135-43.

Selenko N, et al. "CD20 antibody (C2B8)-induced apoptosis of lymphoma cells promotes phagocytosis by dendritic cells and cross-priming of CD8+ cytotoxic T cells," Leukemia. Oct. 2001;15(10):1619-26.

Seong J, et al. "Radiation-induced alteration of pain-related signals in an animal model with bone invasion from cancer." Ann N Y Acad Sci. Dec. 2004;1030:179-86.

Seybold VS. "The role of peptides in central sensitization," Handb Exp Pharmacol. 2009;(194):451-91.

Shaw NE, et al. "The effect of monoclonal antibodies to calcitonin gene-related peptide (CGRP) on CGRP-induced vasodilatation in pig coronary artery rings," Br J Pharmacol. May 1992;106(1):196-8.

Sheets MD, et al. "Efficient construction of a large nonimmune phage antibody library: the production of high-affinity human single-chain antibodies to protein antigens," Proc Natl Acad Sci U S A. May 26, 1998;95(11):6157-62.

Sheftell FD, et al. "Naratriptan in the preventive treatment of refractory transformed migraine: a prospective pilot study," Headache. Nov.-Dec. 2005;45(10):1400-6.

Shen YT, et al. "Functional role of alpha-calcitonin gene-related peptide in the regulation of the cardiovascular system," J Pharmacol Exp Ther. Aug. 2001;298(2):551-8.

Shevel E. "The extracranial vascular theory of migraine—a great story confirmed by the facts," Headache. Mar. 2011;51(3):409-17.

Shields RL, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.

Shulkes A, et al. "Production of calcitonin gene related peptide, calcitonin and PTH-related protein by a prostatic adenocarcinoma," Clin Endocrinol (Oxf). May 1991;34(5):387-93.

Silberstein S, et al. "Botulinum toxin type A as a migraine preventive treatment. For the Botox Migraine Clinical Research Group," Headache. Jun. 2000;40(6):445-50.

Silberstein SD, "Practice parameter: evidence-based guidelines for migraine headache (an evidence-based review): report of the Quality Standards Subcommittee of the American Academy of Neurology," Neurology. Sep. 26, 2000;55(6):754-62.

Silberstein SD. "Emerging target-based paradigms to prevent and treat migraine," Clin Pharmacol Ther. Jan. 2013;93(1):78-85.

Silverman AJ, et al. "Mast cells migrate from blood to brain," J Neurosci. Jan. 1, 2000;20(1):401-8.

Simmons LC, et al. "Expression of full-length immunoglobulins in *Escherichia coli*: rapid and efficient production of aglycosylated antibodies," J Immunol Methods. May 1, 2002;263(1-2):133-47.

(56) References Cited

OTHER PUBLICATIONS

Sixt ML, et al. "Calcitonin gene-related peptide receptor antagonist olcegepant acts in the spinal trigeminal nucleus," Brain. Nov. 2009;132(Pt 11):3134-41.
Skofitsch G, et al. "Comparative immunohistochemical distribution of amylin-like and calcitonin gene related peptide like immunoreactivity in the rat central nervous system," Can J Physiol Pharmacol. Jul. 1995;73(7):945-56.
Smillie SJ, et al. "Calcitonin gene-related peptide (CGRP) and its role in hypertension," Neuropeptides. Apr. 2011;45(2):93-104.
Smith KA, et al. "Demystified . . . recombinant antibodies," J Clin Pathol. Sep. 2004;57(9):912-7.
Smith TW, et al. "Reversal of advanced digoxin intoxication with Fab fragments of digoxin-specific antibodies." N Engl J Med. Apr. 8, 1976;294(15):797-800.
Smith-Gill SJ, et al. "Contributions of immunoglobulin heavy and light chains to antibody specificity for lysozyme and two haptens." J Immunol. Dec. 15, 1987;139(12):4135-44.
Solomon S. "Major therapeutic advances in the past 25 years," Headache. Apr. 2007;47 Suppl 1:S20-2.
Song MK, et al. "Light chain of natural antibody plays a dominant role in protein antigen binding." Biochem Biophys Res Commun. Feb. 16, 2000;268(2):390-4.
Spetz AC, et al. "Momentary increase in plasma calcitonin gene-related peptide is involved in hot flashes in men treated with castration for carcinoma of the prostate," J Urol. Nov. 2001;166(5):1720-3.
Sprenger T, et al. "Migraine pathogenesis and state of pharmacological treatment options," BMC Med. Nov. 16, 2009;7:71.
Stensrud P, et al. "Comparative trial of Tenormin (atenolol) and Inderal (propranolol) in migraine," Headache. Jul. 1980;20(4):204-7.
Storer RJ, et al. "Calcitonin gene-related peptide (CGRP) modulates nociceptive trigeminovascular transmission in the cat," Br J Pharmacol. Aug. 2004;142(7):1171-81.
Stovner LJ, et al. "New drugs for migraine," J Headache Pain. Dec. 2009;10(6):395-406.
Strassman AM, et al. "On the origin of headaches," Endeavour. 1997;21(3):97-100.
Strassman AM, et al. "Response properties of dural nociceptors in relation to headache," J Neurophysiol. Mar. 2006;95(3):1298-306.
Subramanian KN, et al. "Safety, tolerance and pharmacokinetics of a humanized monoclonal antibody to respiratory syncytial virus in premature infants and infants with bronchopulmonary dysplasia," MEDI-493 Study Group, Pediatr Infect Dis J. Feb. 1998;17(2):110-5.
Tam SH, et al. "Abciximab (ReoPro, chimeric 7E3 Fab) demonstrates equivalent affinity and functional blockade of glycoprotein IIb/IIIa and alpha(v)beta3 integrins," Circulation. Sep. 15, 1998;98(11):1085-91.
Tamura M, et al. "Structural correlates of an anticarcinoma antibody: identification of specificity-determining residues (SDRs) and development of a minimally immunogenic antibody variant by retention of SDRs only." J Immunol. Feb. 1, 2000;164(3):1432-41.
Tan et al., "Demonstration of the neurotransmitter role of calcitonin gene-related peptides (CGRP) by immunoblockade with anti-CGRP monoclonal antibodies," Br J Pharmacol. Mar. 1994;111(3):703-10.
Tan KK, et al. "Calcitonin gene-related peptide as an endogenous vasodilator: immunoblockade studies in vivo with an anti-calcitonin gene-related peptide monoclonal antibody and its Fab' fragment." Clin Sci (Lond). Dec. 1995;89(6):565-73.
Tanaka H, et al. "Inhibition of calcitonin gene-related peptide (CGRP) has the potential to.extend first-phase insulin secretion," Exp Clin Endocrinol Diabetes. May 2013;121(5):280-5.
Taylor AW, et al. "Suppression of nitric oxide generated by inflammatory macrophages by calcitonin gene-related peptide in aqueous humor," Invest Ophthalmol Vis Sci. Jul. 1998;39(8):1372-8.
Tedstone, et al. "The effect of islet amyloid polypeptide (amylin) and calcitonin gene-related peptide on glucose removal in the anaesthetized rat and on insulin secretion from rat pancreatic islets in vitro," Biosci Rep. Aug. 1990;10(4):339-45.
Tepper SJ, Bigal ME, et al. "Botulinum toxin type A in the treatment of refractory headache." In Olsen J, Silberstein SD, Tfelt-Hansen P, eds. Preventive Pharmacotherapy of Headache Disorders. Copenhagen: Oxford University Press, 2004, Chapter 20.
Tepper SJ, et al. "Botulinum neurotoxin type A in the preventive treatment of refractory headache: a review of 100 consecutive cases," Headache. Sep. 2004;44(8):794-800.
Tepper SJ, et al. "Clinical and preclinical rationale for CGRP-receptor antagonists in the treatment of migraine," Headache. Sep. 2008;48(8):1259-68.
Tepper SJ, et al. "Mechanisms of action of the 5-HT1B/1D receptor agonists," Arch Neurol. Jul. 2002;59(7):1084-8.
Teva Pharmaceutical Industries Ltd., Press Release, "Teva to Acquire Labrys Biologics, Inc.", Jun. 3, 2014. 4 pages.
Tfelt-Hansen P, et al. "Effervescent metoclopramide and aspirin (Migravess) versus effervescent aspirin or placebo for migraine attacks: a double-blind study," Cephalalgia. Jun. 1984;4(2):107-11.
Tfelt-Hansen P, et al. "Possible site of action of CGRP antagonists in migraine," Cephalalgia. Apr. 2011;31(6):748-50.
Tfelt-Hansen PC. "Verisimilitude (or "truthlikeness") as an alternative to pro and cons: migraine and cluster headache mechanisms," J Headache Pain. Oct. 2010;11(5):379-89.
Theoharides TC, et al. "The role of mast cells in migraine pathophysiology," Brain Res Brain Res Rev. Jul. 2005;49(1):65-76.
Thomas TC, et al. "Inhibition of complement activity by humanized anti-C5 antibody and single-chain Fv," Mol Immunol. Dec. 1996;33(17-18):1389-401.
Tjen-A-Looi S, et al. "CGRP and somatostatin modulate chronic hypoxic pulmonary hypertension," Am J Physiol. Sep. 1992;263(3 Pt 2):H681-90.
Toda M, et al. "Neuronal system-dependent facilitation of tumor angiogenesis and tumor growth by calcitonin gene-related peptide," Proc Natl Acad Sci U S A. Sep. 9, 2008;105(36):13550-5.
Todd J. Schwedt et al: "14th International Headache Congress: Basic Science Highlights", Headache, vol. 50, No. 3, Mar. 1, 2010 (Mar. 1, 2010), pp. 520-526.
Tokuda Y, et al. "Dose escalation and pharmacokinetic study of a humanized anti-HER2 monoclonal antibody in patients with HER2/neu-overexpressing metastatic breast cancer," Br J Cancer. Dec. 1999;81(8):1419-25.
Tsujikawa K, et al. "Hypertension and dysregulated proinflammatory cytokine production in receptor activity-modifying protein 1-deficient mice," Proc Natl Acad Sci U S A. Oct. 16, 2007;104(42):16702-7.
Turner LC, et al. "A neural shift theory of migraine," Neuroepidemiology. 1993;12(4):249-50.
Tvedskov JF, et al. "No increase of calcitonin gene-related peptide in jugular blood during.migraine." Ann Neurol. Oct. 2005;58(4):561-8.
Tzabazis AZ, et al. "Antihyperalgesic effect of a recombinant herpes virus encoding antisense for calcitonin gene-related peptide." Anesthesiology. Jun. 2007;106(6):1196-203.
Uhr M, et al. "Penetration of endogenous steroid hormones corticosterone, cortisol, aldosterone and progesterone into the brain is enhanced in mice deficient for both mdr1a and mdr1b P-glycoproteins," J Neuroendocrinol. Sep. 2002;14(9):753-9.
Unger J. "Migraine headaches: a historical prospective, a glimpse into the future, and migraine epidemiology," Dis Mon. Oct. 2006;52(10):367-84.
Vajdos FF, et al. "Comprehensive functional maps of the antigen-binding site of an anti-ErbB2 antibody obtained with shotgun scanning mutagenesis." J Mol Biol. Jul. 5, 2002;320(2):415-28.
Van der Schueren BJ, et al. "Calcitonin gene-related peptide8-37 antagonizes capsaicin-induced vasodilation in the skin: evaluation of a human in vivo pharmacodynamic model," J Pharmacol Exp Ther. Apr. 2008;325(1):248-55.
van Rossum D, et al. "Neuroanatomical localization, pharmacological characterization and functions of CGRP, related peptides and their receptors," Neurosci Biobehav Rev. Sep. 1997;21(5):649-78.

(56) References Cited

OTHER PUBLICATIONS

Vater A, et al. "Short bioactive Spiegelmers to migraine-associated calcitonin gene-related peptide rapidly identified by a novel approach: tailored-SELEX." Nucleic Acids Res. Nov. 1, 2003;31(21):e130.

Vaughan TJ, et al. "Human antibodies with sub-nanomolar affinities isolated from a large non-immunized phage display library," Nat Biotechnol. Mar. 1996;14(3):309-14.

Villalón CM, et al. "The role of CGRP in the pathophysiology of migraine and efficacy of CGRP receptor antagonists as acute antimigraine drugs," Pharmacol Ther. Dec. 2009;124(3):309-23.

Vincent A, et al. "Molecular targets for autoimmune and genetic disorders of neuromuscular transmission," Eur J Biochem. Dec. 2000;267(23):6717-28.

Vogler B, et al. "Role of melatonin in the pathophysiology of migraine: implications for treatment," CNS Drugs. 2006;20(5):343-50.

Volcy M, et al. "Botulinum toxin A for the treatment of greater occipital neuralgia and trigeminal neuralgia: a case report with pathophysiological considerations," Cephalalgia. Mar. 2006;26(3):336-40.

von Mehren M, et al. "Monoclonal antibody therapy for cancer," Annu Rev Med. 2003;54:343-69.

Wachter C, et al. "Visceral vasodilatation and somatic vasoconstriction evoked by acid challenge of the rat gastric mucosa: diversity of mechanisms," J Physiol. Jul. 15, 1995;486 ( Pt 2):505-16.

Wacnik PW, et al. "Tumor-induced mechanical hyperalgesia involves CGRP receptors and altered innervation and vascularization of DsRed2 fluorescent hindpaw tumors." Pain. May 2005;115(1-2):95-106.

Waeber C, et al. "Migraine as an inflammatory disorder." Neurology. May 24, 2005;64(10 Suppl 2):S9-15.

Walker CS, et al. "Mice lacking the neuropeptide alpha-calcitonin gene-related peptide are protected against diet-induced obesity," Endocrinology. Sep. 2010;151(9):4257-69.

Walker CS, et al. "Regulation of signal transduction by calcitonin gene-related peptide receptors," Trends Pharmacol Sci. Oct. 2010;31(10):476-83.

Ward ES, et al. "Binding activities of a repertoire of single immunoglobulin variable domains secreted from *Escherichia coli*." Nature. Oct. 12, 1989;341(6242):544-6.

Weir AN, et al. "Formatting antibody fragments to mediate specific therapeutic functions," Biochem Soc Trans. Aug. 2002;30(4):512-6.

Welch KM, et al. "Mismatch in how oestrogen modulates molecular and neuronal function may explain menstrual migraine," Neurol Sci. May 2006;27 Suppl 2:S190-2.

Werther WA, et al. "Humanization of an anti-lymphocyte function-associated antigen (LFA)-1 monoclonal antibody and reengineering of the humanized antibody for binding to rhesus LFA-1," J Immunol. Dec. 1, 1996;157(11):4986-95.

Wick EC, et al. "Transient receptor potential vanilloid 1, calcitonin gene-related peptide, and substance P mediate nociception in acute pancreatitis." Am J Physiol Gastrointest Liver Physiol. May 2006;290(5):G959-69. Epub Jan. 6, 2006.

Willats WG. "Phage display: practicalities and prospects," Plant Mol Biol. Dec. 2002;50(6):837-54.

Williamson DJ, et al. "Intravital microscope studies on the effects of neurokinin agonists and calcitonin gene-related peptide on dural vessel diameter in the anaesthetized rat," Cephalalgia. Jun. 1997;17(4):518-24.

Williamson DJ, et al. "Neurogenic inflammation in the context of migraine," Microsc Res Tech. May 1, 2001;53(3):167-78.

Williamson DJ, et al. "Sumatriptan inhibits neurogenic vasodilation of dural blood vessels in the anaesthetized rat—intravital microscope studies," Cephalalgia. Jun. 1997;17(4):525-31.

Williamson DJ, et al. "The anti-migraine 5-HT(16/1D) agonist rizatriptan inhibits neurogenic dural vasodilation in anaesthetized guinea-pigs," Br J Pharmacol. Aug. 2001;133(7):1029-34.

Williamson DJ, et al. "The novel anti-migraine agent rizatriptan inhibits neurogenic dural vasodilation and extravasation," Eur J Pharmacol. Jun. 5, 1997;328(1):61-4.

Wimalawansa SJ, et al. "Comparative study of distribution and biochemical characterization of brain calcitonin gene-related peptide receptors in five different species," Neuroscience. May 1993;54(2):513-9.

Wimalawansa SJ, et al. "Validation, role in perioperative assessment, and clinical applications of an immunoradiometric assay for human calcitonin," Peptides. 1995;16(2):307-12.

Wimalawansa SJ. "Amylin, calcitonin gene-related peptide, calcitonin, and adrenomedullin: a peptide superfamily," Crit Rev Neurobiol. 1997;11(2-3):167-239.

Wimalawansa SJ. "Calcitonin gene-related peptide and its receptors: molecular genetics, physiology, pathophysiology, and therapeutic potentials," Endocr Rev. Oct. 1996;17(5):533-85.

Wimalawansa SJ. "Effects of in vivo stimulation on molecular forms of circulatory calcitonin and calcitonin gene-related peptide in man," Mol Cell Endocrinol. May 28, 1990;71(1):13-9.

Winkler K, et al. "Changing the antigen binding specificity by single point mutations of an anti-p24 (HIV-1) antibody." J Immunol. Oct. 15, 2000;165(8):4505-14.

Winter G, et al. "Making antibodies by phage display technology," Annu Rev Immunol. 1994;12:433-55.

Wong G, et al. "Safety and tolerability of LBR-101, a humanized monoclonal antibody that blocks the binding of CGRP to its receptor," Labrys Biologics Poster, 1 page, 2013 International Headache Congress.

Wong HC, et al. "Monoclonal antibody to rat alpha-CGRP: production, characterization, and in vivo immunoneutralization activity." Hybridoma. Feb. 1993;12(1):93-106.

Wong HC, et al. "Preparation of a monoclonal antibody to rat alpha-CGRP for in vivo immunoneutralization of peptides." Ann N Y Acad Sci. Jun. 30, 1992;657:525-7.

Wu D, et al. "Development and potential of non-peptide antagonists for calcitonin-gene- related peptide (CGRP) receptors: evidence for CGRP receptor heterogeneity," Biochem Soc Trans. Aug. 2002;30(4):468-73.

Wu H, et al. "Humanization of a murine monoclonal antibody by simultaneous optimization of framework and CDR residues." J Mol Biol. Nov. 19, 1999;294(1):151-62.

Wu H, et al. "Humanized antibodies and their applications," Methods. May 2005;36(1):1-2.

Wyon Y, et al. "Postmenopausal women with vasomotor symptoms have increased urinary excretion of calcitonin gene-related peptide," Maturitas. Nov. 16, 1998;30(3):289-94.

Xu, F.T. Study on the Mechanism of SP and CGRP in the Chronic Pain and Knee Joint Master Thesis. Guangxi Medical University. May 2005. (in Chinese with English abstract).

Yallampalli C, et al. "Calcitonin gene-related peptide in pregnancy and its emerging receptor heterogeneity," Trends Endocrinol Metab. Aug. 2002;13(6):263-9.

Yoshikawa R, et al. "Suppression of ovalbumin-induced allergic diarrhea by diminished intestinal peristalsis in RAMP1-deficient mice," Biochem Biophys Res Commun. Jul. 8, 2011;410(3):389-93.

Yu LC, et al. "Roles of calcitonin gene-related peptide and its receptors in pain-related behavioral responses in the central nervous system," Neurosci Biobehav Rev. Sep. 2009;33(8):1185-91.

Zeller J, et al. "CGRP function-blocking antibodies inhibit neurogenic vasodilatation without affecting heart rate or arterial blood pressure in the rat." Br J Pharmacol. Dec. 2008;155(7):1093-103. doi: 10.1038/bjp.2008.334. Epub Sep. 8, 2008.

Zhang L, et al. "Arthritic calcitonin/alpha calcitonin gene-related peptide knockout mice have reduced nociceptive hypersensitivity," Pain. Jan. 2001;89(2-3):265-73.

Zhang M, et al. "Rheumatoid factor specificity of a VH3-encoded antibody is dependent on the heavy chain CDR3 region and is independent of protein a binding." J Immunol. Sep. 1, 1998;161(5):2284-9.

Zhuang X, et al. "Brain mast cell degranulation regulates blood-brain barrier," J Neurobiol. Dec. 1996;31(4):393-403.

(56) References Cited

OTHER PUBLICATIONS

Zittel et al., "Role of spinal afferents and calcitonin gene-related peptide in the postoperative gastric ileus in anesthetized rats," Ann Surg. Jan. 1994;219(1):79-87.
Zittel TT, et al. "Calcitonin gene-related peptide and spinal afferents partly mediate postoperative colonic ileus in the rat," Surgery. May 1998;123(5):518-27.
Zuckier LS, et al. "Chimeric human-mouse IgG antibodies with shuffled constant region exons demonstrate that multiple domains contribute to in vivo half-life," Cancer Res. Sep. 1, 1998;58(17):3905-8.

\* cited by examiner

Ab1 Heavy chain (chimera) Full length protein sequence

QSLEESGGRLVTPGTPLTLTCTVSGLDLSSYYMQWVRQAPGKGLEWIGVIGNDNTYYASWAKGRFTISRASSTTVDLKMTS
LTTEDTATYFCARGDIWGPGTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPCPAPELLGGPSVFLFPPKPKDTLMISRTP
EVTCVVVDVSHEDPEVKFNWYVDGVEVHNAKTKPREHQYASTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 4)

Ab1 Variable region heavy chain (chimera) protein sequence

QSLEESGGRLVTPGTPLTLTCTVSGLDLSSYYMQWVRQAPGKGLEWIGVIGNDNTYYASWAKGRFTISRASSTTVDLKMTS
LTTEDTATYFCARGDIWGPGTLVTVSS (SEQ ID NO: 3)

Ab1 Variable region heavy chain (chimera) protein sequence. CDR1: Bold; CDR2: Underlined; CDR3: Italic.

QSLEESGGRLVTPGTPLTLTCTVSGLDLSSYYMQWVRQAPGKGLEWIGVIGNDNTYYASWAKGRFTISRASSTTVDLKMTS
LTTEDTATYFCARG*DI*WGPGTLVTVSS (SEQ ID NO: 3)

Ab1 Variable region heavy chain (chimera) DNA sequence. CDR1: Bold; CDR2: Underlined; CDR3: Italic.

CAGTCGCTGGAGGAGTCCGGGGGTCCGGCTGGTCACGCCTGGGACACCCCTGACACTCACCTGCACCGTCTCTGGACTCG
ACCTCAGTAGCTACTACATGCAATGGGTCCGCCAGGCTCCAGGGAAGGGGCTGGAATGGATCGGAGTGATTGGTATTA
ATGATAACACATACTACGCGAGCTGGGCGAAAGGCCGATTCACCATCTCCAGAGACGGCCTGTGTGACCACGTGATCTGA
AAATGACCAGTCTGACACCGAGGACACGGCCACCTATTTCTGTGCCAGAGGGGG*CGTCTGGGGCCCAGGCACCCTCGT*
CACCGTCTCGAGC (SEQ ID NO: 143)

FIGURE 1B

Ab1 Heavy chain (chimera) Full length DNA sequence.

CAGTCGCTGGAGGAGTCCGGGGGTCGCCTGGTCACGCCTGGGACACCCTGACACTCACCTGCACAGTCTCTGACTCG
ACCTCAGTAGCTACTACATGTCATGGGTCCGCCAGGCTCCAGGGAAGGGGCTGGAATGGATCGGAGTCATTGGTATTA
ATGATAACACATATACGGAGCTGGGCAAAGGCGAATTCACCATCTCCAGAGGCTGTCGACCAGGTGATCTGA
AAATGACCAGTCTGAAACCACTGTGCCAGAGGACACTGCCGTCTATTCTGTGCCAGAGGGGACATTCGGGCCAGGCACCCTG
TCACCGTCTCGAGCTCCACCAAGGGCCCATCGGTCTTCCCCCTGGCACCCTCCTCCAAGAGCACCTCTGGGGGCAC
AGCGGCCCTGGGCTGCCTGGTCAAGGACTACTTCCCCGAACCGGTGACGGTGTCGTGGAACTCAGGCGCCCTGACCAG
CGGCGTGCACACCTTCCCGGCTGTCCTACAGTCCTCAGGACTCTACTCCCTCAGCAGCGTGGTGACCGTGCCCTCCAGC
AGCTTGGGCACCCAGACCTACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGACCGTCAGTCTTCCTCTTC
CCCCCAAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGGCAGCCCCGAGAACCACAG
GTGTACACCCTGCCCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTGCTGGACT
CCGACGGCTCCTTCTTCCTCTACAGCAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTCTCCGGGTAAATGA (SEQ ID NO: 144)

Ab1 Light chain (chimera) Full length protein sequence.

QVLTQTASPVSAAVGSTVTINCQASQSVYDNNYLAWYQQKPCQPPKQLIYSTSTLASGVSSRFKGSGSGTQFLTISDLECAD
AATYYCLGSYDCSSGDCVFGGGTEVVKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC (SEQ ID NO: 2)

Ab1 Variable region light chain (chimera) protein sequence.

QVLTQTASPVSAAVGSTVTINCQASQSVYDNNYLAWYQQKPCQPPKQLIYSTSTLASGVSSRFKGSGSGTQFLTISDLECAD
AATYYCLGSYDCSSGDCVFGGGTEVVKR (SEQ ID NO: 1)

FIGURE 1C

Ab1 Variable region light chain (chimera) protein sequence. CDR1: Bold; CDR2: Underlined; CDR3: Italics.

QVLTQTASPVSAAVGSTVTINCQASQSVYDNNYLAWYQQKPGQPPKQLIY<u>STSTLAS</u>GVSSRFKGSGSGTQFTLTISDLECA
DAATYYC*LGSYDCSGDCFV*FGGGTEVVVKR (SEQ ID NO: 1)

Ab1 Variable region light chain (chimera) DNA sequence. CDR1: Bold; CDR2: Underlined; CDR3: Italics.

CAAGTGCTGACCCAGACTGCATCCCCGTGTCTGCAGTGTGGGAAGCACAGTCACCATCAATTGC**CAGGCCAGTCAG
AGTGTTTATGATAACAACTACCTAGCC**TGGTATCAGCAGAAACCAGGGCAGCCTCCAAGCAACTGATCTATTCTAC
<u>ATCCACTCTGGCATC</u>GGGGTCTCATCGCGGTTCAAAGGCAGTGGATCTGGGACACAGTTCACTCTCACCATCAGTGAC
CTGGAGTGTGCCGATGCTGCCACTTACTACTGT*CTAGGCAGTTATGATTGTAGTGGTGATTGTTTTGTT*TTCGGCGGAG
GGACCGAGGTGGTGGTCAAACGT (SEQ ID NO: 141)

Ab1 Light chain (chimera) Full length DNA sequence.

CAAGTGCTGACCCAGACTGCATCCCCGTGTCTGCAGTGTGGGAAGCACAGTCACCATCAATTGCCAGGCCAGTCAG
AGTGTTTATGATAACAACTACCTAGCCTGGTATCAGCAGAAACCAGGGCAGCCTCCAAGCAACTGATCTATTCTACAT
CCACTCTGGCATCGGGGTCTCATCGCGGTTCAAAGGCAGTGGATCTGGGACACAGTTCACTCTCACCATCAGTGACCT
GGAGTGTGCCGATGCTGCCACTTACTACTGTCTAGGCAGTTATGATTGTAGTGGTGATTGTTTTGTTTTCGGCGGAG
GGACCGAGGTGGTGGTCAAACGTACGGTGCTGCACCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTACAGTGGAAGGTGATAACGCC
CTCCAATCGGGTAACTCCCAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAGGGCCTGAGCTCGCCCGTC
ACAAAGAGCTTCAACAGGGGAGAGTGTTAG (SEQ ID NO: 142)

Ab2 Heavy chain (humanized) Full length protein sequence – mammalian produced.

EVQLVESGGGLVQPGGSLRLSCAVSGLDLSSYYMQWVRQAPGKGLEWVGVIGINDNTYYASWAKGRFTISRDNSKTTVYL
QMNSLRAEDTAVYFCARGDIWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYASTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 14)

Ab2 Variable region heavy chain (humanized) protein sequence.

EVQLVESGGGLVQPGGSLRLSCAVSGLDLSSYYMQWVRQAPGKGLEWVG<u>VIGINDNTYYASWAKG</u>RFTISRDNSKTTVYL
QMNSLRAEDTAVYFCARG*DI*WGQGTLVTVSS (SEQ ID NO: 13)

Ab2 Variable region heavy chain (humanized) protein sequence. CDR1: Bold; CDR2: Underlined; CDR3: Italics.

EVQLVESGGGLVQPGGSLRLSCAVSGLDLSSYYMQWVRQAPGKGLEWVG<u>VIGINDNTYYASWAKG</u>RFTISRDNSKTTVYL
QMNSLRAEDTAVYFCARG*DI*WGQGTLVTVSS (SEQ ID NO: 13)

Ab2 Variable region heavy chain (humanized) DNA sequence. CDR1: Bold; CDR2: Underlined; CDR3: Italics.

GAGGTGCAGCTGGTGGAGTCTGGGGGAGGCTTGGTCCAGCCTGGGGGGTCCCTGAGACTCTCTGTGTGCAGTCTCTGGAC
TCGACCTCAGTAGCTACTACTACATGCAATGGGTCCGTCAGGCTCCAGGGAAGGGTCTGGAGTGGGTCGGAGTCATTGGTA
TCAATGATAACACATACTACGCGAGTTGGGCGAAAGGCGATTCAGCCGATTCACCATCTCCAGAGACAATTCCAAGACGGTGT
ATCTTCAAATGAACAGCCTGAGAGCTGAGGACACTGCTGTCTATTTCTGTGCTAGAGGG*GACATT*TGGGGCCAAGGGAC
CCTCGTCACCGTCTCGAGC (SEQ ID NO: 153)

FIGURE 2B

Ab2 Heavy chain (humanized) Full length DNA sequence – mammalian produced

GAGGTGCAGCTTGTGGAGTCTGGGGGAGGCTTGGTCCAGCCTGGGGGGTCCCTGAGACTCTCCTGTGCAGTCTCTGGAC
TCGACCTCAGTAGTACTACATACTACGAGAGCTGGATGCAATGGGTCCGTCCAGGCTCCAGGGAAGGGGCTGGAGTGGGTCATTGGTA
TCAATGATAACACCATACTCGAGAGCTGGGAAAGGCTGATTCACCATCTCCAGAGACATCCAAGACCACGGTGT
ATCTCAAATGAACAGCCTGAGAGCTGTGTGTAGAGGACATGTGTAGAGGACATGGGGCAAGGGA
CCCTCGTCACGTCTGAAGCGCCTGCGTCAAGGACTACTTCCCCGACCGTGTCGGTGACCCTCAGAGCACCTCTGG
GGCCACAGCGGCGTGCACACCTTCCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACCAAGGTGGACAAGAGAGTT
GAGCCCAAATCTTGTGACAAAACCCACACATGCCCACCGTGCCCAGCACCTGAACTCCTGGGGGGACCGTCAGTCTTC
TCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACAGCAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAAC
CACAGGTGTACACCCTGCCCCCATCCCGGGAGGAGATGACCAAGAACCAGGTCAGCCTGACCTGCCTGGTCAAGGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAATGA (SEQ ID
NO: 154)

Ab2 Light chain (humanized) Full length protein sequence

QVLTQSPSSLSASVGDRVTINCQASQSVYDNNYLAWYQQKPGKVPKQLIYSTSTLASGVPSRFSGSGSGTDFTLTISSLQPED
VATYYCLGSYDCSSGDCFVFGGGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC  (SEQ ID NO: 12)

Ab2 Variable region Light chain (humanized) protein sequence

QVLTQSPSSLSASVGDRVTINCQASQSVYDNNYLAWYQQKPGKVPKQLIYSTSTLASGVPSRFSGSGSGTDFTLTISSLQPED
VATYYCLGSYDCSSGDCFVFGGGTKVEIKR  (SEQ ID NO: 11)

FIGURE 2C

Ab2 Variable region Light chain (humanized) protein sequence. CDR1: Bold; CDR2: Underlined; CDR3: Italics.

QVLTQSPSSLSASVGDRVTINCQASQSVYDNNYLAWYQQKPGKVPKQLIYSTSTLASGVPSRFSGSGSGTDFTLTISSLQPED
VATYYC*LGSYDCSSGDCF*FGGGTKVEIKR (SEQ ID NO: 11)

Ab2 Variable region Light chain (humanized) DNA sequence. CDR1: Bold; CDR2: Underlined; CDR3: Italics.

CAAGTGCTGACCCAGTCTCCATCTCCCTGTCTGCATCTGTAGGAGACAGAGTCACCATCAATTGC**CAGGCCAGTCAG
AGTGTTTATGATAACAACTACCTAG**CCTGGTATCAGCAGAAACCAGGGAAAGTTCCTAAGCAACTGATCTATTCTAC
ATCCACTCTGGCATCTGGGGTCCCATCTCGTTCAGTGGCAGTGGATCTGGGACAGATTTCACTCTCACCATCAGCAGC
CTGCAGCCTGAAGATGTTGCAACTTATTACTGTC*TAGGCAGTTATGATTGTAGTAGTGGTGATTGTTTT*GGCGGAG
GAACCAAGGTGGAAATCAAACGT (SEQ ID NO: 151)

Ab2 Light chain (humanized) Full length DNA sequence.

CAAGTGCTGACCCAGTCTCCATCTCCCTGTCTGCATCTGTAGGAGACAGAGTCACCATCAATTGCCAGGCCAGTCAGA
GTGTTTATGATAACAACTACCTAGCCTGGTATCAGCAGAAACCAGGGAAAGTTCCTAAGCAACTGATCTATTCTACATC
CACTCTGGCATCTGGGGTCCCATCTCGTTCAGTGGCAGTGGATCTGGGACAGATTTCACTCTCACCATCAGCAGCCTG
CAGCCTGAAGATGTTGCAACTTATTACTGTCTAGGCAGTTATGATTGTAGTAGTGGTGATTGTTTTGGCGGAGG
AACCAAGGTGGAAATCAAACGTACGGTGGCTGCTCCATCTGTCTTCATCTTCCCGCCAAGTACAGTGGAAGGTGGATAACGCC
TCCAATCGGGTAACTCCCAGGAGAGTGTCACAGAGAAACAAAGTCTACGCCCTCAGCAGCCACCCTGA
CGCTGAGCAAAGCAGACTACGAGAAACACAAAGTCTACGCCTGCGAAGTCACCCATCAGGGCCTGAGCTCGCCGTCA
CAAAGAGCTTCAACAGGGGAGAGTGTTAG (SEQ ID NO: 152)

Ab3 Heavy chain (humanized) Full length protein sequence – yeast produced

EVQLVESGGGLVQPGGSLRLSCAVSGIDIWQQTLVTVSSASTKGPSVFPLAPSSKSTSGGTAALGCLVKDYFPEPVTVSWNSGALTSGV
QMNSLRAEDTAVYFCARGDIWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 24)

Ab3 Variable region heavy chain (humanized) protein sequence

EVQLVESGGGLVQPGGSLRLSCAVSGIDLSSYYMQWVRQAPGKGLEWVGVIGINDNTYYASWAKGRFTISRDNSKTTVYL
QMNSLRAEDTAVYFCARGDIWGQGTLVTVSS (SEQ ID NO: 23)

Ab3 Variable region heavy chain (humanized) protein sequence. CDR1: Bold; CDR2: Underlined; CDR3: Italics.

EVQLVESGGGLVQPGGSLRLSCAVSGIDLSSYYMQWVRQAPGKGLEWVGVIGINDNTYYASWAKGRFTISRDNSKTTVYL
QMNSLRAEDTAVYFCARG*DI*WGQGTLVTVSS (SEQ ID NO: 23)

Ab3 Variable region heavy chain (humanized) DNA sequence. CDR1: Bold; CDR2: Underlined; CDR3: Italics.

GAGGTCCAGCTGGTGGAGTCTGGGGGAGGCTTGGTCCAGCCTGGGGGGTCCCTGAGACTCTCCTGTGCAGTCTCTGGAC
TCGACCTCAGTAGCTACTACATGCAATGGGTCCGCCAGGCTCCAGGGAAGGGGCTGGAGTGGGTCGGAGTTATTGGTA
TCAATGATAACACATATACAGCCTCGTGGGCGAAAGGCCGATTCACCATCTCCAGAGACAATTCCAAGACCACGGTGTA
TCTTCAAATGAACAGCCTGAGAGCTGAGGACACTGCTGTGTATATTCTGTGCTAGAGGGGGACATCTGGGGCCAAGGGAC
CCTCGTCACCGTCTCGAGC (SEQ ID NO: 16)

FIGURE 3B

Ab3 Heavy chain (humanized) Full length DNA sequence – yeast produced.

GAGGTGCAGCTGGTGGAGTCTGGGGGAGGCTTGGTGCAGCCTGGGGGGTCCCTGAGACTCTCCTGTGCAGTCTCTGGAC
TCGACCTCAGTCAGTACTACTACTACATGCAATGGGTCCAGCAGGCTCCAGGAAAGGGCTGGAGTCGGAGTCATTGTA
TCAATGATATACACATACTACGCCAGCTGGGCGAAAGGCCGATTCACCATCTCCAGAGACAATTCCAAGAACACGTGT
ATCTTCAAATGAACAGCCTGAGAGCTGAAGACACTGCTGTGTATTTCTGTGCTAGAGGGACATCTGCGGCAAGGGA
CCCTGTCGTCAGCGCCTCGAGCGCCTCCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACCAAGGTGGACAAGCGAGTT
GAGCCCAAATCTTGTGACAAAACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACGGCAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAAC
CACAGGTGTACACCCTGCCCCCATCCCGGGAGGAGATGACCAAGAACCAGGTCAGCCTGACCTGCCTGGTCAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCCCGGGTAAATGA (SEQ ID NO: 164)

Ab3 Light chain (humanized) Full length protein sequence.

QVLTQSPSSLSASVGDRVTINCQASQSVYDNNYLAWYQQKPGKVPKQLIYSTSTLASGVPSRFSGSGSGTDFTLTISSLQPED
VATYYCLGSYDCSSGDCFVFGGGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC (SEQ ID NO: 22)

Ab3 Variable region Light chain (humanized) protein sequence.

QVLTQSPSSLSASVGDRVTINCQASQSVYDNNYLAWYQQKPGKVPKQLIYSTSTLASGVPSRFSGSGSGTDFTLTISSLQPED
VATYYCLGSYDCSSGDCFVFGGGTKVEIKR (SEQ ID NO: 21)

FIGURE 3C

Ab3 Variable region Light chain (humanized) protein sequence. CDR1: Bold; CDR2: Underlined; CDR3: Italics.

QVLTQSPSSLSASVGDRVTINCQASQSVYDNNYLAWYQQKPGKVPKQLIYSTSTLASGVPSRFSGSGSGTDFTLTISSLQPED
VATYYC*LGSYDCSSGDCF*FGGGTKVEIKR (SEQ ID NO: 21)

Ab3 Variable region Light chain (humanized) DNA sequence. CDR1: Bold; CDR2: Underlined; CDR3: Italics.

CAAGTGCTGACCCAGTCTCCATCTCCCGTCTCCGTGTCTGCAGCAGAGTCACCATCAATTGC**CAGGCCAGTCAG
AGTGTTTATGATAACAACTACCTAGC**CTGGTATCAGCAGAAACCAGGGAAAGTTCCTAAGCAACTGATCTATTCTAC
ATCCACTCTGGCATCTGGGGTCCCATCTCGTTCAGTGGCAGTGGATCTGGGACAGATTTCACTCTCACCATCAGCAGC
CTGCAGCCTGAAGATGTTGCAACTTATTACTGT*CTAGGCAGTTATGATTGTAGTAGTGGTGATTGTTTTT*TTCGGCGGAG
GAACCAAGGTGGAAATCAAACGT (SEQ ID NO: 161)

Ab3 Light chain (humanized) Full length DNA sequence.

CAAGTGCTGACCCAGTCTCCATCTCCCGTCTCCGTGTCTGCAGCAGAGTCACCATCAATTGCCAGGCCAGTCAGA
GTGTTTATGATAACAACTACCTAGCCTGGTATCAGCAGAAACCAGGGAAAGTTCCTAAGCAACTGATCTATTCTACATC
CACTCTGGCATCTGGGGTCCCATCTCGTTCAGTGGCAGTGGATCTGGGACAGATTTCACTCTCACCATCAGCAGCCTG
CAGCCTGAAGATGTTGCAACTTATTACTGTCTAGGCAGTTATGATTGTAGTAGTGGTGATTGTTTTTTCGGCGGAGG
AACCAAGGTGGAAATCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG (SEQ ID NO: 162)

Ab4 Heavy chain (chimera) Full length protein sequence.

QSLEESGGRLVTPGTPLTLTCSVSGIDLSGYYMNWVRQAPGKGLEWIGVIGINGATYYASWAKGRFTISKTSSTTVDLKMTS LTTEDTATYFCARGDIWGPGTLVTVSSASTKGPSVFPLAPSSKSTSGTAALGCLVKDYFPEPVTVSWNSGALTSGVHTFPAV LQSSGLYSLSSVVTVPSSSLGTQTYICNVNHKPSNTKVDKRVEPKSCDKTHTCPPCPAPELLGGPSVFLFPPKPKDTLMISRTP EVTCVVVDVSHEDPEVKFNWYVDGVEVHNAKTKPREEQYASTYRVVSVLTVLHQDWLNGKEYKCKVSNKALPAPIEKTIS KAKGQPREPQVYTLPPSREEMTKNQVSLTCLVKGFYPSDIAVEWESNGQPENNYKTTPPVLDSDGSFFLYSKLTVDKSRWQ QGNVFSCSVMHEALHNHYTQKSLSLSPGK (SEQ ID NO: 34)

Ab4 Variable region heavy chain (chimera) protein sequence.

QSLEESGGRLVTPGTPLTLTCSVSGIDLSGYYMNWVRQAPGKGLEWIGVIGINGATYYASWAKGRFTISKTSSTTVDLKMTS LTTEDTATYFCARGDIWGPGTLVTVSS (SEQ ID NO: 33)

Ab4 Variable region heavy chain (chimera) protein sequence. CDR1: Bold; CDR2: Underlined; CDR3: Italics.

QSLEESGGRLVTPGTPLTLTCSVSGIDLSGYYMNWVRQAPGKGLEWIG<u>VIGINGATYYASWAKG</u>RFTISKTSSTTVDLKMTS LTTEDTATYFCAR*GDI*WGPGTLVTVSS (SEQ ID NO: 33)

Ab4 Variable region heavy chain (chimera) DNA sequence. CDR1: Bold; CDR2: Underlined; CDR3: Italics.

CAGTCGCTGGAGGAGTCGGGGGGTCCGGCTGGTGACTCCGGGGACACCCCTGACACTCACCTGTTCCGTCTCTGGCATCG ACCTCAGTGGCTACTACATGAACTGGGTCCGCCAGTCTCCAGGGAAGGGGCTGGAATGGATCGGAGTCATTGGTATT AATGGTGCACTACTTACTACGCGTCGTGGGCGAAAGGCCGGATTCACCATCTCCAAAACCTCGTCGACCACGGTGGATCTG AAAATGACCAGTCTGACAACGGAGGACACGGCCACCTATTTCTGTGCCAGAGG*GGACATC*TGGGGCCCGGGCACCCTC GTCACCGTCTCGAGC (SEQ ID NO: 173)

FIGURE 4B

Ab4 Heavy chain (chimera) Full length DNA sequence:

CAGTCCTGGAGGAGTCCCTGCCTGCTTGGTCCTGGTCACACTGGGACACCCTGACACTGGTTCGTTCGTTCTGCCATCG
ACCTCAGTGGCTACTACTACATGGAACTGGTTCGCCAGGCTCCAGGGAAGGGGCTGGAATGGGTGGCAGTCATTGGTATTA
ATGTGCACATACTACTACGCAGACAGTGTGAAGGGCCGATTCACCATCTCCAAACCTGTGACACACGTGGATCGA
AAATGACCAGTCTGACAGCCTGCCTGGTGAGCAGACGGCCACCTATTCTGTGCAGGGGACATCTGGGCGCCCACCTCG
TCACCGTCTCGAGCGCCTCCACCAAGGGCCCATCCGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTGGTGACCGTGCCCTCCAGC
AGCTTGGGCACCCAGACCTACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGACCGTCAGTCTTCCTCTTCC
CCCCAAAACCCAAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCGGGAGGAGCAG
TACGCCAGCACGTACCGTGTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTGCTGGACT
CCGACGGCTCCTTCTTCCTCTACAGCAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTCTCCGGGTAAATGA (SEQ ID NO: 174)

Ab4 Light chain (chimera) Full length protein sequence:

QVLTQTPSPVSAAVGSTVTINCQASQSVYHNTYLAWYQQKPGQPPKQLIYDASTLASGVPSRFSGSGSGTQFTLTISGVQCND
AAYYCLGSYDCTNGDCFVFGGGTEVVVKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC (SEQ ID NO: 32)

Ab4 Variable region light chain (chimera) protein sequence:

QVLTQTPSPVSAAVGSTVTINCQASQSVYHNTYLAWYQQKPGQPPKQLIYDASTLASGVPSRFSGSGSGTQFTLTISGVQCND
AAYYCLGSYDCTNGDCFVFGGGTEVVVKR (SEQ ID NO: 31)

FIGURE 4C

Ab4 Variable region light chain (chimera) protein sequence. CDR1: Bold; CDR2: Underlined; CDR3: Italics

QVLTQTPSPVSAAVGSTVTINCQASQSVYHNTYLAWYQQKPGQPPKQLIYDASTLASGVPSRFSGSGSGTQFTLTISGVQCN
DAAAYYC*LGSYDCTNGDCFI*FGGGTEVVVKR (SEQ ID NO: 31)

Ab4 Variable region light chain (chimera) DNA sequence. CDR1: Bold; CDR2: Underlined; CDR3: Italics

CAAGTGCTGACCCAGACTCCATCCCCGTGTCTGCAGTCCCAGGTCACCATCACATCAATGCCAGGCCCAGTCAG
AGTGTTTATCATAACACCTACCTGGCCTGGTATCAGCAGAAGCCAGGGCAGCCTCCCAAACTACTGATCTATGATGC
ATCCACTCTGGCATCTGGGGTCCCATCGCGGTTCAGCGGCCAGTGGATCTGGGACACAGTTCACTCTCACCATCAGCGGC
GTGCAGTGTAACGATGCCGCCGCTTACTACTGTCT*GGGCAGTTATGATTGTACTAATGGTGATTGTTTTATT*TTCGGCGGAG
GGACCGAGGTGGTGGTCAAACGT (SEQ ID NO: 171)

Ab4 Light chain (chimera) Full length DNA sequence

CAAGTGCTGACCCAGACTCCATCCCCGTGTCTGCAGTCCCAGGTCACCATCAATGCCAGGCCCAGTCAGA
GTGTTTATCATAACACCTACCTGGCCTGGTATCAGCAGAAGCCAGGGCAGCCTCCAAACTACTGATCTATGATGC
CACTCTGGCCTCTGGGGTCCCATCGCGGTTCAGCGGCCAGTGGATCTGGGACACAGTTCACTCTCACCATCAGCGGCGTG
CAGTGTAACGATGCCGCCGCTTACTACTGTCTGGGCAGTTATGATTGTACTAATGGTGATTGTTTTATTTTCGGCGGAGG
GACCGAGGTGGTGGTCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG (SEQ ID NO: 172)

Ab5 Heavy chain (humanized) Full length protein sequence – mammalian produced

EVQLVESGGGLVQPGGSLRLSCAVSGIDLSGYYMNWVRQAPGKGLEWVGVIGINGATYYASWAKGRFTISRDNSKTTVYL
QMNSLRAEDTAVYFCARGDIWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYASTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 44)

Ab5 Variable region heavy chain (humanized) protein sequence

EVQLVESGGGLVQPGGSLRLSCAVSGIDLSGYYMNWVRQAPGKGLEWVGVIGINGATYYASWAKGRFTISRDNSKTTVYL
QMNSLRAEDTAVYFCARGDIWGQGTLVTVSS (SEQ ID NO: 43)

Ab5 Variable region heavy chain (humanized) protein sequence. CDR1: Bold; CDR2: Underlined; CDR3: Italics.

EVQLVESGGGLVQPGGSLRLSCAVSGIDLSGYYMNWVRQAPGKGLEWVG<u>VIGINGATYYASWAKG</u>RFTISRDNSKTTVYL
QMNSLRAEDTAVYFCARG*DI*WGQGTLVTVSS (SEQ ID NO: 43)

Ab5 Variable region heavy chain (humanized) DNA sequence. CDR1: Bold; CDR2: Underlined; CDR3: Italics.

GAGGTGCAGCTGTGGAGTCTGGGGGAGACTTGGTGCAGCCTGGGGGGTCCCTGAGACTCTCCTGTGCAGTCTCTGGA
TCGACCTCAGTGGCTACTACATGAACTGGGTCCGTCAGGCTCCAGGGAAGGGGCTGGAGTGGGTCGGAGTCATTGGT
<u>ATTAATGGTGCCACATACTACGCGAGCTGGGCGAAAGGC</u>CGATTCACCATCTCCAGAGACAATTCCAAGACCACGGTG
TATCTTCAAATGAACAGCCTGAGAGACACTGCTGTGTATTTCTGTGCTAGA*GGGGAC*ATTTGGGGCCAAGGGA
CCCTGGTCACCGTCTCGAGC (SEQ ID NO: 183)

FIGURE 5B

Ab5 Heavy chain (humanized) Full length DNA sequence – mammalian produced

GAGGTGTCCAGCTTGTGGAGTCTGGAGGTCTGGGGGAGGCTTGGTCCAGCCTGGGGGGGTCCCTGAGACTCTCCTGTGCAGTCTCTGGAA
TGACCTCAGTGGCTACTACATACTGCGCAGTCGGAACTGAACTGGGTCCGTCAGGCTCCAGGGAAGGGCTGGAGTGGGTCGGAGTCATTGGTA
TTAATGGTGCCACATATTACTGCGCAGTCGGCGAAAGGCCGATTCACCATCTCCAGAGACAATTCCAAGACACATTGTATCTGCAAATGAA
ATCTTCAAATGAACAGCCTGAGAGCCTGAGAGGACACTGCTGTGTATTCTGTGCTAGAGGGGACATTGGGGCAAGGGACACTCTGG
GGCCACAGGGACCACGGTCACCGTCTCCTCAGCCTCCACCAAGGGCCCATCCGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAGAGTT
GAGCCCAAATCTTGTGACAAAACTCACACATGCCCACCGTGCCCAGCACCTGAACTCCTGGGGGGACCGTCAGTCTTC
TCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACGCCAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAAC
CACAGGTGTACACCCTGCCCCCATCCCGGGATGAGCTGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAATGA (SEQ ID NO: 184)

Ab5 Light chain (humanized) Full length protein sequence

QVLTQSPSSLSASVGDRVTINCQASQSVYHNTYLAWYQQKPGKVPKQLIYDASTLASGVPSRFSGSGSGTDFTLTISSLQPED
VATYYCLGSYDCTNGDCFVFGGGTKVEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC (SEQ ID NO: 42)

Ab5 Variable region Light chain (humanized) protein sequence

QVLTQSPSSLSASVGDRVTINCQASQSVYHNTYLAWYQQKPGKVPKQLIYDASTLASGVPSRFSGSGSGTDFTLTISSLQPED
VATYYCLGSYDCTNGDCFVFGGGTKVEIKR (SEQ ID NO: 41)

FIGURE 5C

Ab5 Variable region Light chain (humanized) protein sequence. CDR1: Bold; CDR2: Underlined; CDR3: Italics.

QVLTQSPSSLSASVGDRVTINCQASQSVYHNTYLAWYQQKPGKVPKQLIY<u>DASTLAS</u>GVPSRFSGSGSGTDFTLTISSLQPED
VATYYC*LGSYDCTNGDCF*FGGGTKVEIKR (SEQ ID NO: 41)

Ab5 Variable region Light chain (humanized) DNA sequence. CDR1: Bold; CDR2: Underlined; CDR3: Italics.

CAAGTGCTGACCCAGTCTCCATCCTCCCTGTCTGCATCTGTAGGAGACAGAGTCACCATCAATTGC**CAGGCCAGTCAG
AGTGTTTATCATAACACCTACCTG**GCCTGGTATCAGCAGAAACCAGGGAAAGTTCCTAAGCAACTGATCTATGAT<u>GC
ATCCACTCTGGCATCTG</u>GGGTCCCATCTCGTTCAGTGGCAGTGGATCTGGGACAGATTTCACTCTCACCATCAGCAGC
CTGCAGCCTGAAGATGTTGCAACTTATTACTGT*CTGGGCAGTTATGATTGTACTAATGGTGATTGTTTTT*TCGGGGGAG
GAACCAAGGTGGAAATCAAACGT (SEQ ID NO: 181)

Ab5 Light chain (humanized) Full length DNA sequence.

CAAGTGCTGACCCAGTCTCCATCCTCCCTGTCTGCATCTGTAGGAGACAGAGTCACCATCAATTGCCAGGCCAGTCAGA
GTGTTTATCATAACACCTACCTGGCCTGGTATCAGCAGAAACCAGGGAAAGTTCCTAAGCAACTGATCTATGATGCATC
CACTCTGGCATCTGGGGTCCCATCTCGTTCAGTGGCAGTGGATCTGGGACAGATTTCACTCTCACCATCAGCAGCCTG
CAGCCTGAAGATGTTGCAACTTATTACTGTCTGGGCAGTTATGATTGTACTAATGGTGATTGTTTTTTCGGGGGAGG
AACCAAGGTGGAAATCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGAGTTCAACAGGGGAGAGTGTTAG (SEQ ID NO: 182)

Ab6 Heavy chain (humanized) Full length protein sequence – yeast produced

EVQLVESGGGLVQPGGSLRLSCAVSGIDLSGYYMNWVRQAPGKGLEWVGVIGINGATYYASWAKGRFTISRDNSKTTVYL
QMNSLRAEDTAVYFCARGDIWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYASTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 54)

Ab6 Variable region heavy chain (humanized) protein sequence.

EVQLVESGGGLVQPGGSLRLSCAVSGIDLSGYYMNWVRQAPGKGLEWVGVIGINGATYYASWAKGRFTISRDNSKTTVYL
QMNSLRAEDTAVYFCARGDIWGQGTLVTVSS (SEQ ID NO: 53)

Ab6 Variable region heavy chain (humanized) protein sequence. CDR1: Bold; CDR2: Underlined; CDR3: Italic.

EVQLVESGGGLVQPGGSLRLSCAVSGIDLSGYYMNWVRQAPGKGLEWVGVIGINGATYYASWAKGRFTISRDNSKTTVYL
QMNSLRAEDTAVYFCARGDIWGQGTLVTVSS (SEQ ID NO: 53)

Ab6 Variable region heavy chain (humanized) DNA sequence. CDR1: Bold; CDR2: Underlined; CDR3: Italic.

GAGGTCCAGCTTGTGGAGTCTGGGGGAGGCTTGGTGCAGCCTGGGGGGTCCCTGAGACTCTCCTGTGCAGTCTCTGGAA
TCGACCTCAGTGGCTACTACATGAACTGGGTCCGTCAGGCTCCAGGGAAGGGGCTGGAGTGGGTGGGAGTCATTGGT
ATTAATGGTGCCACATACTACGCCAGCTGGGCGAAAGGCCGATTCACCATCTCCAGAGACAATTCCAAGACCACGGTG
TATCTTCAAATGAACAGCCTGAGAGCTGAGGACACTGCTGTGTATTCTGTGCTAGA*GGGGATCTGGGATCTGGGACGTTCTCGAGC* (SEQ ID NO: 193)

FIGURE 6B

Ab6 Heavy chain (humanized) Full length DNA sequence – yeast produced

GAGGTGCAGCTTGTGGAGTCTGGGGGAGGCTTGGTCCAGCCTGGGGGGTCCCTGAGACTCTCCTGTGCAGTCTCTGAA
TCGACTCAGTGGTACTACTACTACGCCAGCTGAACTGAATGGGTCCGTCAGGCTCCAGGGAAGGGGTTGGAGTGGGTCGCAGTCATTGGTA
TTAATGGTGCCACATACTACGCCGAGTCTGGGCGAAAGGCCGATTCACCATCTCCAGAGACAATTCAAGAACCACGTGT
ATCTTCAAATGAACAGCCTGAGAGCTGAGGACACTGCTGTGTATTTCTGTGCTAGAGGGACATCTGGGCTCAAGGGA
CCCTCGTCACCGTCTCGAGCGCCTCCACCAAGGGCCCATCGGTCTTCCCCCTGGCTCCCTGCACCTCCAGAGCACCCTG
GGGCACAGCGGCGTGCACACCTTCCCGGCTGTCCTACAGTCCTCAGGACTCTACTCCCTCAGCAGCGTGGTGACCGTCCC
GACCAGCGGCGTGCACACCTTCCCGGCTGTCCTACAGTCCTCAGGACTCTACTCCCTCAGCAGCGTGGTGACCGTGCCC
TCCAGCAGCTTGGGCACCCAGACCTACACCTGCAACGTGAATCACAAGCCCAGCAACACCAAGGTGGACGCGGAGAGTT
GAGCCCAAATCTTGTGACAAAACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACGCCAAGCACGTCTCAACAAAGCCCTCGAGGTGCTCACCGTCCTGCACCAGGACTGGCTGAATGGCAAGGAGTACA
AGTGCAAGGTCTCCAACAAAGCCCTCCCATCCGAGAAAACCATCTCCAAAGCCAAAGGGCAGCCCCGAGAA
CCACAGGTGTACACCCTGCCCCCATCCCGGGAGGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGAACGTCTTCTC
ATGCTCCGTGATGCATGAGGCTCTGCACAACCACTACACGCAGAAGAGCCTCTCCCTGTCTCCGGGTAAATGA (SEQ ID NO: 194)

Ab6 Light chain (humanized) Full length protein sequence.

QVLTQSPSSLSASVGDRVTINCQASQSVYHNTYLAWYQQKPGKVPKQLIYDASTLASGVPSRFSGSGSGTDFTLTISSLQPED
VATYYCLGSYDCTNGDCFVFGGGTKVEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC (SEQ ID NO: 52)

Ab6 Variable region Light chain (humanized) protein sequence.

QVLTQSPSSLSASVGDRVTINCQASQSVYHNTYLAWYQQKPGKVPKQLIYDASTLASGVPSRFSGSGSGTDFTLTISSLQPED
VATYYCLGSYDCTNGDCFVFGGGTKVEIKR (SEQ ID NO: 51)

FIGURE 6C

Ab6 Variable region Light chain (humanized) protein sequence. CDR1: Bold; CDR2: Underlined; CDR3: Italics

QVLTQSPSSLSASVGDRVTINCQASQSVYHNTYLAWYQQKPGKVPKQLIYDASTLASGVPSRFSGSGSGTDFTLTISSLQPED
VATYYCL*GSYDCTNGIDCF*FGGGTKVEICR (SEQ ID NO: 51)

Ab6 Variable region Light chain (humanized) DNA sequence. CDR1: Bold; CDR2: Underlined; CDR3: Italics

CAAGTGCTGACCCAGTCTCCATCCTCCCTGTCTGCATCTGTAGGAGACAGAGTCACCATCAATTGCCAGGCCAGTCAG
AGTGTTTATCATAACACCTACCTGGCCTGGTATCAGCAGAAACCAGGGAAAGTTCCTAAGCAACTGATCTATGATGC
ATCCACTCTGGCATCTGGGGTCCATCTCGGTTCAGTGGCAGTGGATCTGGGACAGATTTCACTCTCACCATCAGC
AGTCTGCAGCCTGAAGATGTTGCAACTTATTACTGT*CTCGGGCAGTTATGATTGTACTAATGGTATTGATTGTTT*TGGCGGAGG
GAACCAAGGTGGAAATCAAACGT (SEQ ID NO: 191)

Ab6 Light chain (humanized) Full length DNA sequence.

CAAGTGCTGACCCAGTCTCCATCCTCCCTGTCTGCATCTGTAGGAGACAGAGTCACCATCAATTGCCAGGCCAGTCAG
AGTGTTTATCATAACACCTACCTGGCCTGGTATCAGCAGAAACCAGGGAAAGTTCCTAAGCAACTGATCTATGATGC
ATCCACTCTGGCATCTGGGGTCCATCTCGGTTCAGTGGCAGTGGATCTGGGACAGATTTCACTCTCACCATCAGCAGTC
TGCAGCCTGAAGATGTTGCAACTTATTACTGTCTCGGGCAGTTATGATTGTACTAATGGTATTGATTGTTTTGGCGGAGG
GAACCAAGGTGGAAATCAAACGTAACGGTGGCTGCACCATCTCTGTCTTCCCACCATCCAGTGAGCAGTTGAAATCT
GGAACTGCCTCTGTTGTGTGCCTGCTGAATAACTTCTATCCCAGAGAGGCCAAAGTACAGTGGAAGGTGGATAACGCC
CTCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG (SEQ ID NO: 192)

Ab7 Heavy chain (chimera) Full length protein sequence.

QEQLKESGRLVTPGTSLTLTCTVSGIDLSNHYMQWVRQAPGKGLEWIGYVGINGRTYYASWAKGRFTISRTSSTTVDLKM
TRLTEEDTATYFCARGDIWGPGTLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCDKTHTCPPCPAPELLGGPSVFLFPPKPKDTLMISR
TPEVTCVVVDVSHEDPEVKFNWYVDGVEVHNAKTKPREEQYASTYRVVSVLTVLHQDWLNGKEYKCKVSNKALPAPIEKT
ISKAKGQPREPQVYTLPPSREEMTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 64)

Ab7 Variable region heavy chain (chimera) protein sequence.

QEQLKESGRLVTPGTSLTLTCTVSGIDLSNHYMQWVRQAPGKGLEWIGYVGINGRTYYASWAKGRFTISRTSSTTVDLKM
TRLTEEDTATYFCARGDIWGPGTLVTVSS (SEQ ID NO: 63)

Ab7 Variable region heavy chain (chimera) protein sequence. CDR1: Bold; CDR2: Underlined; CDR3: Italics.

QEQLKESGRLVTPGTSLTLTCTVSGIDLSNHYMQWVRQAPGKGLEWIG*YVGINGRTYYASWAKG*RFTISRTSSTTVDLKM
TRLTEEDTATYFCARG*DI*WGPGTLVTVSS (SEQ ID NO: 63)

Ab7 Variable region heavy chain (chimera) DNA sequence. CDR1: Bold; CDR2: Underlined; CDR3: Italics.

CAGGAGCAGCTGAAGGAGTCCGGAGGCGGGTCGCTGGTCACCCCTGGGACACTCCTGACACTCACCTGCACCGTCTCTGGA
ATCGACCTCAGTAACCACTACATGCAATGGGTCCGCCAGGCTCCAGGAAGGGCTCTGGAGTGGATCGGATACGTTGG
TATTAATGGTCGTACATATTACGCGTCGTGGAAGGCGATTCACCATCTCCAGAACCTCGTCGACCGTCGAT
CTGAAAATGACCAGGCTGACAACCGAGGACACGGCCACCTATTTCTGTGCCAGAGGGGA*CATT*TGGGGCCCAGGCACC
CTGGTCACCGTCTCGAGC (SEQ ID NO: 203)

FIGURE 7B

Ab7 Heavy chain (chimera) Full length DNA sequence

CAGGAGCAGCTGAAGGAGTCCGGGGGTCCGGTCACCTGGTCACCTGCACCGTCTGA
ATCGACCTCAGTAACACTACTACGCGAGTCAATGGGTCCCCAGGCTCCAGGAAGGGCTGGAGTGGATCGGAGTCGTTGGT
ATTAATGTGCACATACTACCCGAGTCTGGGCGAAAGGCCGATTCACCATCTCCAGAGACACCTCGACCAGGTGGAT
CTGAAAATGACCAGCCTGAGGCTGAACCGAGGACACCGCCACCTATTCTGTGCCAGAGGACATCGGCCCCAGGCACC
CTGGTCACCGTCTCGGCGCCTCCACCAAGGGCCCATCCGTCTTCCCCCTGGCACCCTCCTCCAAGAGCACCTCTGGG
GCACAGCGCCTGGCTGCCTGGTCAAGGACTACTTCCCCGAACCGGTGACGGTGTCGTGGAACTCAGGCGCCCTGA
CCAGCGGCGTGCACACCTTCCCGGCTGTCCTACAGTCCTCAGGACTCTACTCCCTCAGCAGCGTGGTGACCGTGCCCTC
CAGCAGCTTGGGCACCCAGACCTACATCTGCAACGTGAATCACAAGCCCAGCAACACCAAGGTGGACAAGAGAGTTGA
GCCCAAATCTTGTGACAAAACTCACACATGCCCACCGTGCCCAGCACCTGAACTCCTGGGGGACCGTCAGTCTTCCTC
TTCCCCCCAAAACCCAAGGACACCCTCATGATCTCCCGGACCCCTGAGGTCACATGCGTGGTGGTGGACGTGAGCCACG
AAGACCCTGAGGTCAAGTTCAACTGGTACGTGGACGGCGTGGAGGTGCATAATGCCAAGACAAAGCCGCGGGAGGAG
CAGTACAACAGCACGTACCGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAAGGGCAGCCCCGAGAACCA
CAGGTGTACACCCTGCCCCCATCCCGGGAGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAGGGGAACGTCTTCTCAT
GCTCCGTGATGCATGAGGCTCTGCACAACCACTACACGCAGAAGAGCCTCTCCCTGTCTCCGGGTAAATGA (SEQ ID NO: 204)

Ab7 Light chain (chimera) Full length protein sequence

QVLTQTASPVSAAVGGSTVTINCQASQSVYNNYLAWYQQKPGQPPKQLIYSTSTLASGVSSRFKGSGSGTQFTLTISDVQCD
DAATYYCLGSYDCSTGDCFVFGGGTEVVVKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC (SEQ ID NO: 62)

Ab7 Variable region light chain (chimera) protein sequence

QVLTQTASPVSAAVGGSTVTINCQASQSVYNNYLAWYQQKPGQPPKQLIYSTSTLASGVSSRFKGSGSGTQFTLTISDVQCD
DAATYYCLGSYDCSTGDCFVFGGGTEVVVKR (SEQ ID NO: 61)

FIGURE 7C

Ab7 Variable region light chain (chimera) protein sequence. CDR1: Bold; CDR2: Underlined; CDR3: Italics.

QVLTQTASPVSAAVGSTVTINCQASQSVYNNYNYLAWYQQKPGQPPKQLIYSETLASGVSSRFKGSGSGTQFTLTISDVQCD
DAATYYC*LGSYDCSTGDCF*FGGGTEVVVKR (SEQ ID NO: 61)

Ab7 Variable region light chain (chimera) DNA sequence. CDR1: Bold; CDR2: Underlined; CDR3: Italics.

CAAGTGCTGACCCAGACTGCATCCCCGTGTCTGCAGCTGTGGAAGCACAGTCACCATCAATTGC**CAGGCCAGTCAG
AGTGTTTATAATTACAACTAC**CTTGCCTGGTATCAGCAGAAACCAGGGCAGCCTCCAAGCAACTGATCTATTCTACA
TCCACTCTGGCATCTGGGGTCTCATGCGGATCAAGGCAGTGGATCTGGACACAGTTCACTCTCACCATCAGCGACGT
TGCAGTGTGACGATGCTGCCACTTACTACTGT*CTAGGCAGTTATGACTGTAGTACTGGTGATTGTTTTGGC*GGGGAGG
GACCGAGGTGGTGGTCAAACGT (SEQ ID NO: 201)

Ab7 Light chain (chimera) Full length DNA sequence.

CAAGTGCTGACCCAGACTGCATCCCCGTGTCTGCAGCTGTGGAAGCACAGTCACCATCAATTGCCAGGCCAGTCAG
AGTGTTTATAATTACAACTACCTTGCCTGGTATCAGCAGAAACCAGGGCAGCCTCCAAGCAACTGATCTATTCTACAT
CCACTCTGGCATCTGGGGTCTCATCGCGGATTCTAGGCAGTGGATCTGGGACACAGTTCACTCTCACCATCAGCGACGT
GCAGTGTGACGATGCTGCCACTTACTACTGTCTAGGCAGTTATGACTGTAGTACTGGTGATTGTTTTGGCGGGGAG
GGACCGAGGTGGTGGTCAAACGTACGGTGGCTGCACCATCTCGTCTTCATCTTCCGCCATCTGATGAGCAGTTGAAATC
TGGAACTGCCTCTGTTGTGTGCCTGCTGAATAACTTCTATCCCAGAGAGGCCAAAGTACAGTGGAAGGTGGATAACGCC
CTCCAATCGGGTAACTCCCAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAGGGCCTGAGCTCGCCCGTC
ACAAAGAGCTTCAACAGGGGAGAGTGTTAG (SEQ ID NO: 202)

Ab8 Heavy chain (humanized) Full length protein sequence

EVQLVESGGGLVQPGGSLRLSCAVSGIDLSNHYMQWVRQAPGKGLEWVGVYGINGRTYYASWAKGRFTISRDNSKTTVYL
QMNSLRAEDTAVYFCARGDIWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYASTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 74)

Ab8 Variable region heavy chain (humanized) protein sequence

EVQLVESGGGLVQPGGSLRLSCAVSGIDLSNHYMQWVRQAPGKGLEWVGVYGINGRTYYASWAKGRFTISRDNSKTTVYL
QMNSLRAEDTAVYFCARGDIWGQGTLVTVSS (SEQ ID NO: 75)

Ab8 Variable region heavy chain (humanized) protein sequence; CDR1: Bold; CDR2: Underlined; CDR3: Italics

EVQLVESGGGLVQPGGSLRLSCAVSGIDLSNHYMQWVRQAPGKGLEWVG<u>VYGINGRTYYASWAKG</u>RFTISRDNSKTTVYL
QMNSLRAEDTAVYFCARG*DIW*GQGTLVTVSS (SEQ ID NO: 73)

Ab8 Variable region heavy chain (humanized) DNA sequence; CDR1: Bold; CDR2: Underlined; CDR3: Italics

GAGGTGCAGCTGGTGGAGTCTGGGGGAGGCTTGGTGCAGCCTGGGGGGTCCCTGAGACTCTCCTGTGCAGTCTCTGGAA
TCGACCTCAGTAACCACTACATGCAATGGGTCCGCCAGGCTCCAGGGAAGGGGCTGGAGTGGGTCGGA<u>GTCTATGGTA
TCAATGGTCGCACATACTACGCGAGCTGGCGCGAAAGG</u>CCGATTCACCATCTCCAGAGACAATTCCAAGACCACGGTGT
ATCTTCAAATGAACAGCCTGAGAGCTGAGGACACTGCTGTGTATTTCTGTGTAGAG*GGGGACATCTGG*GGCCAAGGGAC
CCTCGTCACCGTCTCGAGC (SEQ ID NO: 213)

FIGURE 8B

Ab8 Heavy chain (humanized) Full length DNA sequence

GAGGTGCAGCTGGTGGAGTCTGGGGGAGGCTTGGTCCAGCCTGGGGGGTCCCTGAGACTCTCCTGTGCAGTCTCTGGAA
TCGACCTCAGTAACTACTACTACATGTCCTGGGTCCGCCAGGCTCCAGGGAAGGGGCTGGAGTGGGTCTCAGTTATTTATACA
TCAATGGTCGCACATACTACGCGGACAGCGTGAAGGGCCGATTCACCATCTCCAGAGACAATTCCAAGAACACACGGTGT
ATCTTCAAATGAACAGCCTGAGAGCTGAGGACACTGCTGTGTATTACTGTGCTAGAGCGGACATCTGGGGCCAAGGGA
CCCTGGTCACCGTCTCGAGCTGCCTCCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACCAAGGTGGACAAGAGAGTT
GAGCCCAAATCTTGTGACAAAACTCACACATGCCCACCGTGCCCAGCACCTGAACTCCTGGGGGGACCGTCAGTCTTC
CTCTTCCCCCCAAAACCCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACAACAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAAC
CACAGGTGTACACCCTGCCCCCATCCCGGGATGAGCTGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTATAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAATGA (SEQ ID
NO: 214)

Ab8 Light chain (humanized) Full length protein sequence

QVLTQSPSSLSASVGDRVTINCQASQSVYNNYLAWYQQKPGKVPKQLIYSTSTLASGVPSRFSGSGSGTDFTLTISSLQPED
VATYYCLGSYDCSTQDCFVFGGGTKVEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC (SEQ ID NO: 72)

Ab8 Variable region Light chain (humanized) protein sequence

QVLTQSPSSLSASVGDRVTINCQASQSVYNNYLAWYQQKPGKVPKQLIYSTSTLASGVPSRFSGSGSGTDFTLTISSLQPED
VATYYCLGSYDCSTQDCFVFGGGTKVEIKR (SEQ ID NO: 71)

FIGURE 8C

Ab8 Variable region Light chain (humanized) protein sequence. CDR1: Bold; CDR2: Underlined; CDR3: Italics

QVLTQSPSSLSASVGDRVTINCQASQSVYNNYNLAWYQQKPGKVPKQLIY<u>STSTLAS</u>GVPSRFSGSGSGTDFTLTISSLQPED
VATYYC*LGSYDCSTGDCFF*FGGGTKVEIKR (SEQ ID NO: 71)

Ab8 Variable region Light chain (humanized) DNA sequence. CDR1: Bold; CDR2: Underlined; CDR3: Italics

CAAGTGCTGACCCAGTCTCCATCCTCCCTGTCTGCATCTGTAGGAGACAGAGTCACCATTAACTGC**CAGGCCAGTCAG
AGTGTTTACAACTACTACCTG**CCTGGTATCAGCAGAAACCAGGGAAAGTTCCTAAGCAACTGATCTAT<u>TCTAC
ATCCACTCTGGCATCTG</u>GGGTCCCATCTCGTTCAGTGGCAGTGGATCTGGGACAGATTTCACTCTCACCATCAGC
AGCCTGCAGCCTGAAGATGTTGCAACTTATTACTGT*CTGGGCAGTTATGACTGTTCTACTGGTGATTGTTTCTTT*TTCGGCGGAG
GAACCAAGGTGGAAATCAAACGT (SEQ ID NO: 211)

Ab8 Light chain (humanized) Full length DNA sequence

CAAGTGCTGACCCAGTCTCCATCCTCCCTGTCTGCATCTGTAGGAGACAGAGTCACCATTAACTGCCAGGCCAGTCAG
AGTGTTTACAACTACTACCTGGCCTGGTATCAGCAGAAACCAGGGAAAGTTCCTAAGCAACTGATCTATTCTACATCC
ACTCTGGCATCTGGGGTCCCATCTCGTTCAGTGGCAGTGGATCTGGGACAGATTTCACTCTCACCATCAGCAGCCTG
CAGCCTGAAGATGTTGCAACTTATTACTGTCTGGGCAGTTATGATGTAGTACTGGTGATTGTTTCTTTTTCGGCGGAGG
AACCAAGGTGGAAATCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCC
CTCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG (SEQ ID NO: 212)

Ab9 Heavy chain (chimera) Full length protein sequence:

QSLEESGGRLVTPGTPLTLTCTVSGIGLSSYYMQWVRQSPGRGLEWIGVIGSDGKTYYATWAKGRFTISKTSSTTVDLRMAS
LTTEDTATYFCTRGDIWGPGTLVTVSSASTKGPSVPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPELLGGPSVFLFPPKPKDTLMISRTP
EVTCVVVDVSHEDPEVKFNWYVDGVEVHNAKTKPREEQYASTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 84)

Ab9 Variable region heavy chain (chimera) protein sequence:

QSLEESGGRLVTPGTPLTLTCTVSGIGLSSYYMQWVRQSPGRGLEWIGVIGSDGKTYYATWAKGRFTISKTSSTTVDLRMAS
LTTEDTATYFCTRGDIWGPGTLVTVSS (SEQ ID NO: 83)

Ab9 Variable region heavy chain (chimera) protein sequence; CDR1: Bold; CDR2: Underlined; CDR3: Italics.

QSLEESGGRLVTPGTPLTLTCTVSGIGLSSYYMQWVRQSPGRGLEWIG<u>VIGSDGKTYYATWAKG</u>RFTISKTSSTTVDLRMAS
LTTEDTATYFCTR*GDI*WGPGTLVTVSS (SEQ ID NO: 83)

Ab9 Variable region heavy chain (chimera) DNA sequence; CDR1: Bold; CDR2: Underlined; CDR3: Italics.

CAGTCCTGGAGGAGTCCGGGGGTCCTGTCACGTCCTGGGACACCCTGACACTCACTTGCACAGTCTCTGGAATCG
GCCTCAGTAGCTACTACATGCAGTGGGTCCGCCAGTCTCCAGGGAAGGGGCTGGAATGGATCGGAATCGTAGT
GATGGTAAGACATACTACGCGACCTGGGCGAAAGGCCGATTCACCATCTCCAAGACCTCGTCGACCACGGTGGATCTG
AGAATGGCCAGTCTGACAACGGAGGACACGGCCACTTATTTCTGTACGAGAGGGGACATCTGGGGACCAGGG
GTCACCGTCTCGAGC (SEQ ID NO: 223)

FIGURE 9B

Ab9 Heavy chain (chimera) Full length DNA sequence

CAGTCCTGGAGGAGTCCGGAGGTCCGGGTCACGTCTGTTGCAGCCTCGGGACACCCCTGACCCTGACCCTGACCTCTCACCTCGCACAGTGAATCG
GCCTCAGTAGTACTACTACATGCAGTGGGTCCGCCAGTCTCCAGGAAGGGGTCTGGAGTGGGTCTCAGGTATTAGATCCACATATCATTGGTAGTG
ATGGTAAGACATACTACGGCGACTCGGTGAAAGGCCGATTCACCATCTCCAGAGACAATTCCAAGAATTCCGTGTCCTGCAGAATGAACAGCCTGA
GAATGGCCAGTCTCGAGGACTCTGAGGACGCGGCAGTCTACATTCTGTCCCGTACCACCGATGGGGACACATCTCTGGGGACCTCTG
TCACCGTCTCAGGCCTCTGCCTCCACCAAGGGCCATCAGGTCTCCCTGGCACCCTCCTCCAAGAGCACCTCTGGGGGCAC
AGCGGCCCTGGGCTGCCTGGTCAAGGACTACTTCCCCGAACCGGTGACGGTGTCGTGGAACTCAGGCGCCCTGACCAG
CGGCGTGCACACCTTCCCGGCTGTCCTACAGTCCTCAGGACTCTACTCCCTCAGCAGCGTGGTGACCGTGCCCTCCAGC
AGCTTGGGCACCCAGACCTACATCTGCAACGTGAATCACAAGCCCAGCAACACCAAGGTGGACAAGAAAGTTGAGCCC
AAATCTTGTGACAAAACTCACACATGCCCACCGTGCCCAGCACCTGAACTCCTGGGGGGACCGTCAGTCTTCCTCTTCC
CCCCAAAACCCAAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCGGGAGGAGCAG
TACGCCAGCACGTACCGTGTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTGCTGGACT
CCGACGGCTCCTTCTTCCTCTACAGCAAGCTCACCGTGGACAAGAGCAGGTGGCAGCAGGGGAACGTCTTCTCATGCTC
CGTGATGCATGAAGCTCTGCACAACCACTACACGCAGAAGAGCCTCTCCCTGTCTCCGGGTAAATGA (SEQ ID NO: 224)

Ab9 Light chain (chimera) Full length protein sequence

QVLTQTPSPVSAAVGSTVTINCQASQNVYNNNYLAWYQQKPGQPPKQLIYSTSTLASGVSSRFRGSGSGTQFTLTISDVQCD
DAATYYCLGSYDCSRGDCFVFGGGTEVVVKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC (SEQ ID NO: 82)

Ab9 Variable region light chain (chimera) protein sequence

QVLTQTPSPVSAAVGSTVTINCQASQNVYNNNYLAWYQQKPGQPPKQLIYSTSTLASGVSSRFRGSGSGTQFTLTISDVQCD
DAATYYCLGSYDCSRGDCFVFGGGTEVVVKR (SEQ ID NO: 81)

FIGURE 9C

Ab9 Variable region light chain (chimera) protein sequence. CDR1: Bold; CDR2: Underlined; CDR3: Italics.

QVLTQTPSPVSAAVGSTVTINCQASQNVYNNNYLAWYQQKPGQPPKQLIY<u>STSTLAS</u>GVSSRFRGSGSGTQFTLTISDVQCD
DAATYYC*LGSYDCSRGDCFF*FGGGTEVVVKR  (SEQ ID NO: 81)

Ab9 Variable region light chain (chimera) DNA sequence. CDR1: Bold; CDR2: Underlined; CDR3: Italics.

CAAGTGCTGACCCAGACTCCATCCCCGTGTCTGCAGCTGTGGAAGCACAGTCACCATCAATTGC**CAGGCCAGTCAG
AATGTTTATAATAACAACTA**CCTAGCCTGGTATCAGCAGAAACCAGGGCAGCCTCCAAGCAACTGATCTATTCTAC
GTCCACTCTGGCATCTGGGGTCTCATCGCGATTCAGAGGCAGTGGATCTGGGACACAGTTCACTCTCACCATCAGCGAC
GTGCAGTGTGACGATGCTGCCACTTACTACTGT*CTAGGCAGTTATGATTGTAGTCGTGGTGATTGTTTTTTT*TTCGGCGGAG
GGACCGAGGTGGTGGTCAAACGT  (SEQ ID NO: 221)

Ab9 Light chain (chimera) Full length DNA sequence.

CAAGTGCTGACCCAGACTCCATCCCCGTGTCTGCAGCTGTGGAAGCACAGTCACCATCAATTGCCAGGCCAGTCAGA
ATGTTTATAATAACAACTACCTAGCCTGGTATCAGCAGAAACCAGGGCAGCCTCCAAGCAACTGATCTATTCTACGTC
CACTCTGGCATCTGGGGTCTCATCGCGATTCAGAGGCAGTGGATCTGGGACACAGTTCACTCTCACCATCAGCGACGTG
CAGTGTGACGATGCTGCCACTTACTACTGTCTAGGCAGTTATGATTGTAGTCGTGGTGATTGTTTTTTTCGGCGGAGG
GACCGAGGTGGTGGTCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG  (SEQ ID NO: 222)

Ab10 Heavy chain (humanized) Full length protein sequence.

EVQLVESGGGLVQPGGSLRLSCAVSGIGLSSYYMQWVRQAPGKGLEWVGVIGSDGKTYYATWAKGRFTISRDNSKTTVYL
QMNSLRAEDTAVYFCTRGDIWGQGTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYASTYRVVSVLTVLHQDWLNGKEYKCKVSNKALPAPI
EKTISKAKGQPREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 94)

Ab10 Variable region heavy chain (humanized) protein sequence.

EVQLVESGGGLVQPGGSLRLSCAVSGIGLSSYYMQWVRQAPGKGLEWVGVIGSDGKTYYATWAKGRFTISRDNSKTTVYL
QMNSLRAEDTAVYFCTRGDIWGQGTLVTVSS (SEQ ID NO: 93)

Ab10 Variable region heavy chain (humanized) protein sequence. CDR1: Bold; CDR2: Underlined; CDR3: Italics.

EVQLVESGGGLVQPGGSLRLSCAVSGIGLSSYYMQWVRQAPGKGLEWVG<u>VIGSDGKTYYATWAKG</u>RFTISRDNSKTTVYL
QMNSLRAEDTAVYFCTR*GDI*WGQGTLVTVSS (SEQ ID NO: 93)

Ab10 Variable region heavy chain (humanized) DNA sequence. CDR1: Bold; CDR2: Underlined; CDR3: Italics.

GAGGTCCAGCTGGTGGAGTCTGGGGGAGGCTTGGTCCAGCCTGGGGGGTCCCTGAGACTCTCCTGTGCAGTCTCTGGAA
TCGGCCTCAGTAGCTACTACATGCAATGGGTCCGTCAGGCTCCAGGGAAGGGGCTGGAGTGGGTCGGAGTCATTGGTA
GTGATGGTAAGACATACTACGCGACCTGGGCGAAAGGCCGATTCACCATCTCCAGAGACAATTCCAAGACCACGGTGT
ATCTTCAAATGAACAGCCTGAGAGCTGAGGACACTGCTGTGTATTTCTGTACCAGAGGGGAT*ATTTGGGGCCAAGGGAC
CCTCGTCACCGTCTCGAGC (SEQ ID NO: 233)

FIGURE 10B

Ab10 Heavy chain (humanized) Full length DNA sequence

GAGGTGCAGCTTGTGGAGTCTGGAGGAGGCTTGGTTCAGCCTGGGGGGTCCTCAGACTCTCCTGTGCAGTCTCTGGAA
TCGGCCAGTAGTACTACTACATGCAATGGGAGGCCAGTCGTCAGGTCCAGGGAAGGGGCTGGAGTGGGTTGGTA
GTATGGTAAGACATATACTACGCAGACTCCGTGAAAGGCCGATTCACCATCTCAAGAGACAATTCCAAGAACACGGTG
ATCTTCAAATGAACAGCCTGAGAGCTGAGGACACTGCTGTGTATATTCTGTACCAGAGAGGACATGGGGCAAGAGA
CCCTGGTCACGTCTCAGGCCTCTCAGCCTCCACCAAGGGCCCATCCGTCTTCCCCCTGGCACCCTCTCCAAGAGCACCTCTGG
GGGCACAGCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACCAAGGTGGACAAGAGAGTT
GAGCCCAAATCTTGTGACAAACTCACACATGCCCACCGTGCCCAGCACCTGAACTCCTGGGGGGACCGTCAGTCTTC
CTCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACGCCAAGTCTAAAGGACGTCCTCAACGTCCTCAACGTCCTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGCAGCCCCGAGAAC
CACAGGTGTACACCCTGCCCCCATCCCGGGAGGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAATGA (SEQ ID NO: 234)

Ab10 Light chain (humanized) Full length protein sequence

QVLTQSPSSLSASVGDRVTINCQASQNVYNNYLAWYQQKPGKVPKQLIYSTSTLASGVPSRFSGSGSGTDFTLTISSLQPED
VATYYCLGSYDCSRGDCFVFGGGTKVEIKRTVAAPSVFIFPPSDEQLKSGTASVVCLLNNFYPREAKVQWKVDNALQSNS
QESVTEQDSKDSTYSLSSTLTLSKADYEKHKVYACEVTHQGLSSPVTKSFNRGEC (SEQ ID NO: 92)

Ab10 Variable region Light chain (humanized) protein sequence

QVLTQSPSSLSASVGDRVTINCQASQNVYNNYLAWYQQKPGKVPKQLIYSTSTLASGVPSRFSGSGSGTDFTLTISSLQPED
VATYYCLGSYDCSRGDCFVFGGGTKVEIKR (SEQ ID NO: 91)

FIGURE 10C

Ab10 Variable region Light chain (humanized) protein sequence. CDR1: Bold; CDR2: Underlined; CDR3: Italics.

QVLTQSPSSLSASVGDRVTINCQASQNVYNNYLAWYQQKPGKVPKQLIYSTSTLASGVPSRFSGSGSGTDFTLTISSLQPED
VATYYCLGSYDCSRGDCFVFGGGTKVEIKR (SEQ ID NO: 91)

Ab10 Variable region Light chain (humanized) DNA sequence. CDR1: Bold; CDR2: Underlined; CDR3: Italics.

CAAGTTGCTGACCCAGTCTCCATCCTCCCTGTCTGCATCTGTAGGAGACAGAGTCACCATCAATTGCCAGGCCAGTCAG
AATGTTTACAATAACAACTACCTAGCCTGGTATCAGCAGAAACCAGGGAAAGTTCCTAAGCAACTGATCTATTCTAC
ATCCACTCTGGCATCTGGGGTCCCATCTCGTTCAGTGGCAGTGGATCTGGGACAGATTTCACTCTCACCATCAGCAGC
CTGCAGCCTGAAGATGTTGCAACTTATTACTGT*CTGGGCAGTTATGATTGTAGTCGTGGTATTGTTTGTTTCGGCGGAG
GAACCAAGGTGGAAATCAAACGT (SEQ ID NO: 231)

Ab10 Light chain (humanized) Full length DNA sequence.

CAAGTTGCTGACCCAGTCTCCATCCTCCCTGTCTGCATCTGTAGGAGACAGAGTCACCATCAATTGCCAGGCCAGTCAGA
ATGTTTACAATAACAACTACCTAGCCTGGTATCAGCAGAAACCAGGGAAAGTTCCTAAGCAACTGATCTATTCTACATC
CACTCTGGCATCTGGGGTCCCATCTCGTTCAGTGGCAGTGGATCTGGGACAGATTTCACTCTCACCATCAGCAGCCTG
CAGCCTGAAGATGTTGCAACTTATTACTGTCTGGGCAGTTATGATTGTAGTCGTGGTATTGTTTGTTTCGGCGGAGG
AACCAAGGTGGAAATCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG (SEQ ID NO: 232)

Ab11 Heavy chain (chimera) Full length protein sequence

QSLEESGGRLVTPGGSLTLTCTVSGIDVTNYYMQWVRQAPGKGLEWIGVIGVNGKRYYASWAKGRFTISKTSSTTVDLKMT
SLTTEDTATYFCARGDWGPGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSCDKTHTCPPCPAPELLGGPSVFLFPPKPKDTLMISRT
PEVTCVVVDVSHEDPEVKFNWYVDGVEVHNAKTKPREEQYASTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 104)

Ab11 Variable region heavy chain (chimera) protein sequence

QSLEESGGRLVTPGGSLTLTCTVSGIDVTNYYMQWVRQAPGKGLEWIGVIGVNGKRYYASWAKGRFTISKTSSTTVDLKMT
SLTTEDTATYFCARGDWGPGTLVTVSS (SEQ ID NO: 103)

Ab11 Variable region heavy chain (chimera) protein sequence. CDR1: Bold; CDR2: Underlined; CDR3: Italics.

QSLEESGGRLVTPGGSLTLTCTVSGIDVTNYYMQWVRQAPGKGLEWIG<u>VIGVNGKRYYASWAKG</u>RFTISKTSSTTVDLKMT
SLTTEDTATYFC*ARGDWGPGTLVTVSS* (SEQ ID NO: 103)

Ab11 Variable region heavy chain (chimera) DNA sequence. CDR1: Bold; CDR2: Underlined; CDR3: Italics.

CAGTCGCTGGAGGAGTCCGGGGGTCCGCTGGTCACGCCTGGGGGATCCCTGACACTCACCTGCACAGTCTCTGGAATCG
ACGTCACTAACTACTATATGCAATGGGTCCGCCAGGCTCCAGGGAAGGGGCTGGAATGGATCGGAGTCATTGGTGTGA
ATGGTAGAGATACTACTACGGCAAGCTGGCCATAAAGGCCGATTCACCATCTCCAAACTCGTCGACCACGGTGGATCTGA
AAATGACCAGTCTGACAACCGAGGACACGGCCACCTATTTCTGTGCCAGAGGCGACTGGGGCCCGGGGACCCTCGT
CACCGTCTCGAGC (SEQ ID NO: 245)

FIGURE 11B

Ab11 Heavy chain (chimera) Full length DNA sequence.

CAGTGCTGCTGGAGGAGTCCGGAGGTCCGGGGGTCCTGGTCACCTGCACACTCACCTGCACAGTCCTGGAATCG
ACGTCACTACTAACTACTATATGCAATGGTCCCGCCAGGCTCCAGGGAAGGGGCTGGAATGGATCGGAGTCATTGGTGTGA
ATGGTAAGAGATACTACCGAGCCTGCGCGAAGGCCGATTCACCATCTCCAAAACCTGCACGTGGATCTGA
AATGACCAGTCGAACCGAGGACACGGCCACCTATTCTGTGCCAGAGGGGGACATCTGGGGCCGGGAACCCTG
TCAACGGTCTGGAGCGCTGCCTGTTCAAGGACTAGTTCCCGGAAACCGGTGTGACTTCCTCAGCAGCCCTGACCAG
AGCGGCCCTGGGCTGCCTGGTCAAGGACTACTTCCCCGAACCGGTGACCGTGTCCTGGAACTCAGGCGCCCTGACCAG
CGGCGTGCACACCTTCCCAGCTGTCCTACAGTCCTCAGGACTCTACTCCCTCAGCAGCGTGGTGACCGTGCCCTCCAGC
AGCTTGGGCACCCAGACCTACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGACCGTCAGTCTTCCTCTTC
CCCCCAAAACCCAAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCGGGAGGAGCAG
TACCAGCAGCACGTACCGTGTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGGCAGCCCCGAGAACCACAG
GTGTACACCCTGCCCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTGCTGGACT
CCGACGGCTCCTTCTTCCTCTACAGCAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTCTCCGGGTAAATGA (SEQ ID NO: 244)

Ab11 Light chain (chimera) Full length protein sequence.

QVLTQTASPVSPAVGSTVTINCRASQSVYYNNYLAWYQQKPGQPPKQLIYSTSTLASGVSSRFKGSGSGTQFTLTISDVQCDD
AATYYCLGSYDCSNGDCFVFGGGTEVVKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSPNRGEC (SEQ ID NO: 102)

Ab11 Variable region light chain (chimera) protein sequence.

QVLTQTASPVSPAVGSTVTINCRASQSVYYNNYLAWYQQKPGQPPKQLIYSTSTLASGVSSRFKGSGSGTQFTLTISDVQCDD
AATYYCLGSYDCSNGDCFVFGGGTEVVKR (SEQ ID NO: 101)

FIGURE 11C

Ab11 Variable region light chain (chimera) protein sequence. CDR1: Bold; CDR2: Underlined; CDR3: Italics.

QVLTQTASPVSPAVGSTVTINCRASQSVYNNYLAWYQQKRGQPPKQLIYSTSILASGVSSRFKGSGSGTQFTLTISDVQCD
DAATYYC*LGSYDCSNGDCF*FGGGTEVVVKR (SEQ ID NO: 101)

Ab11 Variable region light chain (chimera) DNA sequence. CDR1: Bold; CDR2: Underlined; CDR3: Italics.

CAGGTGCTGACCCAGACTGCATCCCCGTGTCTCCAGTGTGGAAGCACAGTCACCATCAATTGCCGGGCCAGTCAG
AGTGTTTATTATAACAACTACCTAGCCTGGTATCAGCAGAAACCAGGGCAGCCTCCCAAGCAACTGATCTATTCTAC
ATCCATCCTGGCATCTGGGGTCTCATCGCGGTTCAAAGGCAGTGGATCTGGGACACAGTTCACTCTCACCATCAGCGAC
GTGCAGTGTGACGATGCTGCCACTTAC*TACTGTCT*GGCAGTTATGATTGTAGTAATGGTGATTGTTTT*TTCGGCGGAG
GGACCGAGGTGGTGGTCAAACGT (SEQ ID NO: 241)

Ab11 Light chain (chimera) Full length DNA sequence.

CAGGTGCTGACCCAGACTGCATCCCCGTGTCTCCAGTGTGGAAGCACAGTCACCATCAATTGCCGGGCCAGTCAGA
GTGTTTATTATAACAACTACCTAGCCTGGTATCAGCAGAAACCAGGGCAGCCTCCCAAGCAACTGATCTATTCTACATC
CATCCTGGCATCTGGGGTCTCATCGCGGTTCAAAGGCAGTGGATCTGGGACACAGTTCACTCTCACCATCAGCGACGTG
CAGTGTGACGATGCTGCCACTTACTACTGTCTGGGCAGTTATGATTGTAGTAATGGTGATTGTTTCGGCGGAGGG
ACCGAGGTGGTGGTCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG (SEQ ID NO: 242)

Ab12 Heavy chain (humanized) Full length protein sequence

EVQLVESGGGLVQPGGSLRLSCAVSGIDYTNYYMQWVRQAPGKGLEWVGVIGVNGKRYYASWAKGRFTISRDNSKTTVYL
QMNSLRAEDTAVYFCARGDIWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTCPPCPAPELLGGPSVFLFPPKPKDTL
MISRTPEVTCVVVDVSHEDPEVKFNWYVDGVEVHNAKTKPREEQYASTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 114)

Ab12 Variable region heavy chain (humanized) protein sequence

EVQLVESGGGLVQPGGSLRLSCAVSGIDYTNYYMQWVRQAPGKGLEWVGVIGVNGKRYYASWAKGRFTISRDNSKTTVYL
QMNSLRAEDTAVYFCARGDIWGQGTLVTVSS (SEQ ID NO: 113)

Ab12 Variable region heavy chain (humanized) protein sequence. CDR1: Bold; CDR2: Underlined; CDR3: Italics

EVQLVESGGGLVQPGGSLRLSCAVSGIDYTNYYMQWVRQAPGKGLEWVG<u>VIGVNGKRYYASWAKG</u>RFTISRDNSKTTVY
LQMNSLRAEDTAVYFCARG*DI*WGQGTLVTVSS (SEQ ID NO: 113)

Ab12 Variable region heavy chain (humanized) DNA sequence. CDR1: Bold; CDR2: Underlined; CDR3: Italics

GAGGTGCAGCTTGTGGAGTCTGGGGGAGGCTTGGTCCAGCCTGGGGGGTCCCTGAGACTCTCTGTGCAGTCTGGAA
TCGACGTCACTAACTACTACATGCAATGGGTCCGTCAGGCTCCAGGGAAGGGTCTGGAGTGGGTGGGAGTCATTGGTG
TGAATGGTAAGAGATACTACGCGAGCTGGGCCGAAGGCGGATTCACCATCTCCAGAGACAATTCCAAGACCACGGTGT
ATCTTCAAATGAACAGCCTGAGAGCTGAGGACACTGCTGTGTATTTCTGTGCCAGAGG*GGACATC*TGGGGCCAAGGGAC
CCTCGTCACCGTCTCGAGC (SEQ ID NO: 253)

FIGURE 12B

Ab12 Heavy chain (humanized) Full length DNA sequence

GAGGTGCAGCTTGTGGAGTCTGGGGGAGGCTTGGTCCAGCCTGGGGGGTCCCTGAGACTCTCCTGTGCAGCCTCTGGA
TCGACCTTCACTAACTACTACATGCGCTGGGTCCGCCAGGCTCCAGGGAAGGGGCTGGAGTGGGTCGGAGTCATTGGTG
TGAATGGTAAGATACTACGCCGAGCTGCCGAAAGGCCGATTCACCATCTCCAGAGACAATGCCAAGAACACACGGTGT
ATCTTCAAATGAACAGCCTGAGAGCTGAGGACACTGCTGTATATTCTGTGCCAGAGGGACATCTGGGCCAAGGGA
CCCTCGTCACCGTCTCGAGCGCCTCCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACCAAGGTGGACAAGAGAGTT
GAGCCCAAATCTTGTGACAAAACTCACACATGCCCACCGTGCCCAGCACCTGAACTCCTGGGGGGACCGTCAGTCTTC
CTCTTCCCCCCAAAACCCAAGGACACCCTCATGATCTCCCGGACCCCTGAGGTCACATGCGTGGTGGTGGACGTGAGCA
CGAAGACCCTGAGGTCAAGTTCAACTGGTACGTGGACGGCGTGGAGGTGCATAATGCCAAGACAAAGCCGCGGGAGG
AGCAGTACAACAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAAC
CACAGGTGTACACCCTGCCCCCATCCCGGGAGGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAATGA (SEQ ID NO: 254)

Ab12 Light chain (humanized) Full length protein sequence

QVLTQSPSSLSASVGDRVTINCRASQSVYYNNYLAWYQQKPGKVPKQLIYSTSTLASGVPSRFSGSGSGTDFTLTISSLQPEDV
ATYYCLGSYDCSNGDCFVFGGGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC (SEQ ID NO: 112)

Ab12 Variable region Light chain (humanized) protein sequence

QVLTQSPSSLSASVGDRVTINCRASQSVYYNNYLAWYQQKPGKVPKQLIYSTSTLASGVPSRFSGSGSGTDFTLTISSLQPEDV
ATYYCLGSYDCSNGDCFVFGGGTKVEIKR (SEQ ID NO: 111)

FIGURE 12C

Ab12 Variable region Light chain (humanized) protein sequence. CDR1: Bold; CDR2: Underlined; CDR3: Italics.

QVLTQSPSSLSASVGDRVTINCRASQSVYYNYLAWYQQKPGKVPKQLIYSTSTLASGVPSRFSGSGSGTDFTLTISSLQPED
VATYYC*LGSYDCSNGDCFF*GGGTKVEIKR (SEQ ID NO: 111)

Ab12 Variable region Light chain (humanized) DNA sequence. CDR1: Bold; CDR2: Underlined; CDR3: Italics.

CAAGTGCTGACCCAGTCCCCATCTCCCTGTCTGCATCTGTAGGAGACAGAGTCACCATCAATTGC**CGGGCCAGTCAG
AGTGTTTACTATAACAACTACCTAGCCTGGTATCAGCAGAAACCAGGGAAAGTTCCTAAGCAACTGATCTAT**TCTAC
ATCCACTCTGCATCTGGGGTCCCATCTCGGTTCAGTGGCAGTGGATCTGGGACAGATTTCACTCTCACCATCAGCAGC
CTGCAGCCTGAAGATGTTGCAACTTATTACTGT*CTGGGCAGTTATGATTGTAGTAATGGTGATTGTTTTGTTT*TCGGCGGAG
GGACCAAGGTGGAAATCAAACGT (SEQ ID NO: 25)

Ab12 Light chain (humanized) Full length DNA sequence.

CAAGTGCTGACCCAGTCCCCATCTCCCTGTCTGCATCTGTAGGAGACAGAGTCACCATCAATTGCCGGGCCAGTCAGA
GTGTTTACTATAACAACTACCTAGCCTGGTATCAGCAGAAACCAGGGAAAGTTCCTAAGCAACTGATCTATTCTACATC
CACTCTGGCATCTGGGGTCCCATCTCGGTTCAGTGGCAGTGGATCTGGGACAGATTTCACTCTCACCATCAGCAGCCTG
CAGCCTGAAGATGTTGCAACTTATTACTGTCTGGGCAGTTATGATTGTAGTAATGGTGATTGTTTTGTTTTCGGCGGAGG
GACCAAGGTGGAAATCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCC
CTCCAATCGGGTAACTCCCAGGAGAGTGTCACAGAGCAGGACAGCAAGGACAGCACCTACAGCCTCAGCAGCACCCTGA
CCCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG (SEQ ID NO: 252)

Ab13 Heavy chain (chimera) Full length protein sequence

QSVEESGGGLVQPEGSLTLTCTASGFDFSSNAMWWVRQAPGKGLEWIGCIYNGDGSTYYASWVNGRFSISKTSSTTVTLQL
NSLTVADTATYYCARDLDLWGPGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPELLGGPSVFLFPPKPKDTLMI
SRTPEVTCVVVDVSHEDPEVKFNWYVDGVEVHNAKTKPREEQYASTYRVVSVLTVLHQDWLNGKEYKCKVSNKALPAPIE
KTISKAKGQPREPQVYTLPPSREEMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 124)

Ab13 Variable region heavy chain (chimera) protein sequence

QSVEESGGGLVQPEGSLTLTCTASGFDFSSNAMWWVRQAPGKGLEWIGCIYNGDGSTYYASWVNGRFSISKTSSTTVTLQL
NSLTVADTATYYCARD*LDL*WGPGTLVTVSS (SEQ ID NO: 123)

Ab13 Variable region heavy chain (chimera) protein sequence: CDR1: Bold; CDR2: Underlined; CDR3: Italics

QSVEESGGGLVQPEGSLTLTCTASGFDFSSNAMWWVRQAPGKGLEWIGCIYNGDGSTYYASWVNGRFSISKTSSTTVTLQL
NSLTVADTATYYCARD*LDL*WGPGTLVTVSS (SEQ ID NO: 123)

Ab13 Variable region heavy chain (chimera) DNA sequence: CDR1: Bold; CDR2: Underlined; CDR3: Italics

CAGTCTGTCGAGGAGAGTGGTGGCGGAGTCCAGCCTGAGGGATCCTGACACTCACCTGCACAGCTCTGGATTC
GACTTCAGTAGCAATGCAATGGATCTGGGTCCGCCAGGCTCCAGGAAAGGGCTGGAGTGGATCGGATGCATTACAA
TGGTGATGGCAGCACATACTACGCGAGCTGGGTGAATGGCCGATTCTCCATCTCCAAAACCTCGTCGACCGTGACT
CTGCAACTGAATAGTCTGACAGTGGCGGACACGGCCACGTATTATTGTGTGCGAGATCTTGACTTGTGGGGCCGGCA
CCCTGGTCACCGTCTCCAGC (SEQ ID NO: 265)

FIGURE 13B

Ab13 Heavy chain (chimera) Full length DNA sequence:

CAGTCGGTGAGGAGTCCGGGGGAGGCCTGGTCCAGCCTGGAGGGATCCCTGACACTTCACTGGCCTCTGGATTC
GACTTCAGTAGCAATGCAATTGTGGTCCGCCAGGCTCCAGGAAGGGGTCTGGAGTGGATCGGATGCATTTACAAT
GGTGATGGCAGCACATACTACGGAGTCGCGGACACCGGCAGTGGAATGGCCGATTCTCAAAACCTCGTCGACGTGACTC
TGCAACTGAATAGTCTGACAGTCGCGGACACCGGCACAGTCTACTATTGTGCGAGAGATCTTGTGGGCGGCAC
CCTCGTCACCGTCTCCACTGGCGTTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCGTGGAACTCAGGCGCCCTG
ACCAGCGGCGTGCACACCTTCCCGGCTGTCCTACAGTCCTCAGGACTCTACTCCCTCAGCAGCGTGGTGACCGTGCCCT
CCAGCAGCTTGGGCACCCAGACCTACATCTGCAACGTGAATCACAAGCCCAGCAACACCAAGGTGGACAAGAAAGTTG
AGCCCAAATCTTGTGACAAAACTCACACATGCCCACCGTGCCCAGCACCTGAACTCCTGGGGGGACCGTCAGTCTTCCT
CTTCCCCCCAAAACCCAAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACAAAGCCGCGGGAGGA
GCAGTACAACAGCACGTACCGTGTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAGCCAAAGGGCAGCCCCGAGAACC
ACAGGTGTACACCCTGCCCCCATCCCGGGAGGAGATGACCAAGAACCAGGTCAGCCTGACCTGCCTGGTCAAAGGCTT
CTATCCCAGCGACATCGCCGTGGAGTGGGAGAGCAATGGGCAGCCGGAGAACAACTACAAGACCACGCCTCCCGTGCT
GGACTCCGACGGCTCCTTCTTCCTCTACAGCAAGCTCACCGTGGACAAGAGCAGGTGGCAGCAGGGGAACGTCTTCTCA
TGCTCCGTGATGCATGAGGCTCTGCACAACCACTACACGCAGAAGAGCCTCTCCCTGTCTCCGGGTAAATGA (SEQ ID NO: 264)

Ab13 Light chain (chimera) Full length protein sequence:

AIVMTQTPSSKSVPVGDTVTINCQASESLYNNNALAWFQQKPGQPPKRLIYDASKLASGVPSRFSGGGSGTQFTLTISGVQCD
DAATYYCGGYRSDSVDGVAFAGGTEVVVKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC (SEQ ID NO: 122)

Ab13 Variable region light chain (chimera) protein sequence:

AIVMTQTPSSKSVPVGDTVTINCQASESLYNNNALAWFQQKPGQPPKRLIYDASKLASGVPSRFSGGGSGTQFTLTISGVQCD
DAATYYCGGYRSDSVDGVAFAGGTEVVVKR (SEQ ID NO: 121)

FIGURE 13C

Ab13 Variable region light chain (chimera) protein sequence. CDR1: Bold; CDR2: Underlined; CDR3: Italics.

AIVMTQTPSSKSVPGDTVTINCQASESLYNNNALAWFQQKPGQPPKRLIYDASKLASGVPSRFSGSGSGTQFTLTISGVQCD
DAATYY*CQGYRSDSVDGVAF*AGGTEVVVKR (SEQ ID NO: 121)

Ab13 Variable region light chain (chimera) DNA sequence. CDR1: Bold; CDR2: Underlined; CDR3: Italics.

GCCATCGTGATGACCCAGACTCCATCTTCCAAGTCTGTCCCTGTGGGAGACACAGTCACCATCAATTGCCAGGCCAGT
GAGAGTCTTTATAATAACAACGCCCTTGCCTGGTTTCAGCAGAAACCAGGGCAGCCTCCCAAGCGCCTGATCTATGA
TGCATCAAACTGGCATCTGGGGTCCCATCGCTTCAGTGGCAGTGGATCTGGGACAGATTCACTCTCACCATCAGT
GGCGTGCAGTGTGACGATGCTGCCACTTACTACTGT*GGGAGGCTACAGAAGTGATAGTGTTGATGGTGTTGCTTTCGGCGGA*
GGGACCGAGGTGGTGGTCAAACGT (SEQ ID NO: 261)

Ab13 Light chain (chimera) Full length DNA sequence.

GCCATCGTGATGACCCAGACTCCATCTTCCAAGTCTGTCCCTGTGGGAGACACAGTCACCATCAATTGCCAGGCCAGTG
AGAGTCTTTATAATAACAACGCCCTTGCCTGGTTTCAGCAGAAACCAGGGCAGCCTCCCAAGCGCCTGATCTATGATGC
ATCCAAACTGGCATCTGGGGTCCCATCGCGTTCAGTGGCAGTGGATCTGGGACAGATTCACTCTCACCATCAGTGGC
GTGCAGTGTGACGATGCTGCCACTTACTACTGTGGGAGGCTACAGAAGTGATAGTGTTGATGGTGTTGCTTTCGGCGGAG
GGACCGAGGTGGTGGTCAAACGTAACTCCAGAGAGGAGTCTCAAGTACACACAAAGAGCAAGAGCACCTCAGCAGCC
TGGAACTGCCTCTGTTGTGCCTGCTGAATAACTTCTATCCCAGAGAGGCCAAAGTACAGTGGAAGGTGGATAACGCC
CTCCAATCGGGTAACTCCCAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAGGGCCTGAGCTCGCCCGTC
ACAAAGAGCTTCAACAGGGGAGAGTGTTAG (SEQ ID NO: 262)

Ab14 Heavy chain (humanized) Full length protein sequence:

EVQLVESGGGLVQPGGSLRLSCAVSGHGLSSYYMQWVRQAPGKGLEWVGVIGSDKTYYATWAKGRFTISRDNSKTTVYL
QMNSLRAEDTAVYFCTRGDIWGQGTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDARVEPKSCDKTHTCPPCPAPELLGGPSVFLFPPKPKDTLM
ISRTPEVTCVVVDVSHEDPEVKFNWYVDGVEVHNAKTKPREEQYASTYRVVSVLTVLHQDWLNGKEYKCKVSNKALPAPI
EKTISKAKGQPREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 134)

Ab14 Variable region heavy chain (humanized) protein sequence:

EVQLVESGGGLVQPGGSLRLSCAVSGHGLSSYYMQWVRQAPGKGLEWVGVIGSDKTYYATWAKGRFTISRDNSKTTVYL
QMNSLRAEDTAVYFCTRGDIWGQGTLVTVSS (SEQ ID NO: 133)

Ab14 Variable region heavy chain (humanized) protein sequence. CDR1: Bold; CDR2: Underlined; CDR3: Italics.

EVQLVESGGGLVQPGGSLRLSCAVSGHGLSSYYMQWVRQAPGKGLEWVG<u>VIGSDKTYYATWAKG</u>RFTISRDNSKTTVYL
QMNSLRAEDTAVYFCTR*GDI*WGQGTLVTVSS (SEQ ID NO: 133)

Ab14 Variable region heavy chain (humanized) DNA sequence. CDR1: Bold; CDR2: Underlined; CDR3: Italics.

GAGGTGCAGCTTGTGGAGTCTGGGGGAGGCTTGGTCCAGCCTGGGGGGTCCCTGAGACTCTCCTGTGCAGTCTCTGGAA
TCGGCCTCAGTAGCTACTACATGCAATGGGTCCGCCAGGCTCCAGGGAAGGGGCTGGAGTGGGTCGGAGTCATTGGTA
GTGATAAGACATACTACGCGGAATGGGCCAAGGGCCGATTCACCATCTCCAGAGACAACTCCAAGACCACGGTGTA
TCTTCAAATGAACAGCCTGAGAGTTGAGGACACTGCTGTGTATTTCTGTACAAGA*GGGGAC*ATCTGGGGCCAAGGGACC
CTGGTCACCGTCTCGAGC (SEQ ID NO: 273)

FIGURE 14B

Ab14 Heavy chain (humanized) Full length DNA sequence:

GAGGTGCAGCTTGTGGAGTCTGGGGGAGGCTTGGTCCAGCCTGGGGGGTCCCTGAGACTCTCCTGTGCAGTCTCTGGAA
TCGGCCTCAGTAGTACTACATGGGCTGGGTCCGTCAGGCTCCAGGGAAGGGGCTGGAGTGGGTCGGAGTCATTGGTA
GTGATGGTAAGACATACTATGCCGATTCAGTGAAAGGCCGATTCACCATCTCCAGAGACAATTCCAAGAACACGGTGT
ATCTTCAAATGAACAGCCTGAGAGCCGAGGACACTGCTGTGTATTTCTGTGCCAGAGACATCTGGGGCCAAGGGA
CCCTCGTCACCGTCTCGAGCGGCCTGGCCTGCCTCCCCAAGTCTTCTCCCCTGGCCCCCTGCTGTGACGGTGACCTCCTGG
GGCACAGCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGACCGTGCCCTCC
TCCAGCAGCTTGGGCACGAAGACCTACACCTGCAACGTAGATCACAAGCCCAGCAACACCAAGGTGGACAAGAGAGTT
GAGCCCAAATCTTGTGACAAAACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACAACAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAAC
CACAGGTGTACACCCTGCCCCCATCCCGGGATGAGCTGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAATGA (SEQ ID NO: 274)

Ab14 Light chain (humanized) Full length protein sequence:

QVLTQSPSSLSASVGDRVTINCQASQNVYNNNYLAWYQQKPGKVPKQLIYSTSTLASGVPSRFSGSGSGTDFTLTISSLQPED
VATYYCLGSYDCSRGDCFVFGGGTKVEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC (SEQ ID NO: 132)

Ab14 Variable region Light chain (humanized) protein sequence:

QVLTQSPSSLSASVGDRVTINCQASQNVYNNNYLAWYQQKPGKVPKQLIYSTSTLASGVPSRFSGSGSGTDFTLTISSLQPED
VATYYCLGSYDCSRGDCFVFGGGTKVEIKR (SEQ ID NO: 131)

FIGURE 14C

Ab14 Variable region Light chain (humanized) protein sequence. CDR1: Bold; CDR2: Underlined; CDR3: Italics.

QVLTQSPSSLSASVGDRVTINCQASQNVYNNNYLAWYQQKPGKVFKQLIY<u>STSTLAS</u>GVPSRFSGSGSGTDFTLTISSLQPED
VATYYC*LGSYDCSRGDCFV*FGGGTKVEIKR (SEQ ID NO: 131)

Ab14 Variable region Light chain (humanized) DNA sequence. CDR1: Bold; CDR2: Underlined; CDR3: Italics.

CAAGTGCTGACCCAGTCCAGTCCTCCATCCCTGTCTGCATCAGTAGGAGACAGAGTCACCATCAATTGC**CAGGCCAGTCAG
AATGTTTACAATAACAACTAC**CTAGCCTGGTATCAGCAGAAACCAGGGAAAGTTCCTAAG<u>CAACTGATCTATTCTAC</u>
<u>ATCCACTCTG</u>GCATCTGGGGTCCCATCTCGTTCAGTGGCAGTGGATCTGGGACAGATTTCACTCTCACCATCAGCAGC
CTGCAGCCTGAAGATGTGCAACTTATTACTGT*CTGGGCAGTTATGATTGTCGTGGCAGGGATTGTTTTGTT*TTCGGCGGAG
GAACCAAGGTTGAAATCAAACGT (SEQ ID NO: 271)

Ab14 Light chain (humanized) Full length DNA sequence.

CAAGTGCTGACCCAGTCCAGTCCTCCATCCCTGTCTGCATCAGTAGGAGACAGAGTCACCATCAATTGCCAGGCCAGTCAGA
ATGTTTACAATAACAACTACCTAGCCTGGTATCAGCAGAAACCAGGGAAAGTTCCTAAGCAACTGATCTATTCTACATC
CACTCTGGCATCTGGGGTCCCATCTCGTTCAGTGGCAGTGGATCTGGGACAGATTTCACTCTCACCATCAGCCTG
CAGCCTGAAGATGTGCAACTTATTACTGTCTGGGCAGTTATGATTGTCGTGGCAGGGATTGTTTTGTTTTCGGCGGAGG
AACCAAGGTTGAAATCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGCAGCAGCAAGTAACGCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG (SEQ ID NO: 272)

Human CGRPα ELISA

Figure 16     Human CGRPα ELISA

Human CGRPα ELISA

Human CGRPα ELISA

Human CGRPα cAMP

Human CGRPα cAMP

Human CGRPα cAMP

Human CGRPα cAMP

Human CGRPα cAMP

Human CGRPα cAMP

Human CGRPβ cAMP

Human CGRPβ cAMP

Human CGRPβ cAMP

Human CGRPβ cAMP

Human CGRPβ cAMP

Rat CGRP cAMP

Rat CGRP cAMP

Rat CGRP cAMP

Rat CGRP cAMP

Rat CGRP cAMP

Rat CGRP cAMP

Rat CGRP cAMP

Rat CGRP cAMP

Figure 38
Inhibition of Radioligand Binding

| | IC$_{50}$ (nM) | K$_I$ (nM) |
|---|---|---|
| Ab1 | 0.585 | 0.46 |
| Ab2 | 0.482 | 0.378 |
| Ab3 | 2.49 | 10.96 |
| Ab4 | 0.579 | 0.455 |
| Ab5 | 0.586 | 0.461 |
| Ab6 | 2.46 | 1.94 |
| Ab7 | 4.53 | 3.56 |
| Ab8 | 0.936 | 0.736 |
| Ab9 | 2.03 | 1.6 |
| Ab10 | 0.28 | 0.22 |
| Ab11 | 2.26 | 1.78 |
| Ab12 | 0.315 | 0.248 |
| Ab13 | 0.335 | 0.264 |

Figure 40. Reduction in Vasodilatation Following Capsaicin Administration

* $p < 0.05$ one-way ANOVA followed by Dunnett's test, comparison to vehicle

SEQUENCE LISTING

```
<160> NUMBER OF SEQ ID NOS: 284

<210> SEQ ID NO 1
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Leu Thr Gln Thr Ala Ser Pro Val Ser Ala Ala Val Gly Ser
1               5                   10                  15

Thr Val Thr Ile Asn Cys Gln Ala Ser Gln Ser Val Tyr Asp Asn Asn
            20                  25                  30

Tyr Leu Ala Trp Tyr Gln Gln Lys Pro Gly Gln Pro Pro Lys Gln Leu
        35                  40                  45

Ile Tyr Ser Thr Ser Thr Leu Ala Ser Gly Val Ser Ser Arg Phe Lys
    50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Leu Gly Ser Tyr Asp Cys Ser
                85                  90                  95

Ser Gly Asp Cys Phe Val Phe Gly Gly Gly Thr Glu Val Val Val Lys
                100                 105                 110

Arg

<210> SEQ ID NO 2
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Leu Thr Gln Thr Ala Ser Pro Val Ser Ala Ala Val Gly Ser
```

```
  1               5                  10                 15
Thr Val Thr Ile Asn Cys Gln Ala Ser Gln Ser Val Tyr Asp Asn Asn
                20                 25                 30

Tyr Leu Ala Trp Tyr Gln Gln Lys Pro Gly Gln Pro Pro Lys Gln Leu
                35                 40                 45

Ile Tyr Ser Thr Ser Thr Leu Ala Ser Gly Val Ser Ser Arg Phe Lys
 50                 55                 60

Gly Ser Gly Ser Gly Thr Gln Phe Thr Leu Thr Ile Ser Asp Leu Glu
 65                 70                 75                 80

Cys Ala Asp Ala Ala Thr Tyr Tyr Cys Leu Gly Ser Tyr Asp Cys Ser
                85                 90                 95

Ser Gly Asp Cys Phe Val Phe Gly Gly Thr Glu Val Val Val Lys
               100                105                110

Arg Thr Val Ala Ala Pro Ser Val Phe Ile Phe Pro Pro Ser Asp Glu
               115                120                125

Gln Leu Lys Ser Gly Thr Ala Ser Val Val Cys Leu Leu Asn Asn Phe
               130                135                140

Tyr Pro Arg Glu Ala Lys Val Gln Trp Lys Val Asp Asn Ala Leu Gln
145                150                155                160

Ser Gly Asn Ser Gln Glu Ser Val Thr Glu Gln Asp Ser Lys Asp Ser
               165                170                175

Thr Tyr Ser Leu Ser Ser Thr Leu Thr Leu Ser Lys Ala Asp Tyr Glu
               180                185                190

Lys His Lys Val Tyr Ala Cys Glu Val Thr His Gln Gly Leu Ser Ser
               195                200                205

Pro Val Thr Lys Ser Phe Asn Arg Gly Glu Cys
               210                215

<210> SEQ ID NO 3
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ser Leu Glu Glu Ser Gly Gly Arg Leu Val Thr Pro Gly Thr Pro
1               5                  10                 15

Leu Thr Leu Thr Cys Thr Val Ser Gly Leu Asp Leu Ser Ser Tyr Tyr
                20                 25                 30

Met Gln Trp Val Arg Gln Ala Pro Gly Lys Gly Leu Glu Trp Ile Gly
                35                 40                 45

Val Ile Gly Ile Asn Asp Asn Thr Tyr Tyr Ala Ser Trp Ala Lys Gly
 50                 55                 60

Arg Phe Thr Ile Ser Arg Ala Ser Ser Thr Thr Val Asp Leu Lys Met
65                  70                 75                 80

Thr Ser Leu Thr Thr Glu Asp Thr Ala Thr Tyr Phe Cys Ala Arg Gly
                85                 90                 95

Asp Ile Trp Gly Pro Gly Thr Leu Val Thr Val Ser Ser
               100                105

<210> SEQ ID NO 4
<211> LENGTH: 439
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 4

```
Gln Ser Leu Glu Glu Ser Gly Gly Arg Leu Val Thr Pro Gly Thr Pro
1               5                   10                  15

Leu Thr Leu Thr Cys Thr Val Ser Gly Leu Asp Leu Ser Ser Tyr Tyr
            20                  25                  30

Met Gln Trp Val Arg Gln Ala Pro Gly Lys Gly Leu Glu Trp Ile Gly
        35                  40                  45

Val Ile Gly Ile Asn Asp Asn Thr Tyr Tyr Ala Ser Trp Ala Lys Gly
    50                  55                  60

Arg Phe Thr Ile Ser Arg Ala Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Arg Val Glu
        195                 200                 205

Pro Lys Ser Cys Asp Lys Thr His Thr Cys Pro Pro Cys Pro Ala Pro
    210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Ala Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400
```

```
Lys Leu Thr Val Asp Lys Ser Arg Trp Gln Gln Gly Asn Val Phe Ser
            405                 410                 415

Cys Ser Val Met His Glu Ala Leu His Asn His Tyr Thr Gln Lys Ser
            420                 425                 430

Leu Ser Leu Ser Pro Gly Lys
        435

<210> SEQ ID NO 5
<211> LENGTH: 13
<212> TYPE: PRT
<213> ORGANISM: Oryctolagus cuniculus

<400> SEQUENCE: 5

Gln Ala Ser Gln Ser Val Tyr Asp Asn Asn Tyr Leu Ala
1               5                   10

<210> SEQ ID NO 6
<211> LENGTH: 7
<212> TYPE: PRT
<213> ORGANISM: Oryctolagus cuniculus

<400> SEQUENCE: 6

Ser Thr Ser Thr Leu Ala Ser
1               5

<210> SEQ ID NO 7
<211> LENGTH: 13
<212> TYPE: PRT
<213> ORGANISM: Oryctolagus cuniculus

<400> SEQUENCE: 7

Leu Gly Ser Tyr Asp Cys Ser Ser Gly Asp Cys Phe Val
1               5                   10

<210> SEQ ID NO 8
<211> LENGTH: 5
<212> TYPE: PRT
<213> ORGANISM: Oryctolagus cuniculus

<400> SEQUENCE: 8

Ser Tyr Tyr Met Gln
1               5

<210> SEQ ID NO 9
<211> LENGTH: 16
<212> TYPE: PRT
<213> ORGANISM: Oryctolagus cuniculus

<400> SEQUENCE: 9

Val Ile Gly Ile Asn Asp Asn Thr Tyr Tyr Ala Ser Trp Ala Lys Gly
1               5                   10                  15

<210> SEQ ID NO 10
<211> LENGTH: 3
<212> TYPE: PRT
<213> ORGANISM: Oryctolagus cuniculus

<400> SEQUENCE: 10

Gly Asp Ile
1

<210> SEQ ID NO 11
<211> LENGTH: 113
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
            100                 105                 110

Arg

<210> SEQ ID NO 12
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
                    195                 200                 205
Pro Val Thr Lys Ser Phe Asn Arg Gly Glu Cys
    210                 215
```

<210> SEQ ID NO 13
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110
```

<210> SEQ ID NO 14
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
```

```
                         165                 170                 175
Ser Ser Val Val Thr Val Pro Ser Ser Leu Gly Thr Gln Thr Tyr
            180                 185                 190

Ile Cys Asn Val Asn His Lys Pro Ser Asn Thr Lys Val Asp Lys Arg
            195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
            275                 280                 285

Gln Tyr Ala Ser Thr Tyr Arg Val Val Ser Val Leu Thr Val Leu His
            290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
            370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 15
<211> LENGTH: 13
<212> TYPE: PRT
<213> ORGANISM: Oryctolagus cuniculus

<400> SEQUENCE: 15

Gln Ala Ser Gln Ser Val Tyr Asp Asn Asn Tyr Leu Ala
1               5                   10

<210> SEQ ID NO 16
<211> LENGTH: 7
<212> TYPE: PRT
<213> ORGANISM: Oryctolagus cuniculus

<400> SEQUENCE: 16

Ser Thr Ser Thr Leu Ala Ser
1               5

<210> SEQ ID NO 17
<211> LENGTH: 13
<212> TYPE: PRT
```

<210> SEQ ID NO 17
<211> LENGTH: (implicit)
<212> TYPE: PRT
<213> ORGANISM: Oryctolagus cuniculus

<400> SEQUENCE: 17

Leu Gly Ser Tyr Asp Cys Ser Gly Asp Cys Phe Val
1               5                   10

<210> SEQ ID NO 18
<211> LENGTH: 5
<212> TYPE: PRT
<213> ORGANISM: Oryctolagus cuniculus

<400> SEQUENCE: 18

Ser Tyr Tyr Met Gln
1               5

<210> SEQ ID NO 19
<211> LENGTH: 16
<212> TYPE: PRT
<213> ORGANISM: Oryctolagus cuniculus

<400> SEQUENCE: 19

Val Ile Gly Ile Asn Asp Asn Thr Tyr Tyr Ala Ser Trp Ala Lys Gly
1               5                   10                  15

<210> SEQ ID NO 20
<211> LENGTH: 3
<212> TYPE: PRT
<213> ORGANISM: Oryctolagus cuniculus

<400> SEQUENCE: 20

Gly Asp Ile
1

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
                20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
            100                 105                 110

Arg

<210> SEQ ID NO 22
<211> LENGTH: 219
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 22

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 23
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
50                  55                  60

Gly Arg Phe Thr Ile Ser Arg Asp Asn Ser Lys Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110
```

<210> SEQ ID NO 24
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro

```
                355                 360                 365
Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 25
<211> LENGTH: 13
<212> TYPE: PRT
<213> ORGANISM: Oryctolagus cuniculus

<400> SEQUENCE: 25

Gln Ala Ser Gln Ser Val Tyr Asp Asn Asn Tyr Leu Ala
1               5                   10

<210> SEQ ID NO 26
<211> LENGTH: 7
<212> TYPE: PRT
<213> ORGANISM: Oryctolagus cuniculus

<400> SEQUENCE: 26

Ser Thr Ser Thr Leu Ala Ser
1               5

<210> SEQ ID NO 27
<211> LENGTH: 13
<212> TYPE: PRT
<213> ORGANISM: Oryctolagus cuniculus

<400> SEQUENCE: 27

Leu Gly Ser Tyr Asp Cys Ser Ser Gly Asp Cys Phe Val
1               5                   10

<210> SEQ ID NO 28
<211> LENGTH: 5
<212> TYPE: PRT
<213> ORGANISM: Oryctolagus cuniculus

<400> SEQUENCE: 28

Ser Tyr Tyr Met Gln
1               5

<210> SEQ ID NO 29
<211> LENGTH: 16
<212> TYPE: PRT
<213> ORGANISM: Oryctolagus cuniculus

<400> SEQUENCE: 29

Val Ile Gly Ile Asn Asp Asn Thr Tyr Tyr Ala Ser Trp Ala Lys Gly
1               5                   10                  15

<210> SEQ ID NO 30
<211> LENGTH: 3
<212> TYPE: PRT
<213> ORGANISM: Oryctolagus cuniculus

<400> SEQUENCE: 30
```

```
Gly Asp Ile
1

<210> SEQ ID NO 31
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Leu Thr Gln Thr Pro Ser Pro Val Ser Ala Ala Val Gly Ser
1               5                   10                  15

Thr Val Thr Ile Asn Cys Gln Ala Ser Gln Ser Val Tyr His Asn Thr
            20                  25                  30

Tyr Leu Ala Trp Tyr Gln Gln Lys Pro Gly Gln Pro Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asn Asp Ala Ala Ala Tyr Tyr Cys Leu Gly Ser Tyr Asp Cys Thr
                85                  90                  95

Asn Gly Asp Cys Phe Val Phe Gly Gly Gly Thr Glu Val Val Val Lys
            100                 105                 110

Arg

<210> SEQ ID NO 32
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Leu Thr Gln Thr Pro Ser Pro Val Ser Ala Ala Val Gly Ser
1               5                   10                  15

Thr Val Thr Ile Asn Cys Gln Ala Ser Gln Ser Val Tyr His Asn Thr
            20                  25                  30

Tyr Leu Ala Trp Tyr Gln Gln Lys Pro Gly Gln Pro Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asn Asp Ala Ala Ala Tyr Tyr Cys Leu Gly Ser Tyr Asp Cys Thr
                85                  90                  95

Asn Gly Asp Cys Phe Val Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215
```

<210> SEQ ID NO 33
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Ser Leu Glu Glu Ser Gly Gly Arg Leu Val Thr Pro Gly Thr Pro
1               5                   10                  15

Leu Thr Leu Thr Cys Ser Val Ser Gly Ile Asp Leu Ser Gly Tyr Tyr
            20                  25                  30

Met Asn Trp Val Arg Gln Ala Pro Gly Lys Gly Leu Glu Trp Ile Gly
        35                  40                  45

Val Ile Gly Ile Asn Gly Ala Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser
            100                 105
```

<210> SEQ ID NO 34
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Ser Leu Glu Glu Ser Gly Gly Arg Leu Val Thr Pro Gly Thr Pro
1               5                   10                  15

Leu Thr Leu Thr Cys Ser Val Ser Gly Ile Asp Leu Ser Gly Tyr Tyr
            20                  25                  30

Met Asn Trp Val Arg Gln Ala Pro Gly Lys Gly Leu Glu Trp Ile Gly
        35                  40                  45

Val Ile Gly Ile Asn Gly Ala Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125
```

```
Gly Gly Thr Ala Ala Leu Gly Cys Leu Val Lys Asp Tyr Phe Pro Glu
        130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Arg Val Glu
        195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Ala Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys
        435

<210> SEQ ID NO 35
<211> LENGTH: 13
<212> TYPE: PRT
<213> ORGANISM: Oryctolagus cuniculus

<400> SEQUENCE: 35

Gln Ala Ser Gln Ser Val Tyr His Asn Thr Tyr Leu Ala
1               5                   10

<210> SEQ ID NO 36
<211> LENGTH: 7
<212> TYPE: PRT
<213> ORGANISM: Oryctolagus cuniculus

<400> SEQUENCE: 36
```

Asp Ala Ser Thr Leu Ala Ser
1               5

<210> SEQ ID NO 37
<211> LENGTH: 13
<212> TYPE: PRT
<213> ORGANISM: Oryctolagus cuniculus

<400> SEQUENCE: 37

Leu Gly Ser Tyr Asp Cys Thr Asn Gly Asp Cys Phe Val
1               5                   10

<210> SEQ ID NO 38
<211> LENGTH: 5
<212> TYPE: PRT
<213> ORGANISM: Oryctolagus cuniculus

<400> SEQUENCE: 38

Gly Tyr Tyr Met Asn
1               5

<210> SEQ ID NO 39
<211> LENGTH: 16
<212> TYPE: PRT
<213> ORGANISM: Oryctolagus cuniculus

<400> SEQUENCE: 39

Val Ile Gly Ile Asn Gly Ala Thr Tyr Tyr Ala Ser Trp Ala Lys Gly
1               5                   10                  15

<210> SEQ ID NO 40
<211> LENGTH: 3
<212> TYPE: PRT
<213> ORGANISM: Oryctolagus cuniculus

<400> SEQUENCE: 40

Gly Asp Ile
1

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg

<210> SEQ ID NO 42
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu

```
                 65                  70                  75                  80
Gln Met Asn Ser Leu Arg Ala Glu Asp Thr Ala Val Tyr Phe Cys Ala
                 85                  90                  95

Arg Gly Asp Ile Trp Gly Gln Gly Thr Leu Val Thr Val Ser Ser
                100                 105                 110

<210> SEQ ID NO 44
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Glu Ser Gly Gly Gly Leu Val Gln Pro Gly Gly
 1               5                  10                  15

Ser Leu Arg Leu Ser Cys Ala Val Ser Gly Ile Asp Leu Ser Gly Tyr
                20                  25                  30

Tyr Met Asn Trp Val Arg Gln Ala Pro Gly Lys Gly Leu Glu Trp Val
                35                  40                  45

Gly Val Ile Gly Ile Asn Gly Ala Thr Tyr Tyr Ala Ser Trp Ala Lys
 50                  55                  60

Gly Arg Phe Thr Ile Ser Arg Asp Asn Ser Lys Thr Thr Val Tyr Leu
 65                  70                  75                  80

Gln Met Asn Ser Leu Arg Ala Glu Asp Thr Ala Val Tyr Phe Cys Ala
                 85                  90                  95

Arg Gly Asp Ile Trp Gly Gln Gly Thr Leu Val Thr Val Ser Ser Ala
                100                 105                 110

Ser Thr Lys Gly Pro Ser Val Phe Pro Leu Ala Pro Ser Ser Lys Ser
                115                 120                 125

Thr Ser Gly Gly Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
                180                 185                 190

Ile Cys Asn Val Asn His Lys Pro Ser Asn Thr Lys Val Asp Lys Arg
            195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
            275                 280                 285

Gln Tyr Ala Ser Thr Tyr Arg Val Val Ser Val Leu Thr Val Leu His
            290                 295                 300

Gln Asp Trp Leu Asn Gly Lys Glu Tyr Lys Cys Lys Val Ser Asn Lys
305                 310                 315                 320
```

```
Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 45
<211> LENGTH: 13
<212> TYPE: PRT
<213> ORGANISM: Oryctolagus cuniculus

<400> SEQUENCE: 45

Gln Ala Ser Gln Ser Val Tyr His Asn Thr Tyr Leu Ala
1               5                   10

<210> SEQ ID NO 46
<211> LENGTH: 7
<212> TYPE: PRT
<213> ORGANISM: Oryctolagus cuniculus

<400> SEQUENCE: 46

Asp Ala Ser Thr Leu Ala Ser
1               5

<210> SEQ ID NO 47
<211> LENGTH: 13
<212> TYPE: PRT
<213> ORGANISM: Oryctolagus cuniculus

<400> SEQUENCE: 47

Leu Gly Ser Tyr Asp Cys Thr Asn Gly Asp Cys Phe Val
1               5                   10

<210> SEQ ID NO 48
<211> LENGTH: 5
<212> TYPE: PRT
<213> ORGANISM: Oryctolagus cuniculus

<400> SEQUENCE: 48

Gly Tyr Tyr Met Asn
1               5

<210> SEQ ID NO 49
<211> LENGTH: 15
<212> TYPE: PRT
<213> ORGANISM: Oryctolagus cuniculus

<400> SEQUENCE: 49

Ile Gly Ile Asn Gly Ala Thr Tyr Tyr Ala Ser Trp Ala Lys Gly
1               5                   10                  15
```

```
<210> SEQ ID NO 50
<211> LENGTH: 3
<212> TYPE: PRT
<213> ORGANISM: Oryctolagus cuniculus

<400> SEQUENCE: 50

Gly Asp Ile
1

<210> SEQ ID NO 51
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg

<210> SEQ ID NO 52
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125
```

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 53
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
            85                  90                  95

Arg Gly Asp Ile Trp Gly Gln Gly Thr Leu Val Thr Val Ser Ser
        100                 105                 110

<210> SEQ ID NO 54
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
            85                  90                  95

```
Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Leu Gly Thr Gln Thr Tyr
            180                 185                 190

Ile Cys Asn Val Asn His Lys Pro Ser Asn Thr Lys Val Asp Ala Arg
    195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
            275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 55
<211> LENGTH: 13
<212> TYPE: PRT
<213> ORGANISM: Oryctolagus cuniculus

<400> SEQUENCE: 55

Gln Ala Ser Gln Ser Val Tyr His Asn Thr Tyr Leu Ala
1               5                   10
```

```
<210> SEQ ID NO 56
<211> LENGTH: 7
<212> TYPE: PRT
<213> ORGANISM: Oryctolagus cuniculus

<400> SEQUENCE: 56

Asp Ala Ser Thr Leu Ala Ser
1               5

<210> SEQ ID NO 57
<211> LENGTH: 13
<212> TYPE: PRT
<213> ORGANISM: Oryctolagus cuniculus

<400> SEQUENCE: 57

Leu Gly Ser Tyr Asp Cys Thr Asn Gly Asp Cys Phe Val
1               5                   10

<210> SEQ ID NO 58
<211> LENGTH: 5
<212> TYPE: PRT
<213> ORGANISM: Oryctolagus cuniculus

<400> SEQUENCE: 58

Gly Tyr Tyr Met Asn
1               5

<210> SEQ ID NO 59
<211> LENGTH: 15
<212> TYPE: PRT
<213> ORGANISM: Oryctolagus cuniculus

<400> SEQUENCE: 59

Ile Gly Ile Asn Gly Ala Thr Tyr Tyr Ala Ser Trp Ala Lys Gly
1               5                   10                  15

<210> SEQ ID NO 60
<211> LENGTH: 3
<212> TYPE: PRT
<213> ORGANISM: Oryctolagus cuniculus

<400> SEQUENCE: 60

Gly Asp Ile
1

<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Leu Thr Gln Thr Ala Ser Pro Val Ser Ala Val Gly Ser
1               5                   10                  15

Thr Val Thr Ile Asn Cys Gln Ala Ser Gln Ser Val Tyr Asn Tyr Asn
                20                  25                  30

Tyr Leu Ala Trp Tyr Gln Gln Lys Pro Gly Gln Pro Pro Lys Gln Leu
            35                  40                  45

Ile Tyr Ser Thr Ser Thr Leu Ala Ser Gly Val Ser Ser Arg Phe Lys
        50                  55                  60

Gly Ser Gly Ser Gly Thr Gln Phe Thr Leu Thr Ile Ser Asp Val Gln
65                  70                  75                  80
```

Cys Asp Asp Ala Ala Thr Tyr Tyr Cys Leu Gly Ser Tyr Asp Cys Ser
                85                  90                  95

Thr Gly Asp Cys Phe Val Phe Gly Gly Gly Thr Glu Val Val Val Lys
            100                 105                 110

Arg

<210> SEQ ID NO 62
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Leu Thr Gln Thr Ala Ser Pro Val Ala Ala Val Gly Ser
1               5                   10                  15

Thr Val Thr Ile Asn Cys Gln Ala Ser Gln Ser Val Tyr Asn Tyr Asn
                20                  25                  30

Tyr Leu Ala Trp Tyr Gln Gln Lys Pro Gly Gln Pro Pro Lys Gln Leu
            35                  40                  45

Ile Tyr Ser Thr Ser Thr Leu Ala Ser Gly Val Ser Ser Arg Phe Lys
        50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Tyr Asp Cys Ser
                85                  90                  95

Thr Gly Asp Cys Phe Val Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 63
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Glu Gln Leu Lys Glu Ser Gly Gly Arg Leu Val Thr Pro Gly Thr
1               5                   10                  15

Ser Leu Thr Leu Thr Cys Thr Val Ser Gly Ile Asp Leu Ser Asn His
            20                  25                  30

```
Tyr Met Gln Trp Val Arg Gln Ala Pro Gly Lys Gly Leu Glu Trp Ile
            35                  40                  45

Gly Val Val Gly Ile Asn Gly Arg Thr Tyr Tyr Ala Ser Trp Ala Lys
 50                      55                  60

Gly Arg Phe Thr Ile Ser Arg Thr Ser Ser Thr Thr Val Asp Leu Lys
 65                  70                  75                  80

Met Thr Arg Leu Thr Thr Glu Asp Thr Ala Thr Tyr Phe Cys Ala Arg
                85                  90                  95

Gly Asp Ile Trp Gly Pro Gly Thr Leu Val Thr Val Ser Ser
            100                 105                 110

<210> SEQ ID NO 64
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Glu Gln Leu Lys Glu Ser Gly Gly Arg Leu Val Thr Pro Gly Thr
 1               5                  10                  15

Ser Leu Thr Leu Thr Cys Thr Val Ser Gly Ile Asp Leu Ser Asn His
            20                  25                  30

Tyr Met Gln Trp Val Arg Gln Ala Pro Gly Lys Gly Leu Glu Trp Ile
            35                  40                  45

Gly Val Val Gly Ile Asn Gly Arg Thr Tyr Tyr Ala Ser Trp Ala Lys
 50                      55                  60

Gly Arg Phe Thr Ile Ser Arg Thr Ser Ser Thr Thr Val Asp Leu Lys
 65                  70                  75                  80

Met Thr Arg Leu Thr Thr Glu Asp Thr Ala Thr Tyr Phe Cys Ala Arg
                85                  90                  95

Gly Asp Ile Trp Gly Pro Gly Thr Leu Val Thr Val Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Arg Val
        195                 200                 205

Glu Pro Lys Ser Cys Asp Lys Thr His Thr Cys Pro Pro Cys Pro Ala
    210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285
```

```
            Tyr Ala Ser Thr Tyr Arg Val Ser Val Leu Thr Val Leu His Gln
                        290                 295                 300
            Asp Trp Leu Asn Gly Lys Glu Tyr Lys Cys Lys Val Ser Asn Lys Ala
            305                 310                 315                 320
            Leu Pro Ala Pro Ile Glu Lys Thr Ile Ser Lys Ala Lys Gly Gln Pro
                            325                 330                 335
            Arg Glu Pro Gln Val Tyr Thr Leu Pro Pro Ser Arg Glu Glu Met Thr
                        340                 345                 350
            Lys Asn Gln Val Ser Leu Thr Cys Leu Val Lys Gly Phe Tyr Pro Ser
                        355                 360                 365
            Asp Ile Ala Val Glu Trp Glu Ser Asn Gly Gln Pro Glu Asn Asn Tyr
                        370                 375                 380
            Lys Thr Thr Pro Pro Val Leu Asp Ser Asp Gly Ser Phe Phe Leu Tyr
            385                 390                 395                 400
            Ser Lys Leu Thr Val Asp Lys Ser Arg Trp Gln Gln Gly Asn Val Phe
                            405                 410                 415
            Ser Cys Ser Val Met His Glu Ala Leu His Asn His Tyr Thr Gln Lys
                        420                 425                 430
            Ser Leu Ser Leu Ser Pro Gly Lys
                        435                 440

<210> SEQ ID NO 65
<211> LENGTH: 13
<212> TYPE: PRT
<213> ORGANISM: Oryctolagus cuniculus

<400> SEQUENCE: 65

Gln Ala Ser Gln Ser Val Tyr Asn Tyr Asn Tyr Leu Ala
1               5                   10

<210> SEQ ID NO 66
<211> LENGTH: 7
<212> TYPE: PRT
<213> ORGANISM: Oryctolagus cuniculus

<400> SEQUENCE: 66

Ser Thr Ser Thr Leu Ala Ser
1               5

<210> SEQ ID NO 67
<211> LENGTH: 13
<212> TYPE: PRT
<213> ORGANISM: Oryctolagus cuniculus

<400> SEQUENCE: 67

Leu Gly Ser Tyr Asp Cys Ser Thr Gly Asp Cys Phe Val
1               5                   10

<210> SEQ ID NO 68
<211> LENGTH: 5
<212> TYPE: PRT
<213> ORGANISM: Oryctolagus cuniculus

<400> SEQUENCE: 68

Asn His Tyr Met Gln
1               5

<210> SEQ ID NO 69
<211> LENGTH: 16
<212> TYPE: PRT
```

<213> ORGANISM: Oryctolagus cuniculus

<400> SEQUENCE: 69

Val Val Gly Ile Asn Gly Arg Thr Tyr Tyr Ala Ser Trp Ala Lys Gly
1               5                   10                  15

<210> SEQ ID NO 70
<211> LENGTH: 3
<212> TYPE: PRT
<213> ORGANISM: Oryctolagus cuniculus

<400> SEQUENCE: 70

Gly Asp Ile
1

<210> SEQ ID NO 71
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asn Tyr Asn
                20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Thr Gly Asp Cys Phe Val Phe Gly Gly Gly Thr Lys Val Glu Ile Lys
            100                 105                 110

Arg

<210> SEQ ID NO 72
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asn Tyr Asn
                20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser

```
                    85                  90                  95
Thr Gly Asp Cys Phe Val Phe Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215
```

<210> SEQ ID NO 73
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Asn His
            20                  25                  30

Tyr Met Gln Trp Val Arg Gln Ala Pro Gly Lys Gly Leu Glu Trp Val
        35                  40                  45

Gly Val Val Gly Ile Asn Gly Arg Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110
```

<210> SEQ ID NO 74
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Asn His
            20                  25                  30

Tyr Met Gln Trp Val Arg Gln Ala Pro Gly Lys Gly Leu Glu Trp Val
        35                  40                  45

Gly Val Val Gly Ile Asn Gly Arg Thr Tyr Tyr Ala Ser Trp Ala Lys
```

```
                    50                  55                  60
Gly Arg Phe Thr Ile Ser Arg Asp Asn Ser Lys Thr Thr Val Tyr Leu
 65                  70                  75                  80

Gln Met Asn Ser Leu Arg Ala Glu Asp Thr Ala Val Tyr Phe Cys Ala
                 85                  90                  95

Arg Gly Asp Ile Trp Gly Gln Gly Thr Leu Val Thr Val Ser Ser Ala
                100                 105                 110

Ser Thr Lys Gly Pro Ser Val Phe Pro Leu Ala Pro Ser Ser Lys Ser
                115                 120                 125

Thr Ser Gly Gly Thr Ala Ala Leu Gly Cys Leu Val Lys Asp Tyr Phe
                130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
                180                 185                 190

Ile Cys Asn Val Asn His Lys Pro Ser Asn Thr Lys Val Asp Lys Arg
                195                 200                 205

Val Glu Pro Lys Ser Cys Asp Lys Thr His Thr Cys Pro Pro Cys Pro
                210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
                275                 280                 285

Gln Tyr Ala Ser Thr Tyr Arg Val Val Ser Val Leu Thr Val Leu His
                290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
                355                 360                 365

Ser Asp Ile Ala Val Glu Trp Glu Ser Asn Gly Gln Pro Glu Asn Asn
                370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
                435                 440

<210> SEQ ID NO 75
<211> LENGTH: 13
<212> TYPE: PRT
<213> ORGANISM: Oryctolagus cuniculus
```

-continued

<400> SEQUENCE: 75

Gln Ala Ser Gln Ser Val Tyr Asn Tyr Asn Tyr Leu Ala
1               5                   10

<210> SEQ ID NO 76
<211> LENGTH: 7
<212> TYPE: PRT
<213> ORGANISM: Oryctolagus cuniculus

<400> SEQUENCE: 76

Ser Thr Ser Thr Leu Ala Ser
1               5

<210> SEQ ID NO 77
<211> LENGTH: 13
<212> TYPE: PRT
<213> ORGANISM: Oryctolagus cuniculus

<400> SEQUENCE: 77

Leu Gly Ser Tyr Asp Cys Ser Thr Gly Asp Cys Phe Val
1               5                   10

<210> SEQ ID NO 78
<211> LENGTH: 5
<212> TYPE: PRT
<213> ORGANISM: Oryctolagus cuniculus

<400> SEQUENCE: 78

Asn His Tyr Met Gln
1               5

<210> SEQ ID NO 79
<211> LENGTH: 16
<212> TYPE: PRT
<213> ORGANISM: Oryctolagus cuniculus

<400> SEQUENCE: 79

Val Val Gly Ile Asn Gly Arg Thr Tyr Tyr Ala Ser Trp Ala Lys Gly
1               5                   10                  15

<210> SEQ ID NO 80
<211> LENGTH: 3
<212> TYPE: PRT
<213> ORGANISM: Oryctolagus cuniculus

<400> SEQUENCE: 80

Gly Asp Ile
1

<210> SEQ ID NO 81
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Leu Thr Gln Thr Pro Ser Pro Val Ser Ala Ala Val Gly Ser
1               5                   10                  15

Thr Val Thr Ile Asn Cys Gln Ala Ser Gln Asn Val Tyr Asn Asn Asn
            20                  25                  30

Tyr Leu Ala Trp Tyr Gln Gln Lys Pro Gly Gln Pro Pro Lys Gln Leu

```
                    35                  40                  45

Ile Tyr Ser Thr Ser Thr Leu Ala Ser Gly Val Ser Ser Arg Phe Arg
 50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Leu Gly Ser Tyr Asp Cys Ser
                     85                  90                  95

Arg Gly Asp Cys Phe Val Phe Gly Gly Gly Thr Glu Val Val Val Lys
                    100                 105                 110

Arg

<210> SEQ ID NO 82
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Leu Thr Gln Thr Pro Ser Pro Val Ser Ala Ala Val Gly Ser
  1               5                  10                  15

Thr Val Thr Ile Asn Cys Gln Ala Ser Gln Asn Val Tyr Asn Asn Asn
                 20                  25                  30

Tyr Leu Ala Trp Tyr Gln Lys Pro Gly Gln Pro Pro Lys Gln Leu
             35                  40                  45

Ile Tyr Ser Thr Ser Thr Leu Ala Ser Gly Val Ser Ser Arg Phe Arg
 50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Leu Gly Ser Tyr Asp Cys Ser
                     85                  90                  95

Arg Gly Asp Cys Phe Val Phe Gly Gly Gly Thr Glu Val Val Val Lys
                    100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 83
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

Gln Ser Leu Glu Glu Ser Gly Gly Arg Leu Val Thr Pro Gly Thr Pro
1               5                   10                  15

Leu Thr Leu Thr Cys Thr Val Ser Gly Ile Gly Leu Ser Ser Tyr Tyr
                20                  25                  30

Met Gln Trp Val Arg Gln Ser Pro Gly Arg Gly Leu Glu Trp Ile Gly
            35                  40                  45

Val Ile Gly Ser Asp Gly Lys Thr Tyr Tyr Ala Thr Trp Ala Lys Gly
        50                  55                  60

Arg Phe Thr Ile Ser Lys Thr Ser Ser Thr Thr Val Asp Leu Arg Met
65                  70                  75                  80

Ala Ser Leu Thr Thr Glu Asp Thr Ala Thr Tyr Phe Cys Thr Arg Gly
                85                  90                  95

Asp Ile Trp Gly Pro Gly Thr Leu Val Thr Val Ser Ser
            100                 105

<210> SEQ ID NO 84
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ser Leu Glu Glu Ser Gly Gly Arg Leu Val Thr Pro Gly Thr Pro
1               5                   10                  15

Leu Thr Leu Thr Cys Thr Val Ser Gly Ile Gly Leu Ser Ser Tyr Tyr
                20                  25                  30

Met Gln Trp Val Arg Gln Ser Pro Gly Arg Gly Leu Glu Trp Ile Gly
            35                  40                  45

Val Ile Gly Ser Asp Gly Lys Thr Tyr Tyr Ala Thr Trp Ala Lys Gly
        50                  55                  60

Arg Phe Thr Ile Ser Lys Thr Ser Ser Thr Thr Val Asp Leu Arg Met
65                  70                  75                  80

Ala Ser Leu Thr Thr Glu Asp Thr Ala Thr Tyr Phe Cys Thr Arg Gly
                85                  90                  95

Asp Ile Trp Gly Pro Gly Thr Leu Val Thr Val Ser Ser Ala Ser Thr
            100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
        130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Arg Val Glu
        195                 200                 205

Pro Lys Ser Cys Asp Lys Thr His Thr Cys Pro Pro Cys Pro Ala Pro
    210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val

```
                    245                 250                 255
Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
            275                 280                 285

Ala Ser Thr Tyr Arg Val Val Ser Val Leu Thr Val Leu His Gln Asp
        290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys
        435

<210> SEQ ID NO 85
<211> LENGTH: 13
<212> TYPE: PRT
<213> ORGANISM: Oryctolagus cuniculus

<400> SEQUENCE: 85

Gln Ala Ser Gln Asn Val Tyr Asn Asn Asn Tyr Leu Ala
1               5                   10

<210> SEQ ID NO 86
<211> LENGTH: 7
<212> TYPE: PRT
<213> ORGANISM: Oryctolagus cuniculus

<400> SEQUENCE: 86

Ser Thr Ser Thr Leu Ala Ser
1               5

<210> SEQ ID NO 87
<211> LENGTH: 13
<212> TYPE: PRT
<213> ORGANISM: Oryctolagus cuniculus

<400> SEQUENCE: 87

Leu Gly Ser Tyr Asp Cys Ser Arg Gly Asp Cys Phe Val
1               5                   10

<210> SEQ ID NO 88
<211> LENGTH: 5
<212> TYPE: PRT
<213> ORGANISM: Oryctolagus cuniculus

<400> SEQUENCE: 88
```

```
Ser Tyr Tyr Met Gln
1               5
```

<210> SEQ ID NO 89
<211> LENGTH: 16
<212> TYPE: PRT
<213> ORGANISM: Oryctolagus cuniculus

<400> SEQUENCE: 89

```
Val Ile Gly Ser Asp Gly Lys Thr Tyr Tyr Ala Thr Trp Ala Lys Gly
1               5                   10                  15
```

<210> SEQ ID NO 90
<211> LENGTH: 3
<212> TYPE: PRT
<213> ORGANISM: Oryctolagus cuniculus

<400> SEQUENCE: 90

```
Gly Asp Ile
1
```

<210> SEQ ID NO 91
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Gln Val Leu Thr Gln Ser Pro Ser Ser Leu Ser Ala Ser Val Gly Asp
1               5                   10                  15

Arg Val Thr Ile Asn Cys Gln Ala Ser Gln Asn Val Tyr Asn Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Arg Gly Asp Cys Phe Val Phe Gly Gly Gly Thr Lys Val Glu Ile Lys
            100                 105                 110

Arg
```

<210> SEQ ID NO 92
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Gln Val Leu Thr Gln Ser Pro Ser Ser Leu Ser Ala Ser Val Gly Asp
1               5                   10                  15

Arg Val Thr Ile Asn Cys Gln Ala Ser Gln Asn Val Tyr Asn Asn Asn
            20                  25                  30

Tyr Leu Ala Trp Tyr Gln Gln Lys Pro Gly Lys Val Pro Lys Gln Leu
        35                  40                  45
```

```
Ile Tyr Ser Thr Ser Thr Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Val Ala Thr Tyr Tyr Cys Leu Gly Ser Tyr Asp Cys Ser
                 85                  90                  95

Arg Gly Asp Cys Phe Val Phe Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215

<210> SEQ ID NO 93
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Val Ser Gly Ile Gly Leu Ser Ser Tyr
                 20                  25                  30

Tyr Met Gln Trp Val Arg Gln Ala Pro Gly Lys Gly Leu Glu Trp Val
             35                  40                  45

Gly Val Ile Gly Ser Asp Gly Lys Thr Tyr Tyr Ala Thr Trp Ala Lys
 50                  55                  60

Gly Arg Phe Thr Ile Ser Arg Asp Asn Ser Lys Thr Thr Val Tyr Leu
 65                  70                  75                  80

Gln Met Asn Ser Leu Arg Ala Glu Asp Thr Ala Val Tyr Phe Cys Thr
                 85                  90                  95

Arg Gly Asp Ile Trp Gly Gln Gly Thr Leu Val Thr Val Ser Ser
                100                 105                 110

<210> SEQ ID NO 94
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Gln Pro Gly Gly
 1               5                  10                  15
```

-continued

```
Ser Leu Arg Leu Ser Cys Ala Val Ser Gly Ile Gly Leu Ser Ser Tyr
         20                  25                  30

Tyr Met Gln Trp Val Arg Gln Ala Pro Gly Lys Gly Leu Glu Trp Val
         35                  40                  45

Gly Val Ile Gly Ser Asp Gly Lys Thr Tyr Tyr Ala Thr Trp Ala Lys
 50                  55                  60

Gly Arg Phe Thr Ile Ser Arg Asp Asn Ser Lys Thr Thr Val Tyr Leu
 65                  70                  75                  80

Gln Met Asn Ser Leu Arg Ala Glu Asp Thr Ala Val Tyr Phe Cys Thr
                 85                  90                  95

Arg Gly Asp Ile Trp Gly Gln Gly Thr Leu Val Thr Val Ser Ser Ala
             100                 105                 110

Ser Thr Lys Gly Pro Ser Val Phe Pro Leu Ala Pro Ser Ser Lys Ser
         115                 120                 125

Thr Ser Gly Gly Thr Ala Ala Leu Gly Cys Leu Val Lys Asp Tyr Phe
     130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                 165                 170                 175

Ser Ser Val Val Thr Val Pro Ser Ser Ser Leu Gly Thr Gln Thr Tyr
             180                 185                 190

Ile Cys Asn Val Asn His Lys Pro Ser Asn Thr Lys Val Asp Lys Arg
         195                 200                 205

Val Glu Pro Lys Ser Cys Asp Lys Thr His Thr Cys Pro Pro Cys Pro
     210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                 245                 250                 255

Val Val Asp Val Ser His Glu Asp Pro Glu Val Lys Phe Asn Trp Tyr
             260                 265                 270

Val Asp Gly Val Glu Val His Asn Ala Lys Thr Lys Pro Arg Glu Glu
         275                 280                 285

Gln Tyr Ala Ser Thr Tyr Arg Val Val Ser Val Leu Thr Val Leu His
     290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                 325                 330                 335

Pro Arg Glu Pro Gln Val Tyr Thr Leu Pro Pro Ser Arg Glu Glu Met
             340                 345                 350

Thr Lys Asn Gln Val Ser Leu Thr Cys Leu Val Lys Gly Phe Tyr Pro
         355                 360                 365

Ser Asp Ile Ala Val Glu Trp Glu Ser Asn Gly Gln Pro Glu Asn Asn
     370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                 405                 410                 415

Phe Ser Cys Ser Val Met His Glu Ala Leu His Asn His Tyr Thr Gln
             420                 425                 430

Lys Ser Leu Ser Leu Ser Pro Gly Lys
```

```
                 435                 440

<210> SEQ ID NO 95
<211> LENGTH: 13
<212> TYPE: PRT
<213> ORGANISM: Oryctolagus cuniculus

<400> SEQUENCE: 95

Gln Ala Ser Gln Asn Val Tyr Asn Asn Asn Tyr Leu Ala
1               5                   10

<210> SEQ ID NO 96
<211> LENGTH: 7
<212> TYPE: PRT
<213> ORGANISM: Oryctolagus cuniculus

<400> SEQUENCE: 96

Ser Thr Ser Thr Leu Ala Ser
1               5

<210> SEQ ID NO 97
<211> LENGTH: 13
<212> TYPE: PRT
<213> ORGANISM: Oryctolagus cuniculus

<400> SEQUENCE: 97

Leu Gly Ser Tyr Asp Cys Ser Arg Gly Asp Cys Phe Val
1               5                   10

<210> SEQ ID NO 98
<211> LENGTH: 5
<212> TYPE: PRT
<213> ORGANISM: Oryctolagus cuniculus

<400> SEQUENCE: 98

Ser Tyr Tyr Met Gln
1               5

<210> SEQ ID NO 99
<211> LENGTH: 16
<212> TYPE: PRT
<213> ORGANISM: Oryctolagus cuniculus

<400> SEQUENCE: 99

Val Ile Gly Ser Asp Gly Lys Thr Tyr Tyr Ala Thr Trp Ala Lys Gly
1               5                   10                  15

<210> SEQ ID NO 100
<211> LENGTH: 3
<212> TYPE: PRT
<213> ORGANISM: Oryctolagus cuniculus

<400> SEQUENCE: 100

Gly Asp Ile
1

<210> SEQ ID NO 101
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101
```

Gln Val Leu Thr Gln Thr Ala Ser Pro Val Ser Pro Ala Val Gly Ser
1               5                   10                  15

Thr Val Thr Ile Asn Cys Arg Ala Ser Gln Ser Val Tyr Tyr Asn Asn
            20                  25                  30

Tyr Leu Ala Trp Tyr Gln Gln Lys Pro Gly Gln Pro Pro Lys Gln Leu
        35                  40                  45

Ile Tyr Ser Thr Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Tyr Asp Cys Ser
                85                  90                  95

Asn Gly Asp Cys Phe Val Phe Gly Gly Gly Thr Glu Val Val Val Lys
            100                 105                 110

Arg

<210> SEQ ID NO 102
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Leu Thr Gln Thr Ala Ser Pro Val Ser Pro Ala Val Gly Ser
1               5                   10                  15

Thr Val Thr Ile Asn Cys Arg Ala Ser Gln Ser Val Tyr Tyr Asn Asn
            20                  25                  30

Tyr Leu Ala Trp Tyr Gln Gln Lys Pro Gly Gln Pro Pro Lys Gln Leu
        35                  40                  45

Ile Tyr Ser Thr Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Tyr Asp Cys Ser
                85                  90                  95

Asn Gly Asp Cys Phe Val Phe Gly Gly Gly Thr Glu Val Val Val Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 103
<211> LENGTH: 109

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Val Thr Asn Tyr Tyr
            20                  25                  30

Met Gln Trp Val Arg Gln Ala Pro Gly Lys Gly Leu Glu Trp Ile Gly
        35                  40                  45

Val Ile Gly Val Asn Gly Lys Arg Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser
            100                 105

<210> SEQ ID NO 104
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Val Thr Asn Tyr Tyr
            20                  25                  30

Met Gln Trp Val Arg Gln Ala Pro Gly Lys Gly Leu Glu Trp Ile Gly
        35                  40                  45

Val Ile Gly Val Asn Gly Lys Arg Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Arg Val Glu
        195                 200                 205
```

```
Pro Lys Ser Cys Asp Lys Thr His Thr Cys Pro Pro Cys Pro Ala Pro
    210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
                275                 280                 285

Ala Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Glu Glu Met Thr Lys
                340                 345                 350

Asn Gln Val Ser Leu Thr Cys Leu Val Lys Gly Phe Tyr Pro Ser Asp
                355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Pro Gly Lys
            435

<210> SEQ ID NO 105
<211> LENGTH: 13
<212> TYPE: PRT
<213> ORGANISM: Oryctolagus cuniculus

<400> SEQUENCE: 105

Arg Ala Ser Gln Ser Val Tyr Tyr Asn Asn Tyr Leu Ala
1               5                   10

<210> SEQ ID NO 106
<211> LENGTH: 7
<212> TYPE: PRT
<213> ORGANISM: Oryctolagus cuniculus

<400> SEQUENCE: 106

Ser Thr Ser Thr Leu Ala Ser
1               5

<210> SEQ ID NO 107
<211> LENGTH: 13
<212> TYPE: PRT
<213> ORGANISM: Oryctolagus cuniculus

<400> SEQUENCE: 107

Leu Gly Ser Tyr Asp Cys Ser Asn Gly Asp Cys Phe Val
1               5                   10
```

```
<210> SEQ ID NO 108
<211> LENGTH: 5
<212> TYPE: PRT
<213> ORGANISM: Oryctolagus cuniculus

<400> SEQUENCE: 108

Asn Tyr Tyr Met Gln
1               5

<210> SEQ ID NO 109
<211> LENGTH: 16
<212> TYPE: PRT
<213> ORGANISM: Oryctolagus cuniculus

<400> SEQUENCE: 109

Val Ile Gly Val Asn Gly Lys Arg Tyr Tyr Ala Ser Trp Ala Lys Gly
1               5                   10                  15

<210> SEQ ID NO 110
<211> LENGTH: 3
<212> TYPE: PRT
<213> ORGANISM: Oryctolagus cuniculus

<400> SEQUENCE: 110

Gly Asp Ile
1

<210> SEQ ID NO 111
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Leu Thr Gln Ser Pro Ser Ser Leu Ser Ala Ser Val Gly Asp
1               5                   10                  15

Arg Val Thr Ile Asn Cys Arg Ala Ser Gln Ser Val Tyr Tyr Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Asn Gly Asp Cys Phe Val Phe Gly Gly Gly Thr Lys Val Glu Ile Lys
            100                 105                 110

Arg

<210> SEQ ID NO 112
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Leu Thr Gln Ser Pro Ser Ser Leu Ser Ala Ser Val Gly Asp
1               5                   10                  15
```

Arg Val Thr Ile Asn Cys Arg Ala Ser Gln Ser Val Tyr Tyr Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Asn Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 113
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Val Thr Asn Tyr
            20                  25                  30

Tyr Met Gln Trp Val Arg Gln Ala Pro Gly Lys Gly Leu Glu Trp Val
        35                  40                  45

Gly Val Ile Gly Val Asn Gly Lys Arg Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 114
<211> LENGTH: 441
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Val Thr Asn Tyr
            20                  25                  30

Tyr Met Gln Trp Val Arg Gln Ala Pro Gly Lys Gly Leu Glu Trp Val
        35                  40                  45

Gly Val Ile Gly Val Asn Gly Lys Arg Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

```
Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 115
<211> LENGTH: 13
<212> TYPE: PRT
<213> ORGANISM: Oryctolagus cuniculus

<400> SEQUENCE: 115

Arg Ala Ser Gln Ser Val Tyr Tyr Asn Asn Tyr Leu Ala
1               5                   10

<210> SEQ ID NO 116
<211> LENGTH: 7
<212> TYPE: PRT
<213> ORGANISM: Oryctolagus cuniculus

<400> SEQUENCE: 116

Ser Thr Ser Thr Leu Ala Ser
1               5

<210> SEQ ID NO 117
<211> LENGTH: 13
<212> TYPE: PRT
<213> ORGANISM: Oryctolagus cuniculus

<400> SEQUENCE: 117

Leu Gly Ser Tyr Asp Cys Ser Asn Gly Asp Cys Phe Val
1               5                   10

<210> SEQ ID NO 118
<211> LENGTH: 5
<212> TYPE: PRT
<213> ORGANISM: Oryctolagus cuniculus

<400> SEQUENCE: 118

Asn Tyr Tyr Met Gln
1               5

<210> SEQ ID NO 119
<211> LENGTH: 16
<212> TYPE: PRT
<213> ORGANISM: Oryctolagus cuniculus

<400> SEQUENCE: 119

Val Ile Gly Val Asn Gly Lys Arg Tyr Tyr Ala Ser Trp Ala Lys Gly
1               5                   10                  15

<210> SEQ ID NO 120
<211> LENGTH: 3
<212> TYPE: PRT
<213> ORGANISM: Oryctolagus cuniculus

<400> SEQUENCE: 120

Gly Asp Ile
1

<210> SEQ ID NO 121
<211> LENGTH: 113
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 121

Ala Ile Val Met Thr Gln Thr Pro Ser Ser Lys Ser Val Pro Val Gly
1               5                   10                  15

Asp Thr Val Thr Ile Asn Cys Gln Ala Ser Glu Ser Leu Tyr Asn Asn
            20                  25                  30

Asn Ala Leu Ala Trp Phe Gln Gln Lys Pro Gly Gln Pro Pro Lys Arg
        35                  40                  45

Leu Ile Tyr Asp Ala Ser Lys Leu Ala Ser Gly Val Pro Ser Arg Phe
    50                  55                  60

Ser Gly Gly Gly Ser Gly Thr Gln Phe Thr Leu Thr Ile Ser Gly Val
65                  70                  75                  80

Gln Cys Asp Asp Ala Ala Thr Tyr Tyr Cys Gly Gly Tyr Arg Ser Asp
                85                  90                  95

Ser Val Asp Gly Val Ala Phe Ala Gly Gly Thr Glu Val Val Val Lys
            100                 105                 110

Arg

<210> SEQ ID NO 122
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Ile Val Met Thr Gln Thr Pro Ser Ser Lys Ser Val Pro Val Gly
1               5                   10                  15

Asp Thr Val Thr Ile Asn Cys Gln Ala Ser Glu Ser Leu Tyr Asn Asn
            20                  25                  30

Asn Ala Leu Ala Trp Phe Gln Gln Lys Pro Gly Gln Pro Pro Lys Arg
        35                  40                  45

Leu Ile Tyr Asp Ala Ser Lys Leu Ala Ser Gly Val Pro Ser Arg Phe
    50                  55                  60

Ser Gly Gly Gly Ser Gly Thr Gln Phe Thr Leu Thr Ile Ser Gly Val
65                  70                  75                  80

Gln Cys Asp Asp Ala Ala Thr Tyr Tyr Cys Gly Gly Tyr Arg Ser Asp
                85                  90                  95

Ser Val Asp Gly Val Ala Phe Ala Gly Gly Thr Glu Val Val Val Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

```
Pro Val Thr Lys Ser Phe Asn Arg Gly Glu Cys
    210                 215
```

<210> SEQ ID NO 123
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Gln Ser Val Glu Glu Ser Gly Gly Leu Val Gln Pro Gly Ser
1               5                   10                  15

Leu Thr Leu Thr Cys Thr Ala Ser Gly Phe Asp Phe Ser Ser Asn Ala
            20                  25                  30

Met Trp Trp Val Arg Gln Ala Pro Gly Lys Gly Leu Glu Trp Ile Gly
        35                  40                  45

Cys Ile Tyr Asn Gly Asp Gly Ser Thr Tyr Tyr Ala Ser Trp Val Asn
    50                  55                  60

Gly Arg Phe Ser Ile Ser Lys Thr Ser Ser Thr Thr Val Thr Leu Gln
65                  70                  75                  80

Leu Asn Ser Leu Thr Val Ala Asp Thr Ala Thr Tyr Tyr Cys Ala Arg
                85                  90                  95

Asp Leu Asp Leu Trp Gly Pro Gly Thr Leu Val Thr Val Ser Ser
            100                 105                 110
```

<210> SEQ ID NO 124
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Gln Ser Val Glu Glu Ser Gly Gly Leu Val Gln Pro Gly Ser
1               5                   10                  15

Leu Thr Leu Thr Cys Thr Ala Ser Gly Phe Asp Phe Ser Ser Asn Ala
            20                  25                  30

Met Trp Trp Val Arg Gln Ala Pro Gly Lys Gly Leu Glu Trp Ile Gly
        35                  40                  45

Cys Ile Tyr Asn Gly Asp Gly Ser Thr Tyr Tyr Ala Ser Trp Val Asn
    50                  55                  60

Gly Arg Phe Ser Ile Ser Lys Thr Ser Ser Thr Thr Val Thr Leu Gln
65                  70                  75                  80

Leu Asn Ser Leu Thr Val Ala Asp Thr Ala Thr Tyr Tyr Cys Ala Arg
                85                  90                  95

Asp Leu Asp Leu Trp Gly Pro Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175
```

```
Ser Ser Val Val Thr Val Pro Ser Ser Leu Gly Thr Gln Thr Tyr
            180                 185                 190

Ile Cys Asn Val Asn His Lys Pro Ser Asn Thr Lys Val Asp Lys Arg
        195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 125
<211> LENGTH: 13
<212> TYPE: PRT
<213> ORGANISM: Oryctolagus cuniculus

<400> SEQUENCE: 125

Gln Ala Ser Glu Ser Leu Tyr Asn Asn Asn Ala Leu Ala
1               5                   10

<210> SEQ ID NO 126
<211> LENGTH: 7
<212> TYPE: PRT
<213> ORGANISM: Oryctolagus cuniculus

<400> SEQUENCE: 126

Asp Ala Ser Lys Leu Ala Ser
1               5

<210> SEQ ID NO 127
<211> LENGTH: 12
<212> TYPE: PRT
<213> ORGANISM: Oryctolagus cuniculus
```

<400> SEQUENCE: 127

Gly Gly Tyr Arg Ser Asp Ser Val Asp Gly Val Ala
1               5                   10

<210> SEQ ID NO 128
<211> LENGTH: 5
<212> TYPE: PRT
<213> ORGANISM: Oryctolagus cuniculus

<400> SEQUENCE: 128

Ser Asn Ala Met Trp
1               5

<210> SEQ ID NO 129
<211> LENGTH: 17
<212> TYPE: PRT
<213> ORGANISM: Oryctolagus cuniculus

<400> SEQUENCE: 129

Cys Ile Tyr Asn Gly Asp Gly Ser Thr Tyr Tyr Ala Ser Trp Val Asn
1               5                   10                  15

Gly

<210> SEQ ID NO 130
<211> LENGTH: 4
<212> TYPE: PRT
<213> ORGANISM: Oryctolagus cuniculus

<400> SEQUENCE: 130

Asp Leu Asp Leu
1

<210> SEQ ID NO 131
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Leu Thr Gln Ser Pro Ser Ser Leu Ser Ala Ser Val Gly Asp
1               5                   10                  15

Arg Val Thr Ile Asn Cys Gln Ala Ser Gln Asn Val Tyr Asn Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Arg Gly Asp Cys Phe Val Phe Gly Gly Gly Thr Lys Val Glu Ile Lys
            100                 105                 110

Arg

<210> SEQ ID NO 132
<211> LENGTH: 219
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 132

Gln Val Leu Thr Gln Ser Pro Ser Ser Leu Ser Ala Ser Val Gly Asp
1               5                   10                  15

Arg Val Thr Ile Asn Cys Gln Ala Ser Gln Asn Val Tyr Asn Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Arg Gly Asp Cys Phe Val Phe Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 133
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Gly Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ser Asp Gly Lys Thr Tyr Tyr Ala Thr Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Thr
                85                  90                  95

Arg Gly Asp Ile Trp Gly Gln Gly Thr Leu Val Thr Val Ser Ser

<210> SEQ ID NO 134
<211> LENGTH: 441
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Gly Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ser Asp Gly Lys Thr Tyr Tyr Ala Thr Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Thr
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350
```

-continued

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 135
<211> LENGTH: 13
<212> TYPE: PRT
<213> ORGANISM: Oryctolagus cuniculus

<400> SEQUENCE: 135

Gln Ala Ser Gln Asn Val Tyr Asn Asn Asn Tyr Leu Ala
1               5                   10

<210> SEQ ID NO 136
<211> LENGTH: 7
<212> TYPE: PRT
<213> ORGANISM: Oryctolagus cuniculus

<400> SEQUENCE: 136

Ser Thr Ser Thr Leu Ala Ser
1               5

<210> SEQ ID NO 137
<211> LENGTH: 13
<212> TYPE: PRT
<213> ORGANISM: Oryctolagus cuniculus

<400> SEQUENCE: 137

Leu Gly Ser Tyr Asp Cys Ser Arg Gly Asp Cys Phe Val
1               5                   10

<210> SEQ ID NO 138
<211> LENGTH: 5
<212> TYPE: PRT
<213> ORGANISM: Oryctolagus cuniculus

<400> SEQUENCE: 138

Ser Tyr Tyr Met Gln
1               5

<210> SEQ ID NO 139
<211> LENGTH: 16
<212> TYPE: PRT
<213> ORGANISM: Oryctolagus cuniculus

<400> SEQUENCE: 139

Val Ile Gly Ser Asp Gly Lys Thr Tyr Tyr Ala Thr Trp Ala Lys Gly
1               5                   10                  15

<210> SEQ ID NO 140
<211> LENGTH: 3
<212> TYPE: PRT
<213> ORGANISM: Oryctolagus cuniculus

<400> SEQUENCE: 140

Gly Asp Ile
1

<210> SEQ ID NO 141
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141

```
caagtgctga cccagactgc atcccccgtg tctgcagctg tgggaagcac agtcaccatc      60
aattgccagg ccagtcagag tgtttatgat aacaactacc tagcctggta tcagcagaaa     120
ccagggcagc ctcccaagca actgatctat tctacatcca ctctggcatc tggggtctca     180
tcgcggttca aaggcagtgg atctgggaca cagttcactc tcaccatcag cgacctggag     240
tgtgccgatg ctgccactta ctactgtcta ggcagttatg attgtagtag tggtgattgt     300
tttgttttcg gcggagggac cgaggtggtg gtcaaacgt                            339
```

<210> SEQ ID NO 142
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142

```
caagtgctga cccagactgc atcccccgtg tctgcagctg tgggaagcac agtcaccatc      60
aattgccagg ccagtcagag tgtttatgat aacaactacc tagcctggta tcagcagaaa     120
ccagggcagc ctcccaagca actgatctat tctacatcca ctctggcatc tggggtctca     180
tcgcggttca aaggcagtgg atctgggaca cagttcactc tcaccatcag cgacctggag     240
tgtgccgatg ctgccactta ctactgtcta ggcagttatg attgtagtag tggtgattgt     300
tttgttttcg gcggagggac cgaggtggtg gtcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660
```

<210> SEQ ID NO 143
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143

```
cagtcgctgg aggagtccgg gggtcgcctg gtcacgcctg gacacccct gacactcacc       60 tgcacagtct ctggactcga cctcagtagc tactacatgc aatgggtccg ccaggctcca     120
gggaaggggc tggaatggat cggagtcatt ggtattaatg ataacacata ctacgcgagc     180
tgggcgaaag gccgattcac catctccaga gcctcgtcga ccacggtgga tctgaaaatg     240
```

```
accagtctga caaccgagga cacggccacc tatttctgtg ccagagggga catctggggc    300
ccaggcaccc tcgtcaccgt ctcgagc                                        327
```

<210> SEQ ID NO 144
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144

```
cagtcgctgg aggagtccgg gggtcgcctg gtcacgcctg ggacacccct gacactcacc     60
tgcacagtct ctggactcga cctcagtagc tactacatgc aatgggtccg ccaggctcca    120 gggaagggc tggaatggat cggagtcatt ggtattaatg ataacacata ctacgcgagc     180
tgggcgaaag gccgattcac catctccaga gcctcgtcga ccacggtgga tctgaaaatg    240
accagtctga caaccgagga cacggccacc tatttctgtg ccagagggga catctggggc    300
ccaggcaccc tcgtcaccgt ctcgagcgcc tccaccaagg gcccatcggt cttccccctg    360
gcaccctcct ccaagagcac ctctgggggc acagcggccc tgggctgcct ggtcaaggac    420
tacttccccg aaccggtgac ggtgtcgtgg aactcaggcg ccctgaccag cggcgtgcac    480
accttcccgg ctgtcctaca gtcctcagga ctctactccc tcagcagcgt ggtgaccgtg    540
ccctccagca gcttgggcac ccagacctac atctgcaacg tgaatcacaa gcccagcaac    600
accaaggtgg acaagagagt tgagcccaaa tcttgtgaca aaactcacac atgcccaccg    660
tgcccagcac ctgaactcct ggggggaccg tcagtcttcc tcttcccccc aaaacccaag    720
gacaccctca tgatctcccg gacccctgag gtcacatgcg tggtggtgga cgtgagccac    780
gaagaccctg aggtcaagtt caactggtac gtggacggcg tggaggtgca taatgccaag    840
acaaagccgc gggaggagca gtacgccagc acgtaccgtg tggtcagcgt cctcaccgtc    900
ctgcaccagg actggctgaa tggcaaggag tacaagtgca aggtctccaa caaagccctc    960
ccagccccca tcgagaaaac catctccaaa gccaaagggc agccccgaga accacaggtg   1020
tacaccctgc cccatcccg ggaggagatg accaagaacc aggtcagcct gacctgcctg    1080
gtcaaaggct tctatcccag cgacatcgcc gtggagtggg agagcaatgg gcagccggag   1140
aacaactaca agaccacgcc tcccgtgctg gactccgacg gctccttctt cctctacagc   1200
aagctcaccg tggacaagag caggtggcag caggggaacg tcttctcatg ctccgtgatg   1260
catgaggctc tgcacaacca ctacacgcag aagagcctct ccctgtctcc gggtaaatga   1320
```

<210> SEQ ID NO 145
<211> LENGTH: 39
<212> TYPE: DNA
<213> ORGANISM: Oryctolagus cuniculus

<400> SEQUENCE: 145

```
caggccagtc agagtgttta tgataacaac tacctagcc                            39
```

<210> SEQ ID NO 146
<211> LENGTH: 21
<212> TYPE: DNA
<213> ORGANISM: Oryctolagus cuniculus

<400> SEQUENCE: 146

```
tctacatcca ctctggcatc t                                               21
```

<210> SEQ ID NO 147
<211> LENGTH: 39
<212> TYPE: DNA
<213> ORGANISM: Oryctolagus cuniculus

<400> SEQUENCE: 147
ctaggcagtt atgattgtag tagtggtgat tgttttgtt                               39

<210> SEQ ID NO 148
<211> LENGTH: 15
<212> TYPE: DNA
<213> ORGANISM: Oryctolagus cuniculus

<400> SEQUENCE: 148
agctactaca tgcaa                                                         15

<210> SEQ ID NO 149
<211> LENGTH: 48
<212> TYPE: DNA
<213> ORGANISM: Oryctolagus cuniculus

<400> SEQUENCE: 149
gtcattggta ttaatgataa cacatactac gcgagctggg cgaaaggc                     48

<210> SEQ ID NO 150
<211> LENGTH: 9
<212> TYPE: DNA
<213> ORGANISM: Oryctolagus cuniculus

<400> SEQUENCE: 150 ggggacatc                                                                 9

<210> SEQ ID NO 151
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
caagtgctga cccagtctcc atcctccctg tctgcatctg taggagacag agtcaccatc         60
aattgccagg ccagtcagag tgtttatgat aacaactacc tagcctggta tcagcagaaa        120
ccagggaaag ttcctaagca actgatctat tctacatcca ctctggcatc tggggtccca        180
tctcgtttca gtggcagtgg atctgggaca gatttcactc tcaccatcag cagcctgcag        240
cctgaagatg ttgcaactta ttactgtcta ggcagttatg attgtagtag tggtgattgt        300
tttgttttcg gcggaggaac caaggtggaa atcaaacgt                               339

<210> SEQ ID NO 152
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
caagtgctga cccagtctcc atcctccctg tctgcatctg taggagacag agtcaccatc         60
aattgccagg ccagtcagag tgtttatgat aacaactacc tagcctggta tcagcagaaa        120

```
ccagggaaag ttcctaagca actgatctat tctacatcca ctctggcatc tggggtccca      180
tctcgtttca gtggcagtgg atctgggaca gatttcactc tcaccatcag cagcctgcag      240
cctgaagatg ttgcaactta ttactgtcta ggcagttatg attgtagtag tggtgattgt      300
tttgttttcg gcggaggaac caaggtggaa atcaaacgta cggtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgttag    660

<210> SEQ ID NO 153
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gaggtgcagc ttgtggagtc tgggggaggc ttggtccagc ctggggggtc cctgagactc       60
tcctgtgcag tctctggact cgacctcagt agctactaca tgcaatgggt ccgtcaggct      120
ccagggaagg ggctggagtg ggtcggagtc attggtatca atgataacac atactacgcg      180
agctgggcga aaggccgatt caccatctcc agagacaatt ccaagaccac ggtgtatctt      240
caaatgaaca gcctgagagc tgaggacact gctgtgtatt tctgtgctag aggggacatc      300
tggggccaag ggaccctcgt caccgtctcg agc                                   333

<210> SEQ ID NO 154
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154
gaggtgcagc ttgtggagtc tgggggaggc ttggtccagc ctggggggtc cctgagactc       60
tcctgtgcag tctctggact cgacctcagt agctactaca tgcaatgggt ccgtcaggct      120
ccagggaagg ggctggagtg ggtcggagtc attggtatca atgataacac atactacgcg      180
agctgggcga aaggccgatt caccatctcc agagacaatt ccaagaccac ggtgtatctt      240
caaatgaaca gcctgagagc tgaggacact gctgtgtatt tctgtgctag aggggacatc      300
tggggccaag ggaccctcgt caccgtctcg agcgcctcca caagggccc atcggtcttc       360 cccctggcac cctcctccaa gagcacctct ggggcacag cggccctggg ctgcctggtc       420
aaggactact ccccgaacc ggtgacggtg tcgtggaact caggcgccct gaccagcggc      480
gtgcacacct tcccggctgt cctacagtcc tcaggactct actccctcag cagcgtggtg      540
accgtgccct ccagcagctt gggcacccag acctacatct gcaacgtgaa tcacaagccc      600
agcaacacca aggtggacaa gagagttgag cccaaatctt gtgacaaaac tcacacatgc      660
ccaccgtgcc cagcacctga actcctgggg ggaccgtcag tcttcctctt ccccccaaaa      720
cccaaggaca cctcatgat ctcccggacc cctgaggtca catgcgtggt ggtggacgtg       780
agccacgaag accctgaggt caagttcaac tggtacgtgg acggcgtgga ggtgcataat       840
```

```
gccaagacaa agccgcggga ggagcagtac gccagcacgt accgtgtggt cagcgtcctc        900
accgtcctgc accaggactg gctgaatggc aaggagtaca agtgcaaggt ctccaacaaa        960
gccctcccag cccccatcga gaaaaccatc tccaaagcca agggcagcc ccgagaacca        1020 caggtgtaca ccctgccccc atcccgggag gagatgacca gaaccaggt cagcctgacc        1080 tgcctggtca aaggcttcta tcccagcgac atcgccgtgg agtgggagag caatgggcag        1140
ccggagaaca actacaagac cacgcctccc gtgctggact ccgacggctc cttcttcctc        1200
tacagcaagc tcaccgtgga caagagcagg tggcagcagg ggaacgtctt ctcatgctcc        1260
gtgatgcatg aggctctgca caaccactac acgcagaaga gcctctccct gtctccgggt        1320
aaatga                                                                 1326
```

<210> SEQ ID NO 155
<211> LENGTH: 39
<212> TYPE: DNA
<213> ORGANISM: Oryctolagus cuniculus

<400> SEQUENCE: 155

```
caggccagtc agagtgttta tgataacaac tacctagcc                              39
```

<210> SEQ ID NO 156
<211> LENGTH: 21
<212> TYPE: DNA
<213> ORGANISM: Oryctolagus cuniculus

<400> SEQUENCE: 156

```
tctacatcca ctctggcatc t                                                 21
```

<210> SEQ ID NO 157
<211> LENGTH: 39
<212> TYPE: DNA
<213> ORGANISM: Oryctolagus cuniculus

<400> SEQUENCE: 157

```
ctaggcagtt atgattgtag tagtggtgat tgttttgtt                              39
```

<210> SEQ ID NO 158
<211> LENGTH: 15
<212> TYPE: DNA
<213> ORGANISM: Oryctolagus cuniculus

<400> SEQUENCE: 158

```
agctactaca tgcaa                                                        15
```

<210> SEQ ID NO 159
<211> LENGTH: 48
<212> TYPE: DNA
<213> ORGANISM: Oryctolagus cuniculus

<400> SEQUENCE: 159

```
gtcattggta tcaatgataa cacatactac gcgagctggg cgaaaggc                    48
```

<210> SEQ ID NO 160
<211> LENGTH: 9
<212> TYPE: DNA
<213> ORGANISM: Oryctolagus cuniculus

<400> SEQUENCE: 160

```
ggggacatc                                                                9
```

<210> SEQ ID NO 161
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
caagtgctga cccagtctcc atcctccctg tctgcatctg taggagacag agtcaccatc      60
aattgccagg ccagtcagag tgtttatgat aacaactacc tagcctggta tcagcagaaa     120
ccagggaaag ttcctaagca actgatctat tctacatcca ctctggcatc tggggtccca     180
tctcgtttca gtggcagtgg atctgggaca gatttcactc tcaccatcag cagcctgcag     240
cctgaagatg ttgcaactta ttactgtcta ggcagttatg attgtagtag tggtgattgt     300
tttgttttcg gcggaggaac caaggtggaa atcaaacgt                            339

<210> SEQ ID NO 162
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
caagtgctga cccagtctcc atcctccctg tctgcatctg taggagacag agtcaccatc      60
aattgccagg ccagtcagag tgtttatgat aacaactacc tagcctggta tcagcagaaa     120
ccagggaaag ttcctaagca actgatctat tctacatcca ctctggcatc tggggtccca     180
tctcgtttca gtggcagtgg atctgggaca gatttcactc tcaccatcag cagcctgcag     240
cctgaagatg ttgcaactta ttactgtcta ggcagttatg attgtagtag tggtgattgt     300
tttgttttcg gcggaggaac caaggtggaa atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 163
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
gaggtgcagc ttgtggagtc tgggggaggc ttggtccagc ctgggggggtc cctgagactc      60 tcctgtgcag tctctggact cgacctcagt agctactaca tgcaatgggt ccgtcaggct     120
ccagggaagg ggctggagtg ggtcggagtc attggtatca atgataacac atactacgcg     180
agctgggcga aaggccgatt caccatctcc agagacaatt ccaagaccac ggtgtatctt     240
caaatgaaca gcctgagagc tgaggacact gctgtgtatt tctgtgctag aggggacatc     300 tgggggccaag ggaccctcgt caccgtctcg agc                                  333

<210> SEQ ID NO 164
<211> LENGTH: 1326
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 164

| | | | | | |
|---|---|---|---|---|---|
| gaggtgcagc | ttgtggagtc | tgggggaggc | ttggtccagc | ctgggggtc | cctgagactc | 60 |
| tcctgtgcag | tctctggact | cgacctcagt | agctactaca | tgcaatgggt | ccgtcaggct | 120 |
| ccagggaagg | ggctggagtg | gtcggagtc | attggtatca | atgataacac | atactacgcg | 180 |
| agctgggcga | aaggccgatt | caccatctcc | agagacaatt | ccaagaccac | ggtgtatctt | 240 |
| caaatgaaca | gcctgagagc | tgaggacact | gctgtgtatt | tctgtgctag | aggggacatc | 300 |
| tggggccaag | ggaccctcgt | caccgtctcg | agcgcctcca | ccaagggccc | atcggtcttc | 360 |
| cccctggcac | cctcctccaa | gagcacctct | ggggcacag | cggccctggg | ctgcctggtc | 420 |
| aaggactact | tccccgaacc | ggtgacggtg | tcgtggaact | caggcgccct | gaccagcggc | 480 |
| gtgcacacct | tcccggctgt | cctacagtcc | tcaggactct | actccctcag | cagcgtggtg | 540 |
| accgtgccct | ccagcagctt | gggcacccag | acctacatct | gcaacgtgaa | tcacaagccc | 600 |
| agcaacacca | aggtggacgc | gagagttgag | cccaaatctt | gtgacaaaac | tcacacatgc | 660 |
| ccaccgtgcc | cagcacctga | actcctgggg | ggaccgtcag | tcttcctctt | ccccccaaaa | 720 |
| cccaaggaca | ccctcatgat | ctcccggacc | cctgaggtca | catgcgtggt | ggtggacgtg | 780 |
| agccacgaag | accctgaggt | caagttcaac | tggtacgtgg | acggcgtgga | ggtgcataat | 840 |
| gccaagacaa | agccgcggga | ggagcagtac | gccagcacgt | accgtgtggt | cagcgtcctc | 900 |
| accgtcctgc | accaggactg | gctgaatggc | aaggagtaca | agtgcaaggt | ctccaacaaa | 960 |
| gccctcccag | cccccatcga | gaaaaccatc | tccaaagcca | aagggcagcc | ccgagaacca | 1020 |
| caggtgtaca | ccctgccccc | atcccgggag | gagatgacca | agaaccaggt | cagcctgacc | 1080 |
| tgcctggtca | aaggcttcta | tcccagcgac | atcgccgtgg | agtgggagag | caatgggcag | 1140 |
| ccggagaaca | actacaagac | cacgcctccc | gtgctggact | ccgacggctc | cttcttcctc | 1200 |
| tacagcaagc | tcaccgtgga | caagagcagg | tggcagcagg | ggaacgtctt | ctcatgctcc | 1260 |
| gtgatgcatg | aggctctgca | caaccactac | acgcagaaga | gcctctccct | gtctccgggt | 1320 |
| aaatga | | | | | 1326 |

<210> SEQ ID NO 165
<211> LENGTH: 39
<212> TYPE: DNA
<213> ORGANISM: Oryctolagus cuniculus

<400> SEQUENCE: 165
caggccagtc agagtgttta tgataacaac tacctagcc        39

<210> SEQ ID NO 166
<211> LENGTH: 21
<212> TYPE: DNA
<213> ORGANISM: Oryctolagus cuniculus

<400> SEQUENCE: 166
tctacatcca ctctggcatc t        21

<210> SEQ ID NO 167

<210> SEQ ID NO 167
<211> LENGTH: 39
<212> TYPE: DNA
<213> ORGANISM: Oryctolagus cuniculus

<400> SEQUENCE: 167
ctaggcagtt atgattgtag tagtggtgat tgttttgtt                    39

<210> SEQ ID NO 168
<211> LENGTH: 15
<212> TYPE: DNA
<213> ORGANISM: Oryctolagus cuniculus

<400> SEQUENCE: 168
agctactaca tgcaa                                              15

<210> SEQ ID NO 169
<211> LENGTH: 48
<212> TYPE: DNA
<213> ORGANISM: Oryctolagus cuniculus

<400> SEQUENCE: 169
gtcattggta tcaatgataa cacatactac gcgagctggg cgaaaggc          48

<210> SEQ ID NO 170
<211> LENGTH: 9
<212> TYPE: DNA
<213> ORGANISM: Oryctolagus cuniculus

<400> SEQUENCE: 170 ggggacatc                                                      9

<210> SEQ ID NO 171
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171
caagtgctga cccagactcc atcccccgtg tctgcagctg tgggaagcac agtcaccatc    60
aattgccagg ccagtcagag tgtttatcat aacacctacc tggcctggta tcagcagaaa   120
ccagggcagc ctcccaaaca actgatctat gatgcatcca ctctggcgtc tggggtccca   180
tcgcggttca gcggcagtgg atctgggaca cagttcactc tcaccatcag cggcgtgcag   240
tgtaacgatg ctgccgctta ctactgtctg ggcagttatg attgtactaa tggtgattgt   300
tttgttttcg gcggagggac cgaggtggtg gtcaaacgt                          339

<210> SEQ ID NO 172
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
caagtgctga cccagactcc atcccccgtg tctgcagctg tgggaagcac agtcaccatc    60
aattgccagg ccagtcagag tgtttatcat aacacctacc tggcctggta tcagcagaaa   120
ccagggcagc ctcccaaaca actgatctat gatgcatcca ctctggcgtc tggggtccca   180
tcgcggttca gcggcagtgg atctgggaca cagttcactc tcaccatcag cggcgtgcag   240

```
tgtaacgatg ctgccgctta ctactgtctg ggcagttatg attgtactaa tggtgattgt    300
tttgttttcg gcggagggac cgaggtggtg gtcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660
```

<210> SEQ ID NO 173
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173

```
cagtcgctgg aggagtccgg gggtcgcctg gtcacgcctg ggacacccct gacactcacc     60
tgttccgtct ctggcatcga cctcagtggc tactacatga actgggtccg ccaggctcca    120 gggaagggc tggaatggat cggagtcatt ggtattaatg gtgccacata ctacgcgagc    180
tgggcgaaag gccgattcac catctccaaa acctcgtcga ccacggtgga tctgaaaatg    240
accagtctga caaccgagga cacggccacc tatttctgtg ccagagggga catctggggc    300
ccgggcaccc tcgtcaccgt ctcgagc                                       327
```

<210> SEQ ID NO 174
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174

```
cagtcgctgg aggagtccgg gggtcgcctg gtcacgcctg ggacacccct gacactcacc     60
tgttccgtct ctggcatcga cctcagtggc tactacatga actgggtccg ccaggctcca    120 gggaagggc tggaatggat cggagtcatt ggtattaatg gtgccacata ctacgcgagc    180
tgggcgaaag gccgattcac catctccaaa acctcgtcga ccacggtgga tctgaaaatg    240
accagtctga caaccgagga cacggccacc tatttctgtg ccagagggga catctggggc    300
ccgggcaccc tcgtcaccgt ctcgagcgcc tccaccaagg gcccatcggt cttccccctg    360
gcaccctcct ccaagagcac ctctgggggc acagcggccc tgggctgcct ggtcaaggac    420
tacttccccg aaccggtgac ggtgtcgtgg aactcaggcg ccctgaccag cggcgtgcac    480
accttcccgc tgtcctaca gtcctcagga ctctactccc tcagcagcgt ggtgaccgtg    540
ccctccagca gcttgggcac ccagacctac atctgcaacg tgaatcacaa gcccagcaac    600
accaaggtgg acaagagagt tgagcccaaa tcttgtgaca aaactcacac atgcccaccg    660
tgcccagcac ctgaactcct ggggggaccg tcagtcttcc tcttcccccc aaaacccaag    720
gacaccctca tgatctcccg gacccctgag gtcacatgcg tggtggtgga cgtgagccac    780
gaagaccctg aggtcaagtt caactggtac gtggacggcg tggaggtgca taatgccaag    840
acaaagccgc gggaggagca gtacgccagc acgtaccgtg tggtcagcgt cctcaccgtc    900
```

-continued

| | |
|---|---|
| ctgcaccagg actggctgaa tggcaaggag tacaagtgca aggtctccaa caaagccctc | 960 |
| ccagccccca tcgagaaaac catctccaaa gccaaagggc agccccgaga accacaggtg | 1020 |
| tacaccctgc ccccatcccg ggaggagatg accaagaacc aggtcagcct gacctgcctg | 1080 |
| gtcaaaggct tctatcccag cgacatcgcc gtggagtggg agagcaatgg gcagccggag | 1140 |
| aacaactaca agaccacgcc tcccgtgctg gactccgacg gctccttctt cctctacagc | 1200 |
| aagctcaccg tggacaagag caggtggcag caggggaacg tcttctcatg ctccgtgatg | 1260 |
| catgaggctc tgcacaacca ctacacgcag aagagcctct ccctgtctcc gggtaaatga | 1320 |

<210> SEQ ID NO 175
<211> LENGTH: 39
<212> TYPE: DNA
<213> ORGANISM: Oryctolagus cuniculus

<400> SEQUENCE: 175
caggccagtc agagtgttta tcataacacc tacctggcc              39

<210> SEQ ID NO 176
<211> LENGTH: 21
<212> TYPE: DNA
<213> ORGANISM: Oryctolagus cuniculus

<400> SEQUENCE: 176
gatgcatcca ctctggcgtc t                                21

<210> SEQ ID NO 177
<211> LENGTH: 39
<212> TYPE: DNA
<213> ORGANISM: Oryctolagus cuniculus

<400> SEQUENCE: 177
ctgggcagtt atgattgtac taatggtgat tgttttgtt              39

<210> SEQ ID NO 178
<211> LENGTH: 15
<212> TYPE: DNA
<213> ORGANISM: Oryctolagus cuniculus

<400> SEQUENCE: 178
ggctactaca tgaac                                       15

<210> SEQ ID NO 179
<211> LENGTH: 48
<212> TYPE: DNA
<213> ORGANISM: Oryctolagus cuniculus

<400> SEQUENCE: 179
gtcattggta ttaatggtgc cacatactac gcgagctggg cgaaaggc    48

<210> SEQ ID NO 180
<211> LENGTH: 9
<212> TYPE: DNA
<213> ORGANISM: Oryctolagus cuniculus

<400> SEQUENCE: 180 ggggacatc                                              9

<210> SEQ ID NO 181
<211> LENGTH: 339
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 181
caagtgctga cccagtctcc atcctccctg tctgcatctg taggagacag agtcaccatc      60
aattgccagg ccagtcagag tgtttatcat aacacctacc tggcctggta tcagcagaaa     120
ccagggaaag ttcctaagca actgatctat gatgcatcca ctctggcatc tggggtccca     180
tctcgtttca gtggcagtgg atctgggaca gatttcactc tcaccatcag cagcctgcag     240
cctgaagatg ttgcaactta ttactgtctg ggcagttatg attgtactaa tggtgattgt     300
tttgttttcg gcggaggaac caaggtggaa atcaaacgt                            339

<210> SEQ ID NO 182
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182
caagtgctga cccagtctcc atcctccctg tctgcatctg taggagacag agtcaccatc      60
aattgccagg ccagtcagag tgtttatcat aacacctacc tggcctggta tcagcagaaa     120
ccagggaaag ttcctaagca actgatctat gatgcatcca ctctggcatc tggggtccca     180
tctcgtttca gtggcagtgg atctgggaca gatttcactc tcaccatcag cagcctgcag     240
cctgaagatg ttgcaactta ttactgtctg ggcagttatg attgtactaa tggtgattgt     300
tttgttttcg gcggaggaac caaggtggaa atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 183
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
gaggtgcagc ttgtggagtc tgggggaggc ttggtccagc ctggggggtc cctgagactc      60
tcctgtgcag tctctggaat cgacctcagt ggctactaca tgaactgggt ccgtcaggct     120
ccagggaagg ggctggagtg ggtcggagtc attggtatta atggtgccac atactacgcg     180
agctgggcga aaggccgatt caccatctcc agagacaatt ccaagaccac ggtgtatctt     240
caaatgaaca gcctgagagc tgaggacact gctgtgtatt tctgtgctag agggacatc     300 tggggccaag ggaccctcgt caccgtctcg agc                                  333

<210> SEQ ID NO 184
<211> LENGTH: 1326
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 184

```
gaggtgcagc ttgtggagtc tgggggaggc ttggtccagc ctgggggtc cctgagactc      60
tcctgtgcag tctctggaat cgacctcagt ggctactaca tgaactgggt ccgtcaggct     120
ccagggaagg gctggagtg gtcggagtc attggtatta atggtgccac atactacgcg       180
agctgggcga aaggccgatt caccatctcc agagacaatt ccaagaccac ggtgtatctt     240
caaatgaaca gcctgagagc tgaggacact gctgtgtatt tctgtgctag aggggacatc    300
tggggccaag ggaccctcgt caccgtctcg agcgcctcca ccaagggccc atcggtcttc    360
cccctggcac cctcctccaa gagcacctct ggggcacag cggccctggg ctgcctggtc     420
aaggactact tccccgaacc ggtgacggtg tcgtggaact caggcgccct gaccagcggc    480
gtgcacacct tcccggctgt cctacagtcc tcaggactct actccctcag cagcgtggtg    540
accgtgccct ccagcagctt gggcacccag acctacatct gcaacgtgaa tcacaagccc    600
agcaacacca aggtggacaa gagagttgag cccaaatctt gtgacaaaac tcacacatgc    660
ccaccgtgcc cagcacctga actcctgggg gaccgtcag tcttcctctt ccccccaaaa    720
cccaaggaca ccctcatgat ctcccggacc cctgaggtca catgcgtggt ggtggacgtg    780
agccacgaag accctgaggt caagttcaac tggtacgtgg acggcgtgga ggtgcataat    840
gccaagacaa agccgcggga ggagcagtac gccagcacgt accgtgtggt cagcgtcctc    900
accgtcctgc accaggactg gctgaatggc aaggagtaca agtgcaaggt ctccaacaaa    960
gccctcccag cccccatcga gaaaaccatc tccaaagcca agggcagcc cgagaaccag   1020
caggtgtaca ccctgccccc atcccgggag gagatgacca gaaccaggt cagcctgacc   1080
tgcctggtca aaggcttcta tcccagcgac atcgccgtgg agtgggagag caatgggcag   1140
ccggagaaca actacaagac cacgcctccc gtgctggact ccgacggctc cttcttcctc   1200
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaatga                                                             1326
```

<210> SEQ ID NO 185
<211> LENGTH: 39
<212> TYPE: DNA
<213> ORGANISM: Oryctolagus cuniculus

<400> SEQUENCE: 185

```
caggccagtc agagtgttta tcataacacc tacctggcc                            39
```

<210> SEQ ID NO 186
<211> LENGTH: 21
<212> TYPE: DNA
<213> ORGANISM: Oryctolagus cuniculus

<400> SEQUENCE: 186

```
gatgcatcca ctctggcatc t                                               21
```

<210> SEQ ID NO 187
<211> LENGTH: 39
<212> TYPE: DNA
<213> ORGANISM: Oryctolagus cuniculus

<400> SEQUENCE: 187

```
ctgggcagtt atgattgtac taatggtgat tgttttgtt                          39
```

<210> SEQ ID NO 188
<211> LENGTH: 15
<212> TYPE: DNA
<213> ORGANISM: Oryctolagus cuniculus

<400> SEQUENCE: 188

```
ggctactaca tgaac                                                    15
```

<210> SEQ ID NO 189
<211> LENGTH: 48
<212> TYPE: DNA
<213> ORGANISM: Oryctolagus cuniculus

<400> SEQUENCE: 189

```
gtcattggta ttaatggtgc cacatactac gcgagctggg cgaaaggc                48
```

<210> SEQ ID NO 190
<211> LENGTH: 9
<212> TYPE: DNA
<213> ORGANISM: Oryctolagus cuniculus

<400> SEQUENCE: 190

```
ggggacatc                                                            9
```

<210> SEQ ID NO 191
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191

```
caagtgctga cccagtctcc atcctccctg tctgcatctg taggagacag agtcaccatc    60
aattgccagg ccagtcagag tgtttatcat aacacctacc tggcctggta tcagcagaaa   120
ccagggaaag ttcctaagca actgatctat gatgcatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtactaa tggtgattgt   300
tttgttttcg gcggaggaac caaggtggaa atcaaacgt                          339
```

<210> SEQ ID NO 192
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

```
caagtgctga cccagtctcc atcctccctg tctgcatctg taggagacag agtcaccatc    60
aattgccagg ccagtcagag tgtttatcat aacacctacc tggcctggta tcagcagaaa   120
ccagggaaag ttcctaagca actgatctat gatgcatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtactaa tggtgattgt   300
tttgttttcg gcggaggaac caaggtggaa atcaaacgta cggtggctgc accatctgtc   360
```

```
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacaggggg agagtgttag    660
```

<210> SEQ ID NO 193
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193

```
gaggtgcagc ttgtggagtc tgggggaggc ttggtccagc ctggggggtc cctgagactc     60
tcctgtgcag tctctggaat cgacctcagt ggctactaca tgaactgggt ccgtcaggct    120
ccagggaagg ggctggagtg ggtcggagtc attggtatta atggtgccac atactacgcg    180
agctgggcga aaggccgatt caccatctcc agagacaatt ccaagaccac ggtgtatctt    240
caaatgaaca gcctgagagc tgaggacact gctgtgtatt tctgtgctag aggggacatc    300
tggggccaag ggaccctcgt caccgtctcg agc                                 333
```

<210> SEQ ID NO 194
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194

```
gaggtgcagc ttgtggagtc tgggggaggc ttggtccagc ctggggggtc cctgagactc     60
tcctgtgcag tctctggaat cgacctcagt ggctactaca tgaactgggt ccgtcaggct    120
ccagggaagg ggctggagtg ggtcggagtc attggtatta atggtgccac atactacgcg    180
agctgggcga aaggccgatt caccatctcc agagacaatt ccaagaccac ggtgtatctt    240
caaatgaaca gcctgagagc tgaggacact gctgtgtatt tctgtgctag aggggacatc    300
tggggccaag ggaccctcgt caccgtctcg agcgcctcca ccaagggccc atcggtcttc    360
cccctggcac cctcctccaa gagcacctct gggggcacag cggccctggg ctgcctggtc    420
aaggactact tccccgaacc ggtgacggtg tcgtggaact caggcgccct gaccagcggc    480
gtgcacacct tcccggctgt cctacagtcc tcaggactct actccctcag cagcgtggtg    540
accgtgccct ccagcagctt gggcacccag acctacatct gcaacgtgaa tcacaagccc    600
agcaacacca aggtggacgc gagagttgag cccaaatctt gtgacaaaac tcacacatgc    660
ccaccgtgcc cagcacctga actcctgggg ggaccgtcag tcttcctctt ccccccaaaa    720
cccaaggaca ccctcatgat ctcccggacc cctgaggtca catgcgtggt ggtggacgtg    780
agccacgaag accctgaggt caagttcaac tggtacgtgg acggcgtgga ggtgcataat    840
gccaagacaa agccgcggga ggagcagtac gccagcacgt accgtgtggt cagcgtcctc    900
accgtcctgc accaggactg gctgaatggc aaggagtaca agtgcaaggt ctccaacaaa    960
gccctcccag cccccatcga gaaaaccatc tccaaagcca aagggcagcc ccgagaacca   1020
caggtgtaca ccctgccccc atcccgggag gagatgacca agaaccaggt cagcctgacc   1080
```

```
tgcctggtca aaggcttcta tcccagcgac atcgccgtgg agtgggagag caatgggcag    1140
ccggagaaca actacaagac cacgcctccc gtgctggact ccgacggctc cttcttcctc    1200
tacagcaagc tcaccgtgga caagagcagg tggcagcagg ggaacgtctt ctcatgctcc    1260
gtgatgcatg aggctctgca caaccactac acgcagaaga gcctctccct gtctccgggt    1320
aaatga                                                                1326
```

<210> SEQ ID NO 195
<211> LENGTH: 39
<212> TYPE: DNA
<213> ORGANISM: Oryctolagus cuniculus

<400> SEQUENCE: 195

```
caggccagtc agagtgttta tcataacacc tacctggcc                              39
```

<210> SEQ ID NO 196
<211> LENGTH: 21
<212> TYPE: DNA
<213> ORGANISM: Oryctolagus cuniculus

<400> SEQUENCE: 196

```
gatgcatcca ctctggcatc t                                                 21
```

<210> SEQ ID NO 197
<211> LENGTH: 39
<212> TYPE: DNA
<213> ORGANISM: Oryctolagus cuniculus

<400> SEQUENCE: 197

```
ctgggcagtt atgattgtac taatggtgat tgttttgtt                              39
```

<210> SEQ ID NO 198
<211> LENGTH: 15
<212> TYPE: DNA
<213> ORGANISM: Oryctolagus cuniculus

<400> SEQUENCE: 198

```
ggctactaca tgaac                                                        15
```

<210> SEQ ID NO 199
<211> LENGTH: 48
<212> TYPE: DNA
<213> ORGANISM: Oryctolagus cuniculus

<400> SEQUENCE: 199

```
gtcattggta ttaatggtgc cacatactac gcgagctggg cgaaaggc                    48
```

<210> SEQ ID NO 200
<211> LENGTH: 9
<212> TYPE: DNA
<213> ORGANISM: Oryctolagus cuniculus

<400> SEQUENCE: 200

```
ggggacatc                                                                9
```

<210> SEQ ID NO 201
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
caagtgctga cccagactgc atcccccgtg tctgcagctg tgggaagcac agtcaccatc    60
aattgccagg ccagtcagag tgtttataat tacaactacc ttgcctggta tcagcagaaa   120
ccagggcagc ctcccaagca actgatctat tctacatcca ctctggcatc tggggtctca   180
tcgcgattca aaggcagtgg atctgggaca cagttcactc tcaccatcag cgacgtgcag   240
tgtgacgatg ctgccactta ctactgtcta ggcagttatg actgtagtac tggtgattgt   300
tttgttttcg gcggagggac cgaggtggtg gtcaaacgt                          339

<210> SEQ ID NO 202
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
caagtgctga cccagactgc atcccccgtg tctgcagctg tgggaagcac agtcaccatc    60
aattgccagg ccagtcagag tgtttataat tacaactacc ttgcctggta tcagcagaaa   120
ccagggcagc ctcccaagca actgatctat tctacatcca ctctggcatc tggggtctca   180
tcgcgattca aaggcagtgg atctgggaca cagttcactc tcaccatcag cgacgtgcag   240
tgtgacgatg ctgccactta ctactgtcta ggcagttatg actgtagtac tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

<210> SEQ ID NO 203
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
caggagcagc tgaaggagtc cggggggtcgc ctggtcacgc ctgggacatc cctgacactc    60
acctgcaccg tctctggaat cgacctcagt aaccactaca tgcaatgggt ccgccaggct   120
ccagggaagg ggctggagtg gatcggagtc gttggtatta atggtcgcac atactacgcg   180
agctgggcga aaggccgatt caccatctcc agaacctcgt cgaccacggt ggatctgaaa   240
atgaccaggc tgacaaccga ggacacggcc acctatttct gtgccagagg ggacatctgg   300
ggcccaggca ccctggtcac cgtctcgagc                                    330

<210> SEQ ID NO 204
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204

```
caggagcagc tgaaggagtc cggggtcgc ctggtcacgc ctgggacatc cctgacactc      60
acctgcaccg tctctggaat cgacctcagt aaccactaca tgcaatgggt ccgccaggct    120
ccagggaagg gctggagtg atcggagtc gttggtatta atggtcgcac atactacgcg     180
agctgggcga aaggccgatt caccatctcc agaacctcgt cgaccacggt ggatctgaaa    240
atgaccaggc tgacaaccga ggacacggcc acctatttct gtgccagagg ggacatctgg    300
ggcccaggca ccctggtcac cgtctcgagc gcctccacca agggcccatc ggtcttcccc    360
ctggcaccct cctccaagag cacctctggg ggcacagcgg ccctgggctg cctggtcaag    420
gactacttcc ccgaaccggt gacggtgtcg tggaactcag cgccctgaca gcggcgtg     480
cacaccttcc cggctgtcct acagtcctca ggactctact ccctcagcag cgtggtgacc    540
gtgccctcca gcagcttggg cacccagacc tacatctgca acgtgaatca caagcccagc    600
aacaccaagg tggacaagag agttgagccc aaatcttgtg acaaaactca cacatgccca    660
ccgtgcccag cacctgaact cctgggggga ccgtcagtct tcctcttccc cccaaaaccc    720
aaggacaccc tcatgatctc ccggacccct gaggtcacat gcgtggtggt ggacgtgagc    780
cacgaagacc ctgaggtcaa gttcaactgg tacgtggacg gcgtggaggt gcataatgcc    840
aagacaaagc cgcgggagga gcagtacgcc agcacgtacc gtgtggtcag cgtcctcacc    900
gtcctgcacc aggactggct gaatggcaag gagtacaagt gcaaggtctc caacaaagcc    960
ctcccagccc ccatcgagaa aaccatctcc aaagccaaag ggcagccccg agaaccacag   1020
gtgtacaccc tgcccccatc ccgggaggag atgaccaaga accaggtcag cctgacctgc   1080
ctggtcaaag gcttctatcc agcgacatc gccgtggagt gggagagcaa tgggcagccg   1140
gagaacaact acaagaccac gcctcccgtg ctggactccg acggctcctt cttcctctac   1200
agcaagctca ccgtggacaa gagcaggtgg cagcagggga acgtcttctc atgctccgtg   1260
atgcatgagg ctctgcacaa ccactacacg cagaagagcc tctccctgtc tccgggtaaa   1320
tga                                                                 1323
```

<210> SEQ ID NO 205
<211> LENGTH: 39
<212> TYPE: DNA
<213> ORGANISM: Oryctolagus cuniculus

<400> SEQUENCE: 205

```
caggccagtc agagtgttta taattacaac taccttgcc                            39
```

<210> SEQ ID NO 206
<211> LENGTH: 21
<212> TYPE: DNA
<213> ORGANISM: Oryctolagus cuniculus

<400> SEQUENCE: 206

```
tctacatcca ctctggcatc t                                               21
```

<210> SEQ ID NO 207
<211> LENGTH: 39
<212> TYPE: DNA
<213> ORGANISM: Oryctolagus cuniculus

<400> SEQUENCE: 207

```
ctaggcagtt atgactgtag tactggtgat tgttttgtt                            39
```

<210> SEQ ID NO 208
<211> LENGTH: 15
<212> TYPE: DNA
<213> ORGANISM: Oryctolagus cuniculus

<400> SEQUENCE: 208
aaccactaca tgcaa                                                          15

<210> SEQ ID NO 209
<211> LENGTH: 48
<212> TYPE: DNA
<213> ORGANISM: Oryctolagus cuniculus

<400> SEQUENCE: 209
gtcgttggta ttaatggtcg cacatactac gcgagctggg cgaaaggc                       48

<210> SEQ ID NO 210
<211> LENGTH: 9
<212> TYPE: DNA
<213> ORGANISM: Oryctolagus cuniculus

<400> SEQUENCE: 210 ggggacatc                                                                   9

<210> SEQ ID NO 211
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
caagtgctga cccagtctcc atcctccctg tctgcatctg taggagacag agtcaccatc           60
aattgccagg ccagtcagag tgtttacaat tacaactacc ttgcctggta tcagcagaaa          120
ccagggaaag ttcctaagca actgatctat tctacatcca ctctggcatc tggggtccca          180
tctcgtttca gtggcagtgg atctgggaca gatttcactc tcaccatcag cagcctgcag          240
cctgaagatg ttgcaactta ttactgtctg ggcagttatg attgtagtac tggtgattgt          300
tttgttttcg gcggaggaac caaggtggaa atcaaacgt                                 339

<210> SEQ ID NO 212
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
caagtgctga cccagtctcc atcctccctg tctgcatctg taggagacag agtcaccatc           60
aattgccagg ccagtcagag tgtttacaat tacaactacc ttgcctggta tcagcagaaa          120
ccagggaaag ttcctaagca actgatctat tctacatcca ctctggcatc tggggtccca          180
tctcgtttca gtggcagtgg atctgggaca gatttcactc tcaccatcag cagcctgcag          240
cctgaagatg ttgcaactta ttactgtctg ggcagttatg attgtagtac tggtgattgt          300
tttgttttcg gcggaggaac caaggtggaa atcaaacgta cggtggctgc accatctgtc          360
ttcatcttcc cgccatctga tgagcagttg aaatctggaa ctgcctctgt tgtgtgcctg          420
ctgaataact tctatcccag agaggccaaa gtacagtgga aggtggataa cgccctccaa          480

```
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggga agagtgttag    660
```

<210> SEQ ID NO 213
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213

```
gaggtgcagc ttgtggagtc tgggggaggc ttggtccagc ctgggggggtc cctgagactc    60 tcctgtgcag tctctggaat cgacctcagt aaccactaca tgcaatgggt ccgtcaggct   120
ccagggaagg ggctggagtg ggtcggagtc gttggtatca atggtcgcac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag gaccctcgt caccgtctcg agc                                  333
```

<210> SEQ ID NO 214
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214

```
gaggtgcagc ttgtggagtc tgggggaggc ttggtccagc ctgggggggtc cctgagactc    60 tcctgtgcag tctctggaat cgacctcagt aaccactaca tgcaatgggt ccgtcaggct   120
ccagggaagg ggctggagtg ggtcggagtc gttggtatca atggtcgcac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag gaccctcgt caccgtctcg agcgcctcca ccaagggccc atcggtcttc   360
cccctggcac cctcctccaa gagcacctct ggggggcacag cggccctggg ctgcctggtc   420
aaggactact cccccgaacc ggtgacggtg tcgtggaact caggcgccct gaccagcggc   480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacaa gagagttgag cccaaatctt gtgacaaaac tcacacatgc   660
ccaccgtgcc cagcacctga actcctgggg ggaccgtcag tcttcctctt ccccccaaaa   720
cccaaggaca cctcatgat ctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag ccccccatcga gaaaaccatc tccaaagcca agggcagcc ccgagaacca   1020 caggtgtaca ccctgccccc atcccgggag gagatgacca gaaccaggt cagcctgacc   1080 tgcctggtca aaggcttcta tcccagcgac atcgccgtgg agtgggagag caatgggcag   1140
```

```
ccggagaaca actacaagac cacgcctccc gtgctggact ccgacggctc cttcttcctc    1200
tacagcaagc tcaccgtgga caagagcagg tggcagcagg ggaacgtctt ctcatgctcc    1260
gtgatgcatg aggctctgca caaccactac acgcagaaga gcctctccct gtctccgggt    1320
aaatga                                                               1326

<210> SEQ ID NO 215
<211> LENGTH: 39
<212> TYPE: DNA
<213> ORGANISM: Oryctolagus cuniculus

<400> SEQUENCE: 215
caggccagtc agagtgttta caattacaac taccttgcc                           39

<210> SEQ ID NO 216
<211> LENGTH: 21
<212> TYPE: DNA
<213> ORGANISM: Oryctolagus cuniculus

<400> SEQUENCE: 216
tctacatcca ctctggcatc t                                              21

<210> SEQ ID NO 217
<211> LENGTH: 39
<212> TYPE: DNA
<213> ORGANISM: Oryctolagus cuniculus

<400> SEQUENCE: 217
ctgggcagtt atgattgtag tactggtgat tgttttgtt                           39

<210> SEQ ID NO 218
<211> LENGTH: 15
<212> TYPE: DNA
<213> ORGANISM: Oryctolagus cuniculus

<400> SEQUENCE: 218
aaccactaca tgcaa                                                     15

<210> SEQ ID NO 219
<211> LENGTH: 48
<212> TYPE: DNA
<213> ORGANISM: Oryctolagus cuniculus

<400> SEQUENCE: 219
gtcgttggta tcaatggtcg cacatactac gcgagctggg cgaaaggc                 48

<210> SEQ ID NO 220
<211> LENGTH: 9
<212> TYPE: DNA
<213> ORGANISM: Oryctolagus cuniculus

<400> SEQUENCE: 220 ggggacatc                                                            9

<210> SEQ ID NO 221
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
```

```
caagtgctga cccagactcc atccccgtg tctgcagctg tgggaagcac agtcaccatc        60
aattgccagg ccagtcagaa tgtttataat aacaactacc tagcctggta tcagcagaaa       120
ccagggcagc ctcccaagca actgatctat tctacgtcca ctctggcatc tggggtctca       180
tcgcgattca gaggcagtgg atctgggaca cagttcactc tcaccatcag cgacgtgcag       240
tgtgacgatg ctgccactta ctactgtcta ggcagttatg attgtagtcg tggtgattgt       300
tttgttttcg gcggagggac cgaggtggtg gtcaaacgt                              339
```

<210> SEQ ID NO 222
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222

```
caagtgctga cccagactcc atccccgtg tctgcagctg tgggaagcac agtcaccatc        60
aattgccagg ccagtcagaa tgtttataat aacaactacc tagcctggta tcagcagaaa       120
ccagggcagc ctcccaagca actgatctat tctacgtcca ctctggcatc tggggtctca       180
tcgcgattca gaggcagtgg atctgggaca cagttcactc tcaccatcag cgacgtgcag       240
tgtgacgatg ctgccactta ctactgtcta ggcagttatg attgtagtcg tggtgattgt       300
tttgttttcg gcggagggac cgaggtggtg gtcaaacgta cggtggctgc accatctgtc       360
ttcatcttcc cgccatctga tgagcagttg aaatctggaa ctgcctctgt tgtgtgcctg       420
ctgaataact tctatcccag agaggccaaa gtacagtgga aggtggataa cgccctccaa       480
tcgggtaact cccaggagag tgtcacagag caggacagca aggacagcac ctacagcctc       540
agcagcaccc tgacgctgag caaagcagac tacgagaaac acaaagtcta cgcctgcgaa       600
gtcacccatc agggcctgag ctcgcccgtc acaaagagct tcaacagggg agagtgttag       660
```

<210> SEQ ID NO 223
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223

```
cagtcgctgg aggagtccgg gggtcgcctg gtcacgcctg gacacccct gacactcacc        60 tgcacagtct ctggaatcgg cctcagtagc tactacatgc agtgggtccg ccagtctcca       120
gggagggggc tggaatggat cggagtcatt ggtagtgatg gtaagacata ctacgcgacc       180
tgggcgaaag gccgattcac catctccaag acctcgtcga ccacggtgga tctgagaatg       240
gccagtctga caaccgagga cacggccacc tatttctgta ccagagggga catctggggc       300
ccggggaccc tcgtcaccgt ctcgagc                                            327
```

<210> SEQ ID NO 224
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224

```
cagtcgctgg aggagtccgg gggtcgcctg gtcacgcctg ggacacccct gacactcacc    60
tgcacagtct ctggaatcgg cctcagtagc tactacatgc agtgggtccg ccagtctcca   120 gggaggggc tggaatggat cggagtcatt ggtagtgatg gtaagacata ctacgcgacc   180
tgggcgaaag gccgattcac catctccaag acctcgtcga ccacggtgga tctgagaatg   240
gccagtctga caaccgagga cacggccacc tatttctgta ccagagggga catctggggc   300
ccggggaccc tcgtcaccgt ctcgagcgcc tccaccaagg gcccatcggt cttcccctg   360 gcaccctcct ccaagagcac ctctgggggc acagcggccc tgggctgcct ggtcaaggac   420
tacttccccg aaccggtgac ggtgtcgtgg aactcaggcg ccctgaccag cggcgtgcac   480
accttcccgg ctgtcctaca gtcctcagga ctctactccc tcagcagcgt ggtgaccgtg   540
ccctccagca gcttgggcac ccagacctac atctgcaacg tgaatcacaa gcccagcaac   600
accaaggtgg acaagagagt tgagcccaaa tcttgtgaca aaactcacac atgcccaccg   660
tgcccagcac ctgaactcct ggggggaccg tcagtcttcc tcttcccccc aaaacccaag   720
gacaccctca tgatctcccg gacccctgag gtcacatgcg tggtggtgga cgtgagccac   780
gaagaccctg aggtcaagtt caactggtac gtggacggcg tggaggtgca taatgccaag   840
acaaagccgc gggaggagca gtacgccagc acgtaccgtg tggtcagcgt cctcaccgtc   900
ctgcaccagg actggctgaa tgcaaggag tacaagtgca aggtctccaa caaagccctc   960
ccagccccca tcgagaaaac catctccaaa gccaagggc agcccgaga accacaggtg   1020 tacaccctgc ccccatcccg ggaggagatg accaagaacc aggtcagcct gacctgcctg   1080
gtcaaaggct tctatcccag cgacatcgcc gtggagtggg agagcaatgg gcagccggag   1140
aacaactaca agaccacgcc tcccgtgctg gactccgacg gctccttctt cctctacagc   1200
aagctcaccg tggacaagag caggtggcag caggggaacg tcttctcatg ctccgtgatg   1260
catgaggctc tgcacaacca ctacacgcag aagagcctct ccctgtctcc gggtaaatga   1320
```

<210> SEQ ID NO 225
<211> LENGTH: 39
<212> TYPE: DNA
<213> ORGANISM: Oryctolagus cuniculus

<400> SEQUENCE: 225

```
caggccagtc agaatgttta taataacaac tacctagcc                           39
```

<210> SEQ ID NO 226
<211> LENGTH: 21
<212> TYPE: DNA
<213> ORGANISM: Oryctolagus cuniculus

<400> SEQUENCE: 226

```
tctacgtcca ctctggcatc t                                              21
```

<210> SEQ ID NO 227
<211> LENGTH: 39
<212> TYPE: DNA
<213> ORGANISM: Oryctolagus cuniculus

<400> SEQUENCE: 227

```
ctaggcagtt atgattgtag tcgtggtgat tgttttgtt                           39
```

<210> SEQ ID NO 228
<211> LENGTH: 15
<212> TYPE: DNA
<213> ORGANISM: Oryctolagus cuniculus

<400> SEQUENCE: 228
agctactaca tgcag                                                        15

<210> SEQ ID NO 229
<211> LENGTH: 48
<212> TYPE: DNA
<213> ORGANISM: Oryctolagus cuniculus

<400> SEQUENCE: 229
gtcattggta gtgatggtaa gacatactac gcgacctggg cgaaaggc                    48

<210> SEQ ID NO 230
<211> LENGTH: 9
<212> TYPE: DNA
<213> ORGANISM: Oryctolagus cuniculus

<400> SEQUENCE: 230 ggggacatc                                                                9

<210> SEQ ID NO 231
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
caagtgctga cccagtctcc atcctccctg tctgcatctg taggagacag agtcaccatc       60
aattgccagg ccagtcagaa tgtttacaat aacaactacc tagcctggta tcagcagaaa      120
ccagggaaag ttcctaagca actgatctat tctacatcca ctctggcatc tggggtccca      180
tctcgtttca gtggcagtgg atctgggaca gatttcactc tcaccatcag cagcctgcag      240
cctgaagatg ttgcaactta ttactgtctg ggcagttatg attgtagtcg tggtgattgt      300
tttgttttcg gcggaggaac caaggtggaa atcaaacgt                             339

<210> SEQ ID NO 232
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
caagtgctga cccagtctcc atcctccctg tctgcatctg taggagacag agtcaccatc       60
aattgccagg ccagtcagaa tgtttacaat aacaactacc tagcctggta tcagcagaaa      120
ccagggaaag ttcctaagca actgatctat tctacatcca ctctggcatc tggggtccca      180
tctcgtttca gtggcagtgg atctgggaca gatttcactc tcaccatcag cagcctgcag      240
cctgaagatg ttgcaactta ttactgtctg ggcagttatg attgtagtcg tggtgattgt      300
tttgttttcg gcggaggaac caaggtggaa atcaaacgta cggtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600

```
gtcacccatc agggcctgag ctcgcccgtc acaaagagct tcaacagggg agagtgttag    660
```

<210> SEQ ID NO 233
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233

```
gaggtgcagc ttgtggagtc tgggggaggc ttggtccagc ctgggggtc  cctgagactc    60
tcctgtgcag tctctggaat cggcctcagt agctactaca tgcaatgggt ccgtcaggct   120
ccagggaagg ggctggagtg ggtcggagtc attggtagtg atggtaagac atactacgcg   180
acctgggcga aaggccgatt caccatctcc agagacaatt ccaagaccac ggtgtatctt   240
caaatgaaca gcctgagagc tgaggacact gctgtgtatt tctgtaccag aggggacatc   300
tggggccaag ggaccctcgt caccgtctcg agc                                 333
```

<210> SEQ ID NO 234
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 234

```
gaggtgcagc ttgtggagtc tgggggaggc ttggtccagc ctgggggtc  cctgagactc    60
tcctgtgcag tctctggaat cggcctcagt agctactaca tgcaatgggt ccgtcaggct   120
ccagggaagg ggctggagtg ggtcggagtc attggtagtg atggtaagac atactacgcg   180
acctgggcga aaggccgatt caccatctcc agagacaatt ccaagaccac ggtgtatctt   240
caaatgaaca gcctgagagc tgaggacact gctgtgtatt tctgtaccag aggggacatc   300
tggggccaag ggaccctcgt caccgtctcg agcgcctcca ccaagggccc atcggtcttc   360
cccctggcac cctcctccaa gagcacctct ggggcacag  cggccctggg ctgcctggtc   420
aaggactact tccccgaacc ggtgacggtg tcgtggaact caggcgccct gaccagcggc   480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacaa gagagttgag cccaaatctt gtgacaaaac tcacacatgc   660
ccaccgtgcc cagcacctga actcctgggg ggaccgtcag tcttcctctt ccccccaaaa   720
cccaaggaca cctcatgat  ctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag cccccatcga gaaaaccatc tccaaagcca agggcagcc  cgagaaccca  1020
caggtgtaca ccctgccccc atcccgggag gagatgacca agaaccaggt cagcctgacc  1080
tgcctggtca aaggcttcta tcccagcgac atcgccgtgg agtgggagag caatgggcag  1140
ccggagaaca actacaagac cacgcctccc gtgctggact ccgacggctc cttcttcctc  1200
tacagcaagc tcaccgtgga caagagcagg tggcagcagg ggaacgtctt ctcatgctcc  1260
gtgatgcatg aggctctgca caaccactac acgcagaaga gcctctccct gtctccgggt  1320
``` aaatga                                                          1326

<210> SEQ ID NO 235
<211> LENGTH: 39
<212> TYPE: DNA
<213> ORGANISM: Oryctolagus cuniculus

<400> SEQUENCE: 235
caggccagtc agaatgttta caataacaac tacctagcc                        39

<210> SEQ ID NO 236
<211> LENGTH: 21
<212> TYPE: DNA
<213> ORGANISM: Oryctolagus cuniculus

<400> SEQUENCE: 236
tctacatcca ctctggcatc t                                           21

<210> SEQ ID NO 237
<211> LENGTH: 39
<212> TYPE: DNA
<213> ORGANISM: Oryctolagus cuniculus

<400> SEQUENCE: 237
ctgggcagtt atgattgtag tcgtggtgat tgttttgtt                        39

<210> SEQ ID NO 238
<211> LENGTH: 15
<212> TYPE: DNA
<213> ORGANISM: Oryctolagus cuniculus

<400> SEQUENCE: 238
agctactaca tgcaa                                                  15

<210> SEQ ID NO 239
<211> LENGTH: 48
<212> TYPE: DNA
<213> ORGANISM: Oryctolagus cuniculus

<400> SEQUENCE: 239
gtcattggta gtgatggtaa gacatactac gcgacctggg cgaaaggc              48

<210> SEQ ID NO 240
<211> LENGTH: 9
<212> TYPE: DNA
<213> ORGANISM: Oryctolagus cuniculus

<400> SEQUENCE: 240 ggggacatc                                                          9

<210> SEQ ID NO 241
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241
caggtgctga cccagactgc atcccccgtg tctccagctg tgggaagcac agtcaccatc      60
aattgccggg ccagtcagag tgtttattat aacaactacc tagcctggta tcagcagaaa     120
ccagggcagc ctcccaagca actgatctat tctacatcca ctctggcatc tggggtctca     180

```
tcgcggttca aaggcagtgg atctgggaca cagttcactc tcaccatcag cgacgtgcag    240
tgtgacgatg ctgccactta ctactgtcta ggcagttatg attgtagtaa tggtgattgt    300
tttgttttcg gcggagggac cgaggtggtg gtcaaacgt                           339
```

<210> SEQ ID NO 242
<211> LENGTH: 660
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 242

```
caggtgctga cccagactgc atccccgtg tctccagctg tgggaagcac agtcaccatc     60
aattgccggg ccagtcagag tgtttattat aacaactacc tagcctggta tcagcagaaa   120
ccagggcagc ctcccaagca actgatctat tctacatcca ctctggcatc tggggtctca   180
tcgcggttca aaggcagtgg atctgggaca cagttcactc tcaccatcag cgacgtgcag   240
tgtgacgatg ctgccactta ctactgtcta ggcagttatg attgtagtaa tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct caacaggggg agagtgttag   660
```

<210> SEQ ID NO 243
<211> LENGTH: 327
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 243

```
cagtcgctgg aggagtccgg gggtcgcctg gtcacgcctg gaggatccct gacactcacc    60
tgcacagtct ctggaatcga cgtcactaac tactatatgc aatgggtccg ccaggctcca   120
gggaaggggc tggaatggat cggagtcatt ggtgtgaatg gtaagagata ctacgcgagc   180
tgggcgaaag gccgattcac catctccaaa acctcgtcga ccacggtgga tctgaaaatg   240
accagtctga caaccgagga cacggccacc tatttctgtg ccagaggcga catctggggc   300
ccggggaccc tcgtcaccgt ctcgagc                                       327
```

<210> SEQ ID NO 244
<211> LENGTH: 1320
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 244

```
cagtcgctgg aggagtccgg gggtcgcctg gtcacgcctg gaggatccct gacactcacc    60
tgcacagtct ctggaatcga cgtcactaac tactatatgc aatgggtccg ccaggctcca   120
gggaaggggc tggaatggat cggagtcatt ggtgtgaatg gtaagagata ctacgcgagc   180
```

```
tgggcgaaag gccgattcac catctccaaa acctcgtcga ccacggtgga tctgaaaatg    240
accagtctga caaccgagga cacggccacc tatttctgtg ccagaggcga catctggggc    300
ccggggaccc tcgtcaccgt ctcgagcgcc tccaccaagg gcccatcggt cttccccctg    360
gcaccctcct ccaagagcac ctctgggggc acagcggccc tgggctgcct ggtcaaggac    420
tacttccccg aaccggtgac ggtgtcgtgg aactcaggcg ccctgaccag cggcgtgcac    480
accttcccgg ctgtcctaca gtcctcagga ctctactccc tcagcagcgt ggtgaccgtg    540
ccctccagca gcttgggcac ccagacctac atctgcaacg tgaatcacaa gcccagcaac    600
accaaggtgg acaagagagt tgagcccaaa tcttgtgaca aaactcacac atgcccaccg    660
tgcccagcac ctgaactcct ggggggaccg tcagtcttcc tcttcccccc aaaacccaag    720
gacaccctca tgatctcccg gacccctgag gtcacatgcg tggtggtgga cgtgagccac    780
gaagaccctg aggtcaagtt caactggtac gtggacggcg tggaggtgca taatgccaag    840
acaaagccgc gggaggagca gtacgccagc acgtaccgtg tggtcagcgt cctcaccgtc    900
ctgcaccagg actggctgaa tggcaaggag tacaagtgca aggtctccaa caaagccctc    960
ccagccccca tcgagaaaac catctccaaa gccaaagggc agccccgaga accacaggtg   1020
tacaccctgc cccatcccg ggaggagatg accaagaacc aggtcagcct gacctgcctg   1080
gtcaaaggct tctatcccag cgacatcgcc gtggagtggg agagcaatgg gcagccggag   1140
aacaactaca agaccacgcc tcccgtgctg gactccgacg gctccttctt cctctacagc   1200
aagctcaccg tggacaagag caggtggcag caggggaacg tcttctcatg ctccgtgatg   1260
catgaggctc tgcacaacca ctacacgcag aagagcctct ccctgtctcc gggtaaatga   1320
```

```
<210> SEQ ID NO 245
<211> LENGTH: 39
<212> TYPE: DNA
<213> ORGANISM: Oryctolagus cuniculus

<400> SEQUENCE: 245
cgggccagtc agagtgttta ttataacaac tacctagcc                             39

<210> SEQ ID NO 246
<211> LENGTH: 21
<212> TYPE: DNA
<213> ORGANISM: Oryctolagus cuniculus

<400> SEQUENCE: 246
tctacatcca ctctggcatc t                                                21

<210> SEQ ID NO 247
<211> LENGTH: 39
<212> TYPE: DNA
<213> ORGANISM: Oryctolagus cuniculus

<400> SEQUENCE: 247
ctaggcagtt atgattgtag taatggtgat tgttttgtt                             39

<210> SEQ ID NO 248
<211> LENGTH: 15
<212> TYPE: DNA
<213> ORGANISM: Oryctolagus cuniculus

<400> SEQUENCE: 248
aactactata tgcaa                                                       15
```

<210> SEQ ID NO 249
<211> LENGTH: 48
<212> TYPE: DNA
<213> ORGANISM: Oryctolagus cuniculus

<400> SEQUENCE: 249
gtcattggtg tgaatggtaa gagatactac gcgagctggg cgaaaggc        48

<210> SEQ ID NO 250
<211> LENGTH: 9
<212> TYPE: DNA
<213> ORGANISM: Oryctolagus cuniculus

<400> SEQUENCE: 250 ggcgacatc        9

<210> SEQ ID NO 251
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
caagtgctga cccagtctcc atcctccctg tctgcatctg taggagacag agtcaccatc        60
aattgccggg ccagtcagag tgtttactat aacaactacc tagcctggta tcagcagaaa       120
ccagggaaag ttcctaagca actgatctat tctacatcca ctctggcatc tggggtccca       180
tctcgtttca gtggcagtgg atctgggaca gatttcactc tcaccatcag cagcctgcag       240
cctgaagatg ttgcaactta ttactgtctg ggcagttatg attgtagtaa tggtgattgt       300
tttgttttcg gcggaggaac caaggtggaa atcaaacgt                             339

<210> SEQ ID NO 252
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
caagtgctga cccagtctcc atcctccctg tctgcatctg taggagacag agtcaccatc        60
aattgccggg ccagtcagag tgtttactat aacaactacc tagcctggta tcagcagaaa       120
ccagggaaag ttcctaagca actgatctat tctacatcca ctctggcatc tggggtccca       180
tctcgtttca gtggcagtgg atctgggaca gatttcactc tcaccatcag cagcctgcag       240
cctgaagatg ttgcaactta ttactgtctg ggcagttatg attgtagtaa tggtgattgt       300
tttgttttcg gcggaggaac caaggtggaa atcaaacgta cggtggctgc accatctgtc       360
ttcatcttcc cgccatctga tgagcagttg aaatctggaa ctgcctctgt tgtgtgcctg       420
ctgaataact tctatcccag agaggccaaa gtacagtgga aggtggataa cgccctccaa       480
tcgggtaact cccaggagag tgtcacagag caggacagca aggacagcac ctacagcctc       540
agcagcaccc tgacgctgag caaagcagac tacgagaaac acaaagtcta cgcctgcgaa       600
gtcacccatc agggcctgag ctcgcccgtc acaaagagct tcaacagggg agagtgttag       660

<210> SEQ ID NO 253
<211> LENGTH: 333

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253

| gaggtgcagc ttgtggagtc tgggggaggc ttggtccagc ctggggggtc cctgagactc | 60 |
| tcctgtgcag tctctggaat cgacgtcact aactactaca tgcaatgggt ccgtcaggct | 120 |
| ccagggaagg ggctggagtg ggtcggagtc attggtgtga atggtaagag atactacgcg | 180 |
| agctgggcga aaggccgatt caccatctcc agagacaatt ccaagaccac ggtgtatctt | 240 |
| caaatgaaca gcctgagagc tgaggacact gctgtgtatt tctgtgccag aggggacatc | 300 |
| tggggccaag ggaccctcgt caccgtctcg agc | 333 |

<210> SEQ ID NO 254
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254

| gaggtgcagc ttgtggagtc tgggggaggc ttggtccagc ctggggggtc cctgagactc | 60 |
| tcctgtgcag tctctggaat cgacgtcact aactactaca tgcaatgggt ccgtcaggct | 120 |
| ccagggaagg ggctggagtg ggtcggagtc attggtgtga atggtaagag atactacgcg | 180 |
| agctgggcga aaggccgatt caccatctcc agagacaatt ccaagaccac ggtgtatctt | 240 |
| caaatgaaca gcctgagagc tgaggacact gctgtgtatt tctgtgccag aggggacatc | 300 |
| tggggccaag ggaccctcgt caccgtctcg agcgcctcca caagggccc atcggtcttc | 360 |
| cccctggcac cctcctccaa gagcacctct gggggcacag cggccctggg ctgcctggtc | 420 |
| aaggactact tccccgaacc ggtgacggtg tcgtggaact caggcgccct gaccagcggc | 480 |
| gtgcacacct tcccggctgt cctacagtcc tcaggactct actccctcag cagcgtggtg | 540 |
| accgtgccct ccagcagctt gggcacccag acctacatct gcaacgtgaa tcacaagccc | 600 |
| agcaacacca aggtggacaa gagagttgag cccaaatctt gtgacaaaac tcacacatgc | 660 |
| ccaccgtgcc cagcacctga actcctgggg ggaccgtcag tcttcctctt ccccccaaaa | 720 |
| cccaaggaca ccctcatgat ctcccggacc cctgaggtca catgcgtggt ggtggacgtg | 780 |
| agccacgaag accctgaggt caagttcaac tggtacgtgg acggcgtgga ggtgcataat | 840 |
| gccaagacaa agccgcggga ggagcagtac gccagcacgt accgtgtggt cagcgtcctc | 900 |
| accgtcctgc accaggactg gctgaatggc aaggagtaca agtgcaaggt ctccaacaaa | 960 |
| gccctcccag cccccatcga gaaaaccatc tccaaagcca agggcagcc cgagaaccca | 1020 |
| caggtgtaca ccctgccccc atcccgggag gagatgacca gaaccaggt cagcctgacc | 1080 |
| tgcctggtca aaggcttcta tcccagcgac atcgccgtgg agtgggagag caatgggcag | 1140 |
| ccggagaaca actacaagac cacgcctccc gtgctggact ccgacggctc cttcttcctc | 1200 |
| tacagcaagc tcaccgtgga caagagcagg tggcagcagg ggaacgtctt ctcatgctcc | 1260 |
| gtgatgcatg aggctctgca caaccactac acgcagaaga gcctctccct gtctccgggt | 1320 |
| aaatga | 1326 |

<210> SEQ ID NO 255

```
<210> SEQ ID NO 255
<211> LENGTH: 39
<212> TYPE: DNA
<213> ORGANISM: Oryctolagus cuniculus

<400> SEQUENCE: 255
cgggccagtc agagtgttta ctataacaac tacctagcc                              39

<210> SEQ ID NO 256
<211> LENGTH: 21
<212> TYPE: DNA
<213> ORGANISM: Oryctolagus cuniculus

<400> SEQUENCE: 256
tctacatcca ctctggcatc t                                                 21

<210> SEQ ID NO 257
<211> LENGTH: 39
<212> TYPE: DNA
<213> ORGANISM: Oryctolagus cuniculus

<400> SEQUENCE: 257
ctgggcagtt atgattgtag taatggtgat tgttttgtt                              39

<210> SEQ ID NO 258
<211> LENGTH: 15
<212> TYPE: DNA
<213> ORGANISM: Oryctolagus cuniculus

<400> SEQUENCE: 258
aactactaca tgcaa                                                        15

<210> SEQ ID NO 259
<211> LENGTH: 48
<212> TYPE: DNA
<213> ORGANISM: Oryctolagus cuniculus

<400> SEQUENCE: 259
gtcattggtg tgaatggtaa gagatactac gcgagctggg cgaaaggc                    48

<210> SEQ ID NO 260
<211> LENGTH: 9
<212> TYPE: DNA
<213> ORGANISM: Oryctolagus cuniculus

<400> SEQUENCE: 260 ggggacatc                                                                9

<210> SEQ ID NO 261
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
gccatcgtga tgacccagac tccatcttcc aagtctgtcc ctgtgggaga cacagtcacc        60
atcaattgcc aggccagtga gagtctttat aataacaacg ccttggcctg gtttcagcag       120
aaaccagggc agcctcccaa gcgcctgatc tatgatgcat ccaaactggc atctggggtc       180
ccatcgcggt tcagtggcgg tgggtctggg acacagttca ctctcaccat cagtggcgtg       240
cagtgtgacg atgctgccac ttactactgt ggaggctaca gaagtgatag tgttgatggt       300
```

```
gttgctttcg ccggagggac cgaggtggtg gtcaaacgt                           339
```

<210> SEQ ID NO 262
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262

```
gccatcgtga tgacccagac tccatcttcc aagtctgtcc ctgtgggaga cacagtcacc    60
atcaattgcc aggccagtga gagtctttat aataacaacg ccttggcctg gtttcagcag   120
aaaccagggc agcctcccaa gcgcctgatc tatgatgcat ccaaactggc atctggggtc   180
ccatcgcggt tcagtggcgg tgggtctggg acacagttca ctctcaccat cagtggcgtg   240
cagtgtgacg atgctgccac ttactactgt ggaggctaca aagtgatag tgttgatggt    300 gttgctttcg ccggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660
```

<210> SEQ ID NO 263
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263

```
cagtcggtgg aggagtccgg gggaggcctg gtccagcctg agggatccct gacactcacc    60
tgcacagcct ctggattcga cttcagtagc aatgcaatgt ggtgggtccg ccaggctcca   120
gggaaggggc tggagtggat cggatgcatt tacaatggtg atggcagcac atactacgcg   180
agctgggtga atgccgatt ctccatctcc aaaacctcgt cgaccacggt gactctgcaa    240
ctgaatagtc tgacagtcgc ggacacggcc acgtattatt gtgcgagaga tcttgacttg   300
tggggcccgg gcaccctcgt caccgtctcg agc                                333
```

<210> SEQ ID NO 264
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264

```
cagtcggtgg aggagtccgg gggaggcctg gtccagcctg agggatccct gacactcacc    60
tgcacagcct ctggattcga cttcagtagc aatgcaatgt ggtgggtccg ccaggctcca   120
gggaaggggc tggagtggat cggatgcatt tacaatggtg atggcagcac atactacgcg   180
agctgggtga atgccgatt ctccatctcc aaaacctcgt cgaccacggt gactctgcaa    240
ctgaatagtc tgacagtcgc ggacacggcc acgtattatt gtgcgagaga tcttgacttg   300
```

```
tggggcccgg gcaccctcgt caccgtctcg agcgcctcca ccaagggccc atcggtcttc    360
cccctggcac cctcctccaa gagcaccttct gggggcacag cggccctggg ctgcctggtc    420
aaggactact tccccgaacc ggtgacggtg tcgtggaact caggcgccct gaccagcggc    480
gtgcacacct tcccggctgt cctacagtcc tcaggactct actccctcag cagcgtggtg    540
accgtgccct ccagcagctt gggcacccag acctacatct gcaacgtgaa tcacaagccc    600
agcaacacca aggtggacaa gagagttgag cccaaatctt gtgacaaaac tcacacatgc    660
ccaccgtgcc cagcacctga actcctgggg ggaccgtcag tcttcctctt ccccccaaaa    720
cccaaggaca ccctcatgat ctcccggacc cctgaggtca catgcgtggt ggtggacgtg    780
agccacgaag accctgaggt caagttcaac tggtacgtgg acggcgtgga ggtgcataat    840
gccaagacaa agccgcggga ggagcagtac gccagcacgt accgtgtggt cagcgtcctc    900
accgtcctgc accaggactg gctgaatggc aaggagtaca agtgcaaggt ctccaacaaa    960
gccctcccag cccccatcga gaaaaccatc tccaaagcca agggcagccc cgagaaccca   1020
caggtgtaca ccctgccccc atcccgggag gagatgacca gaaccaggt cagcctgacc    1080 tgcctggtca aaggcttcta tcccagcgac atcgccgtgg agtgggagag caatgggcag   1140
ccggagaaca actacaagac cacgcctccc gtgctggact ccgacggctc cttcttcctc   1200
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaatga                                                               1326

<210> SEQ ID NO 265
<211> LENGTH: 39
<212> TYPE: DNA
<213> ORGANISM: Oryctolagus cuniculus

<400> SEQUENCE: 265
caggccagtg agagtcttta taataacaac gccttggcc                            39

<210> SEQ ID NO 266
<211> LENGTH: 21
<212> TYPE: DNA
<213> ORGANISM: Oryctolagus cuniculus

<400> SEQUENCE: 266
gatgcatcca aactggcatc t                                               21

<210> SEQ ID NO 267
<211> LENGTH: 36
<212> TYPE: DNA
<213> ORGANISM: Oryctolagus cuniculus

<400> SEQUENCE: 267
ggaggctaca gaagtgatag tgttgatggt gttgct                               36

<210> SEQ ID NO 268
<211> LENGTH: 15
<212> TYPE: DNA
<213> ORGANISM: Oryctolagus cuniculus

<400> SEQUENCE: 268
agcaatgcaa tgtgg                                                      15

<210> SEQ ID NO 269
<211> LENGTH: 51
```

<212> TYPE: DNA
<213> ORGANISM: Oryctolagus cuniculus

<400> SEQUENCE: 269
tgcatttaca atggtgatgg cagcacatac tacgcgagct gggtgaatgg c    51

<210> SEQ ID NO 270
<211> LENGTH: 12
<212> TYPE: DNA
<213> ORGANISM: Oryctolagus cuniculus

<400> SEQUENCE: 270
gatcttgact tg    12

<210> SEQ ID NO 271
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgt                          339

<210> SEQ ID NO 272
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

<210> SEQ ID NO 273
<211> LENGTH: 333
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 273

```
gaggtgcagc ttgtggagtc tgggggaggc ttggtccagc ctggggggtc cctgagactc      60
tcctgtgcag tctctggaat cggcctcagt agctactaca tgcaatgggt ccgtcaggct     120
ccagggaagg ggctggagtg ggtcggagtc attggtagtg atggtaagac atactacgcg     180
acctgggcga aaggccgatt caccatctcc agagacaatt ccaagaccac ggtgtatctt     240
caaatgaaca gcctgagagc tgaggacact gctgtgtatt tctgtaccag aggggacatc     300
tggggccaag ggaccctcgt caccgtctcg agc                                  333
```

<210> SEQ ID NO 274
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274

```
gaggtgcagc ttgtggagtc tgggggaggc ttggtccagc ctggggggtc cctgagactc      60
tcctgtgcag tctctggaat cggcctcagt agctactaca tgcaatgggt ccgtcaggct     120
ccagggaagg ggctggagtg ggtcggagtc attggtagtg atggtaagac atactacgcg     180
acctgggcga aaggccgatt caccatctcc agagacaatt ccaagaccac ggtgtatctt     240
caaatgaaca gcctgagagc tgaggacact gctgtgtatt tctgtaccag aggggacatc     300
tggggccaag ggaccctcgt caccgtctcg agcgcctcca ccaagggccc atcggtcttc     360
cccctggcac cctcctccaa gagcacctct ggggcacag cggccctggg ctgcctggtc      420
aaggactact ccccgaacc ggtgacggtg tcgtggaact caggcgccct gaccagcggc     480
gtgcacacct tcccggctgt cctacagtcc tcaggactct actccctcag cagcgtggtg     540
accgtgccct ccagcagctt gggcacccag acctacatct gcaacgtgaa tcacaagccc     600
agcaacacca aggtggacgc gagagttgag cccaaatctt gtgacaaaac tcacacatgc     660
ccaccgtgcc cagcacctga actcctgggg ggaccgtcag tcttcctctt ccccccaaaa     720
cccaaggaca ccctcatgat ctcccggacc cctgaggtca catgcgtggt ggtggacgtg     780
agccacgaag accctgaggt caagttcaac tggtacgtgg acggcgtgga ggtgcataat     840
gccaagacaa agccgcggga ggagcagtac gccagcacgt accgtgtggt cagcgtcctc     900
accgtcctgc accaggactg gctgaatggc aaggagtaca agtgcaaggt ctccaacaaa     960
gccctcccag cccccatcga gaaaaccatc tccaaagcca aagggcagcc ccgagaacca    1020
caggtgtaca ccctgccccc atcccgggag gagatgacca agaaccaggt cagcctgacc    1080
tgcctggtca aaggcttcta tcccagcgac atcgccgtgg agtgggagag caatgggcag    1140
ccggagaaca actacaagac cacgcctccc gtgctggact ccgacggctc cttcttcctc    1200
tacagcaagc tcaccgtgga caagagcagg tggcagcagg ggaacgtctt ctcatgctcc    1260
gtgatgcatg aggctctgca caaccactac acgcagaaga gcctctccct gtctccgggt    1320
aaatga                                                              1326
```

<210> SEQ ID NO 275
<211> LENGTH: 39
<212> TYPE: DNA
<213> ORGANISM: Oryctolagus cuniculus

```
<400> SEQUENCE: 275
caggccagtc agaatgttta caataacaac tacctagcc                              39

<210> SEQ ID NO 276
<211> LENGTH: 21
<212> TYPE: DNA
<213> ORGANISM: Oryctolagus cuniculus

<400> SEQUENCE: 276
tctacatcca ctctggcatc t                                                 21

<210> SEQ ID NO 277
<211> LENGTH: 39
<212> TYPE: DNA
<213> ORGANISM: Oryctolagus cuniculus

<400> SEQUENCE: 277
ctgggcagtt atgattgtag tcgtggtgat tgttttgtt                              39

<210> SEQ ID NO 278
<211> LENGTH: 15
<212> TYPE: DNA
<213> ORGANISM: Oryctolagus cuniculus

<400> SEQUENCE: 278
agctactaca tgcaa                                                        15

<210> SEQ ID NO 279
<211> LENGTH: 48
<212> TYPE: DNA
<213> ORGANISM: Oryctolagus cuniculus

<400> SEQUENCE: 279
gtcattggta gtgatggtaa gacatactac gcgacctggg cgaaaggc                    48

<210> SEQ ID NO 280
<211> LENGTH: 9
<212> TYPE: DNA
<213> ORGANISM: Oryctolagus cuniculus

<400> SEQUENCE: 280 ggggacatc                                                                9

<210> SEQ ID NO 281
<211> LENGTH: 37
<212> TYPE: PRT
<213> ORGANISM: Homo sapiens
<220> FEATURE:
<223> OTHER INFORMATION: C-term amidated

<400> SEQUENCE: 281

Ala Cys Asp Thr Ala Thr Cys Val Thr His Arg Leu Ala Gly Leu Leu
 1               5                  10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 282
<211> LENGTH: 37
<212> TYPE: PRT
<213> ORGANISM: Homo sapiens
```

```
<220> FEATURE:
<223> OTHER INFORMATION: C-term amidated

<400> SEQUENCE: 282

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 283
<211> LENGTH: 105
<212> TYPE: PRT
<213> ORGANISM: Homo sapiens

<400> SEQUENCE: 283

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 284
<211> LENGTH: 330
<212> TYPE: PRT
<213> ORGANISM: Homo sapiens

<400> SEQUENCE: 284

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

-continued

```
            145                 150                 155                 160
Tyr Val Asp Gly Val Glu Val His Asn Ala Lys Thr Lys Pro Arg Glu
                    165                 170                 175

Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

ANTI-CGRP COMPOSITIONS AND USE THEREOF

This application is a divisional of U.S. Utility application Ser. No. 13/476,465 filed May 21, 2012, and claims the benefit of U.S. Provisional Application No. 61/488,660 filed May 20, 2011, entitled "ANTI-CGRP COMPOSITIONS AND USE THEREOF" both of which are hereby incorporated by reference in their entirety.

The instant application contains a Sequence Listing which has been submitted in ASCII format via EFS-Web and is hereby incorporated by reference in its entirety. Said ASCII copy, created on Sep. 6, 2016 is named 43257o2403.txt and is 203,877 bytes in size.

BACKGROUND OF THE INVENTION

Field of the Invention

This invention pertains to antibodies and fragments thereof (including Fab fragments) having binding specificity to human Calcitonin Gene Related Peptide (hereinafter "CGRP"). The invention also pertains to methods of screening for diseases and disorders associated with CGRP, and methods of preventing or treating diseases and disorders associated with CGRP by administering said antibodies or fragments thereof.

Description of Related Art

Calcitonin Gene Related Peptide (CGRP) is produced as a multifunctional neuropeptide of 37 amino acids in length. Two forms of CGRP, the CGRP-alpha and CGRP-beta forms, exist in humans and have similar activities. CGRP-alpha and CGRP-beta differ by three amino acids in humans, and are derived from different genes. The CGRP family of peptides includes amylin, adrenomedullin, and calcitonin, although each has distinct receptors and biological activities. Doods, H., *Curr. Op. Invest. Drugs*, 2(9):1261-68 (2001).

CGRP is released from numerous tissues such as trigeminal nerves, which when activated release neuropeptides within the meninges, mediating neurogenic inflammation that is characterized by vasodilation, vessel leakage, and mast-cell degradation. Durham, P. L., *New Eng. J. Med.*, 350 (11):1073-75 (2004). The biological effects of CGRP are mediated via the CGRP receptor (CGRP-R), which consists of a seven-transmembrane component, in conjunction with a receptor-associated membrane protein (RAMP). CGRP-R further requires the activity of the receptor component protein (RCP), which is essential for an efficient coupling to adenylate cyclase through G proteins and the production of cAMP. Doods, H., *Curr. Op. Invest. Drugs*, 2(9):1261-68 (2001).

Migraines are neurovascular disorder affecting approximately 10% of the adult population in the U.S., and are typically accompanied by intense headaches. Approximately 20-30% f migraine sufferers experience aura, comprising focal neurological phenomena that precede and/or accompany the event. CGRP is believe t play a prominent role in the development of migraines. For example, plasma concentrations of CGRP were identified elevated in jugular venous blood during the headache phase of migraines, to the exclusion of other neuropeptides. Moreover, according to Arulmozhi et al, the following has been identified in migraine sufferers: (1) a strong correlation between plasma CGRP concentrations and migraines, (2) the infusion of CGRP produced a migraine-like headache, (3) baseline CGRP levels were elevated, and (4) changes in plasma CGRP levels during migraine attacks significantly correlated with headache intensity. Arulmozhi, B. K., et al., Vas. Pharma., 43; 176-187 (2005).

One effective treatment for migraines is the administration of triptans, which are a family of tryptamine-based drugs, including sumatriptan and rizatriptan. Members of this family have an affinity for multiple serotonin receptors, including $5\text{-HT}_{1B}$, $5\text{-HT}_{1D}$, and $5\text{-HT}_{1F}$. Members of this family of drugs selectively constrict cerebral vessels, but also cause vasoconstrictive effects on coronary vessels. Durham, P. L., *New Eng. J. Med.*, 350 (11):1073-75 (2004). There is a theoretical risk of coronary spasm in patients with established heart disease following administration, and cardiac events after taking triptans may rarely occur. Noted to be contraindicated for patients with coronary vascular disease.

Similarly, pain may often be addressed through the administration of certain narcotics or non-steroidal anti-inflammatory drugs (NSAIDs). However, the administration of these treatments may occur at the cost of certain negative consequences. NSAIDs have the potential to cause kidney failure, intestinal bleeding, and liver dysfunction. Narcotics have the potential to cause nausea, vomiting, impaired mental functioning, and addiction. Therefore, it is desirable to identify alternative treatments for pain in order to avoid certain of these negative consequences.

CGRP is believed to play a role in a multitude of diseases and disorders, including but not limited to migraines, headaches, and pain.

For example, CGRP reportedly may correlate to or even pay a causal play a role in overactive bladder. Evidence that CGRP may correlate to overactive bladder condition includes the fact that CGRP is present in urinary tract, DRG and spinal cord—(Wharton et al., 1986 Neurosci (3):727) and also that C-fiber afferents are critical for carrying impulses involved in micturition to spinal cord (Yoshida et al., 2011 J Pharmacol Sci (112):128). Further, it has been reported that the intravesical administration of Botox suppresses CGRP and significantly reduces intercontraction interval in acetic acid-induced bladder pain model (Chuang et al., 2004 J Urol (172):1529; Chuang et al., 2009 J Urol (182):786)

Evidence that CGRP may play a causal role in this condition is a recent published patent application containing data purportedly suggesting that an anti-CGRP Ab disclosed therein reduced the number of bladder contractions in a turpentine-oil induced overactive bladder model—(Pfizer WO 2011/024113)).

Due to the perceived involvement of CGRP in these and other disorders, there remains a need in the art for compositions and methods useful for preventing or treating diseases and disorders associated with CGRP, while avoiding adverse side effects. There remains a need in the art for compositions or methods that reduce or inhibit diseases or disorders associated with CGRP, such as migraines, headaches, overactive bladder, and pain.

BRIEF SUMMARY OF THE INVENTION

The present invention is directed to specific antibodies and fragments thereof having binding specificity for CGRP, in particular antibodies having desired epitopic specificity, high affinity or avidity and/or functional properties. Another embodiment of this invention relates to the antibodies described herein comprising the sequences of the $V_H$, $V_L$ and CDR polypeptides described herein and the polynucleotides encoding them. A preferred embodiment of the invention is directed to chimeric or humanized antibodies and fragments thereof (including Fab fragments) capable of binding to CGRP and/or inhibiting the biological activities mediated by the binding of CGRP to the CGRP receptor ("CGRP-R").

In another preferred embodiment of the invention, full length antibodies and Fab fragments thereof are contemplated that inhibit the CGRP-alpha-, CGRP-beta-, and rat CGRP-driven production of cAMP. In a further preferred embodiment of the invention, full length and Fab fragments thereof are contemplated that reduce vasodilation in a recipient following administration.

In another embodiment of the invention, chimeric or humanized antibodies and fragments thereof (including Fab fragments) capable of binding to CGRP are useful in methods directed to reducing, treating, or preventing migraines (with or without aura), cancer or tumors, angiogenesis associated with cancer or tumor growth, angiogenesis associated with cancer or tumor survival, weight loss, pain, hemiplegic migraines, cluster headaches, migrainous neuralgia, chronic headaches, tension headaches, general headaches, hot flushes, chronic paroxysomal hemicrania, secondary headaches due to an underlying structural problem in the head or neck, cranial neuralgia, sinus headaches (such as for example associated with sinusitis), and allergy-induced headaches or migraines. The antibodies and antibody fragments of the present invention particularly have utility in treating, preventing, ameliorating, controlling or reducing the risk of one or more of the following conditions or diseases: overactive bladder and other urinary conditions including bladder infection, pain; chronic pain; neurogenic inflammation and inflammatory pain; neuropathic pain; eye pain; tooth pain; post-surgical pain, trauma related pain, burn related pain, diabetes; non-insulin dependent diabetes mellitus and other inflammatory autoimmune disorders, vascular disorders: inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases including pruritis, neurogenic cutaneous redness, skin rosaceousness and erythema; inflammatory bowel disease, irritable bowel syndrome, cystitis; dysmenorrhea, and other conditions that potentially may be treated or prevented or the symptoms ameliorated by antagonism of CGRP receptors. Of particular importance is the acute or prophylactic treatment of headache, including migraine and cluster headache, and other pain related conditions as well as overactive bladder.

In another embodiment of the invention, chimeric or humanized antibodies and fragments thereof (including Fab fragments) capable of binding to CGRP are preferably useful in methods directed to reducing, treating, or preventing gastro-esophageal reflux and visceral pain associated with gastro-esophageal reflux, dyspepsia, irritable bowel syndrome, inflammatory bowel disease, Crohn's disease, ileitis, ulcerative colitis, renal colic, dysmenorrhea, cystitis, menstrual period, labor, menopause, prostatitis, r pancreatitis.

In another embodiment of the invention these antibodies and humanized versions may be derived from rabbit immune cells (B lymphocytes) and may be selected based on their homology (sequence identity) to human germ line sequences. These antibodies may require minimal or no sequence modifications thereby facilitating retention of functional properties after humanization. A further embodiment of the invention is directed to fragments from anti-CGRP antibodies encompassing $V_H$, $V_L$ and CDR polypeptides, e.g., derived from rabbit immune cells and the polynucleotides encoding the same, as well as the use of these antibody fragments and the polynucleotides encoding them in the creation of novel antibodies and polypeptide compositions capable of binding to CGRP and/or CGRP/CGRP-R complexes.

The invention also contemplates conjugates of anti-CGRP antibodies and binding fragments thereof conjugated to one or more functional or detectable moieties. The invention also contemplates methods of making said chimeric or humanized anti-CGRP r anti-CGRP/CGRP-R complex antibodies and binding fragments thereof. In one embodiment, binding fragments include, but are not limited to, Fab, Fab', F(ab')$_2$, Fv, scFv fragments, SMIPs (small molecule immunopharmaceuticals), camelbodies, nanobodies, and IgNAR.

Embodiments of the invention pertain to the use of anti-CGRP antibodies and binding fragments thereof for the diagnosis, assessment and treatment of diseases and disorders associated with CGRP or aberrant expression thereof. The invention also contemplates the use of fragments of anti-CGRP antibodies for the diagnosis, assessment and treatment of diseases and disorders associated with CGRP or aberrant expression thereof. Other embodiments of the invention relate to the production of anti-CGRP antibodies or fragments thereof in recombinant host cells, for example mammalian cells such as CHO, NSO or HEK 293 cells, or yeast cells (for example diploid yeast such as diploid *Pichia*) and other yeast strains.

BRIEF DESCRIPTION OF THE SEVERAL VIEWS OF THE DRAWINGS

FIG. 1A-C provides polynucleotide and polypeptide sequences corresponding to the full-length Antibody Ab1.

FIG. 2 A-C provides polynucleotide and polypeptide sequences corresponding to the full-length Antibody Ab2.

FIG. 3A-C provides polynucleotide and polypeptide sequences corresponding to the full-length Antibody Ab3.

FIG. 4A-C provides polynucleotide and polypeptide sequences corresponding to the full-length Antibody Ab4.

FIG. 5A-C provides polynucleotide and polypeptide sequences corresponding to the full-length Antibody Ab5.

FIG. 6A-C provides polynucleotide and polypeptide sequences corresponding to the full-length Antibody Ab6.

FIG. 7A-C provides polynucleotide and polypeptide sequences corresponding to the full-length Antibody Ab7.

FIG. 8A-C provides polynucleotide and polypeptide sequences corresponding to the full-length Antibody Ab8.

FIG. 9A-C provides polynucleotide and polypeptide sequences corresponding to the full-length Antibody Ab9.

FIG. 10A-C provides polynucleotide and polypeptide sequences corresponding to the full-length Antibody Ab10.

FIG. 11A-C provides polynucleotide and polypeptide sequences corresponding to the full-length Antibody Ab11.

FIG. 12A-C provides polynucleotide and polypeptide sequences corresponding to the full-length Antibody Ab12.

FIG. 13A-C provides polynucleotide and polypeptide sequences corresponding to the full-length Antibody Ab13.

FIG. 14A-C provides polynucleotide and polypeptide sequences corresponding to the full-length Antibody Ab14.

FIG. 38 demonstrates the inhibition of binding of radiolabeled CGRP to CGRP-R by antibodies Ab1-Ab13, obtained following the protocol in Example 6 infra.

DETAILED DESCRIPTION OF PREFERRED EMBODIMENTS

Definitions

Figure 15:
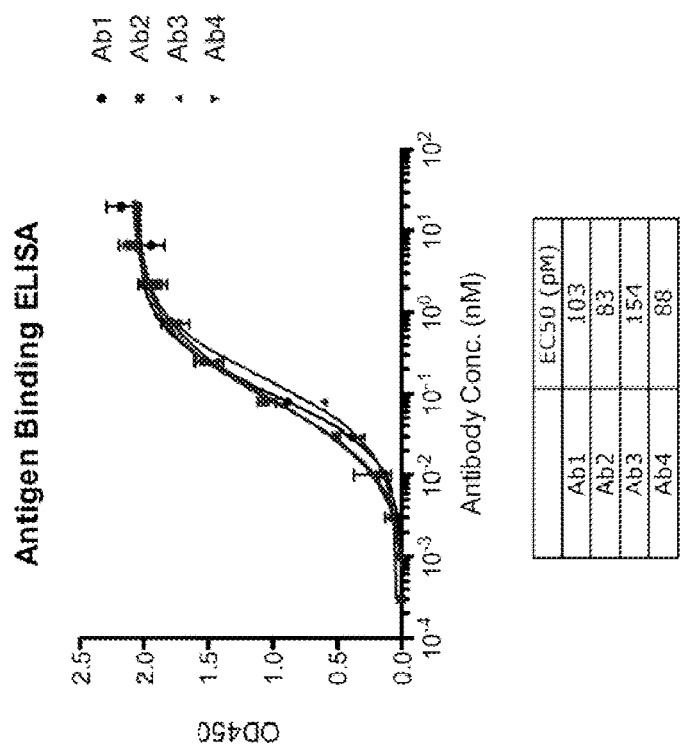
FIG. 15 provides the CGRP-alpha ELISA binding data obtained following the protocol in Example 1 infra for antibodies Ab1, Ab2, Ab3, and Ab4.
Figure 16:
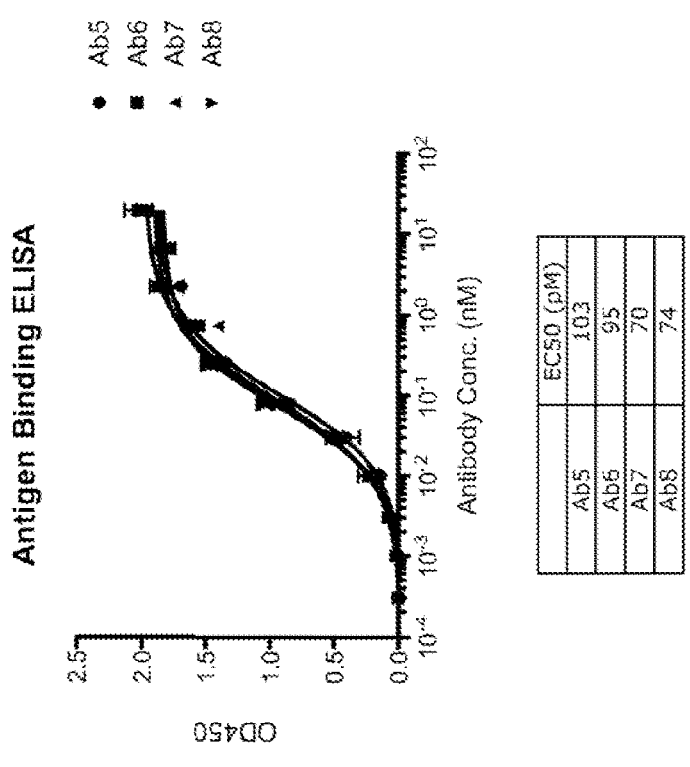
FIG. 16 provides the CGRP-alpha ELISA binding data obtained following the protocol in Example 1 infra for antibodies Ab5, Ab6, Ab7, and Ab8.
Figure 17:
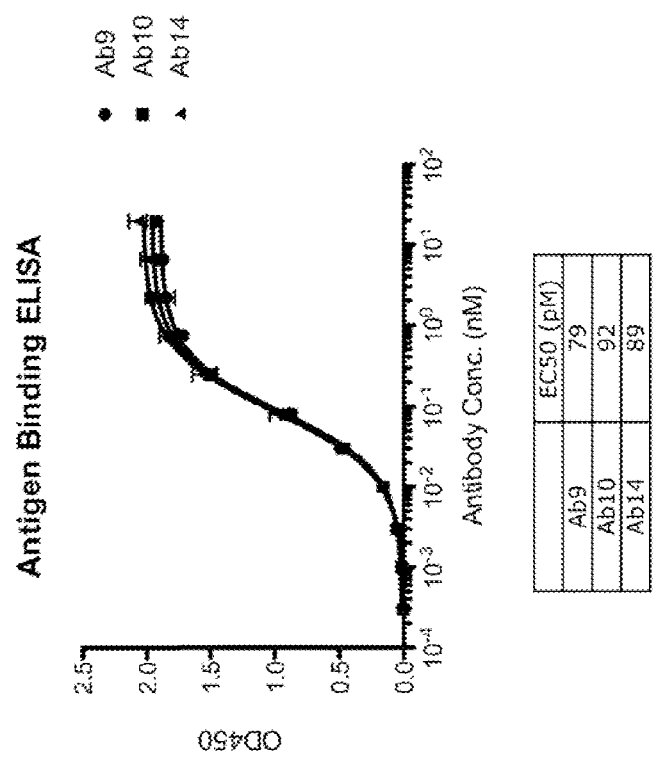
FIG. 17 provides the CGRP-alpha ELISA binding data obtained following the protocol in Example 1 infra for antibodies Ab9, Ab10, and Ab14.
Figure 18:
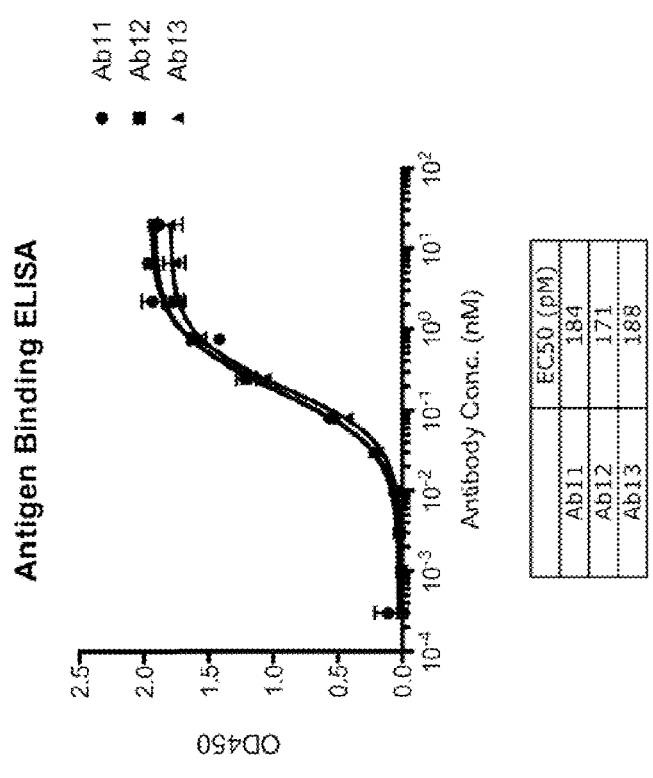
FIG. 18 provides the CGRP-alpha ELISA binding data obtained following the protocol in Example 1 infra for antibodies Ab11, Ab12, and Ab13.
Figure 19:
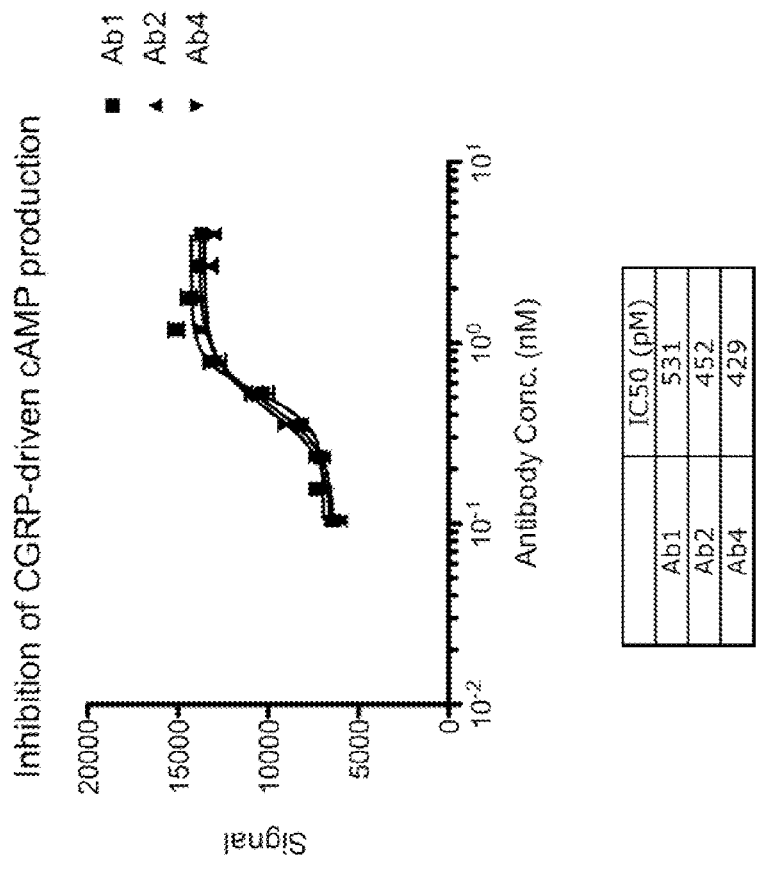
FIG. 19 demonstrates the inhibition of CGRP-alpha-driven cAMP production by antibodies Ab1, Ab2, and Ab4, obtained following the protocol in Example 1 infra.
Figure 20:
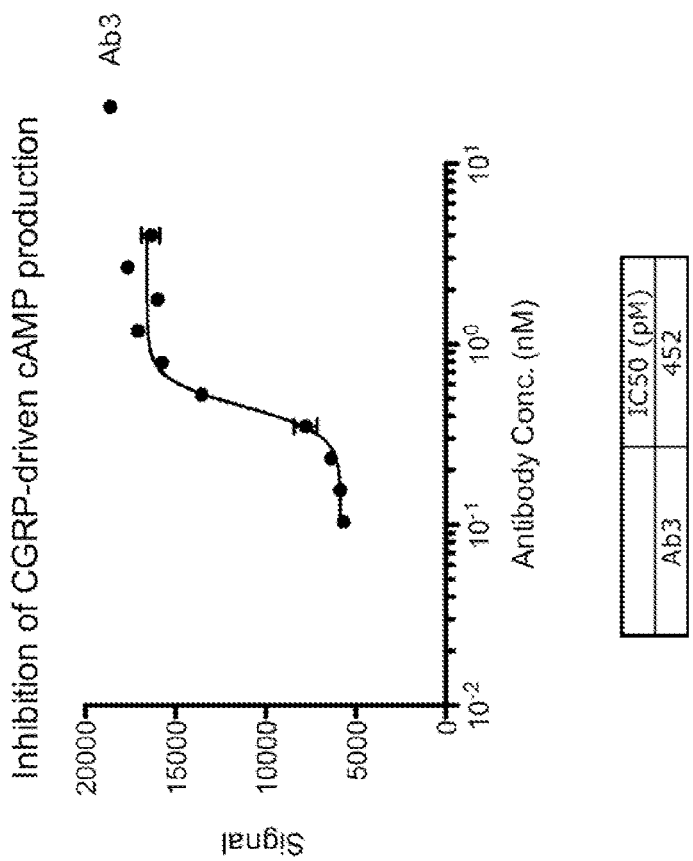
FIG. 20 demonstrates the inhibition of CGRP-alpha-driven cAMP production by antibody Ab3, obtained following the protocol in Example 1 infra.
Figure 21:
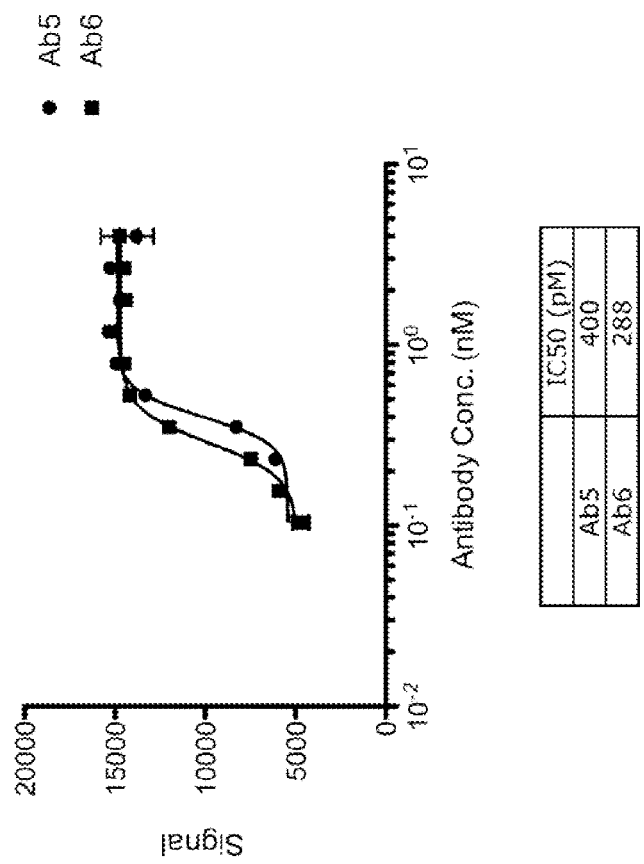
FIG. 21 demonstrates the inhibition of CGRP-alpha-driven cAMP production by antibodies Ab5 and Ab6, obtained following the protocol in Example 1 infra.
Figure 22:
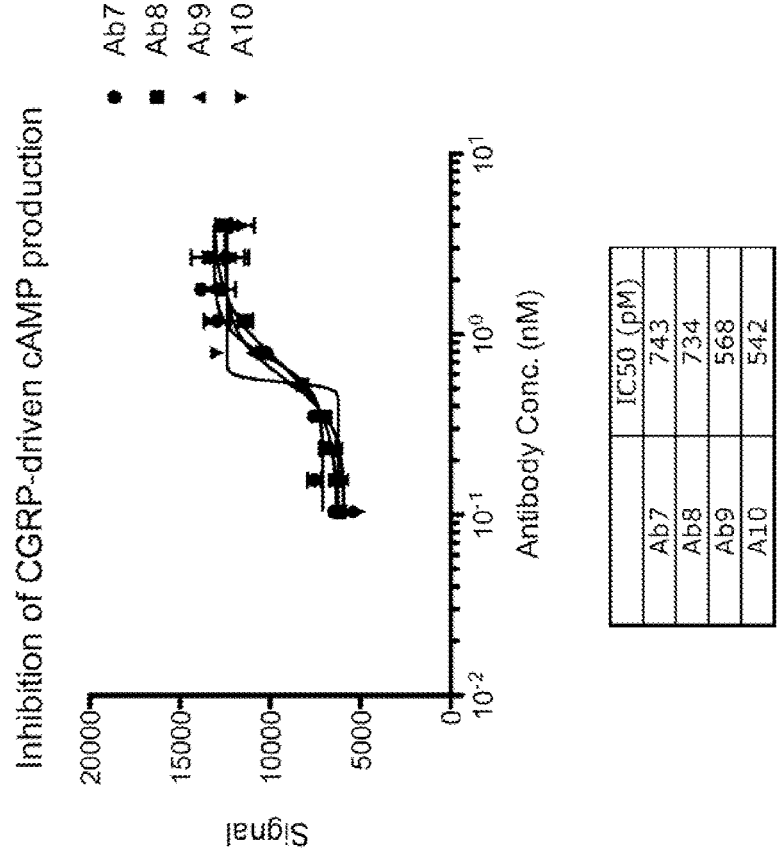
FIG. 22 demonstrates the inhibition of CGRP-alpha-driven cAMP production by antibodies Ab7, Ab8, Ab9, and Ab10, obtained following the protocol in Example 1 infra.
Figure 23:
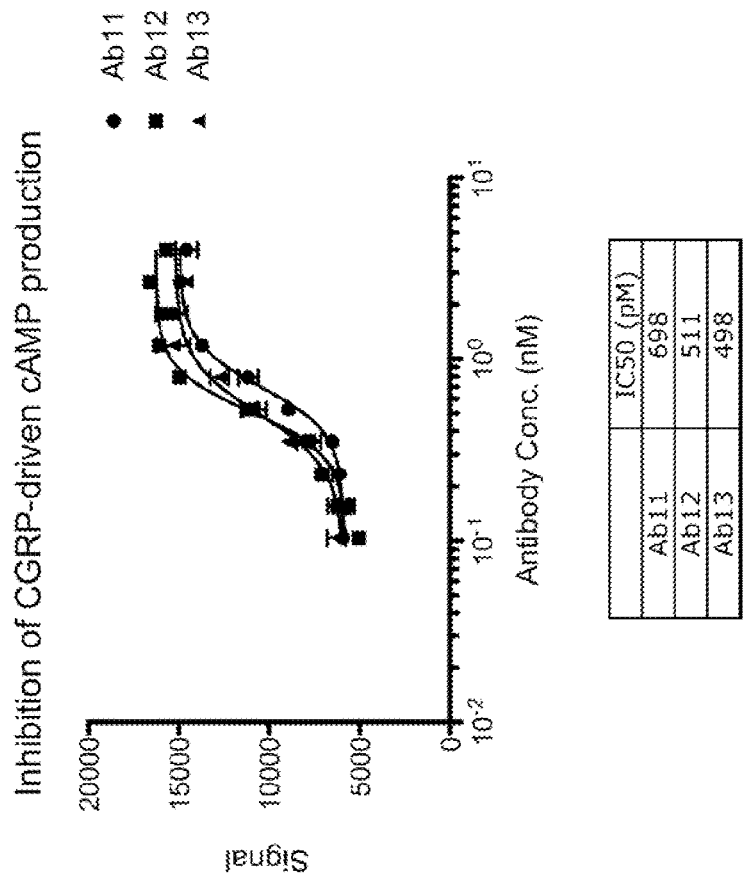
FIG. 23 demonstrates the inhibition of CGRP-alpha-driven cAMP production by antibodies Ab11, Ab12, and Ab13, obtained following the protocol in Example 1 infra.
Figure 24:
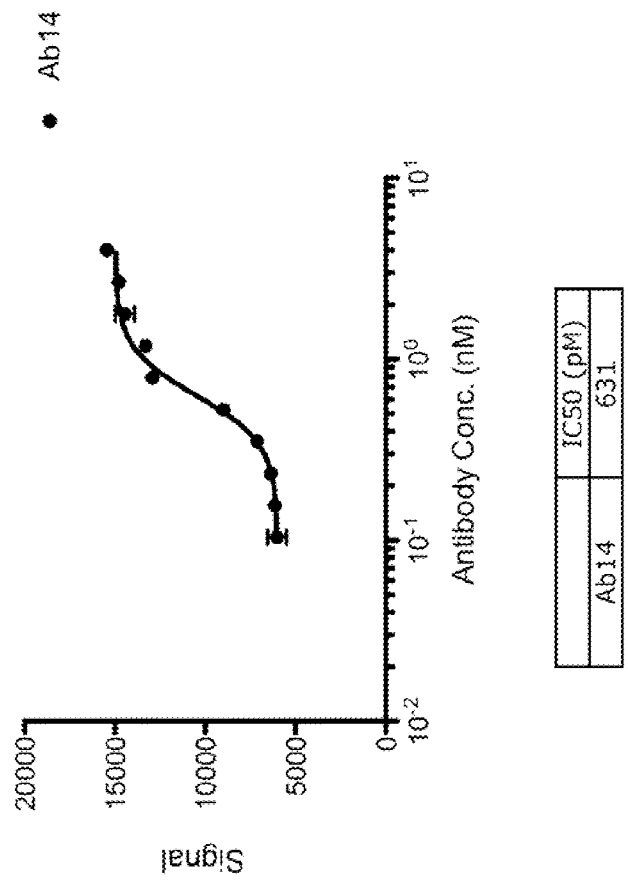
FIG. 24 demonstrates the inhibition of CGRP-alpha-driven cAMP production by antibody Ab14, obtained following the protocol in Example 1 infra.
Figure 25:
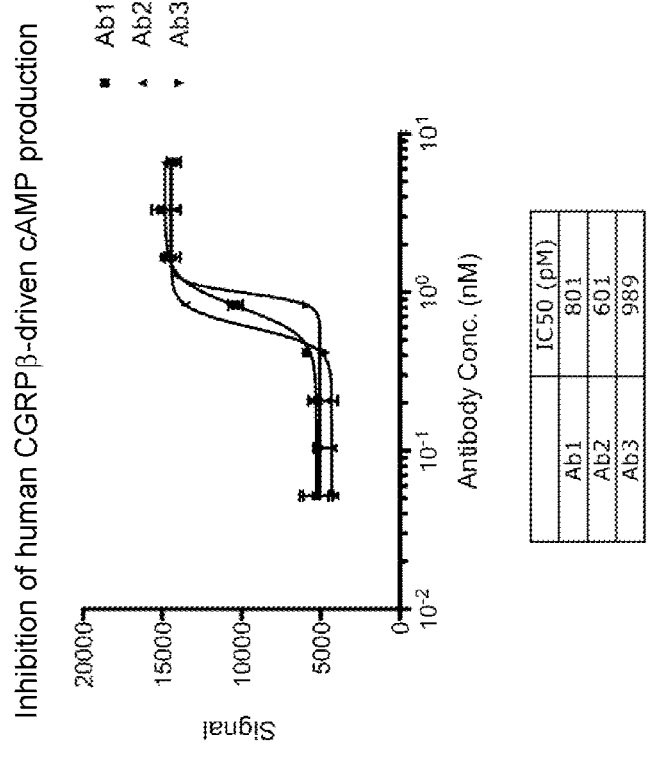
FIG. 25 demonstrates the inhibition of CGRP-beta-driven cAMP production by antibodies Ab1, Ab2, and Ab3, obtained following the protocol in Example 1 infra.
Figure 26:
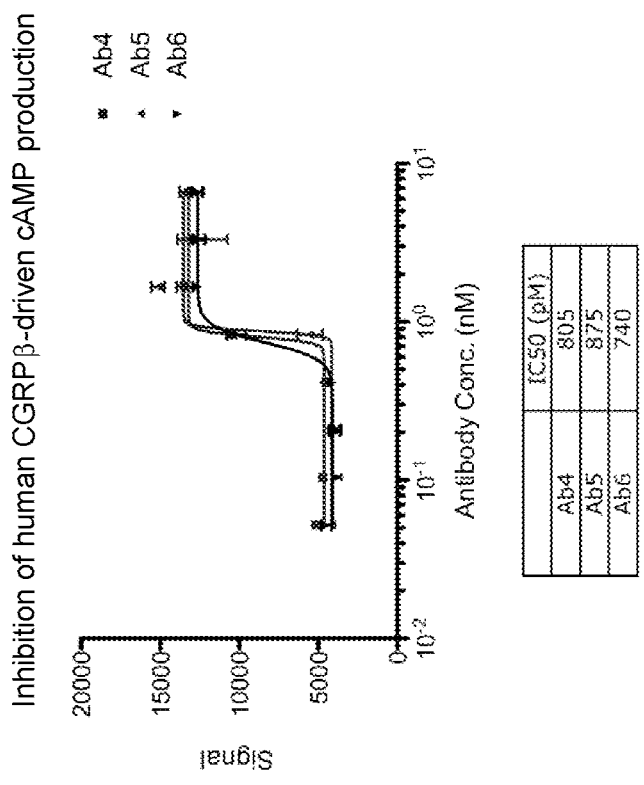
FIG. 26 demonstrates the inhibition of CGRP-beta-driven cAMP production by antibodies Ab4, Ab5 and Ab6, obtained following the protocol in Example 1 infra.
Figure 27:
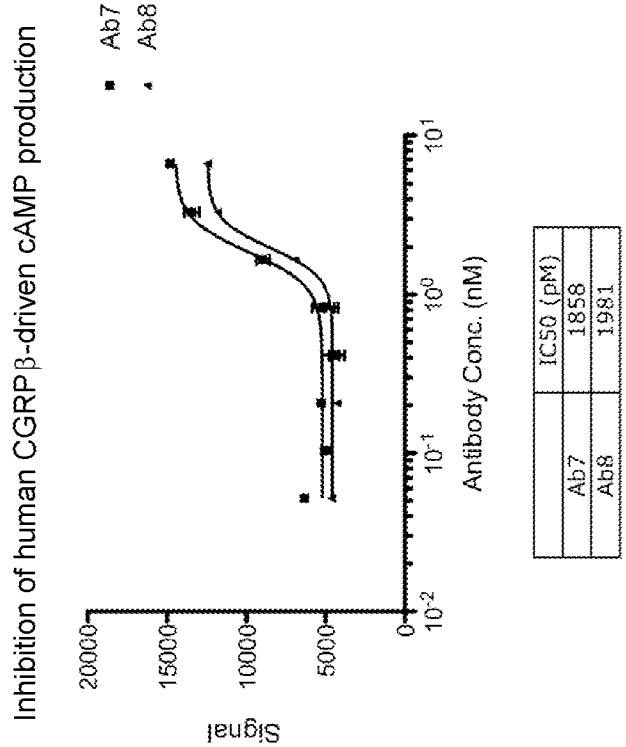
FIG. 27 demonstrates the inhibition of CGRP-beta-driven cAMP production by antibodies Ab7 and Ab8 obtained following the protocol in Example 1 infra.
Figure 28:
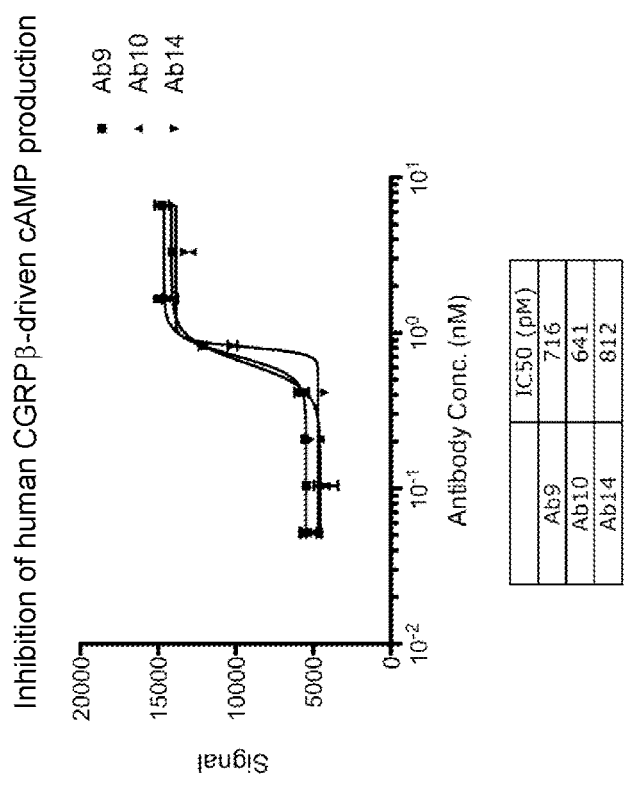
FIG. 28 demonstrates the inhibition of CGRP-beta-driven cAMP production by antibodies Ab9, Ab10, and Ab14, obtained following the protocol in Example 1 infra.
Figure 29:
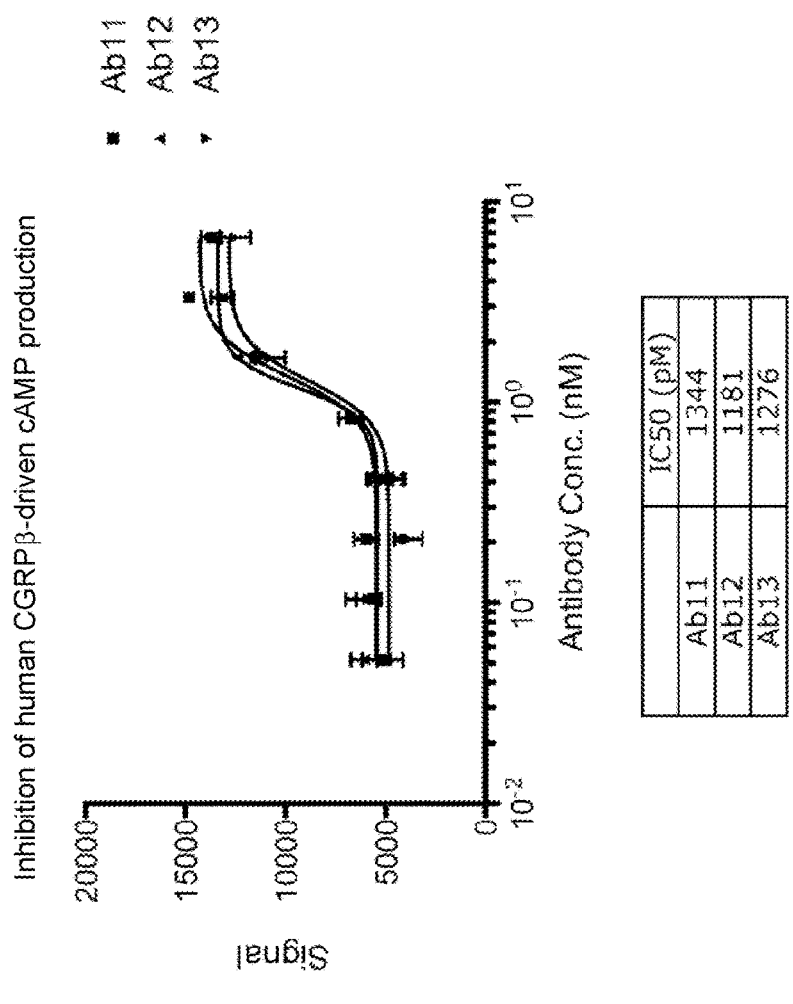
FIG. 29 demonstrates the inhibition of CGRP-beta-driven cAMP production by antibodies Ab11, Ab12, and Ab13, obtained following the protocol in Example 1 infra.
Figure 30:
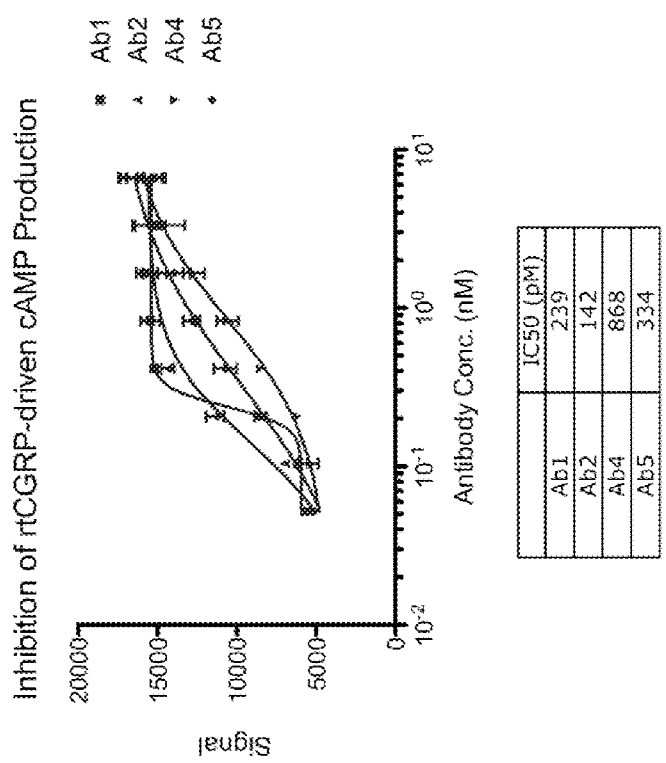
FIG. 30 demonstrates the inhibition of rat CGRP-driven cAMP production by antibodies Ab1, Ab2, Ab4 and Ab5 obtained following the protocol in Example 1 infra.
Figure 31:
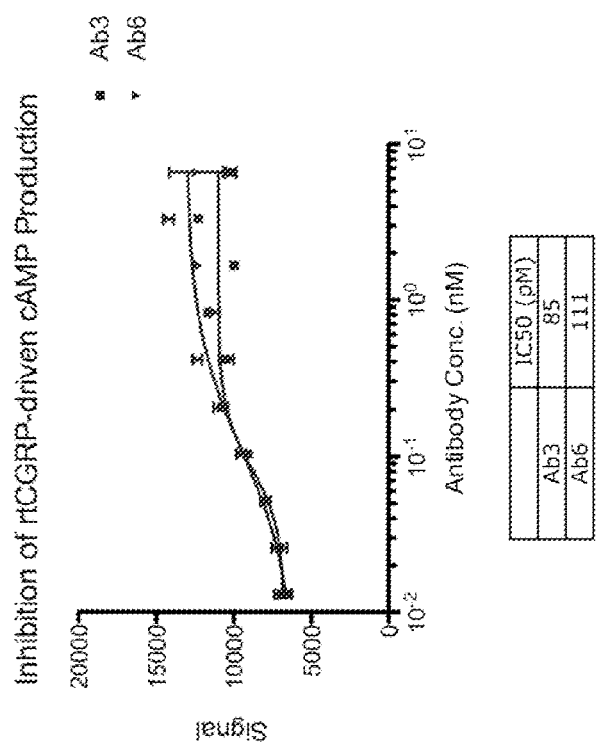
FIG. 31 demonstrates the inhibition of rat CGRP-driven cAMP production by antibodies Ab3 and Ab6, obtained following the protocol in Example 1 infra.
Figure 32:
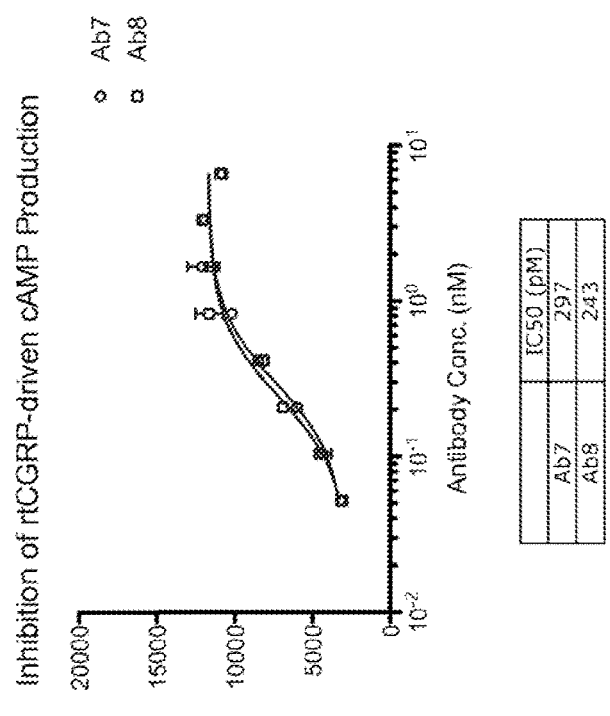
FIG. 32 demonstrates the inhibition of rat CGRP-driven cAMP production by antibodies Ab7 and Ab8, obtained following the protocol in Example 1 infra.
Figure 33:
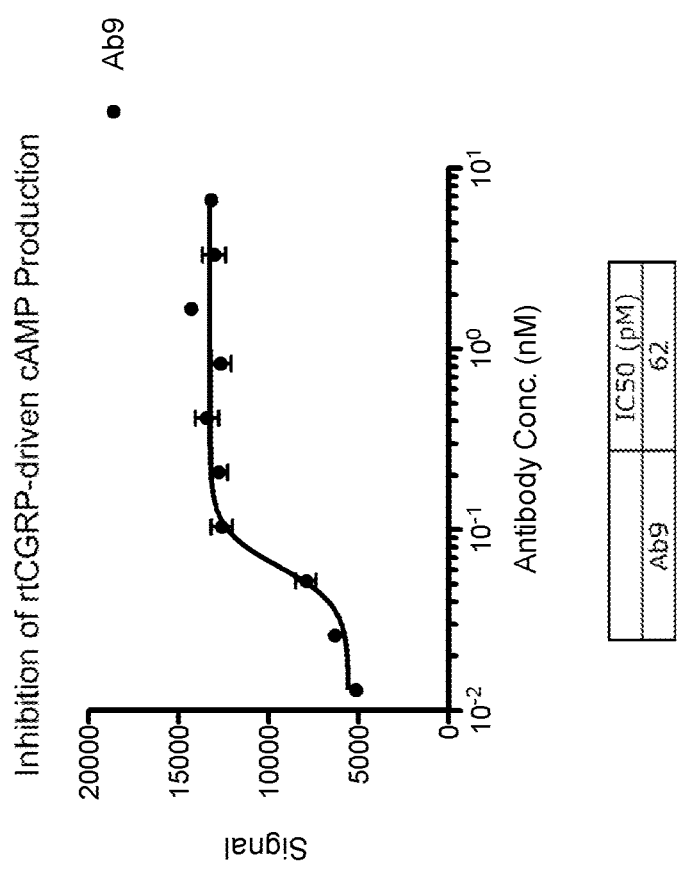
FIG. 33 demonstrates the inhibition of rat CGRP-driven cAMP production by antibody Ab9, obtained following the protocol in Example 1 infra.
Figure 34:
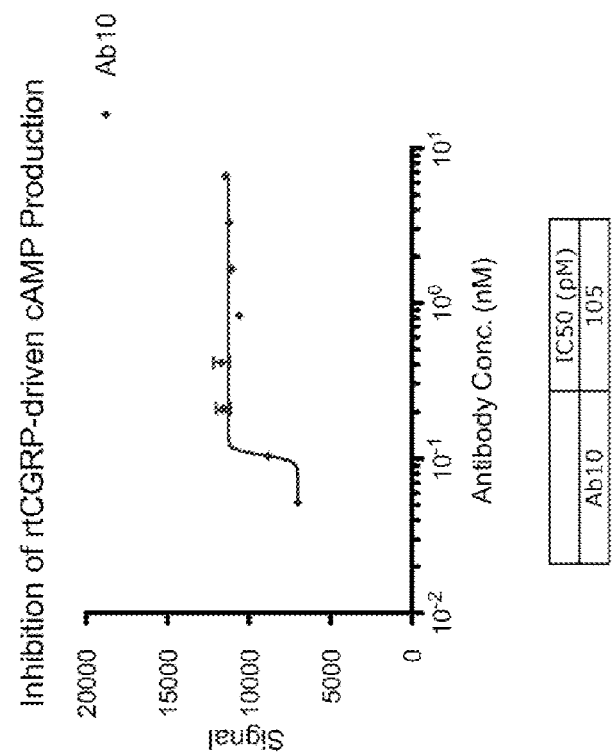
FIG. 34 demonstrates the inhibition of rat CGRP-driven cAMP production by antibody Ab10, obtained following the protocol in Example 1 infra.
Figure 35:
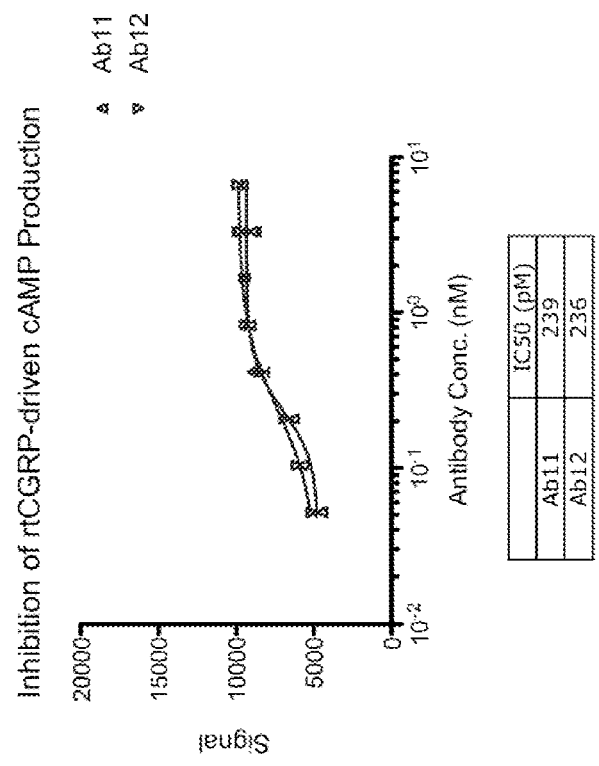
FIG. 35 demonstrates the inhibition of rat CGRP-driven cAMP production by antibodies Ab11 and Ab12, obtained following the protocol in Example 1 infra.
Figure 36:
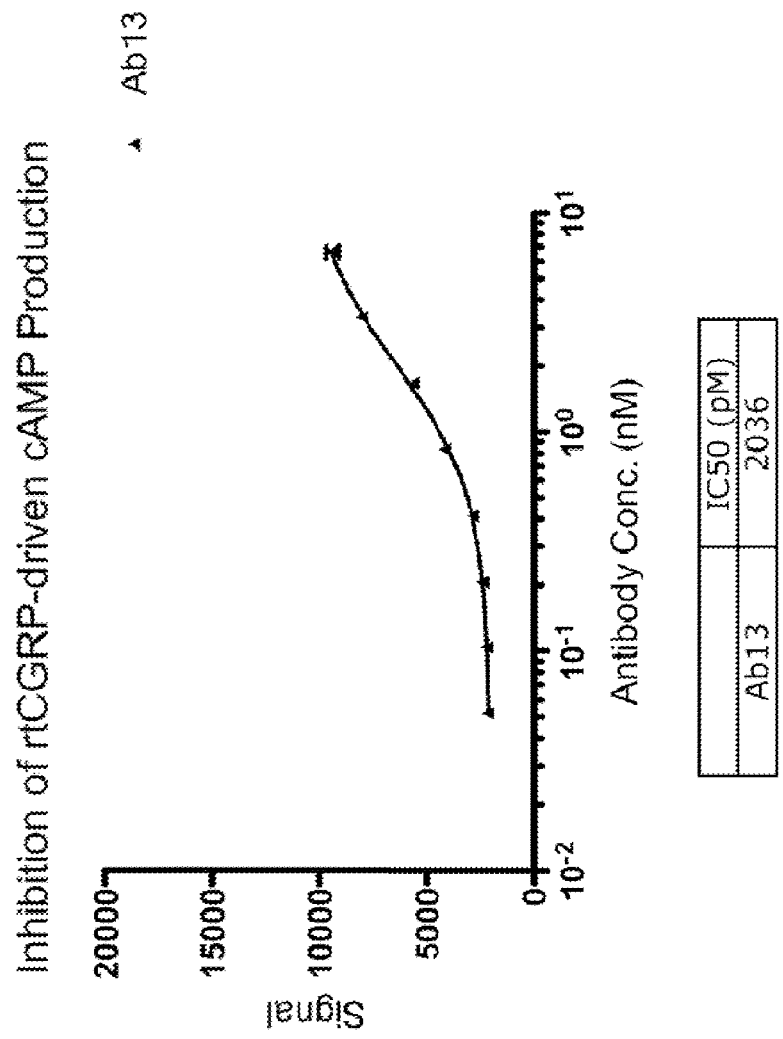
FIG. 36 demonstrates the inhibition of rat CGRP-driven cAMP production by antibody Ab13, obtained following the protocol in Example 1 infra.
Figure 37:
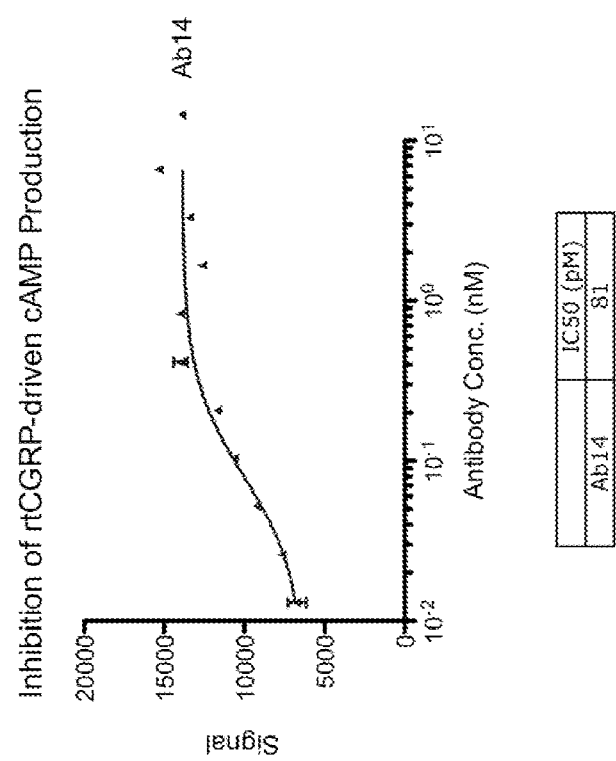
FIG. 37 demonstrates the inhibition of rat CGRP-driven cAMP production by antibody Ab14, obtained following the protocol in Example 1 infra.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope or the present invention which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Calcitonin Gene Related Peptide (CGRP): As used herein, CGRP encompasses not only the following *Homo sapiens* CGRP-alpha and *Homo sapiens* CGRP-beta amino acid sequences available from American Peptides (Sunnyvale Calif.) and Bachem (Torrance, Calif.):
CGRP-alpha: ACDTATCVTHRLAGLLSRSGGVVKNN-FVPTNVGSKAF-NH$_2$ (SEQ ID NO: 281), wherein the N-terminal phenylalanine is amidated;
CGRP-beta: ACNTATCVTHRLAGLLSRSGGMVKSN-FVPTNVGSKAF-NH$_2$ (SEQ ID NO: 282), wherein the N-terminal phenylalanine is amidated; but also any membrane-bound forms of these CGRP amino acid sequences, as well as mutants (mutiens), splice variants, isoforms, orthologues, homologues and variants of this sequence.

Mating competent yeast species: In the present invention this is intended to broadly encompass any diploid or tetraploid yeast which can be grown in culture. Such species of yeast may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or spheroplast fusion.

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Terrapisispora; Torulaspora; Williopsis;* and *Zygosaccharomyces.* Other types of yeast potentially useful in the invention include *Yarrowia; Rhodosporidium; Candida; Hansemula; Filobasium; Sporidiobolus; Bullera; Lencosporididum* and *Filobasidella.*

In a preferred embodiment of the invention, the mating competent yeast is a member of the genus *Pichia.* In a further preferred embodiment of the invention, the mating competent yeast of the genus *Pichia* is one of the following species: *Pichia pastoris, Pichia menthanolica,* and *Hansemula polymorpha (Pichia angusta).* In a particularly preferred embodiment of the invention, the mating competent yeast of the genus *Pichia* is the species *Pichia pastoris.*

Haploid Yeast Cell: A cell having a single copy of each gene of its normal genomic (chromosomal) complement.

Polyploid Yeast Cell: A cell having more than one copy of its normal genomic (chromosomal) complement.

Diploid Yeast Cell: A cell having two copies (alleles) of essentially every gene of its normal genomic complement, typically formed by the process of fusion (mating) of two haploid cells.

Tetraploid Yeast Cell: A cell having four copies (alleles) of essentially every gene of its normal genomic complement, typically formed by the process of fusion (mating) of two haploid cells. Tetraploids may carry two, three, four or more different expression cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [adc his] haploid to obtain diploid [his]; and a [met arg] haploid can be mated with |ade arg| haploid to obtain diploid [arg]; then the diploid |his|×diploid [arg] to obtain a tetraploid prototroph. It will be understood by those of skill in the art that reference to the benefits and uses of diploid cells may also apply to tetraploid cells.

Yeast Mating: The process by which two haploid yeast cells naturally fuse to form one diploid yeast cell.

Meiosis: The process by which a diploid yeast cell undergoes reductive division to form four haploid spore products. Each spore may then germinate and form a haploid vegetatively growing cell line.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two temperature sensitive ("ts") mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

Expression Vector: These DNA vectors contain elements that facilitate manipulation for the expression of a foreign protein within the target host cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press.

Expression vectors for use in the methods of the invention will further include yeast specific sequences, including a selectable auxotrophic or drug marker for identifying transformed yeast strains. A drug marker may further be used to amplify copy number of the vector in a yeast host cell.

The polypeptide coding sequence of interest is operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e g a signal sequence, and the like. A yeast origin of replication is optional, as expression vectors are often integrated into the yeast genome. In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide, a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination *Pichia* transformation is described in Cregg et al. (1985) Mol. Cell. Biol. 5:3376-3385.

Examples of suitable promoters from *Pichia* include the AOX1 and promoter (Cregg et al (1989) Mol. Cell. Biol. 9:1316-1323); ICL1 promoter (Menendez et al. (2003) *Yeast* 20(13):1097-108); glyceraldehyde-3-phosphate dehydrogenase promoter (GAP) (Waterham et al. (1997) *Gene* 186(1): 37-44); and FLD1 promoter (Shen et al. (1998) *Gene* 216(1):93-102). The GAP promoter is a strong constitutive promoter and the AOX and FLD1 promoters are inducible.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 pre-protoxin sequence, PHA-E, FACE, human MCP-1, human scrum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been round 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a mixture of lambda and *E. coli*-encoded recombination proteins. Recombination occurs between specific attachment (att) sites on the interacting DNA molecules. For a description of att sites see Weisberg and Landy (1983) Site-Specific Recombination in Phage Lambda, in *Lambda II*, Weisberg, ed. (Cold Spring Harbor, N.Y.: Cold Spring Harbor Press), pp. 211-250. The DNA segments flanking the recombination sites are switched, such that after recombination, the all sites are hybrid sequences comprised or sequences donated by each parental vector. The recombination can occur between DNAs of any topology.

Att sites may be introduced into a sequence of interest by ligating the sequence of interest into an appropriate vector; generating a PCR product containing att B sites through the use of specific primers, generating a cDNA library cloned into an appropriate vector containing att sites, and the like.

Folding, as used herein, refers to the three-dimensional structure of polypeptides and proteins, where interactions between amino acid residues act to stabilize the structure. While non-covalent interactions are important in determining structure, usually the proteins or interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity. e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein), cyclophilin, and the like. In one embodiment of the invention, each of the haploid parental strains expresses a distinct folding enzyme, e.g. one strain may express BIP, and the other strain may express PDI or combinations thereof.

The terms "desired protein" or "desired antibody" are used interchangeably and refer generally to a parent antibody specific to a target, i.e., CGRP or a chimeric or humanized antibody or a binding portion thereof derived therefrom as described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described, and others may be raised by methods well-known in the art. Examples thereof include chimeric antibodies, human antibodies and other non-human mammalian antibodies, humanized antibodies, single chain antibodies (such as scFvs), camelbodies, nanobodies, IgNAR (single-chain antibodies derived from sharks), small-modular immunopharmaceuticals (SMIPs), and antibody fragments such as Fabs, Fab', F(ab')$_2$ and the like. See Streltsov V A, et al., Structure of a shark IgNAR antibody variable domain and modeling of an early-developmental isotype. Protein Sci. 2005 November; 14(11):2901-9. Epub 2005 Sep. 30; Greenberg A S, et al., A new antigen receptor gene family that undergoes rearrangement and extensive somatic diversification in sharks. Nature. 1995 Mar. 9; 374(6518):168-73; Nuttall S D, et al., Isolation of the new antigen receptor from wobbegong sharks, and use as a scaffold for the display of protein loop libraries, Mol Immunol. 2001 August; 38(4): 313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, and IgG4 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention Examples of additional effector molecules are provided infra.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291-294). Polymerase chain reaction or PCR is a prototype of nucleic acid amplification, and use of PCR herein should be considered exemplary of other suitable amplification techniques.

The general structure of antibodies in vertebrates now is well understood (Edelman, G. M., Ann. N.Y. Acad. Sci. 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_C$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e. the antigen eliciting it). There are five known major classes of constant regions that determine the class of the immunoglobulin molecule (IgG, IgM, IgA, IgD, and IgE corresponding to γ, μ, α, δ, and ε (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, F. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)).

The expressions "framework region" or "FR" refer to one or more of the framework regions within the variable regions of the light and heavy chains of an antibody (See Kabat, E. A. et al., Sequences of Proteins of Immunological Interest. National Institutes of Health, Bethesda, Md., (1987)). These expressions include those amino acid sequence regions interposed between the CDRs within the variable regions of the light and heavy chains of an antibody.

Anti-CGRP Antibodies and Binding Fragments Thereof Having Binding Activity for CGRP Antibody Ab1

In one embodiment, the invention includes chimeric antibodies having binding specificity to CGRP and possessing a variable light chain sequence comprising the sequence set forth below:

```
                                              (SEQ ID NO: 1)
QVLTQTASPVSAAVGSTVTINCQASQSVYDNNYLAWYQQKPGQPPKQLIY

STSTLASGVSSRFKGSGSGTQFTLTISDLECADAATYYCLGSYDCSSGDC

FVFGGGTEVVVKR.
```

The invention also includes chimeric antibodies having binding specificity to CGRP and possessing a light chain sequence comprising the sequence set forth below

```
                                              (SEQ ID NO: 2)
QVLTQTASPVSAAVGSTVTINCQASQSVYDNNYLAWYQQKPGQPPKQLIY

STSTLASGVSSRFKGSGSGTQFTLTISDLECADAATYYCLGSYDCSSGDC

FVFGGGTEVVVKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.
```

The invention further includes chimeric antibodies having binding specificity to CGRP and possessing a variable heavy chain sequence comprising the sequence set forth below:

```
                                              (SEQ ID NO: 3)
QSLEESGGRLVTPGTPLTLTCTVSGLDLSSYYMQWVRQAPGKGLEWIGVI

GINDNTYYASWAKGRFTISRASSTTVDLKMTSLTTEDTATYFCARGDIWG

PGTLVTVSS.
```

The invention also includes chimeric antibodies having binding specificity to CGRP and possessing a heavy chain sequence comprising the sequence set forth below:

```
                                              (SEQ ID NO: 4)
QSLEESGGRLVTPGTPLTLTCTVSGLDLSSYYMQWVRQAPGKGLEWIGVI

GINDNTYYASWAKGRFTISRASSTTVDLKMTSLTTEDTATYFCARGDIWG

PGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSN

TKVDKRVEPKSCDKTHTCPPCPAPELLGGPSVFLFPPKPKDTLMISRTPE

VTCVVVDVSHEDPEVKFNWYVDGVEVHNAKTKPREEQYASTYRVVSVLTV

LHQDWLNGKEYKCKVSNKALPAPIEKTISKAKGQPREPQVYTLPPSREEM

TKNQVSLTCLVKGFYPSDIAVEWESNGQPENNYKTTPPVLDSDGSFFLYS

KLTVDKSRWQQGNVFSCSVMHEALHNHYTQKSLSLSPGK.
```

The invention further contemplates antibodies comprising one or more of the polypeptide sequences of SEQ ID NO: 5; SEQ ID NO: 6; and SEQ ID NO: 7 which correspond to the complementarity-determining regions (CDRs, or hypervariable regions) of the variable light chain sequence of SEQ ID NO: 1 or the light chain sequence of SEQ ID NO: 2, and/or one or more of the polypeptide sequences of SEQ ID NO: 8; SEQ ID NO: 9; and SEQ ID NO: 10 which correspond to the complementarity-determining regions (CDRs, or hypervariable regions) of the variable heavy chain sequence of SEQ ID NO: 3 or the heavy chain sequence of SEQ ID NO: 4, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to CGRP. In one embodiment of the invention, antibody fragments of the invention comprise, or alternatively consist of, the polypeptide sequence of SEQ ID NO: 1 or SEQ ID NO: 2. In another embodiment of the invention, antibody fragments of the invention comprise, or alternatively consist of, the polypeptide sequence of SEQ ID NO: 3 or SEQ ID NO: 4.

In a further embodiment of the invention, fragments of the antibody having binding specificity to CGRP comprise, or alternatively consist of, one or more of the polypeptide sequences of SEQ ID NO: 5; SEQ ID NO: 6; and SEQ ID NO: 7 which correspond to the complementarity-determining regions (CDRs, or hypervariable regions) of the variable light chain sequence of SEQ ID NO: 1 or the light chain sequence of SEQ ID NO: 2.

In a further embodiment of the invention, fragments of the antibody having binding specificity to CGRP comprise, or alternatively consist of, one or more of the polypeptide sequences of SEQ ID NO: 8; SEQ ID NO: 9; and SEQ ID NO: 10 which correspond to the complementarity-determining regions (CDRs, or hypervariable regions) of the variable heavy chain sequence of SEQ ID NO: 3 or the heavy chain sequence of SEQ ID NO: 4.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 1; the variable heavy chain region of SEQ ID NO: 3; the complementarity-determining regions (SEQ ID NO: 5; SEQ ID NO: 6; and SEQ ID NO: 7) of the variable light chain region of SEQ ID NO: 1; and the complementarity-determining regions (SEQ ID NO: 8; SEQ ID NO: 9; and SEQ ID NO: 10) of the variable heavy chain region of SEQ ID NO: 3.

In a particularly preferred embodiment of the invention, the chimeric anti-CGRP antibody is Ab1, comprising, or alternatively consisting of, SEQ ID NO: 2 and SEQ ID NO: 4, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab1, the Fab fragment includes the variable light chain sequence of SEQ ID NO: 1 and the variable heavy chain sequence of SEQ ID NO: 3. This embodiment of the invention further contemplates additions, deletions, and variants of SEQ ID NO: 1 and/or SEQ ID NO: 3 in said Fab while retaining binding specificity for CGRP.

In one embodiment of the invention described herein (infra), Fab fragments may be produced by enzymatic digestion (e.g., papain) of Ab1. In another embodiment of the invention, anti-CGRP antibodies such as Ab1 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab2

In one embodiment, the invention includes humanized antibodies having binding specificity to CGRP and possessing a variable light chain sequence comprising the sequence set forth below:

```
                                              (SEQ ID NO: 11)
QVLTQSPSSLSASVGDRVTINCQASQSVYDNNYLAWYQQKPGKVPKQLIY

STSTLASGVPSRFSGSGSGTDFTLTISSLQPEDVATYYCLGSYDCSSGDC

FVFGGGTKVEIKR.
```

The invention also includes humanized antibodies having binding specificity to CGRP and possessing a light chain sequence comprising the sequence set forth below:

```
                                              (SEQ ID NO: 12)
QVLTQSPSSLSASVGDRVTINCQASQSVYDNNYLAWYQQKPGKVPKQLIY

STSTLASGVPSRFSGSGSGTDFTLTISSLQPEDVATYYCLGSYDCSSGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.
```

The invention further includes humanized antibodies having binding specificity to CGRP and possessing a variable heavy chain sequence comprising the sequence set forth below:

```
                                              (SEQ ID NO: 13)
EVQLVESGGGLVQPGGSLRLSCAVSGLDLSSYYMQWVRQAPGKGLEWVGV

IGINDNTYYASWAKGRFTISRDNSKTTVYLQMNSLRAEDTAVYFCARGDI

WGQGTLVTVSS.
```

The invention also includes humanized antibodies having binding specificity to CGRP and possessing a heavy chain sequence comprising the sequence set forth below:

(SEQ ID NO: 14)
EVQLVESGGGLVQPGGSLRLSCAVSGLDLSSYYMQWVRQAPGKGLEWVGV

IGINDNTYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDKRVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The invention further contemplates antibodies comprising one or more of the polypeptide sequences of SEQ ID NO: 15; SEQ ID NO: 16; and SEQ ID NO: 17 which correspond to the complementarity-determining regions (CDRs, or hypervariable regions) of the variable light chain sequence of SEQ ID NO: 11 or the light chain sequence of SEQ ID NO: 12, and/or one or more of the polypeptide sequences of SEQ ID NO: 18; SEQ ID NO: 19; and SEQ ID NO: 20 which correspond to the complementarity-determining regions (CDRs, or hypervariable regions) of the variable heavy chain sequence of SEQ ID NO: 13 or the heavy chain sequence of SEQ ID NO: 14, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to CGRP. In one embodiment of the invention, antibody fragments of the invention comprise, or alternatively consist of, the polypeptide sequence of SEQ ID NO: 11 or SEQ ID NO: 12. In another embodiment of the invention, antibody fragments of the invention comprise, or alternatively consist of, the polypeptide sequence of SEQ ID NO: 13 or SEQ ID NO: 14.

In a further embodiment of the invention, fragments of the antibody having binding specificity to CGRP comprise, or alternatively consist of, one or more of the polypeptide sequences of SEQ ID NO: 15; SEQ ID NO: 16; and SEQ ID NO: 17 which correspond to the complementarity-determining regions (CDRs, or hypervariable regions) of the variable light chain sequence of SEQ ID NO: 11 or the light chain sequence of SEQ ID NO: 12.

In a further embodiment of the invention, fragments of the antibody having binding specificity to CGRP comprise, or alternatively consist of, one or more of the polypeptide sequences of SEQ ID NO: 18; SEQ ID NO: 19; and SEQ ID NO: 20 which correspond to the complementarity-determining regions (CDRs, or hypervariable regions) of the variable heavy chain sequence of SEQ ID NO: 13 or the heavy chain sequence of SEQ ID NO: 14.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 11; the variable heavy chain region of SEQ ID NO: 13; the complementarity-determining regions (SEQ ID NO: 15; SEQ ID NO: 16; and SEQ ID NO: 17) of the variable light chain region of SEQ ID NO: 11; and the complementarity-determining regions (SEQ ID NO: 18; SEQ ID NO: 19; and SEQ ID NO: 20) of the variable heavy chain region of SEQ ID NO: 13.

In a particularly preferred embodiment of the invention, the humanized anti-CGRP antibody is Ab2, comprising, or alternatively consisting of, SEQ ID NO: 12 and SEQ ID NO: 14, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab2, the Fab fragment includes the variable light chain sequence of SEQ ID NO: 11 and the variable heavy chain sequence of SEQ ID NO: 13. This embodiment of the invention further contemplates additions, deletions, and variants of SEQ ID NO: 11 and/or SEQ ID NO: 13 in said Fab while retaining binding specificity for CGRP.

In one embodiment of the invention described herein (infra), Fab fragments may be produced by enzymatic digestion (e.g., papain) of Ab2. In another embodiment of the invention, anti-CGRP antibodies such as Ab2 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab3

In one embodiment, the invention includes humanized antibodies having binding specificity to CGRP and possessing a variable light chain sequence comprising the sequence set forth below:

(SEQ ID NO: 21)
QVLTQSPSSLSASVGDRVTINCQASQSVYDNNYLAWYQQKPGKVPKQLIY

STSTLASGVPSRFSGSGSGTDFTLTISSLQPEDVATYYCLGSYDCSSGDC

FVFGGGTKVEIKR.

The invention also includes humanized antibodies having binding specificity to CGRP and possessing a light chain sequence comprising the sequence set forth below:

(SEQ ID NO: 22)
QVLTQSPSSLSASVGDRVTINCQASQSVYDNNYLAWYQQKPGKVPKQLIY

STSTLASGVPSRFSGSGSGTDFTLTISSLQPEDVATYYCLGSYDCSSGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes humanized antibodies having binding specificity to CGRP and possessing a variable heavy chain sequence comprising the sequence set forth below:

(SEQ ID NO: 23)
EVQLVESGGGLVQPGGSLRLSCAVSGLDLSSYYMQWVRQAPGKGLEWVGV

IGINDNTYYASWAKGRFTISRDNSKTTVYLQMNSLRAEDTAVYFCARGDI

WGQGTLVTVSS.

The invention also includes humanized antibodies having binding specificity to CGRP and possessing a heavy chain sequence comprising the sequence set forth below:

(SEQ ID NO: 24)
EVQLVESGGGLVQPGGSLRLSCAVSGLDLSSYYMQWVRQAPGKGLEWVGV

IGINDNTYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDARVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The invention further contemplates antibodies comprising one or more of the polypeptide sequences of SEQ ID NO: 25; SEQ ID NO: 26; and SEQ ID NO: 27 which correspond to the complementarity-determining regions (CDRs, or hypervariable regions) of the variable light chain sequence of SEQ ID NO: 21 or the light chain sequence of SEQ ID NO: 22, and/or one or more of the polypeptide sequences of SEQ ID NO: 28; SEQ ID NO: 29; and SEQ ID NO: 30 which correspond to the complementarity-determining regions (CDRs, or hypervariable regions) of the variable heavy chain sequence of SEQ ID NO: 23 or the heavy chain sequence of SEQ ID NO: 24, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to CGRP. In one embodiment of the invention, antibody fragments of the invention comprise, or alternatively consist of, the polypeptide sequence of SEQ ID NO: 21 or SEQ ID NO: 22. In another embodiment of the invention, antibody fragments of the invention comprise, or alternatively consist of, the polypeptide sequence of SEQ ID NO: 23 or SEQ ID NO: 24.

In a further embodiment of the invention, fragments of the antibody having binding specificity to CGRP comprise, or alternatively consist of, one or more of the polypeptide sequences of SEQ ID NO: 25; SEQ ID NO: 26; and SEQ ID NO: 27 which correspond to the complementarity-determining regions (CDRs, or hypervariable regions) of the variable light chain sequence of SEQ ID NO: 21 or the light chain sequence of SEQ ID NO: 22.

In a further embodiment of the invention, fragments of the antibody having binding specificity to CGRP comprise, or alternatively consist of, one or more of the polypeptide sequences of SEQ ID NO: 28; SEQ ID NO: 29; and SEQ ID NO: 30 which correspond to the complementarity-determining regions (CDRs, or hypervariable regions) of the variable heavy chain sequence of SEQ ID NO: 23 or the heavy chain sequence of SEQ ID NO: 24.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 21; the variable heavy chain region of SEQ ID NO: 23; the complementarity-determining regions (SEQ ID NO: 25; SEQ ID NO: 26; and SEQ ID NO: 27) of the variable light chain region of SEQ ID NO: 21; and the complementarity-determining regions (SEQ ID NO: 28; SEQ ID NO: 29; and SEQ ID NO: 30) of the variable heavy chain region of SEQ ID NO: 23.

In a particularly preferred embodiment of the invention, the chimeric anti-CGRP antibody is Ab3, comprising, or alternatively consisting of, SEQ ID NO: 22 and SEQ ID NO: 24, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab3, the Fab fragment includes the variable light chain sequence of SEQ ID NO: 21 and the variable heavy chain sequence of SEQ ID NO: 23. This embodiment of the invention further contemplates additions, deletions, and variants of SEQ ID NO: 21 and/or SEQ ID NO: 23 in said Fab while retaining binding specificity for CGRP.

In one embodiment of the invention described herein (infra), Fab fragments may be produced by enzymatic digestion (e.g., papain) of Ab3. In another embodiment of the invention, anti-CGRP antibodies such as Ab3 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab4

In one embodiment, the invention includes chimeric antibodies having binding specificity to CGRP and possessing a variable light chain sequence comprising the sequence set forth below:

(SEQ ID NO: 31)
QVLTQTPSPVSAAVGSTVTINCQASQSVYHNTYLAWYQQKPGQPPKQLIY

DASTLASGVPSRFSGSGSGTQFTLTISGVQCNDAAAYYCLGSYDCTNGDC

FVFGGGTEVVVKR.

The invention also includes chimeric antibodies having binding specificity to CGRP and possessing a light chain sequence comprising the sequence set forth below:

(SEQ ID NO: 32)
QVLTQTPSPVSAAVGSTVTINCQASQSVYHNTYLAWYQQKPGQPPKQLIY

DASTLASGVPSRFSGSGSGTQFTLTISGVQCNDAAAYYCLGSYDCTNGDC

FVFGGGTEVVVKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes chimeric antibodies having binding specificity to CGRP and possessing a variable heavy chain sequence comprising the sequence set forth below:

(SEQ ID NO: 33)
QSLEESGGRLVTPGTPLTLTCSVSGIDLSGYYMNWVRQAPGKGLEWIGVI

GINGATYYASWAKGRFTISKTSSTTVDLKMTSLTTEDTATYFCARGDIWG

PGTLVTVSS.

The invention also includes chimeric antibodies having binding specificity to CGRP and possessing a heavy chain sequence comprising the sequence set forth below:

(SEQ ID NO: 34)
QSLEESGGRLVTPGTPLTLTCSVSGIDLSGYYMNWVRQAPGKGLEWIGVI

GINGATYYASWAKGRFTISKTSSTTVDLKMTSLTTEDTATYFCARGDIWG

PGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSN

TKVDKRVEPKSCDKTHTCPPCPAPELLGGPSVFLFPPKPKDTLMISRTPE

VTCVVVDVSHEDPEVKFNWYVDGVEVHNAKTKPREEQYASTYRVVSVLTV

LHQDWLNGKEYKCKVSNKALPAPIEKTISKAKGQPREPQVYTLPPSREEM

TKNQVSLTCLVKGFYPSDIAVEWESNGQPENNYKTTPPVLDSDGSFFLYS

KLTVDKSRWQQGNVFSCSVMHEALHNHYTQKSLSLSPGK.

The invention further contemplates antibodies comprising one or more of the polypeptide sequences of SEQ ID NO: 35; SEQ ID NO: 36; and SEQ ID NO: 37 which correspond to the complementarity-determining regions (CDRs, or hypervariable regions) or the variable light chain sequence of SEQ ID NO: 31 or the light chain sequence of SEQ ID NO: 32, and/or one or more of the polypeptide sequences of SEQ ID NO: 38; SEQ ID NO: 39; and SEQ ID NO: 40 which correspond to the complementarity-determining regions (CDRs, or hypervariable regions) of the variable heavy chain sequence of SEQ ID NO: 33 or the heavy chain sequence of SEQ ID NO: 34, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to CGRP. In one embodiment of the invention, antibody fragments of the invention comprise, or alternatively consist of, the polypeptide sequence of SEQ ID NO: 31 or SEQ ID NO: 32. In another embodiment of the invention, antibody fragments of the invention comprise, or alternatively consist of, the polypeptide sequence of SEQ ID NO: 33 or SEQ ID NO: 34.

In a further embodiment of the invention, fragments of the antibody having binding specificity to CGRP comprise, or alternatively consist of, one or more of the polypeptide sequences of SEQ ID NO: 35; SEQ ID NO: 36; and SEQ ID NO: 37 which correspond to the complementarity-determining regions (CDRs, or hypervariable regions) of the variable light chain sequence of SEQ ID NO: 31 or the light chain sequence of SEQ ID NO: 32.

In a further embodiment of the invention, fragments of the antibody having binding specificity to CGRP comprise, or alternatively consist of, one or more of the polypeptide sequences of SEQ ID NO: 38; SEQ ID NO: 39; and SEQ ID NO: 40 which correspond to the complementarity-determining regions (CDRs, or hypervariable regions) of the variable heavy chain sequence of SEQ ID NO: 33 or the heavy chain sequence of SEQ ID NO: 34.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 31; the variable heavy chain region of SEQ ID NO: 33; the complementarity-determining regions (SEQ ID NO: 35; SEQ ID NO: 36; and SEQ ID NO: 37) of the variable light chain region of SEQ ID NO: 31; and the complementarity-determining regions (SEQ ID NO: 38; SEQ ID NO: 39; and SEQ ID NO: 40) of the variable heavy chain region of SEQ ID NO: 33.

In a particularly preferred embodiment of the invention, the humanized anti-CGRP antibody is Ab4, comprising, or alternatively consisting of, SEQ ID NO: 32 and SEQ ID NO: 34, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab4, the Fab fragment includes the variable light chain sequence of SEQ ID NO: 31 and the variable heavy chain sequence of SEQ ID NO: 33. This embodiment of the invention further contemplates additions, deletions, and variants of SEQ ID NO: 31 and/or SEQ ID NO: 33 in said Fab while retaining binding specificity for CGRP.

In one embodiment of the invention described herein (infra), Fab fragments may be produced by enzymatic digestion (e.g., papain) of Ab4. In another embodiment of the invention, anti-CGRP antibodies such as Ab4 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab5

In one embodiment, the invention includes humanized antibodies having binding specificity to CGRP and possessing a variable light chain sequence comprising the sequence set forth below:

(SEQ ID NO: 41)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKR.

The invention also includes humanized antibodies having binding specificity to CGRP and possessing a light chain sequence comprising the sequence set forth below:

(SEQ ID NO: 42)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes humanized antibodies having binding specificity to CGRP and possessing a variable heavy chain sequence comprising the sequence set forth below:

(SEQ ID NO: 43)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSS.

The invention also includes humanized antibodies having binding specificity to CGRP and possessing a heavy chain sequence comprising the sequence set forth below:

(SEQ ID NO: 44)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDKRVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The invention further contemplates antibodies comprising one or more of the polypeptide sequences of SEQ ID NO: 45; SEQ ID NO: 46; and SEQ ID NO: 47 which correspond to the complementarity-determining regions (CDRs, or hypervariable regions) of the variable light chain sequence of SEQ ID NO: 41 or the light chain sequence of SEQ ID NO: 42, and/or one or more of the polypeptide sequences of SEQ ID NO: 48; SEQ ID NO: 49; and SEQ ID NO: 50 which correspond to the complementarity-determining regions (CDRs, or hypervariable regions) of the variable heavy chain sequence of SEQ ID NO: 43 or the heavy chain sequence of SEQ ID NO: 44, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 41 or SEQ ID NO: 42. In another embodiment of the invention, antibody fragments of the invention comprise, or alternatively consist of, the polypeptide sequence of SEQ ID NO: 43 or SEQ ID NO: 44.

In a further embodiment of the invention, fragments of the antibody having binding specificity to CGRP comprise, or alternatively consist of, one or more of the polypeptide sequences of SEQ ID NO: 45; SEQ ID NO: 46; and SEQ ID NO: 47 which correspond to the complementarity-determining regions (CDRs, or hypervariable regions) of the variable light chain sequence of SEQ ID NO: 41 or the light chain sequence of SEQ ID NO: 42.

In a further embodiment of the invention, fragments of the antibody having binding specificity to CGRP comprise, or alternatively consist of, one or more of the polypeptide sequences of SEQ ID NO: 48; SEQ ID NO: 49; and SEQ ID NO: 50 which correspond to the complementarity-determining regions (CDRs, or hypervariable regions) of the variable heavy chain sequence of SEQ ID NO: 43 or the heavy chain sequence of SEQ ID NO: 44.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 41; the variable heavy chain region of SEQ ID NO: 43; the complementarity-determining regions (SEQ ID NO: 45; SEQ ID NO: 46; and SEQ ID NO: 47) of the variable light chain region of SEQ ID NO: 41; and the complementarity-determining regions (SEQ ID NO: 48; SEQ ID NO: 49; and SEQ ID NO: 50) of the variable heavy chain region of SEQ ID NO: 43.

In a particularly preferred embodiment of the invention, the chimeric anti-CGRP antibody is Ab5, comprising, or alternatively consisting of, SEQ ID NO: 42 and SEQ ID NO: 44, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab5, the Fab fragment includes the variable light chain sequence of SEQ ID NO: 41 and the variable heavy chain sequence of SEQ ID NO: 43. This embodiment of the invention further contemplates additions, deletions, and variants of SEQ ID NO: 41 and/or SEQ ID NO: 43 in said Fab while retaining binding specificity for CGRP.

In one embodiment of the invention described herein (infra), Fab fragments may be produced by enzymatic digestion (e.g., papain) of Ab5. In another embodiment of the invention, anti-CGRP antibodies such as Ab5 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab6

In one embodiment, the invention includes humanized antibodies having binding specificity to CGRP and possessing a variable light chain sequence comprising the sequence set forth below:

(SEQ ID NO: 51)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKR.

The invention also includes humanized antibodies having binding specificity to CGRP and possessing a light chain sequence comprising the sequence set forth below:

(SEQ ID NO: 52)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes humanized antibodies having binding specificity to CGRP and possessing a variable heavy chain sequence comprising the sequence set forth below:

(SEQ ID NO: 53)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSS.

The invention also includes humanized antibodies having binding specificity to CGRP and possessing a heavy chain sequence comprising the sequence set forth below:

(SEQ ID NO: 54)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDARVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The invention further contemplates antibodies comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 52, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 54, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 51 or SEQ ID NO: 52. In another embodiment of the invention, antibody fragments of the invention comprise, or alternatively consist of, the polypeptide sequence of SEQ ID NO: 53 or SEQ ID NO: 54.

In a further embodiment of the invention, fragments of the antibody having binding specificity to CGRP comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 52.

In a further embodiment of the invention, fragments of the antibody having binding specificity to CGRP comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 54.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53.

In a particularly preferred embodiment of the invention, the humanized anti-CGRP antibody is Ab6, comprising, or alternatively consisting of, SEQ ID NO: 52 and SEQ ID NO: 54, and having at least one of the biological activities set forth herein.

In a further particularly preferred embodiment of the invention, antibody fragments comprise, or alternatively consist of Fab (fragment antigen binding) fragments having binding specificity for CGRP. With respect to antibody Ab6, the Fab fragment includes the variable light chain sequence of SEQ ID NO: 51 and the variable heavy chain sequence of SEQ ID NO: 53. This embodiment of the invention further contemplates additions, deletions, and variants of SEQ ID NO: 51 and/or SEQ ID NO: 53 in said Fab while retaining binding specificity for CGRP.

In one embodiment of the invention described herein (infra), Fab fragments may be produced by enzymatic digestion (e.g., papain) of Ab6. In another embodiment of the invention, anti-CGRP antibodies such as Ab6 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab7

In one embodiment, the invention includes chimeric antibodies having binding specificity to CGRP and possessing a variable light chain sequence comprising the sequence set forth below:

(SEQ ID NO: 61)
QVLTQTASPVSAAVGSTVTINCQASQSVYNYNYLAWYQQKPGQPPKQLIY
STSTLASGVSSRFKGSGSGTQFTLTISDVQCDDAATYYCLGSYDCSTGDC
FVFGGGTEVVVKR.

The invention also includes chimeric antibodies having binding specificity to CGRP and possessing a light chain sequence comprising the sequence set forth below:

(SEQ ID NO: 62)
QVLTQTASPVSAAVGSTVTINCQASQSVYNYNYLAWYQQKPGQPPKQLIY
STSTLASGVSSRFKGSGSGTQFTLTISDVQCDDAATYYCLGSYDCSTGDC
FVFGGGTEVVVKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC.

The invention further includes chimeric antibodies having binding specificity to CGRP and possessing a variable heavy chain sequence comprising the sequence set forth below:

(SEQ ID NO: 63)
QEQLKESGGRLVTPGTSLTLTCTVSGIDLSNHYMQWVRQAPGKGLEWIGV
VGINGRTYYASWAKGRFTISRTSSTTVDLKMTRLTTEDTATYFCARGDIW
GPGTLVTVSS.

The invention also includes chimeric antibodies having binding specificity to CGRP and possessing a heavy chain sequence comprising the sequence set forth below:

(SEQ ID NO: 64)
QEQLKESGGRLVTPGTSLTLTCTVSGIDLSNHYMQWVRQAPGKGLEWIGV
VGINGRTYYASWAKGRFTISRTSSTTVDLKMTRLTTEDTATYFCARGDIW
GPGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPS
NTKVDKRVEPKSCDKTHTCPPCPAPELLGGPSVFLFPPKPKDTLMISRTP
EVTCVVVDVSHEDPEVKFNWYVDGVEVHNAKTKPREEQYASTYRVVSVLT
VLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLY
SKLTVDKSRWQQGNVFSCSVMHEALHNHYTQKSLSLSPGK.

The invention further contemplates antibodies comprising one or more of the polypeptide sequences of SEQ ID NO: 65; SEQ ID NO: 66; and SEQ ID NO: 67 which correspond to the complementarity-determining regions (CDRs, or hypervariable regions) of the variable light chain sequence of SEQ ID NO: 61 or the light chain sequence of SEQ ID NO: 62, and/or one or more of the polypeptide sequences of SEQ ID NO: 68; SEQ ID NO: 69; and SEQ ID NO: 70 which correspond to the complementarity-determining regions (CDRs, or hypervariable regions) of the variable heavy chain sequence of SEQ ID NO: 63 or the heavy chain sequence of SEQ ID NO: 64, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 61 or SEQ ID NO: 62. In another embodiment of the invention, antibody fragments of the invention comprise, or alternatively consist of, the polypeptide sequence of SEQ ID NO: 63 or SEQ ID NO: 64.

In a further embodiment of the invention, fragments of the antibody having binding specificity to CGRP comprise, or alternatively consist of, one or more of the polypeptide sequences of SEQ ID NO: 65; SEQ ID NO: 66; and SEQ ID NO: 67 which correspond to the complementarity-determining regions (CDRs, or hypervariable regions) of the variable light chain sequence of SEQ ID NO: 61 or the light chain sequence of SEQ ID NO: 62.

In a further embodiment of the invention, fragments of the antibody having binding specificity to CGRP comprise, or alternatively consist of, one or more of the polypeptide sequences of SEQ ID NO: 68; SEQ ID NO: 69; and SEQ ID NO: 70 which correspond to the complementarity-determining regions (CDRs, or hypervariable regions) of the variable heavy chain sequence of SEQ ID NO: 63 or the heavy chain sequence of SEQ ID NO: 64.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 61; the variable heavy chain region of SEQ ID NO: 63; the complementarity-determining regions (SEQ ID NO: 65; SEQ ID NO: 66; and SEQ ID NO: 67) of the variable light chain region of SEQ ID NO: 61; and the complementarity-determining regions (SEQ ID NO: 68; SEQ ID NO: 69; and SEQ ID NO: 70) of the variable heavy chain region of SEQ ID NO: 63.

In a particularly preferred embodiment of the invention, the chimeric anti-CGRP antibody is Ab7, comprising, or alternatively consisting of, SEQ ID NO: 62 and SEQ ID NO: 64, and having at least one or the biological activities set forth herein.

In a further particularly preferred embodiment of the invention, antibody fragments comprise, or alternatively consist of, Fab (fragment antigen binding) fragments having binding specificity for CGRP. With respect to antibody Ab7, the Fab fragment includes the variable light chain sequence of SEQ ID NO: 61 and the variable heavy chain sequence of SEQ ID NO: 63. This embodiment of the invention further contemplates additions, deletions, and variants of SEQ ID NO: 61 and/or SEQ ID NO: 63 in said Fab while retaining binding specificity for CGRP.

In one embodiment of the invention described herein (infra), Fab fragments may be produced by enzymatic digestion (e.g., papain) of Ab7. In another embodiment of the invention, anti-CGRP antibodies such as Ab7 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab8

In one embodiment, the invention includes humanized antibodies having binding specificity to CGRP and possessing a variable light chain sequence comprising the sequence set forth below:

(SEQ ID NO: 71)
QVLTQSPSSLSASVGDRVTINCQASQSVYNYNYLAWYQQKPGKVPKQLIY

STSTLASGVPSRFSGSGSGTDFTLTISSLQPEDVATYYCLGSYDCSTGDC

FVFGGGTKVEIKR.

The invention also includes humanized antibodies having binding specificity to CGRP and possessing a light chain sequence comprising the sequence set forth below:

(SEQ ID NO: 72)
QVLTQSPSSLSASVGDRVTINCQASQSVYNYNYLAWYQQKPGKVPKQLIY

STSTLASGVPSRFSGSGSGTDFTLTISSLQPEDVATYYCLGSYDCSTGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes humanized antibodies having binding specificity to CGRP and possessing a variable heavy chain sequence comprising the sequence set forth below:

(SEQ ID NO: 73)
EVQLVESGGGLVQPGGSLRLSCAVSGIDLSNHYMQWVRQAPGKGLEWVGV

VGINGRTYYASWAKGRFTISRDNSKTTVYLQMNSLRAEDTAVYFCARGDI

WGQGTLVTVSS.

The invention also includes humanized antibodies having binding specificity to CGRP and possessing a heavy chain sequence comprising the sequence set forth below:

(SEQ ID NO: 74)
EVQLVESGGGLVQPGGSLRLSCAVSGIDLSNHYMQWVRQAPGKGLEWVGV

VGINGRTYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDKRVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The invention further contemplates antibodies comprising one or more of the polypeptide sequences of SEQ ID NO: 75; SEQ ID NO: 76; and SEQ ID NO: 77 which correspond to the complementarity-determining regions (CDRs, or hypervariable regions) of the variable light chain sequence of SEQ ID NO: 71 or the light chain sequence of SEQ ID NO: 72, and/or one or more of the polypeptide sequences of SEQ ID NO: 78; SEQ ID NO: 79; and SEQ ID NO: 80 which correspond to the complementarity-determining regions (CDRs, or hypervariable regions) of the variable heavy chain sequence of SEQ ID NO: 73 or the heavy chain sequence of SEQ ID NO: 74, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 71 or SEQ ID NO: 72. In another embodiment of the invention, antibody fragments of the invention comprise, or alternatively consist of, the polypeptide sequence of SEQ ID NO: 73 or SEQ ID NO: 74.

In a further embodiment of the invention, fragments of the antibody having binding specificity to CGRP comprise, or alternatively consist of, one or more of the polypeptide sequences of SEQ ID NO: 75; SEQ ID NO: 76; and SEQ ID NO: 77 which correspond to the complementarity-determining regions (CDRs, or hypervariable regions) of the variable light chain sequence of SEQ ID NO: 71 or the light chain sequence of SEQ ID NO: 72.

In a further embodiment of the invention, fragments of the antibody having binding specificity to CGRP comprise, or alternatively consist of, one or more of the polypeptide sequences of SEQ ID NO: 78; SEQ ID NO: 79; and SEQ ID NO: 80 which correspond to the complementarity-determining regions (CDRs, or hypervariable regions) of the variable heavy chain sequence of SEQ ID NO: 73 or the heavy chain sequence of SEQ ID NO: 74.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 71; the variable heavy chain region of SEQ ID NO: 73; the complementarity-determining regions (SEQ ID NO: 75; SEQ ID NO: 76; and SEQ ID NO: 77) of the variable light chain region of SEQ ID NO: 71; and the complementarity-determining regions (SEQ ID NO: 78; SEQ ID NO: 79; and SEQ ID NO: 80) of the variable heavy chain region of SEQ ID NO: 73.

In a particularly preferred embodiment of the invention, the humanized anti-CGRP antibody is Ab8, comprising, or alternatively consisting of, SEQ ID NO: 72 and SEQ ID NO: 74, and having at least one or the biological activities set forth herein.

In a further particularly preferred embodiment of the invention, antibody fragments comprise, or alternatively consist of Fab (fragment antigen binding) fragments having binding specificity for CGRP. With respect to antibody Ab8, the Fab fragment includes the variable light chain sequence of SEQ ID NO: 71 and the variable heavy chain sequence of SEQ ID NO: 73. This embodiment of the invention further contemplates additions, deletions, and variants of SEQ ID NO: 71 and/or SEQ ID NO: 73 in said Fab while retaining binding specificity for CGRP.

In one embodiment of the invention described herein (infra), Fab fragments may be produced by enzymatic digestion (e.g., papain) of Ab8. In another embodiment of the invention, anti-CGRP antibodies such as Ab8 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab9

In one embodiment, the invention includes chimeric antibodies having binding specificity to CGRP and possessing a variable light chain sequence comprising the sequence set forth below:

```
                                              (SEQ ID NO: 81)
QVLTQTPSPVSAAVGSTVTINCQASQNVYNNNYLAWYQQKPGQPPKQLIY

STSTLASGVSSRFRGSGSGTQFTLTISDVQCDDAATYYCLGSYDCSRGDC

FVFGGGTEVVVKR.
```

The invention also includes chimeric antibodies having binding specificity to CGRP and possessing a light chain sequence comprising the sequence set forth below:

```
                                              (SEQ ID NO: 82)
QVLTQTPSPVSAAVGSTVTINCQASQNVYNNNYLAWYQQKPGQPPKQLIY

STSTLASGVSSRFRGSGSGTQFTLTISDVQCDDAATYYCLGSYDCSRGDC

FVFGGGTEVVVKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.
```

The invention further includes chimeric antibodies having binding specificity to CGRP and possessing a variable heavy chain sequence comprising the sequence set forth below:

```
                                              (SEQ ID NO: 83)
QSLEESGGRLVTPGTPLTLTCTVSGIGLSSYYMQWVRQSPGRGLEWIGVI

GSDGKTYYATWAKGRFTISKTSSTTVDLRMASLTTEDTATYFCTRGDIWG

PGTLVTVSS.
```

The invention also includes chimeric antibodies having binding specificity to CGRP and possessing a heavy chain sequence comprising the sequence set forth below:

```
                                              (SEQ ID NO: 84)
QSLEESGGRLVTPGTPLTLTCTVSGIGLSSYYMQWVRQSPGRGLEWIGVI

GSDGKTYYATWAKGRFTISKTSSTTVDLRMASLTTEDTATYFCTRGDIWG

PGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSN

TKVDKRVEPKSCDKTHTCPPCPAPELLGGPSVFLFPPKPKDTLMISRTPE

VTCVVVDVSHEDPEVKFNWYVDGVEVHNAKTKPREEQYASTYRVVSVLTV

LHQDWLNGKEYKCKVSNKALPAPIEKTISKAKGQPREPQVYTLPPSREEM

TKNQVSLTCLVKGFYPSDIAVEWESNGQPENNYKTTPPVLDSDGSFFLYS

KLTVDKSRWQQGNVFSCSVMHEALHNHYTQKSLSLSPGK.
```

The invention further contemplates antibodies comprising one or more of the polypeptide sequences of SEQ ID NO: 85; SEQ ID NO: 86; and SEQ ID NO: 87 which correspond to the complementarity-determining regions (CDRs, or hypervariable regions) of the variable light chain sequence of SEQ ID NO: 81 or the light chain sequence of SEQ ID NO: 82, and/or one or more of the polypeptide sequences of SEQ ID NO: 88; SEQ ID NO: 89; and SEQ ID NO: 90 which correspond to the complementarity-determining regions (CDRs, or hypervariable regions) of the variable heavy chain sequence of SEQ ID NO: 83 or the heavy chain sequence of SEQ ID NO: 84, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 81 or SEQ ID NO: 82. In another embodiment of the invention, antibody fragments of the invention comprise, or alternatively consist of, the polypeptide sequence of SEQ ID NO: 83 or SEQ ID NO: 84.

In a further embodiment of the invention, fragments of the antibody having binding specificity to CGRP comprise, or alternatively consist of, one or more of the polypeptide sequences of SEQ ID NO: 85; SEQ ID NO: 86; and SEQ ID NO: 87 which correspond to the complementarity-determining regions (CDRs, or hypervariable regions) of the variable light chain sequence of SEQ ID NO: 81 or the light chain sequence of SEQ ID NO: 82.

In a further embodiment of the invention, fragments of the antibody having binding specificity to CGRP comprise, or alternatively consist of, one or more of the polypeptide sequences of SEQ ID NO: 88; SEQ ID NO: 89; and SEQ ID NO: 90 which correspond to the complementarity-determining regions (CDRs, or hypervariable regions) of the variable heavy chain sequence of SEQ ID NO: 83 or the heavy chain sequence of SEQ ID NO: 84.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 81; the variable heavy chain region of SEQ ID NO: 83; the complementarity-determining regions (SEQ ID NO: 85; SEQ ID NO: 86; and SEQ ID NO: 87) of the variable light chain region of SEQ ID NO: 81; and the complementarity-determining regions (SEQ ID NO: 88; SEQ ID NO: 89; and SEQ ID NO: 90) of the variable heavy chain region of SEQ ID NO: 83.

In a particularly preferred embodiment of the invention, the chimeric anti-CGRP antibody is Ab9, comprising, or alternatively consisting of, SEQ ID NO: 82 and SEQ ID NO: 84, and having at least one or the biological activities set forth herein.

In a further particularly preferred embodiment of the invention, antibody fragments comprise, or alternatively consist of, Fab (fragment antigen binding) fragments having binding specificity for CGRP. With respect to antibody Ab9, the Fab fragment includes the variable light chain sequence of SEQ ID NO: 81 and the variable heavy chain sequence of SEQ ID NO: 83. This embodiment of the invention further contemplates additions, deletions, and variants of SEQ ID NO: 81 and/or SEQ ID NO: 83 in said Fab while retaining binding specificity for CGRP.

In one embodiment of the invention described herein (infra), Fab fragments may be produced by enzymatic digestion (e.g., papain) of Ab9. In another embodiment of the invention, anti-CGRP antibodies such as Ab9 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab10

In one embodiment, the invention includes humanized antibodies having binding specificity to CGRP and possessing a variable light chain sequence comprising the sequence set forth below:

(SEQ ID NO: 91)
QVLTQSPSSLSASVGDRVTINCQASQNVYNNNYLAWYQQKPGKVPKQLIY

STSTLASGVPSRFSGSGSGTDFTLTISSLQPEDVATYYCLGSYDCSRGDC

FVFGGGTKVEIKR.

The invention also includes humanized antibodies having binding specificity to CGRP and possessing a light chain sequence comprising the sequence set forth below:

(SEQ ID NO: 92)
QVLTQSPSSLSASVGDRVTINCQASQNVYNNNYLAWYQQKPGKVPKQLIY

STSTLASGVPSRFSGSGSGTDFTLTISSLQPEDVATYYCLGSYDCSRGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes humanized antibodies having binding specificity to CGRP and possessing a variable heavy chain sequence comprising the sequence set forth below:

(SEQ ID NO: 93)
EVQLVESGGGLVQPGGSLRLSCAVSGIGLSSYYMQWVRQAPGKGLEWVGV

IGSDGKTYYATWAKGRFTISRDNSKTTVYLQMNSLRAEDTAVYFCTRGDI

WGQGTLVTVSS.

The invention also includes humanized antibodies having binding specificity to CGRP and possessing a heavy chain sequence comprising the sequence set forth below:

(SEQ ID NO: 94)
EVQLVESGGGLVQPGGSLRLSCAVSGIGLSSYYMQWVRQAPGKGLEWVGV

IGSDGKTYYATWAKGRFTISRDNSKTTVYLQMNSLRAEDTAVYFCTRGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDKRVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The invention further contemplates antibodies comprising one or more of the polypeptide sequences of SEQ ID NO: 95; SEQ ID NO: 96; and SEQ ID NO: 97 which correspond to the complementarity-determining regions (CDRs, or hypervariable regions) of the variable light chain sequence of SEQ ID NO: 91 or the light chain sequence of SEQ ID NO: 92, and/or one or more of the polypeptide sequences of SEQ ID NO: 98; SEQ ID NO: 99; and SEQ ID NO: 100 which correspond to the complementarity-determining regions (CDRs, or hypervariable regions) of the variable heavy chain sequence of SEQ ID NO: 93 or the heavy chain sequence of SEQ ID NO: 94, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 91 or SEQ ID NO: 92. In another embodiment of the invention, antibody fragments of the invention comprise, or alternatively consist of, the polypeptide sequence of SEQ ID NO: 93 or SEQ ID NO: 94.

In a further embodiment of the invention, fragments of the antibody having binding specificity to CGRP comprise, or alternatively consist of, one or more of the polypeptide sequences of SEQ ID NO: 95; SEQ ID NO: 96; and SEQ ID NO: 97 which correspond to the complementarity-determining regions (CDRs, or hypervariable regions) of the variable light chain sequence of SEQ ID NO: 91 or the light chain sequence of SEQ ID NO: 92.

In a further embodiment of the invention, fragments of the antibody having binding specificity to CGRP comprise, or alternatively consist of, one or more of the polypeptide sequences of SEQ ID NO: 98; SEQ ID NO: 99; and SEQ ID NO: 100 which correspond to the complementarity-determining regions (CDRs, or hypervariable regions) of the variable heavy chain sequence of SEQ ID NO: 93 or the heavy chain sequence of SEQ ID NO: 94.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 91; the variable heavy chain region of SEQ ID NO: 93; the complementarity-determining regions (SEQ ID NO: 95; SEQ ID NO: 96; and SEQ ID NO: 97) of the variable light chain region of SEQ ID NO: 91; and the complementarity-determining regions (SEQ ID NO: 98; SEQ ID NO: 99; and SEQ ID NO: 100) of the variable heavy chain region of SEQ ID NO: 93.

In a particularly preferred embodiment of the invention, the humanized anti-CGRP antibody is Ab10, comprising, or alternatively consisting of, SEQ ID NO: 92 and SEQ ID NO: 94, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab10, the Fab fragment includes the variable light chain sequence of SEQ ID NO: 91 and the variable heavy chain sequence of SEQ ID NO: 93. This embodiment of the invention further contemplates additions, deletions, and variants of SEQ ID NO: 91 and/or SEQ ID NO: 93 in said Fab while retaining binding specificity for CGRP.

In one embodiment of the invention described herein (infra), Fab fragments may be produced by enzymatic digestion (e.g., papain) of Ab10. In another embodiment of the invention, anti-CGRP antibodies such as Ab10 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab11

In one embodiment, the invention includes chimeric antibodies having binding specificity to CGRP and possessing a variable light chain sequence comprising the sequence set forth below:

(SEQ ID NO: 101)
QVLTQTASPVSPAVGSTVTINCRASQSVYYNNYLAWYQQKPGQPPKQLIY

STSTLASGVSSRFKGSGSGTQFTLTISDVQCDDAATYYCLGSYDCSNGDC

FVFGGGTEVVVKR.

The invention also includes chimeric antibodies having binding specificity to CGRP and possessing a light chain sequence comprising the sequence set forth below:

(SEQ ID NO: 102)
QVLTQTASPVSPAVGSTVTINCRASQSVYYNNYLAWYQQKPGQPPKQLIY

STSTLASGVSSRFKGSGSGTQFTLTISDVQCDDAATYYCLGSYDCSNGDC

FVFGGGTEVVVKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes chimeric antibodies having binding specificity to CGRP and possessing a variable heavy chain sequence comprising the sequence set forth below:

(SEQ ID NO: 103)
QSLEESGGRLVTPGGSLTLTCTVSGIDVTNYYMQWVRQAPGKGLEWIGVI

GVNGKRYYASWAKGRFTISKTSSTTVDLKMTSLTTEDTATYFCARGDIWG

PGTLVTVSS.

The invention also includes chimeric antibodies having binding specificity to CGRP and possessing a heavy chain sequence comprising the sequence set forth below:

(SEQ ID NO: 104)
QSLEESGGRLVTPGGSLTLTCTVSGIDVTNYYMQWVRQAPGKGLEWIGVI

GVNGKRYYASWAKGRFTISKTSSTTVDLKMTSLTTEDTATYFCARGDIWG

PGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSN

-continued
TKVDKRVEPKSCDKTHTCPPCPAPELLGGPSVFLFPPKPKDTLMISRTPE

VTCVVVDVSHEDPEVKFNWYVDGVEVHNAKTKPREEQYASTYRVVSVLTV

LHQDWLNGKEYKCKVSNKALPAPIEKTISKAKGQPREPQVYTLPPSREEM

TKNQVSLTCLVKGFYPSDIAVEWESNGQPENNYKTTPPVLDSDGSFFLYS

KLTVDKSRWQQGNVFSCSVMHEALHNHYTQKSLSLSPGK.

The invention further contemplates antibodies comprising one or more of the polypeptide sequences of SEQ ID NO: 105; SEQ ID NO: 106; and SEQ ID NO: 107 which correspond to the complementarity-determining regions (CDRs, or hypervariable regions) of the variable light chain sequence of SEQ ID NO: 101 or the light chain sequence of SEQ ID NO: 102, and/or one or more of the polypeptide sequences of SEQ ID NO: 108; SEQ ID NO: 109; and SEQ ID NO: 110 which correspond to the complementarity-determining regions (CDRs, or hypervariable regions) of the variable heavy chain sequence of SEQ ID NO: 103 or the heavy chain sequence of SEQ ID NO: 104, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 101 or SEQ ID NO: 102. In another embodiment of the invention, antibody fragments of the invention comprise, or alternatively consist of, the polypeptide sequence of SEQ ID NO: 103 or SEQ ID NO: 104.

In a further embodiment of the invention, fragments of the antibody having binding specificity to CGRP comprise, or alternatively consist of, one or more of the polypeptide sequences of SEQ ID NO: 105; SEQ ID NO: 106; and SEQ ID NO: 107 which correspond to the complementarity-determining regions (CDRs, or hypervariable regions) of the variable light chain sequence of SEQ ID NO: 101 or the light chain sequence of SEQ ID NO: 102.

In a further embodiment of the invention, fragments of the antibody having binding specificity to CGRP comprise, or alternatively consist of, one or more of the polypeptide sequences of SEQ ID NO: 108; SEQ ID NO: 109; and SEQ ID NO: 110 which correspond to the complementarity-determining regions (CDRs, or hypervariable regions) of the variable heavy chain sequence of SEQ ID NO: 103 or the heavy chain sequence of SEQ ID NO: 104.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 101; the variable heavy chain region of SEQ ID NO: 103; the complementarity-determining regions (SEQ ID NO: 105; SEQ ID NO: 106; and SEQ ID NO: 107) of the variable light chain region of SEQ ID NO: 101; and the complementarity-determining regions (SEQ ID NO: 108; SEQ ID NO: 109; and SEQ ID NO: 110) of the variable heavy chain region of SEQ ID NO: 103.

In a particularly preferred embodiment of the invention, the chimeric anti-CGRP antibody is Ab11, comprising, or alternatively consisting of, SEQ ID NO: 102 and SEQ ID NO: 104, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab11, the Fab fragment includes the variable light chain sequence of SEQ ID NO: 101 and the variable heavy chain sequence of SEQ ID NO: 103. This embodiment of the invention further contemplates additions, deletions, and variants of SEQ ID NO: 101 and/or SEQ ID NO: 103 in said Fab while retaining binding specificity for CGRP.

In one embodiment of the invention described herein (infra), Fab fragments may be produced by enzymatic digestion (e.g., papain) of Ab11. In another embodiment of the invention, anti-CGRP antibodies such as Ab11 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab12

In one embodiment, the invention includes humanized antibodies having binding specificity to CGRP and possessing a variable light chain sequence comprising the sequence set forth below:

(SEQ ID NO: 111)
QVLTQSPSSLSASVGDRVTINCRASQSVYYNNYLAWYQQKPGKVPKQLIY

STSTLASGVPSRFSGSGSGTDFTLTISSLQPEDVATYYCLGSYDCSNGDC

FVFGGGTKVEIKR.

The invention also includes humanized antibodies having binding specificity to CGRP and possessing a light chain sequence comprising the sequence set forth below:

(SEQ ID NO: 112)
QVLTQSPSSLSASVGDRVTINCRASQSVYYNNYLAWYQQKPGKVPKQLIY

STSTLASGVPSRFSGSGSGTDFTLTISSLQPEDVATYYCLGSYDCSNGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes humanized antibodies having binding specificity to CGRP and possessing a variable heavy chain sequence comprising the sequence set forth below:

(SEQ ID NO: 113)
EVQLVESGGGLVQPGGSLRLSCAVSGIDVTNYYMQWVRQAPGKGLEWVGV

IGVNGKRYYASWAKGRFTISRDNSKTTVYLQMNSLRAEDTAVYFCARGDI

WGQGTLVTVSS.

The invention also includes humanized antibodies having binding specificity to CGRP and possessing a heavy chain sequence comprising the sequence set forth below:

(SEQ ID NO: 114)
EVQLVESGGGLVQPGGSLRLSCAVSGIDVTNYYMQWVRQAPGKGLEWVGV

IGVNGKRYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDKRVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The invention further contemplates antibodies comprising one or more of the polypeptide sequences of SEQ ID NO: 115; SEQ ID NO: 116; and SEQ ID NO: 117 which correspond to the complementarity-determining regions (CDRs, or hypervariable regions) of the variable light chain sequence of SEQ ID NO: 111 or the light chain sequence of SEQ ID NO: 112, and/or one or more of the polypeptide sequences of SEQ ID NO: 118; SEQ ID NO: 119; and SEQ ID NO: 120 which correspond to the complementarity-determining regions (CDRs, or hypervariable regions) of the variable heavy chain sequence of SEQ ID NO: 113 or the heavy chain sequence of SEQ ID NO: 114, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 111 or SEQ ID NO: 112. In another embodiment of the invention, antibody fragments of the invention comprise, or alternatively consist of, the polypeptide sequence of SEQ ID NO: 113 or SEQ ID NO: 114.

In a further embodiment of the invention, fragments of the antibody having binding specificity to CGRP comprise, or alternatively consist of, one or more of the polypeptide sequences of SEQ ID NO: 115; SEQ ID NO: 116; and SEQ ID NO: 117 which correspond to the complementarity-determining regions (CDRs, or hypervariable regions) of the variable light chain sequence of SEQ ID NO: 111 or the light chain sequence of SEQ ID NO: 112.

In a further embodiment of the invention, fragments of the antibody having binding specificity to CGRP comprise, or alternatively consist of, one or more of the polypeptide sequences of SEQ ID NO: 118; SEQ ID NO: 119; and SEQ ID NO: 120 which correspond to the complementarity-determining regions (CDRs, or hypervariable regions) of the variable heavy chain sequence of SEQ ID NO: 113 or the heavy chain sequence of SEQ ID NO: 114.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 111; the variable heavy chain region of SEQ ID NO: 113; the complementarity-determining regions (SEQ ID NO: 115; SEQ ID NO: 116; and SEQ ID NO: 117) of the variable light chain region of SEQ ID NO: 111; and the complementarity-determining regions (SEQ ID NO: 118; SEQ ID NO: 119; and SEQ ID NO: 120) of the variable heavy chain region of SEQ ID NO: 113.

In a particularly preferred embodiment of the invention, the humanized anti-CGRP antibody is Ab12, comprising, or alternatively consisting of, SEQ ID NO: 112 and SEQ ID NO: 114, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab12, the Fab fragment includes the variable light chain sequence of SEQ ID NO: 111 and the variable heavy chain sequence of SEQ ID NO: 113. This embodiment of the invention further contemplates additions, deletions, and variants of SEQ ID NO: 111 and/or SEQ ID NO: 113 in said Fab while retaining binding specificity for CGRP.

In one embodiment of the invention described herein (infra), Fab fragments may be produced by enzymatic digestion (e.g., papain) of Ab12. In another embodiment of the invention, anti-CGRP antibodies such as Ab12 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab13

In one embodiment, the invention includes chimeric antibodies having binding specificity to CGRP and possessing a variable light chain sequence comprising the sequence set forth below:

(SEQ ID NO: 121)
AIVMTQTPSSKSVPVGDTVTINCQASESLYNNNALAWFQQKPGQPPKRLI

YDASKLASGVPSRFSGGGSGTQFTLTISGVQCDDAATYYCGGYRSDSVDG

VAFAGGTEVVVKR.

The invention also includes chimeric antibodies having binding specificity to CGRP and possessing a light chain sequence comprising the sequence set forth below:

(SEQ ID NO: 122)
AIVMTQTPSSKSVPVGDTVTINCQASESLYNNNALAWFQQKPGQPPKRLI

YDASKLASGVPSRFSGGGSGTQFTLTISGVQCDDAATYYCGGYRSDSVDG

VAFAGGTEVVVKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes chimeric antibodies having binding specificity to CGRP and possessing a variable heavy chain sequence comprising the sequence set forth below:

(SEQ ID NO: 123)
QSVEESGGGLVQPEGSLTLTCTASGFDFSSNAMWWVRQAPGKGLEWIGII

YNGDGSTYYASWVNGRFSISKTSSTTVTLQLNSLTVADTATYYCARDLDL

WGPGTLVTVSS.

The invention also includes chimeric antibodies having binding specificity to CGRP and possessing a heavy chain sequence comprising the sequence set forth below:

(SEQ ID NO: 124)
QSVEESGGGLVQPEGSLTLTCTASGFDFSSNAMWWVRQAPGKGLEWIGCI

YNGDGSTYYASWVNGRFSISKTSSTTVTLQLNSLTVADTATYYCARDLDL

WGPGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDKRVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The invention further contemplates antibodies comprising one or more of the polypeptide sequences of SEQ ID NO: 125; SEQ ID NO: 126; and SEQ ID NO: 127 which correspond to the complementarity-determining regions (CDRs, or hypervariable regions) of the variable light chain sequence of SEQ ID NO: 121 or the light chain sequence of SEQ ID NO: 122, and/or one or more of the polypeptide sequences of SEQ ID NO: 128; SEQ ID NO: 129; and SEQ ID NO: 130 which correspond to the complementarity-determining regions (CDRs, or hypervariable regions) of the variable heavy chain sequence of SEQ ID NO: 123 or the heavy chain sequence of SEQ ID NO: 124, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 121 or SEQ ID NO: 122. In another embodiment of the invention, antibody fragments of the invention comprise, or alternatively consist of, the polypeptide sequence of SEQ ID NO: 123 or SEQ ID NO: 124.

In a further embodiment of the invention, fragments of the antibody having binding specificity to CGRP comprise, or alternatively consist of, one or more of the polypeptide sequences of SEQ ID NO: 125; SEQ ID NO: 126; and SEQ ID NO: 127 which correspond to the complementarity-determining regions (CDRs, or hypervariable regions) of the variable light chain sequence of SEQ ID NO: 121 or the light chain sequence of SEQ ID NO: 122.

In a further embodiment of the invention, fragments of the antibody having binding specificity to CGRP comprise, or alternatively consist of, one or more of the polypeptide sequences of SEQ ID NO: 128; SEQ ID NO: 129; and SEQ ID NO: 130 which correspond to the complementarity-determining regions (CDRs, or hypervariable regions) of the variable heavy chain sequence of SEQ ID NO: 123 or the heavy chain sequence of SEQ ID NO: 124.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 121; the variable heavy chain region of SEQ ID NO: 123; the complementarity-determining regions (SEQ ID NO: 125; SEQ ID NO: 126; and SEQ ID NO: 127) of the variable light chain region of SEQ ID NO: 121; and the complementarity-determining regions (SEQ ID NO: 128; SEQ ID NO: 129; and SEQ ID NO: 130) of the variable heavy chain region of SEQ ID NO: 123.

In a particularly preferred embodiment of the invention, the chimeric anti-CGRP antibody is Ab13, comprising, or alternatively consisting of, SEQ ID NO: 122 and SEQ ID NO: 124, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab13, the Fab fragment includes the variable light chain sequence of SEQ ID NO: 121 and the variable heavy chain sequence of SEQ ID NO: 123. This embodiment of the invention further contemplates additions, deletions, and variants of SEQ ID NO: 121 and/or SEQ ID NO: 123 in said Fab while retaining binding specificity for CGRP.

In one embodiment of the invention described herein (infra), Fab fragments may be produced by enzymatic digestion (e.g., papain) of Ab13. In another embodiment of the invention, anti-CGRP antibodies such as Ab13 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab14

In one embodiment, the invention includes humanized antibodies having binding specificity to CGRP and possessing a variable light chain sequence comprising the sequence set forth below:

```
                                        (SEQ ID NO: 131)
QVLTQSPSSLSASVGDRVTINCQASQNVYNNNYLAWYQQKPGKVPKQLIY

STSTLASGVPSRFSGSGSGTDFTLTISSLQPEDVATYYCLGSYDCSRGDC

FVFGGGTKVEIKR.
```

The invention also includes humanized antibodies having binding specificity to CGRP and possessing a light chain sequence comprising the sequence set forth below:

```
                                        (SEQ ID NO: 132)
QVLTQSPSSLSASVGDRVTINCQASQNVYNNNYLAWYQQKPGKVPKQLIY

STSTLASGVPSRFSGSGSGTDFTLTISSLQPEDVATYYCLGSYDCSRGDC

FVFGGGTKVEIKRTVAAPSVFIFPPSDEQLKSGTASVVCLLNNFYPREAK
```

```
VQWKVDNALQSGNSQESVTEQDSKDSTYSLSSTLTLSKADYEKHKVYACE

VTHQGLSSPVTKSFNRGEC.
```

The invention further includes humanized antibodies having binding specificity to CGRP and possessing a variable heavy chain sequence comprising the sequence set forth below:

```
                                        (SEQ ID NO: 133)
EVQLVESGGGLVQPGGSLRLSCAVSGIGLSSYYMQWVRQAPGKGLEWVGV

IGSDGKTYYATWAKGRFTISRDNSKTTVYLQMNSLRAEDTAVYFCTRGDI

WGQGTLVTVSS.
```

The invention also includes humanized antibodies having binding specificity to CGRP and possessing a heavy chain sequence comprising the sequence set forth below:

```
                                        (SEQ ID NO: 134)
EVQLVESGGGLVQPGGSLRLSCAVSGIGLSSYYMQWVRQAPGKGLEWVGV

IGSDGKTYYATWAKGRFTISRDNSKTTVYLQMNSLRAEDTAVYFCTRGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDARVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALIINIIYTQKSLSLSPGK.
```

The invention further contemplates antibodies comprising one or more of the polypeptide sequences of SEQ ID NO: 135; SEQ ID NO: 136; and SEQ ID NO: 137 which correspond to the complementarity-determining regions (CDRs, or hypervariable regions) of the variable light chain sequence of SEQ ID NO: 131 or the light chain sequence of SEQ ID NO: 132, and/or one or more of the polypeptide sequences of SEQ ID NO: 138; SEQ ID NO: 139; and SEQ ID NO: 140 which correspond to the complementarity-determining regions (CDRs, or hypervariable regions) of the variable heavy chain sequence of SEQ ID NO: 133 or the heavy chain sequence of SEQ ID NO: 134, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all to them.

The invention also contemplates fragments of the antibody having binding specificity to CGRP. In one embodiment of the invention, antibody fragments of the invention comprise, or alternatively consist of, the polypeptide sequence of SEQ ID NO: 131 or SEQ ID NO: 132. In another embodiment of the invention, antibody fragments of the invention comprise, or alternatively consist of, the polypeptide sequence of SEQ ID NO: 133 or SEQ ID NO: 134.

In a further embodiment of the invention, fragments of the antibody having binding specificity to CGRP comprise, or alternatively consist of, one or more of the polypeptide sequences of SEQ ID NO: 135; SEQ ID NO: 136; and SEQ ID NO: 137 which correspond to the complementarity-determining regions (CDRs, or hypervariable regions) of the variable light chain sequence of SEQ ID NO: 131 or the light chain sequence of SEQ ID NO: 132.

In a further embodiment of the invention, fragments of the antibody having binding specificity to CGRP comprise, or alternatively consist of, one or more of the polypeptide sequences of SEQ ID NO: 138; SEQ ID NO: 139; and SEQ ID NO: 140 which correspond to the complementarity-determining regions (CDRs, or hypervariable regions) of the variable heavy chain sequence of SEQ ID NO: 133 or the heavy chain sequence of SEQ ID NO: 134.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 131; the variable heavy chain region of SEQ ID NO: 133; the complementarity-determining regions (SEQ ID NO: 135; SEQ ID NO: 136; and SEQ ID NO: 137) of the variable light chain region of SEQ ID NO: 131; and the complementarity-determining regions (SEQ ID NO: 138; SEQ ID NO: 139; and SEQ ID NO: 140) of the variable heavy chain region of SEQ ID NO: 133.

In a particularly preferred embodiment of the invention, the humanized anti-CGRP antibody is Ab14, comprising, or alternatively consisting of, SEQ ID NO: 132 and SEQ ID NO: 134, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab14, the Fab fragment includes the variable light chain sequence of SEQ ID NO: 131 and the variable heavy chain sequence of SEQ ID NO: 133. This embodiment of the invention further contemplates additions, deletions, and variants of SEQ ID NO: 131 and/or SEQ ID NO: 133 in said Fab while retaining binding specificity for CGRP.

In one embodiment of the invention described herein (infra), Fab fragments may be produced by enzymatic digestion (e.g., papain) of Ab14. In another embodiment of the invention, anti-CGRP antibodies such as Ab14 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

In another embodiment, antibody fragments may be present in one or more of the following non-limiting forms: Fab, Fab', F(ab')$_2$, Fv and single chain Fv antibody forms. In a preferred embodiment, the anti-CGRP antibodies described herein further comprises the kappa constant light chain sequence comprising the sequence set forth below:

```
                                        (SEQ ID NO: 283)
VAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSF

NRGEC.
```

In another preferred embodiment, the anti-CGRP antibodies described herein further comprises the gamma-1 constant heavy chain polypeptide sequence comprising the sequence set forth below:

```
                                        (SEQ ID NO: 284)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In another embodiment, the invention contemplates an isolated anti-CGRP antibody comprising a $V_H$ polypeptide sequence selected from: SEQ ID NO: 3, 13, 23, 33, 43, 53, 63, 73, 83, 93, 103, 113, 123, or 133, or a variant thereof; and further comprising a $V_L$ polypeptide sequence selected from: SEQ ID NO: 1, 11, 21, 31, 41, 51, 61, 71, 81, 91, 101, 111, 121, or 131, or a variant thereof, wherein one or more or the framework residues (FR residues) in said $V_H$ or $V_L$ polypeptide has been substituted with another amino acid residue resulting in an anti-CGRP antibody that specifically binds CGRP. The invention contemplates humanized and chimeric forms of these antibodies. The chimeric antibodies may include an Fc derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

In one embodiment of the invention, the antibodies or $V_H$ or $V_L$ polypeptides originate or are selected from one or more rabbit B cell populations prior to initiation of the humanization process referenced herein.

In another embodiment of the invention, the anti-CGRP antibodies and fragments thereof do not have binding specificity for CGRP-R. In a further embodiment of the invention, the anti-CGRP antibodies and fragments thereof inhibit the association of CGRP with CGRP-R. In another embodiment of the invention, the anti-CGRP antibodies and fragments thereof inhibit the association of CGRP with CGRP-R and/or additional proteins and/or multimers thereof, and/or antagonizes the biological effects thereof.

As stated above herein, antibodies and fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Antibodies or fragments thereof may also be chemically modified to provide additional advantages such as increased solubility, stability and circulating time (in vivo half-life) of the polypeptide, or decreased immunogenicity (See U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol and the like. The antibodies and fragments thereof may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for case in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

There are a number of attachment methods available to those skilled in the art, See e.g., EP 0 401 384, herein incorporated by reference (coupling PEG to G-CSF), See also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues, those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof).

Alternatively, antibodies or fragments thereof may have increased in vivo half lives via fusion with albumin (including but not limited to recombinant human serum albumin or fragments or variants thereof (See, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)) or other circulating blood proteins such as transferrin or ferritin. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. Polynucleotides encoding fusion proteins of the invention are also encompassed by the invention.

Regarding detectable moieties, further exemplary enzymes include, but are not limited to, horseradish peroxidase, acetylcholinesterase, alkaline phosphatase, beta-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent moieties include, but are not limited to, luminol. Further exemplary bioluminescent materials include, but are not limited to, luciferin and acquorin. Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), deto-rubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin. Toxic enzymes from plants and bacteria such as ricin, diphtheria toxin and *Pseudomonas* toxin may be conjugated to the humanized or chimeric antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof with or without the use of a complex-forming agent. Such radionuclides include beta-emitters such as Phosphorus-32 ($^{32}$P), Scandium-47 ($^{47}$Sc), Copper-67 ($^{67}$Cu), Gallium-67 ($^{67}$Ga), Yttrium-88 ($^{88}$Y), Yttrium-90 ($^{90}$Y), Iodine-125 ($^{125}$I), Iodine-131 ($^{131}$I), Samarium-153 ($^{153}$Sm), Lutetium-177 ($^{177}$Lu), Rhenium-186 ($^{186}$Re) or Rhenium-188 ($^{188}$Re), and alpha-emitters such as Astatine-211 ($^{211}$At), Lead-212 ($^{212}$Pb), Bismuth-212 ($^{212}$Bi) or -213 ($^{213}$Bi) or Actinium-225 ($^{225}$Ac).

Methods are known in the art for conjugating an antibody or binding fragment thereof to a detectable moiety and the like, such as for example those methods described by Hunter et al, Nature 144:945 (1962); David et al, Biochemistry 13:1014 (1974); Pain et al, J. Immunol. Meth. 40:219 (1981); and Nygren, J., Histochem. and Cytochem. 30:407 (1982).

Embodiments described herein further include variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antibody fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antibody fragments, variable regions and CDRs set forth herein. Methods for determining homology between nucleic acid and amino acid sequences are well known to those of ordinary skill in the art.

In another embodiment, the invention further contemplates the above-recited polypeptide homologs of the antibody fragments, variable regions and CDRs set forth herein further having anti-CGRP activity. Non-limiting examples of anti-CGRP activity are set forth herein, for example, in the section "Additional Exemplary Embodiments of the Invention" below.

In another embodiment, the invention further contemplates the generation and use of anti-idiotypic antibodies that bind any of the foregoing sequences. In an exemplary embodiment, such an anti-idiotypic antibody could be administered to a subject who has received an anti-CGRP antibody to modulate, reduce, or neutralize, the effect of the anti-CGRP antibody. Such anti-idiotypic antibodies could also be useful for treatment of an autoimmune disease characterized by the presence of anti-CGRP antibodies. A further exemplary use of such anti-idiotypic antibodies is for detection of the anti-CGRP antibodies of the present invention, for example to monitor the levels of the anti-CGRP antibodies present in a subject's blood or other bodily fluids.

The present invention also contemplates anti-CGRP antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.
Additional Exemplary Embodiments of the Invention In another embodiment, the invention contemplates one or more anti-human CGRP antibodies or antibody fragments thereof which specifically bind to the same overlapping linear or conformational epitope(s) and/or competes for binding to the same overlapping linear or conformational epitope(s) on an intact human CGRP polypeptide or fragment thereof as an anti-human CGRP antibody selected from Ab1, Ab2, Ab3, Ab4, Ab5, Ab6, Ab7, Ab8, Ab9, Ab10, Ab11, Ab12, Ab13, or Ab14. In a preferred embodiment, the anti-human CGRP antibody or fragment thereof specifically binds to the same overlapping linear or conformational epitope(s) and/or competes for binding to the same overlapping linear or conformational epitope(s) on an intact human CGRP polypeptide or a fragment thereof as Ab3, Ab6, Ab13, or Ab14.

A preferred embodiment of the invention is directed to chimeric or humanized antibodies and fragments thereof (including Fab fragments) having binding specificity for CGRP and inhibiting biological activities mediated by the binding of CGRP to the CGRP receptor. In a particularly preferred embodiment of the invention, the chimeric or humanized anti-CGRP antibodies are selected from Ab3, Ab6, Ab13, or Ab14.

In a further embodiment of the invention is contemplated a method of reducing, treating or preventing diseases or disorders associated with CGRP by affecting those biological activities mediated via CGRP, thereby avoiding the biological activities mediated via binding of CGRP to CGRP-R. In one embodiment, the disease or disorder associated with CGRP is migraine or another disorder wherein CGRP elicits pain, headache, pain, cancer, overactive bladder, or weightloss. A further non-limiting listing of diseases and disorders associated with CGRP is provided herein.

Another preferred embodiment of the invention contemplates the use of Fab polypeptide sequences for the treatment of migraines and headaches in a patient. Non-limiting types of migraines and headaches that may be treated using Fab polypeptide sequences are provided elsewhere in this disclosure.

In another embodiment of the invention, the anti-human CGRP antibody is an antibody which specifically binds to the same overlapping linear or conformational epitopes on an intact CGRP polypeptide or fragment thereof that is (are) specifically bound by Ab3, Ab6, Ab13, or Ab14 as ascertained by epitopic mapping using overlapping linear peptide fragments which span the full length of the native human CGRP polypeptide.

The invention is also directed to an anti-CGRP antibody that binds with the same CGRP epitope and/or competes with an anti-CGRP antibody for binding to CGRP as an antibody or antibody fragment disclosed herein, including but not limited to an anti-CGRP antibody selected from Ab1, Ab2, Ab3, Ab4, Ab5, Ab6, Ab7, Ab8, Ab9, Ab10, Ab11, Ab12, Ab13, or Ab14.

In another embodiment, the invention is also directed to an isolated anti-CGRP antibody or antibody fragment comprising one or more of the CDRs contained in the $V_H$ polypeptide sequences selected from: 3, 13, 23, 33, 43, 53, 63, 73, 83, 93, 103, 113, 123, or 133, or a variant thereof, and/or one or more of the CDRs contained in the $V_L$ polypeptide sequences selected from: 1, 11, 21, 31, 41, 51, 61, 71, 81, 91, 101, 111, 121, or 131, or a variant thereof.

In one embodiment of the invention, the anti-human CGRP antibody discussed in the two prior paragraphs comprises at least 2 complementarity determining regions (CDRs) in each the variable light and the variable heavy regions which are identical to those contained in an anti-human CGRP antibody selected from Ab1, Ab2, Ab3, Ab4, Ab5, Ab6, Ab7, Ab8, Ab9, Ab10, Ab1, Ab12, Ab13, or Ab14.

In a preferred embodiment, the anti-human CGRP antibody discussed above comprises at least 2 complementarity determining regions (CDRs) in each the variable light and the variable heavy regions which are identical to those contained in Ab3 or Ab6. In another embodiment, all of the CDRs of the anti-human CGRP antibody discussed above are identical to the CDRs contained in an anti-human CGRP antibody selected from Ab1, Ab2, Ab3, Ab4, Ab5, Ab6, Ab7, Ab8, Ab9, Ab10, Ab11, Ab12, Ab13, or Ab14. In a preferred embodiment of the invention, all of the CDRs of the anti-human CGRP antibody discussed above are identical to the CDRs contained in an anti-human CGRP antibody selected from Ab3 or Ab6.

The invention further contemplates that the one or more anti-human CGRP antibodies discussed above are aglycosylated; that contain an Fc region that has been modified to alter effector function, half-life, proteolysis, and/or glycosylation; are human, humanized, single chain or chimeric; and are a humanized antibody derived from a rabbit (parent) anti-human CGRP antibody.

The invention further contemplates one or more anti-human CGRP antibodies wherein the framework regions (FRs) in the variable light region and the variable heavy regions of said antibody respectively are human FRs which are unmodified or which have been modified by the substitution of one or more human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

In one embodiment of the invention, the anti-human CGRP antibody or fragment specifically binds to CGRP expressing human cells and/or to circulating soluble CGRP molecules in vivo, including CGRP expressed on or by human cells in a patient with a disease associated with cells that express CGRP.

In another embodiment, the disease is selected from migraines (with or without aura), weight loss, cancer or tumors, angiogenesis associated with cancer or tumor growth, angiogenesis associated with cancer or tumor survival, hemiplagic migraines, cluster headaches, migrainous neuralgia, chronic headaches, tension headaches, general headaches, hot flushes, chronic paroxysomal hemicrania, secondary headaches due to an underlying structural problem in the head or neck, cranial neuralgia, sinus headaches (such as for example associated with sinusitis), allergy-induced headaches or migraines, pain, inflammatory pain, post-operative incision pain, complex regional pain syndrome, cancer pain, primary or metastatic bone cancer pain, fracture pain, chronic pain, osteoporotic fracture pain, pain resulting from burn, osteoporosis, gout joint pain, abdominal pain, pain associated with sickle cell crises, and other nociceptic pain, as well as hepatocellular carcinoma, breast cancer, liver cirrhosis, neurogenic pain, neuropathic pain, nociceptic pain, trigeminal neuralgia, post-herpetic neuralgia, phantom limb pain, fibromyalgia, menstrual pain, ovarialgia, reflex sympathetic dystrophy, neurogenic pain, osteoarthritis or rheumatoid arthritis pain, lower back pain, diabetic neuropathy, sciatica, or pain or visceral pain associated with: gastro-esophageal reflux, dyspepsia, irritable bowel syndrome, irritable colon, spastic colon, mucous colitis, inflammatory bowel disease, Crohn's disease, ileitis, ulcerative colitis, renal colic, dysmenorrhea, cystitis, menstrual period, labor, menopause, prostatitis, pancreatitis, renal colic, dysmenorrhea cystitis, including interstitial cystitis (IC), surgery associated with the ileus, diverticulitis, peritonitis, pericarditis, hepatitis, appendicitis, colitis, cholecystitis, endometriosis, chronic and/or acute pancreatitis, myocardial infarction, kidney pain, pleural pain, prostatitis, pelvic pain, trauma to an organ, chronic nociceptive pain, chronic neuropathic pain, chronic inflammatory pain, fibromyalgia, breakthrough pain and persistent pain.

In another embodiment of the invention, the disease is cancer pain arising from malignancy or from cancer preferably selected from one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumours, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumours, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukaemia, primary or secondary bone cancer, tumours that metastasize to the bone, tumours infiltrating the nerve and hollow viscus, tumours near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

The invention further contemplates anti-human CGRP antibodies or fragments directly or indirectly attached to a detectable label or therapeutic agent.

The invention also contemplates one or more nucleic acid sequences which result in the expression of an anti-human CGRP antibody or antibody fragment as set forth above, including those comprising, or alternatively consisting of, yeast or human preferred codons. The invention also contemplates vectors (including plasmids or recombinant viral vectors) comprising said nucleic acid sequence(s). The invention also contemplates host cells or recombinant host cells expressing at least one of the antibodies set forth above, including a mammalian, yeast, bacterial, and insect cells. In a preferred embodiment, the host cell is a yeast cell. In a further preferred embodiment, the yeast cell is a diploidal yeast cell. In a more preferred embodiment, the yeast cell is a *Pichia* yeast.

The invention also contemplates a method of treatment comprising administering to a patient with a disease or condition associated with CGRP expressing cells a therapeutically effective amount of at least one anti-human CGRP antibody or fragment described herein. The invention also contemplates that the treatment method may involve the administration of two or more anti-CGRP antibodies or fragments thereof and disclosed herein. If more than one antibody is administered to the patient, the multiple antibodies may be administered simultaneously or concurrently, or may be staggered in their administration. The diseases that may be treated are presented in the non-limiting list set forth above and elsewhere herein. In a preferred embodiment, the disease is selected from migraine, headache, weight loss, pain, cancer pain or neuropathic pain. In another embodiment the treatment further includes the administration of another therapeutic agent or regimen selected from chemotherapy, radiotherapy, cytokine administration or gene therapy.

In a non-limiting embodiment of the invention, another therapeutic agent or regimen includes Taxol (paclitaxel) or its derivatives, platinum compounds such as carboplatin or cisplatin, anthrocyclines such as doxorubicin, alkylating agents such as cyclophosphamide, anti-metabolites such as 5-fluorouracil, or etoposide.

The invention further contemplates a method of in vivo imaging which detects the presence of cells which express CGRP comprising administering a diagnostically effective amount of at least one anti-human CGRP antibody. In one embodiment, said administration further includes the administration of a radionuclide or fluorophore that facilitates detection of the antibody at CGRP expressing disease sites. In a further embodiment, the results of said in vivo imaging method are used to facilitate the design of an appropriate therapeutic regimen, including therapeutic regimens including radiotherapy, chemotherapy or a combination thereof.

The anti-CGRP activity of the anti-CGRP antibodies of the present invention, and fragments thereof having binding specificity to CGRP, may also be described by their strength of binding or their affinity for CGRP. In one embodiment of the invention, the anti-CGRP antibodies of the present invention, and fragments thereof having binding specificity to CGRP, bind to CGRP with a dissociation constant ($K_D$) of less than or equal to $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, or $10^{-13}$ M. Preferably, the anti-CGRP antibodies and fragments thereof bind CGRP with a dissociation constant of less than or equal to $10^{-11}$ M, $5 \times 10^{-12}$ M, or $10^{-12}$ M. In another embodiment of the invention, the anti-CGRP antibodies of the present invention, and fragments thereof having binding specificity to CGRP, bind to a linear or conformational CGRP epitope.

In another embodiment of the invention, the anti-CGRP activity of the anti-CGRP antibodies of the present invention, and fragments thereof having binding specificity to CGRP, bind to CGRP with an off-rate of less than or equal to $10^{-4}$ S$^{-1}$, $5 \times 10^{-5}$ S$^{-1}$, $10^{-5}$ S$^{-1}$, $5 \times 10^{-6}$ S$^{-1}$, $10^{-6}$ S$^{-1}$, $5 \times 10^{-7}$ S$^{-1}$, or $10^{-4}$ S$^{-1}$.

In a further embodiment of the invention, the anti-CGRP activity of the anti-CGRP antibodies of the present invention, and fragments thereof having binding specificity to CGRP, exhibit anti-CGRP activity by preventing, ameliorating or reducing the symptoms of, or alternatively treating, diseases and disorders associated with CGRP. Non-limiting examples of diseases and disorders associated with CGRP are set forth herein.

Polynucleotides Encoding Anti-CGRP Antibody Polypeptides

Antibody Ab1

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 1:

(SEQ ID NO: 141)
CAAGTGCTGACCCAGACTGCATCCCCCGTGTCTGCAGCTGTGGGAAGCAC

AGTCACCATCAATTGCCAGGCCAGTCAGAGTGTTTATGATAACAACTACC

TAGCCTGGTATCAGCAGAAACCAGGGCAGCCTCCCAAGCAACTGATCTAT

TCTACATCCACTCTGGCATCTGGGGTCTCATCGCGGTTCAAAGGCAGTGG

ATCTGGGACACAGTTCACTCTCACCATCAGCGACCTGGAGTGTGCCGATG

CTGCCACTTACTACTGTCTAGGCAGTTATGATTGTAGTAGTGGTGATTGT

TTTGTTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 2:

(SEQ ID NO: 142)
CAAGTGCTGACCCAGACTGCATCCCCCGTGTCTGCAGCTGTGGGAAGCAC

AGTCACCATCAATTGCCAGGCCAGTCAGAGTGTTTATGATAACAACTACC

TAGCCTGGTATCAGCAGAAACCAGGGCAGCCTCCCAAGCAACTGATCTAT

TCTACATCCACTCTGGCATCTGGGGTCTCATCGCGGTTCAAAGGCAGTGG

ATCTGGGACACAGTTCACTCTCACCATCAGCGACCTGGAGTGTGCCGATG

CTGCCACTTACTACTGTCTAGGCAGTTATGATTGTAGTAGTGGTGATTGT

TTTGTTTTCGGCGGAGGGACCGAGGTGGTGGTCAAACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.

In another embodiment of the invention, polynucleotides of the invention comprise, or alternatively consist of, the following polynucleotide sequence encoding the variable heavy chain polypeptide sequence of SEQ ID NO: 3:

(SEQ ID NO: 143)
CAGTCGCTGGAGGAGTCCGGGGGTCGCCTGGTCACGCCTGGGACACCCCT

GACACTCACCTGCACAGTCTCTGGACTCGACCTCAGTAGCTACTACATGC

AATGGGTCCGCCAGGCTCCAGGGAAGGGGCTGGAATGGATCGGAGTCATT

GGTATTAATGATAACACATACTACGCGAGCTGGGCGAAAGGCCGATTCAC

CATCTCCAGAGCCTCGTCGACCACGGTGGATCTGAAAATGACCAGTCTGA

CAACCGAGGACACGGCCACCTATTTCTGTGCCAGAGGGGACATCTGGGGC

CCAGGCACCCTCGTCACCGTCTCGAGC.

In one embodiment of the invention, polynucleotides of the invention comprise, or alternatively consist of, the following polynucleotide sequence encoding the heavy chain polypeptide sequence or SEQ ID NO: 4:

(SEQ ID NO: 144)
CAGTCGCTGGAGGAGTCCGGGGGTCGCCTGGTCACGCCTGGGACACCCCT

GACACTCACCTGCACAGTCTCTGGACTCGACCTCAGTAGCTACTACATGC

-continued

```
AATGGGTCCGCCAGGCTCCAGGGAAGGGGCTGGAATGGATCGGAGTCATT

GGTATTAATGATAACACATACTACGCGAGCTGGGCGAAAGGCCGATTCAC

CATCTCCAGAGCCTCGTCGACCACGGTGGATCTGAAAATGACCAGTCTGA

CAACCGAGGACACGGCCACCTATTTCTGTGCCAGAGGGGACATCTGGGGC

CCAGGCACCCTCGTCACCGTCTCGAGCGCCTCCACCAAGGGCCCATCGGT

CTTCCCCCTGGCACCCTCCTCCAAGAGCACCTCTGGGGGCACAGCGGCCC

TGGGCTGCCTGGTCAAGGACTACTTCCCCGAACCGGTGACGGTGTCGTGG

AACTCAGGCGCCCTGACCAGCGGCGTGCACACCTTCCCGGCTGTCCTACA

GTCCTCAGGACTCTACTCCCTCAGCAGCGTGGTGACCGTGCCCTCCAGCA

GCTTGGGCACCCAGACCTACATCTGCAACGTGAATCACAAGCCCAGCAAC

ACCAAGGTGGACAAGAGAGTTGAGCCCAAATCTTGTGACAAAACTCACAC

ATGCCCACCGTGCCCAGCACCTGAACTCCTGGGGGGACCGTCAGTCTTCC

TCTTCCCCCCAAAACCCAAGGACACCCTCATGATCTCCCGGACCCCTGAG

GTCACATGCGTGGTGGTGGACGTGAGCCACGAAGACCCTGAGGTCAAGTT

CAACTGGTACGTGGACGGCGTGGAGGTGCATAATGCCAAGACAAAGCCGC

GGGAGGAGCAGTACGCCAGCACGTACCGTGTGGTCAGCGTCCTCACCGTC

CTGCACCAGGACTGGCTGAATGGCAAGGAGTACAAGTGCAAGGTCTCCAA

CAAAGCCCTCCCAGCCCCCATCGAGAAAACCATCTCCAAAGCCAAAGGGC

AGCCCCGAGAACCACAGGTGTACACCCTGCCCCCATCCCGGGAGGAGATG

ACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACA

AGACCACGCCTCCCGTGCTGGACTCCGACGGCTCCTTCTTCCTCTACAGC

AAGCTCACCGTGGACAAGAGCAGGTGGCAGCAGGGGAACGTCTTCTCATG

CTCCGTGATGCATGAGGCTCTGCACAACCACTACACGCAGAAGAGCCTCT

CCCTGTCTCCGGGTAAATGA.
```

In a further embodiment of the invention, polynucleotides encoding antibody fragments having binding specificity to CGRP comprise, or alternatively consist of, one or more of the polynucleotide sequences of SEQ ID NO: 145; SEQ ID NO: 146; and SEQ ID NO: 147 which correspond to polynucleotides encoding the complementarity-determining regions (CDRs, or hypervariable regions) of the light chain variable sequence of SEQ ID NO: 1 or the light chain sequence of SEQ ID NO: 2.

In a further embodiment of the invention, polynucleotides encoding antibody fragments having binding specificity to CGRP comprise, or alternatively consist of, one or more of the polynucleotide sequences of SEQ ID NO: 148; SEQ ID NO: 149; and SEQ ID NO: 150 which correspond to polynucleotides encoding the complementarity-determining regions (CDRs, or hypervariable regions) of the heavy chain variable sequence of SEQ ID NO: 3 or the heavy chain sequence of SEQ ID NO: 4.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 141 encoding the light chain variable sequence of SEQ ID NO: 1; the polynucleotide SEQ ID NO: 142 encoding the light chain sequence of SEQ ID NO: 2; the polynucleotide SEQ ID NO: 143 encoding the heavy chain variable sequence of SEQ ID NO: 3; the polynucleotide SEQ ID NO: 144 encoding the heavy chain sequence of SEQ ID NO: 4; polynucleotides encoding the complementarity-determining regions (SEQ ID NO: 145; SEQ ID NO: 146; and SEQ ID NO: 147) of the light chain variable sequence of SEQ ID NO: 1 or the light chain sequence of SEQ ID NO: 2; and polynucleotides encoding the complementarity-determining regions (SEQ ID NO: 148; SEQ ID NO: 149; and SEQ ID NO: 150) of the heavy chain variable sequence of SEQ ID NO: 3 or the heavy chain sequence of SEQ ID NO: 4.

In a preferred embodiment of the invention, polynucleotides of the invention comprise, or alternatively consist of, polynucleotides encoding Fab (fragment antigen binding) fragments having binding specificity for CGRP. With respect to antibody Ab1, the polynucleotides encoding the full length Ab1 antibody comprise, or alternatively consist of, the polynucleotide SEQ ID NO: 142 encoding the light chain sequence of SEQ ID NO: 2 and the polynucleotide SEQ ID NO: 144 encoding the heavy chain sequence of SEQ ID NO: 4.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab1 following expression of the full-length polynucleotides in a suitable host. In another embodiment of the invention, anti-CGRP antibodies such as Ab1 or Fab fragments thereof may be produced via expression of Ab1 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab2

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 11:

(SEQ ID NO: 151)
```
CAAGTGCTGACCCAGTCTCCATCCTCCCTGTCTGCATCTGTAGGAGACAG

AGTCACCATCAATTGCCAGGCCAGTCAGAGTGTTTATGATAACAACTACC

TAGCCTGGTATCAGCAGAAACCAGGGAAAGTTCCTAAGCAACTGATCTAT

TCTACATCCACTCTGGCATCTGGGGTCCCATCTCGTTTCAGTGGCAGTGG

ATCTGGGACAGATTTCACTCTCACCATCAGCAGCCTGCAGCCTGAAGATG

TTGCAACTTATTACTGTCTAGGCAGTTATGATTGTAGTAGTGGTGATTGT

TTTGTTTTCGGCGGAGGAACCAAGGTGGAAATCAAACGT.
```

In one embodiment of the invention, polynucleotides of the invention comprise, or alternatively consist of, the following polynucleotide sequence encoding the light chain polypeptide sequence or SEQ ID NO: 12:

(SEQ ID NO: 152)
CAAGTGCTGACCCAGTCTCCATCCTCCCTGTCTGCATCTGTAGGAGACAG

AGTCACCATCAATTGCCAGGCCAGTCAGAGTGTTTATGATAACAACTACC

TAGCCTGGTATCAGCAGAAACCAGGGAAAGTTCCTAAGCAACTGATCTAT

TCTACATCCACTCTGGCATCTGGGGTCCCATCTCGTTTCAGTGGCAGTGG

ATCTGGGACAGATTTCACTCTCACCATCAGCAGCCTGCAGCCTGAAGATG

TTGCAACTTATTACTGTCTAGGCAGTTATGATTGTAGTAGTGGTGATTGT

TTTGTTTTCGGCGGAGGAACCAAGGTGGAAATCAAACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.

In another embodiment of the invention, polynucleotides of the invention comprise, or alternatively consist of, the following polynucleotide sequence encoding the variable heavy chain polypeptide sequence or SEQ ID NO: 13:

(SEQ ID NO: 153)
GAGGTGCAGCTTGTGGAGTCTGGGGGAGGCTTGGTCCAGCCTGGGGGGTC

CCTGAGACTCTCCTGTGCAGTCTCTGGACTCGACCTCAGTAGCTACTACA

TGCAATGGGTCCGTCAGGCTCCAGGGAAGGGGCTGGAGTGGGTCGGAGTC

ATTGGTATCAATGATAACACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 14:

(SEQ ID NO: 154)
GAGGTGCAGCTTGTGGAGTCTGGGGGAGGCTTGGTCCAGCCTGGGGGGTC

CCTGAGACTCTCCTGTGCAGTCTCTGGACTCGACCTCAGTAGCTACTACA

TGCAATGGGTCCGTCAGGCTCCAGGGAAGGGGCTGGAGTGGGTCGGAGTC

ATTGGTATCAATGATAACACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGCGCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACAAGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.

In a further embodiment of the invention, polynucleotides encoding antibody fragments having binding specificity to CGRP comprise, or alternatively consist of, one or more of the polynucleotide sequences of SEQ ID NO: 155; SEQ ID NO: 156; and SEQ ID NO: 157 which correspond to polynucleotides encoding the complementarity-determining regions (CDRs, or hypervariable regions) of the light chain variable sequence of SEQ ID NO: 11 or the light chain sequence of SEQ ID NO: 12.

In a further embodiment of the invention, polynucleotides encoding antibody fragments having binding specificity to CGRP comprise, or alternatively consist of, one or more of the polynucleotide sequences of SEQ ID NO: 158; SEQ ID NO: 159; and SEQ ID NO: 160 which correspond to polynucleotides encoding the complementarity-determining regions (CDRs, or hypervariable regions) of the heavy chain variable sequence of SEQ ID NO: 13 or the heavy chain sequence of SEQ ID NO: 14.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 151 encoding the light chain variable sequence of SEQ ID NO: 11; the polynucleotide SEQ ID NO: 152 encoding the light chain sequence of SEQ ID NO: 12; the polynucleotide SEQ ID NO: 153 encoding the heavy chain variable sequence of SEQ ID NO: 13; the polynucleotide SEQ ID NO: 154 encoding the heavy chain sequence of SEQ ID NO: 14; polynucleotides encoding the complementarity-determining regions (SEQ ID NO: 155; SEQ ID NO: 156; and SEQ ID NO: 157) of the light chain variable sequence of SEQ ID NO: 11 or the light chain sequence of SEQ ID NO: 12; and polynucleotides encoding the complementarity-determining regions (SEQ ID NO: 158; SEQ ID NO: 159; and SEQ ID NO: 160) of the heavy chain variable sequence of SEQ ID NO: 13 or the heavy chain sequence of SEQ ID NO: 14.

In a preferred embodiment of the invention, polynucleotides of the invention comprise, or alternatively consist of, polynucleotides encoding Fab (fragment antigen binding) fragments having binding specificity for CGRP. With respect to antibody Ab2, the polynucleotides encoding the full length Ab2 antibody comprise, or alternatively consist of, the polynucleotide SEQ ID NO: 152 encoding the light chain sequence of SEQ ID NO: 12 and the polynucleotide SEQ ID NO: 154 encoding the heavy chain sequence of SEQ ID NO: 14.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab2 following expression of the full-length polynucleotides in a suitable host. In another embodiment of the invention, anti-CGRP antibodies such as Ab2 or Fab fragments thereof may be produced via expression of Ab2 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab3

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 21:

(SEQ ID NO: 161)
CAAGTGCTGACCCAGTCTCCATCCTCCCTGTCTGCATCTGTAGGAGACAG

AGTCACCATCAATTGCCAGGCCAGTCAGAGTGTTTATGATAACAACTACC

TAGCCTGGTATCAGCAGAAACCAGGGAAAGTTCCTAAGCAACTGATCTAT

TCTACATCCACTCTGGCATCTGGGGTCCCATCTCGTTTCAGTGGCAGTGG

ATCTGGGACAGATTTCACTCTCACCATCAGCAGCCTGCAGCCTGAAGATG

TTGCAACTTATTACTGTCTAGGCAGTTATGATTGTAGTAGTGGTGATTGT

TTTGTTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 22:

(SEQ ID NO: 162)
CAAGTGCTGACCCAGTCTCCATCCTCCCTGTCTGCATCTGTAGGAGACAG

AGTCACCATCAATTGCCAGGCCAGTCAGAGTGTTTATGATAACAACTACC

TAGCCTGGTATCAGCAGAAACCAGGGAAAGTTCCTAAGCAACTGATCTAT

TCTACATCCACTCTGGCATCTGGGGTCCCATCTCGTTTCAGTGGCAGTGG

ATCTGGGACAGATTTCACTCTCACCATCAGCAGCCTGCAGCCTGAAGATG

TTGCAACTTATTACTGTCTAGGCAGTTATGATTGTAGTAGTGGTGATTGT

TTTGTTTTCGGCGGAGGAACCAAGGTGGAAATCAAACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.

In another embodiment of the invention, polynucleotides of the invention comprise, or alternatively consist of, the following polynucleotide sequence encoding the variable heavy chain polypeptide sequence of SEQ ID NO: 23:

(SEQ ID NO: 163)
GAGGTGCAGCTTGTGGAGTCTGGGGGAGGCTTGGTCCAGCCTGGGGGGTC

CCTGAGACTCTCCTGTGCAGTCTCTGGACTCGACCTCAGTAGCTACTACA

TGCAATGGGTCCGTCAGGCTCCAGGGAAGGGGCTGGAGTGGGTCGGAGTC

ATTGGTATCAATGATAACACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 24:

(SEQ ID NO: 164)
GAGGTGCAGCTTGTGGAGTCTGGGGGAGGCTTGGTCCAGCCTGGGGGGTC

CCTGAGACTCTCCTGTGCAGTCTCTGGACTCGACCTCAGTAGCTACTACA

TGCAATGGGTCCGTCAGGCTCCAGGGAAGGGGCTGGAGTGGGTCGGAGTC

ATTGGTATCAATGATAACACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGCGCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACGCGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

-continued

```
CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.
```

In a further embodiment of the invention, polynucleotides encoding antibody fragments having binding specificity to CGRP comprise, or alternatively consist of, one or more of the polynucleotide sequences of SEQ ID NO: 165; SEQ ID NO: 166; and SEQ ID NO: 167 which correspond to polynucleotides encoding the complementarity-determining regions (CDRs, or hypervariable regions) of the light chain variable sequence of SEQ ID NO: 21 or the light chain sequence of SEQ ID NO: 22.

In a further embodiment of the invention, polynucleotides encoding antibody fragments having binding specificity to CGRP comprise, or alternatively consist of, one or more of the polynucleotide sequences of SEQ ID NO: 168; SEQ ID NO: 169; and SEQ ID NO: 170 which correspond to polynucleotides encoding the complementarity-determining regions (CDRs, or hypervariable regions) of the heavy chain variable sequence of SEQ ID NO: 23 or the heavy chain sequence of SEQ ID NO: 24.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 161 encoding the light chain variable sequence of SEQ ID NO: 21; the polynucleotide SEQ ID NO: 162 encoding the light chain sequence of SEQ ID NO: 22; the polynucleotide SEQ ID NO: 163 encoding the heavy chain variable sequence of SEQ ID NO: 23; the polynucleotide SEQ ID NO: 164 encoding the heavy chain sequence of SEQ ID NO: 24; polynucleotides encoding the complementarity-determining regions (SEQ ID NO: 165; SEQ ID NO: 166; and SEQ ID NO: 167) of the light chain variable sequence of SEQ ID NO: 21 or the light chain sequence of SEQ ID NO: 22; and polynucleotides encoding the complementarity-determining regions (SEQ ID NO: 168; SEQ ID NO: 169; and SEQ ID NO: 170) of the heavy chain variable sequence of SEQ ID NO: 23 or the heavy chain sequence of SEQ ID NO: 24.

In a preferred embodiment of the invention, polynucleotides of the invention comprise, or alternatively consist of, polynucleotides encoding Fab (fragment antigen binding) fragments having binding specificity for CGRP. With respect to antibody Ab3, the polynucleotides encoding the full length Ab3 antibody comprise, or alternatively consist of, the polynucleotide SEQ ID NO: 162 encoding the light chain sequence of SEQ ID NO: 22 and the polynucleotide SEQ ID NO: 164 encoding the heavy chain sequence of SEQ ID NO: 24.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab3 following expression of the full-length polynucleotides in a suitable host. In another embodiment of the invention, anti-CGRP antibodies such as Ab3 or Fab fragments thereof may be produced via expression of Ab3 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab4

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 31:

```
                                      (SEQ ID NO: 171)
CAAGTGCTGACCCAGACTCCATCCCCCGTGTCTGCAGCTGTGGGAAGCAC

AGTCACCATCAATTGCCAGGCCAGTCAGAGTGTTTATCATAACACCTACC

TGGCCTGGTATCAGCAGAAACCAGGGCAGCCTCCCAAACAACTGATCTAT

GATGCATCCACTCTGGCGTCTGGGGTCCCATCGCGGTTCAGCGGCAGTGG

ATCTGGGACACAGTTCACTCTCACCATCAGCGGCGTGCAGTGTAACGATG

CTGCCGCTTACTACTGTCTGGGCAGTTATGATTGTACTAATGGTGATTGT

TTTGTTTTCGGCGGAGGGACCGAGGTGGTGGTCAAACGT.
```

In one embodiment of the invention, polynucleotides of the invention comprise, or alternatively consist of, the following polynucleotide sequence encoding the light chain polypeptide sequence or SEQ ID NO: 32:

```
                                      (SEQ ID NO: 172)
CAAGTGCTGACCCAGACTCCATCCCCCGTGTCTGCAGCTGTGGGAAGCAC

AGTCACCATCAATTGCCAGGCCAGTCAGAGTGTTTATCATAACACCTACC

TGGCCTGGTATCAGCAGAAACCAGGGCAGCCTCCCAAACAACTGATCTAT

GATGCATCCACTCTGGCGTCTGGGGTCCCATCGCGGTTCAGCGGCAGTGG

ATCTGGGACACAGTTCACTCTCACCATCAGCGGCGTGCAGTGTAACGATG

CTGCCGCTTACTACTGTCTGGGCAGTTATGATTGTACTAATGGTGATTGT

TTTGTTTTCGGCGGAGGGACCGAGGTGGTGGTCAAACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.
```

In another embodiment of the invention, polynucleotides of the invention comprise, or alternatively consist of, the following polynucleotide sequence encoding the variable heavy chain polypeptide sequence of SEQ ID NO: 33:

```
                                          (SEQ ID NO: 173)
CAGTCGCTGGAGGAGTCCGGGGGTCGCCTGGTCACGCCTGGGACACCCCT

GACACTCACCTGTTCCGTCTCTGGCATCGACCTCAGTGGCTACTACATGA

ACTGGGTCCGCCAGGCTCCAGGGAAGGGGCTGGAATGGATCGGAGTCATT

GGTATTAATGGTGCCACATACTACGCGAGCTGGGCGAAAGGCCGATTCAC

CATCTCCAAAACCTCGTCGACCACGGTGGATCTGAAAATGACCAGTCTGA

CAACCGAGGACACGGCCACCTATTTCTGTGCCAGAGGGGACATCTGGGGC

CCGGGCACCCTCGTCACCGTCTCGAGC.
```

In one embodiment of the invention, polynucleotides of the invention comprise, or alternatively consist of, the following polynucleotide sequence encoding the heavy chain polypeptide sequence of SEQ ID NO: 34:

```
                                          (SEQ ID NO: 174)
CAGTCGCTGGAGGAGTCCGGGGGTCGCCTGGTCACGCCTGGGACACCCCT

GACACTCACCTGTTCCGTCTCTGGCATCGACCTCAGTGGCTACTACATGA

ACTGGGTCCGCCAGGCTCCAGGGAAGGGGCTGGAATGGATCGGAGTCATT

GGTATTAATGGTGCCACATACTACGCGAGCTGGGCGAAAGGCCGATTCAC

CATCTCCAAAACCTCGTCGACCACGGTGGATCTGAAAATGACCAGTCTGA

CAACCGAGGACACGGCCACCTATTTCTGTGCCAGAGGGGACATCTGGGGC

CCGGGCACCCTCGTCACCGTCTCGAGCGCCTCCACCAAGGGCCCATCGGT

CTTCCCCCTGGCACCCTCCTCCAAGAGCACCTCTGGGGGCACAGCGGCCC

TGGGCTGCCTGGTCAAGGACTACTTCCCCGAACCGGTGACGGTGTCGTGG

AACTCAGGCGCCCTGACCAGCGGCGTGCACACCTTCCCGGCTGTCCTACA

GTCCTCAGGACTCTACTCCCTCAGCAGCGTGGTGACCGTGCCCTCCAGCA

GCTTGGGCACCCAGACCTACATCTGCAACGTGAATCACAAGCCCAGCAAC

ACCAAGGTGGACAAGAGAGTTGAGCCCAAATCTTGTGACAAAACTCACAC

ATGCCCACCGTGCCCAGCACCTGAACTCCTGGGGGGACCGTCAGTCTTCC

TCTTCCCCCCAAAACCCAAGGACACCCTCATGATCTCCCGGACCCCTGAG

GTCACATGCGTGGTGGTGGACGTGAGCCACGAAGACCCTGAGGTCAAGTT

CAACTGGTACGTGGACGGCGTGGAGGTGCATAATGCCAAGACAAAGCCGC

GGGAGGAGCAGTACGCCAGCACGTACCGTGTGGTCAGCGTCCTCACCGTC

CTGCACCAGGACTGGCTGAATGGCAAGGAGTACAAGTGCAAGGTCTCCAA

CAAAGCCCTCCCAGCCCCCATCGAGAAAACCATCTCCAAAGCCAAAGGGC

AGCCCCGAGAACCACAGGTGTACACCCTGCCCCCATCCCGGGAGGAGATG

ACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACA

AGACCACGCCTCCCGTGCTGGACTCCGACGGCTCCTTCTTCCTCTACAGC

AAGCTCACCGTGGACAAGAGCAGGTGGCAGCAGGGGAACGTCTTCTCATG

CTCCGTGATGCATGAGGCTCTGCACAACCACTACACGCAGAAGAGCCTCT

CCCTGTCTCCGGGTAAATGA.
```

In a further embodiment of the invention, polynucleotides encoding antibody fragments having binding specificity to CGRP comprise, or alternatively consist of, one or more of the polynucleotide sequences of SEQ ID NO: 175; SEQ ID NO: 176; and SEQ ID NO: 177 which correspond to polynucleotides encoding the complementarity-determining regions (CDRs, or hypervariable regions) of the light chain variable sequence of SEQ ID NO: 31 or the light chain sequence of SEQ ID NO: 32.

In a further embodiment of the invention, polynucleotides encoding antibody fragments having binding specificity to CGRP comprise, or alternatively consist of, one or more of the polynucleotide sequences of SEQ ID NO: 178; SEQ ID NO: 179; and SEQ ID NO: 180 which correspond to polynucleotides encoding the complementarity-determining regions (CDRs, or hypervariable regions) of the heavy chain variable sequence of SEQ ID NO: 33 or the heavy chain sequence of SEQ ID NO: 34.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 171 encoding the light chain variable sequence of SEQ ID NO: 31; the polynucleotide SEQ ID NO: 172 encoding the light chain sequence of SEQ ID NO: 32; the polynucleotide SEQ ID NO: 173 encoding the heavy chain variable sequence of SEQ ID NO: 33; the polynucleotide SEQ ID NO: 174 encoding the heavy chain sequence of SEQ ID NO: 34; polynucleotides encoding the complementarity-determining regions (SEQ ID NO: 175; SEQ ID NO: 176; and SEQ ID NO: 177) of the light chain variable sequence of SEQ ID NO: 31 or the light chain sequence of SEQ ID NO: 32; and polynucleotides encoding the complementarity-determining regions (SEQ ID NO: 178; SEQ ID NO: 179; and SEQ ID NO: 180) of the heavy chain variable sequence of SEQ ID NO: 33 or the heavy chain sequence of SEQ ID NO: 34.

In a preferred embodiment of the invention, polynucleotides of the invention comprise, or alternatively consist of, polynucleotides encoding Fab (fragment antigen binding) fragments having binding specificity for CGRP. With respect to antibody Ab4, the polynucleotides encoding the full length Ab4 antibody comprise, or alternatively consist of, the polynucleotide SEQ ID NO: 172 encoding the light chain sequence of SEQ ID NO: 32 and the polynucleotide SEQ ID NO: 174 encoding the heavy chain sequence of SEQ ID NO: 34.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab4 following expression of the full-length polynucleotides in a suitable host. In another embodiment of the invention, anti-CGRP antibodies such as Ab4 or Fab fragments thereof may be produced via expression of Ab4 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab5

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 41:

```
                                        (SEQ ID NO: 181)
CAAGTGCTGACCCAGTCTCCATCCTCCCTGTCTGCATCTGTAGGAGACAG

AGTCACCATCAATTGCCAGGCCAGTCAGAGTGTTTATCATAACACCTACC

TGGCCTGGTATCAGCAGAAACCAGGGAAAGTTCCTAAGCAACTGATCTAT

GATGCATCCACTCTGGCATCTGGGGTCCCATCTCGTTTCAGTGGCAGTGG

ATCTGGGACAGATTTCACTCTCACCATCAGCAGCCTGCAGCCTGAAGATG

TTGCAACTTATTACTGTCTGGGCAGTTATGATTGTACTAATGGTGATTGT

TTTGTTTTCGGCGGAGGAACCAAGGTGGAAATCAAACGT.
```

In one embodiment of the invention, polynucleotides of the invention comprise, or alternatively consist of, the following polynucleotide sequence encoding the light chain polypeptide sequence of SEQ ID NO: 42:

```
                                        (SEQ ID NO: 182)
CAAGTGCTGACCCAGTCTCCATCCTCCCTGTCTGCATCTGTAGGAGACAG

AGTCACCATCAATTGCCAGGCCAGTCAGAGTGTTTATCATAACACCTACC

TGGCCTGGTATCAGCAGAAACCAGGGAAAGTTCCTAAGCAACTGATCTAT

GATGCATCCACTCTGGCATCTGGGGTCCCATCTCGTTTCAGTGGCAGTGG

ATCTGGGACAGATTTCACTCTCACCATCAGCAGCCTGCAGCCTGAAGATG

TTGCAACTTATTACTGTCTGGGCAGTTATGATTGTACTAATGGTGATTGT

TTTGTTTTCGGCGGAGGAACCAAGGTGGAAATCAAACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.
```

In another embodiment of the invention, polynucleotides of the invention comprise, or alternatively consist of, the following polynucleotide sequence encoding the variable heavy chain polypeptide sequence of SEQ ID NO: 43:

```
                                        (SEQ ID NO: 183)
GAGGTGCAGCTTGTGGAGTCTGGGGGAGGCTTGGTCCAGCCTGGGGGGTC

CCTGAGACTCTCCTGTGCAGTCTCTGGAATCGACCTCAGTGGCTACTACA

TGAACTGGGTCCGTCAGGCTCCAGGGAAGGGGCTGGAGTGGGTCGGAGTC

ATTGGTATTAATGGTGCCACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGC.
```

In one embodiment of the invention, polynucleotides of the invention comprise, or alternatively consist of, the following polynucleotide sequence encoding the heavy chain polypeptide sequence of SEQ ID NO: 44:

```
                                        (SEQ ID NO: 184)
GAGGTGCAGCTTGTGGAGTCTGGGGGAGGCTTGGTCCAGCCTGGGGGGTC

CCTGAGACTCTCCTGTGCAGTCTCTGGAATCGACCTCAGTGGCTACTACA

TGAACTGGGTCCGTCAGGCTCCAGGGAAGGGGCTGGAGTGGGTCGGAGTC

ATTGGTATTAATGGTGCCACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGCGCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACAAGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.
```

In a further embodiment of the invention, polynucleotides encoding antibody fragments having binding specificity to CGRP comprise, or alternatively consist of, one or more of the polynucleotide sequences of SEQ ID NO: 185; SEQ ID NO: 186; and SEQ ID NO: 187 which correspond to polynucleotides encoding the complementarity-determining regions (CDRs, or hypervariable regions) or the light chain variable sequence of SEQ ID NO: 41 or the light chain sequence of SEQ ID NO: 42.

In a further embodiment of the invention, polynucleotides encoding antibody fragments having binding specificity to CGRP comprise, or alternatively consist of, one or more of the polynucleotide sequences of SEQ ID NO: 188; SEQ ID NO: 189; and SEQ ID NO: 190 which correspond to polynucleotides encoding the complementarity-determining regions (CDRs, or hypervariable regions) of the heavy chain variable sequence of SEQ ID NO: 43 or the heavy chain sequence of SEQ ID NO: 44.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 181 encoding the light chain variable sequence of SEQ ID NO: 41; the polynucleotide SEQ ID NO: 182 encoding the light chain sequence of SEQ ID NO: 42; the polynucleotide SEQ ID NO: 183 encoding the heavy chain variable sequence of SEQ ID NO: 43; the polynucleotide SEQ ID NO: 184 encoding the heavy chain sequence of SEQ ID NO: 44; polynucleotides encoding the complementarity-determining regions (SEQ ID NO: 185; SEQ ID NO: 186; and SEQ ID NO: 187) of the light chain variable sequence of SEQ ID NO: 41 or the light chain sequence of SEQ ID NO: 42; and polynucleotides encoding the complementarity-determining regions (SEQ ID NO: 188; SEQ ID NO: 189; and SEQ ID NO: 190) of the heavy chain variable sequence of SEQ ID NO: 43 or the heavy chain sequence of SEQ ID NO: 44.

In a preferred embodiment of the invention, polynucleotides of the invention comprise, or alternatively consist of, polynucleotides encoding Fab (fragment antigen binding) fragments having binding specificity for CGRP. With respect to antibody Ab5, the polynucleotides encoding the full length Ab5 antibody comprise, or alternatively consist of, the polynucleotide SEQ ID NO: 182 encoding the light chain sequence of SEQ ID NO: 42 and the polynucleotide SEQ ID NO: 184 encoding the heavy chain sequence of SEQ ID NO: 44.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab5 following expression of the full-length polynucleotides in a suitable host. In another embodiment of the invention, anti-CGRP antibodies such as Ab5 or Fab fragments thereof may be produced via expression of Ab5 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab6

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 51:

(SEQ ID NO: 191)
CAAGTGCTGACCCAGTCTCCATCCTCCCTGTCTGCATCTGTAGGAGACAG

AGTCACCATCAATTGCCAGGCCAGTCAGAGTGTTTATCATAACACCTACC

TGGCCTGGTATCAGCAGAAACCAGGGAAAGTTCCTAAGCAACTGATCTAT

GATGCATCCACTCTGGCATCTGGGGTCCCATCTCGTTTCAGTGGCAGTGG

ATCTGGGACAGATTTCACTCTCACCATCAGCAGCCTGCAGCCTGAAGATG

TTGCAACTTATTACTGTCTGGGCAGTTATGATTGTACTAATGGTGATTGT

TTTGTTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 52:

(SEQ ID NO: 192)
CAAGTGCTGACCCAGTCTCCATCCTCCCTGTCTGCATCTGTAGGAGACAG

AGTCACCATCAATTGCCAGGCCAGTCAGAGTGTTTATCATAACACCTACC

TGGCCTGGTATCAGCAGAAACCAGGGAAAGTTCCTAAGCAACTGATCTAT

GATGCATCCACTCTGGCATCTGGGGTCCCATCTCGTTTCAGTGGCAGTGG

ATCTGGGACAGATTTCACTCTCACCATCAGCAGCCTGCAGCCTGAAGATG

TTGCAACTTATTACTGTCTGGGCAGTTATGATTGTACTAATGGTGATTGT

TTTGTTTTCGGCGGAGGAACCAAGGTGGAAATCAAACGTACGGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.

In another embodiment of the invention, polynucleotides of the invention comprise, or alternatively consist of, the following polynucleotide sequence encoding the variable heavy chain polypeptide sequence of SEQ ID NO: 53:

(SEQ ID NO: 193)
GAGGTGCAGCTTGTGGAGTCTGGGGGAGGCTTGGTCCAGCCTGGGGGGTC

CCTGAGACTCTCCTGTGCAGTCTCTGGAATCGACCTCAGTGGCTACTACA

TGAACTGGGTCCGTCAGGCTCCAGGGAAGGGGCTGGAGTGGGTCGGAGTC

ATTGGTATTAATGGTGCCACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 54:

(SEQ ID NO: 194)
GAGGTGCAGCTTGTGGAGTCTGGGGGAGGCTTGGTCCAGCCTGGGGGGTC

CCTGAGACTCTCCTGTGCAGTCTCTGGAATCGACCTCAGTGGCTACTACA

-continued
```
TGAACTGGGTCCGTCAGGCTCCAGGGAAGGGGCTGGAGTGGGTCGGAGTC

ATTGGTATTAATGGTGCCACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGCGCCTCCACCAAGGGCCC

ATCGGTCTTCCCCCTGGCACCCTCCTCCAAGAGCACCTCTGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACGCGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.
```

In a further embodiment of the invention, polynucleotides encoding antibody fragments having binding specificity to CGRP comprise, or alternatively consist of, one or more of the polynucleotide sequences of SEQ ID NO: 195; SEQ ID NO: 196; and SEQ ID NO: 197 which correspond to polynucleotides encoding the complementarity-determining regions (CDRs, or hypervariable regions) of the light chain variable sequence of SEQ ID NO: 51 or the light chain sequence of SEQ ID NO: 52.

In a further embodiment of the invention, polynucleotides encoding antibody fragments having binding specificity to CGRP comprise, or alternatively consist of, one or more of the polynucleotide sequences of SEQ ID NO: 198; SEQ ID NO: 199; and SEQ ID NO: 200 which correspond to polynucleotides encoding the complementarity-determining regions (CDRs, or hypervariable regions) of the heavy chain variable sequence of SEQ ID NO: 53 or the heavy chain sequence of SEQ ID NO: 54.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 191 encoding the light chain variable sequence of SEQ ID NO: 51; the polynucleotide SEQ ID NO: 192 encoding the light chain sequence of SEQ ID NO: 52; the polynucleotide SEQ ID NO: 193 encoding the heavy chain variable sequence of SEQ ID NO: 53; the polynucleotide SEQ ID NO: 194 encoding the heavy chain sequence of SEQ ID NO: 54; polynucleotides encoding the complementarity-determining regions (SEQ ID NO: 195; SEQ ID NO: 196; and SEQ ID NO: 197) of the light chain variable sequence of SEQ ID NO: 51 or the light chain sequence of SEQ ID NO: 52; and polynucleotides encoding the complementarity-determining regions (SEQ ID NO: 198; SEQ ID NO: 199; and SEQ ID NO: 200) of the heavy chain variable sequence of SEQ ID NO: 53 or the heavy chain sequence of SEQ ID NO: 54.

In a preferred embodiment of the invention, polynucleotides of the invention comprise, or alternatively consist of, polynucleotides encoding Fab (fragment antigen binding) fragments having binding specificity for CGRP. With respect to antibody Ab6, the polynucleotides encoding the full length Ab6 antibody comprise, or alternatively consist of, the polynucleotide SEQ ID NO: 192 encoding the light chain sequence of SEQ ID NO: 52 and the polynucleotide SEQ ID NO: 194 encoding the heavy chain sequence of SEQ ID NO: 54.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab6 following expression of the full-length polynucleotides in a suitable host. In another embodiment of the invention, anti-CGRP antibodies such as Ab6 or Fab fragments thereof may be produced via expression of Ab6 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab7

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 61:

```
                                         (SEQ ID NO: 201)
CAAGTGCTGACCCAGACTGCATCCCCCGTGTCTGCAGCTGTGGGAAGCAC

AGTCACCATCAATTGCCAGGCCAGTCAGAGTGTTTATAATTACAACTACC

TTGCCTGGTATCAGCAGAAACCAGGGCAGCCTCCCAAGCAACTGATCTAT

TCTACATCCACTCTGGCATCTGGGGTCTCATCGCGATTCAAAGGCAGTGG

ATCTGGGACACAGTTCACTCTCACCATCAGCGACGTGCAGTGTGACGATG

CTGCCACTTACTACTGTCTAGGCAGTTATGACTGTAGTACTGGTGATTGT

TTTGTTTTCGGCGGAGGGACCGAGGTGGTGGTCAAACGT.
```

In one embodiment of the invention, polynucleotides of the invention comprise, or alternatively consist of, the following polynucleotide sequence encoding the light chain polypeptide sequence of SEQ ID NO: 62:

(SEQ ID NO: 202)
CAAGTGCTGACCCAGACTGCATCCCCCGTGTCTGCAGCTGTGGGAAGCAC

AGTCACCATCAATTGCCAGGCCAGTCAGAGTGTTTATAATTACAACTACC

TTGCCTGGTATCAGCAGAAACCAGGGCAGCCTCCCAAGCAACTGATCTAT

TCTACATCCACTCTGGCATCTGGGGTCTCATCGCGATTCAAAGGCAGTGG

ATCTGGGACACAGTTCACTCTCACCATCAGCGACGTGCAGTGTGACGATG

CTGCCACTTACTACTGTCTAGGCAGTTATGACTGTAGTACTGGTGATTGT

TTTGTTTTCGGCGGAGGGACCGAGGTGGTGGTCAAACGT ACGGTGGCTG

CACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAA

AGTACAGTGGAAGGTGGATAACGCCCTCCAATCGGGTAACTCCCAGGAGA

GTGTCACAGAGCAGGACAGCAAGGACAGCACCTACAGCCTCAGCAGCACC

CTGACGCTGAGCAAAGCAGACTACGAGAAACACAAAGTCTACGCCTGCGA

AGTCACCCATCAGGGCCTGAGCTCGCCCGTCACAAAGAGCTTCAACAGGG

GAGAGTGTTAG.

In another embodiment of the invention, polynucleotides of the invention comprise, or alternatively consist of, the following polynucleotide sequence encoding the variable heavy chain polypeptide sequence of SEQ ID NO: 63:

(SEQ ID NO: 203)
CAGGAGCAGCTGAAGGAGTCCGGGGGTCGCCTGGTCACGCCTGGGA

CATCCCTGACACTCACCTGCACCGTCTCTGGAATCGACCTCAGTAACCAC

TACATGCAATGGGTCCGCCAGGCTCCAGGGAAGGGGCTGGAGTGGATCGG

AGTCGTTGGTATTAATGGTCGCACATACTACGCGAGCTGGGCGAAAGGCC

GATTCACCATCTCCAGAACCTCGTCGACCACGGTGGATCTGAAAATGACC

AGGCTGACAACCGAGGACACGGCCACCTATTTCTGTGCCAGAGGGGACAT

CTGGGGCCCAGGCACCCTGGTCACCGTCTCGAGC.

In one embodiment of the invention, polynucleotides of the invention comprise, or alternatively consist of, the following polynucleotide sequence encoding the heavy chain polypeptide sequence of SEQ ID NO: 64:

(SEQ ID NO: 204)
CAGGAGCAGCTGAAGGAGTCCGGGGGTCGCCTGGTCACGCCTGGGACATC

CCTGACACTCACCTGCACCGTCTCTGGAATCGACCTCAGTAACCACTACA

TGCAATGGGTCCGCCAGGCTCCAGGGAAGGGGCTGGAGTGGATCGGAGTC

GTTGGTATTAATGGTCGCACATACTACGCGAGCTGGGCGAAAGGCCGATT

CACCATCTCCAGAACCTCGTCGACCACGGTGGATCTGAAAATGACCAGGC

TGACAACCGAGGACACGGCCACCTATTTCTGTGCCAGAGGGGACATCTGG

GGCCCAGGCACCCTGGTCACCGTCTCGAGCGCCTCCACCAAGGGCCCATC

GGTCTTCCCCCTGGCACCCTCCTCCAAGAGCACCTCTGGGGGCACAGCGG

CCCTGGGCTGCCTGGTCAAGGACTACTTCCCCGAACCGGTGACGGTGTCG

TGGAACTCAGGCGCCCTGACCAGCGGCGTGCACACCTTCCCGGCTGTCCT

ACAGTCCTCAGGACTCTACTCCCTCAGCAGCGTGGTGACCGTGCCCTCCA

GCAGCTTGGGCACCCAGACCTACATCTGCAACGTGAATCACAAGCCCAGC

AACACCAAGGTGGACAAGAGAGTTGAGCCCAAATCTTGTGACAAAACTCA

CACATGCCCACCGTGCCCAGCACCTGAACTCCTGGGGGGACCGTCAGTCT

TCCTCTTCCCCCCAAAACCCAAGGACACCCTCATGATCTCCCGGACCCCT

GAGGTCACATGCGTGGTGGTGGACGTGAGCCACGAAGACCCTGAGGTCAA

GTTCAACTGGTACGTGGACGGCGTGGAGGTGCATAATGCCAAGACAAAGC

CGCGGGAGGAGCAGTACGCCAGCACGTACCGTGTGGTCAGCGTCCTCACC

GTCCTGCACCAGGACTGGCTGAATGGCAAGGAGTACAAGTGCAAGGTCTC

CAACAAAGCCCTCCCAGCCCCCATCGAGAAAACCATCTCCAAAGCCAAAG

GGCAGCCCCGAGAACCACAGGTGTACACCCTGCCCCCATCCCGGGAGGAG

ATGACCAAGAACCAGGTCAGCCTGACCTGCCTGGTCAAAGGCTTCTATCC

CAGCGACATCGCCGTGGAGTGGGAGAGCAATGGGCAGCCGGAGAACAACT

ACAAGACCACGCCTCCCGTGCTGGACTCCGACGGCTCCTTCTTCCTCTAC

AGCAAGCTCACCGTGGACAAGAGCAGGTGGCAGCAGGGGAACGTCTTCTC

ATGCTCCGTGATGCATGAGGCTCTGCACAACCACTACACGCAGAAGAGCC

TCTCCCTGTCTCCGGGTAAATGA.

In a further embodiment of the invention, polynucleotides encoding antibody fragments having binding specificity to CGRP comprise, or alternatively consist of, one or more of the polynucleotide sequences of SEQ ID NO: 205; SEQ ID NO: 206; and SEQ ID NO: 207 which correspond to polynucleotides encoding the complementarity-determining regions (CDRs, or hypervariable regions) of the light chain variable sequence of SEQ ID NO: 61 or the light chain sequence of SEQ ID NO: 62.

In a further embodiment of the invention, polynucleotides encoding antibody fragments having binding specificity to CGRP comprise, or alternatively consist of, one or more of the polynucleotide sequences of SEQ ID NO: 208; SEQ ID NO: 209; and SEQ ID NO: 210 which correspond to polynucleotides encoding the complementarity-determining regions (CDRs, or hypervariable regions) of the heavy chain variable sequence of SEQ ID NO: 63 or the heavy chain sequence of SEQ ID NO: 64.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 201 encoding the light chain variable sequence of SEQ ID NO: 61; the polynucleotide SEQ ID NO: 202 encoding the light chain sequence of SEQ ID NO: 62; the polynucleotide SEQ ID NO: 203 encoding the heavy chain variable sequence of SEQ ID NO: 63; the polynucleotide SEQ ID NO: 204 encoding the heavy chain sequence of SEQ ID NO: 64; polynucleotides encoding the complementarity-determining regions (SEQ ID NO: 205; SEQ ID NO: 206; and SEQ ID NO: 207) of the light chain variable sequence of SEQ ID NO: 61 or the light chain sequence of SEQ ID NO: 62; and polynucleotides encoding the complementarity-determining regions (SEQ ID NO: 208; SEQ ID NO: 209; and SEQ ID NO: 210) of the heavy chain variable sequence of SEQ ID NO: 63 or the heavy chain sequence of SEQ ID NO: 64.

In a preferred embodiment of the invention, polynucleotides of the invention comprise, or alternatively consist of, polynucleotides encoding Fab (fragment antigen binding) fragments having binding specificity for CGRP. With respect to antibody Ab7, the polynucleotides encoding the full length Ab7 antibody comprise, or alternatively consist of, the polynucleotide SEQ ID NO: 202 encoding the light chain sequence of SEQ ID NO: 62 and the polynucleotide SEQ ID NO: 204 encoding the heavy chain sequence of SEQ ID NO: 64.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab7 following expression of the full-length polynucleotides in a suitable host. In another embodiment of the invention, anti-CGRP antibodies such as Ab7 or Fab fragments thereof may be produced via expression of Ab7 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab8

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 71:

(SEQ ID NO: 211)
CAAGTGCTGACCCAGTCTCCATCCTCCCTGTCTGCATCTGTAGGAGAC

AGAGTCACCATCAATTGCCAGGCCAGTCAGAGTGTTTACAATTACAACTA

CCTTGCCTGGTATCAGCAGAAACCAGGGAAAGTTCCTAAGCAACTGATCT

ATTCTACATCCACTCTGGCATCTGGGGTCCCATCTCGTTTCAGTGGCAGT

GGATCTGGGACAGATTTCACTCTCACCATCAGCAGCCTGCAGCCTGAAGA

TGTTGCAACTTATTACTGTCTGGGCAGTTATGATTGTAGTACTGGTGATT

GTTTTGTTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 72:

(SEQ ID NO: 212)
CAAGTGCTGACCCAGTCTCCATCCTCCCTGTCTGCATCTGTAGGAGAC

AGAGTCACCATCAATTGCCAGGCCAGTCAGAGTGTTTACAATTACAACTA

CCTTGCCTGGTATCAGCAGAAACCAGGGAAAGTTCCTAAGCAACTGATCT

ATTCTACATCCACTCTGGCATCTGGGGTCCCATCTCGTTTCAGTGGCAGT

GGATCTGGGACAGATTTCACTCTCACCATCAGCAGCCTGCAGCCTGAAGA

TGTTGCAACTTATTACTGTCTGGGCAGTTATGATTGTAGTACTGGTGATT

GTTTTGTTTTCGGCGGAGGAACCAAGGTGGAAATCAAACGTACGGTGGCT

-continued
GCACCATCTGTCTTCATCTTCCCGCCATCTGATGAGCAGTTGAAATCTGG

AACTGCCTCTGTTGTGTGCCTGCTGAATAACTTCTATCCCAGAGAGGCCA

AAGTACAGTGGAAGGTGGATAACGCCCTCCAATCGGGTAACTCCCAGGAG

AGTGTCACAGAGCAGGACAGCAAGGACAGCACCTACAGCCTCAGCAGCAC

CCTGACGCTGAGCAAAGCAGACTACGAGAAACACAAAGTCTACGCCTGCG

AAGTCACCCATCAGGGCCTGAGCTCGCCCGTCACAAAGAGCTTCAACAGG

GGAGAGTGTTAG.

In another embodiment of the invention, polynucleotides of the invention comprise, or alternatively consist of, the following polynucleotide sequence encoding the variable heavy chain polypeptide sequence of SEQ ID NO: 73:

(SEQ ID NO: 213)
GAGGTGCAGCTTGTGGAGTCTGGGGGAGGCTTGGTCCAGCCTGGGGG

GTCCCTGAGACTCTCCTGTGCAGTCTCTGGAATCGACCTCAGTAACCACT

ACATGCAATGGGTCCGTCAGGCTCCAGGGAAGGGGCTGGAGTGGGTCGGA

GTCGTTGGTATCAATGGTCGCACATACTACGCGAGCTGGGCGAAAGGCCG

ATTCACCATCTCCAGAGACAATTCCAAGACCACGGTGTATCTTCAAATGA

ACAGCCTGAGAGCTGAGGACACTGCTGTGTATTTCTGTGCTAGAGGGGAC

ATCTGGGGCCAAGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 74:

(SEQ ID NO: 214)
GAGGTGCAGCTTGTGGAGTCTGGGGGAGGCTTGGTCCAGCCTGGGGGGTC

CCTGAGACTCTCCTGTGCAGTCTCTGGAATCGACCTCAGTAACCACTACA

TGCAATGGGTCCGTCAGGCTCCAGGGAAGGGGCTGGAGTGGGTCGGAGTC

GTTGGTATCAATGGTCGCACATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCTAGAGGGGACATC

TGGGGCCAAGGGACCCTCGTCACCGTCTCGAGCGCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACAAGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

-continued
```
CTCCAACAAAGCCCTCCCAGCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.
```

In a further embodiment of the invention, polynucleotides encoding antibody fragments having binding specificity to CGRP comprise, or alternatively consist of, one or more of the polynucleotide sequences of SEQ ID NO: 215; SEQ ID NO: 216; and SEQ ID NO: 217 which correspond to polynucleotides encoding the complementarity-determining regions (CDRs, or hypervariable regions) of the light chain variable sequence of SEQ ID NO: 71 or the light chain sequence of SEQ ID NO: 72.

In a further embodiment of the invention, polynucleotides encoding antibody fragments having binding specificity to CGRP comprise, or alternatively consist of, one or more of the polynucleotide sequences of SEQ ID NO: 218; SEQ ID NO: 219; and SEQ ID NO: 220 which correspond to polynucleotides encoding the complementarity-determining regions (CDRs, or hypervariable regions) of the heavy chain variable sequence of SEQ ID NO: 73 or the heavy chain sequence of SEQ ID NO: 74.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 211 encoding the light chain variable sequence of SEQ ID NO: 71; the polynucleotide SEQ ID NO: 212 encoding the light chain sequence of SEQ ID NO: 72; the polynucleotide SEQ ID NO: 213 encoding the heavy chain variable sequence of SEQ ID NO: 73; the polynucleotide SEQ ID NO: 214 encoding the heavy chain sequence of SEQ ID NO: 74; polynucleotides encoding the complementarity-determining regions (SEQ ID NO: 215; SEQ ID NO: 216; and SEQ ID NO: 217) of the light chain variable sequence of SEQ ID NO: 71 or the light chain sequence of SEQ ID NO: 72; and polynucleotides encoding the complementarity-determining regions (SEQ ID NO: 218; SEQ ID NO: 219; and SEQ ID NO: 220) of the heavy chain variable sequence of SEQ ID NO: 73 or the heavy chain sequence of SEQ ID NO: 74.

In a preferred embodiment of the invention, polynucleotides of the invention comprise, or alternatively consist of, polynucleotides encoding Fab (fragment antigen binding) fragments having binding specificity for CGRP. With respect to antibody Ab8, the polynucleotides encoding the full length Ab8 antibody comprise, or alternatively consist of, the polynucleotide SEQ ID NO: 212 encoding the light chain sequence of SEQ ID NO: 72 and the polynucleotide SEQ ID NO: 214 encoding the heavy chain sequence of SEQ ID NO: 74.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab8 following expression of the full-length polynucleotides in a suitable host. In another embodiment of the invention, anti-CGRP antibodies such as Ab8 or Fab fragments thereof may be produced via expression of Ab8 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab9

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 81:

```
                                            (SEQ ID NO: 221)
CAAGTGCTGACCCAGACTCCATCCCCCGTGTCTGCAGCTGTGGGAAG

CACAGTCACCATCAATTGCCAGGCCAGTCAGAATGTTTATAATAACAACT

ACCTAGCCTGGTATCAGCAGAAACCAGGGCAGCCTCCCAAGCAACTGATC

TATTCTACGTCCACTCTGGCATCTGGGGTCTCATCGCGATTCAGAGGCAG

TGGATCTGGGACACAGTTCACTCTCACCATCAGCGACGTGCAGTGTGACG

ATGCTGCCACTTACTACTGTCTAGGCAGTTATGATTGTAGTCGTGGTGAT

TGTTTTGTTTTCGGCGGAGGGACCGAGGTGGTGGTCAAACGT.
```

In one embodiment of the invention, polynucleotides of the invention comprise, or alternatively consist of, the following polynucleotide sequence encoding the light chain polypeptide sequence of SEQ ID NO: 82:

```
                                            (SEQ ID NO: 222)
CAAGTGCTGACCCAGACTCCATCCCCCGTGTCTGCAGCTGTGGGAAG

CACAGTCACCATCAATTGCCAGGCCAGTCAGAATGTTTATAATAACAACT

ACCTAGCCTGGTATCAGCAGAAACCAGGGCAGCCTCCCAAGCAACTGATC

TATTCTACGTCCACTCTGGCATCTGGGGTCTCATCGCGATTCAGAGGCAG

TGGATCTGGGACACAGTTCACTCTCACCATCAGCGACGTGCAGTGTGACG

ATGCTGCCACTTACTACTGTCTAGGCAGTTATGATTGTAGTCGTGGTGAT

TGTTTTGTTTTCGGCGGAGGGACCGAGGTGGTGGTCAAACGTACGGTGGC

TGCACCATCTGTCTTCATCTTCCCGCCATCTGATGAGCAGTTGAAATCTG

GAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGA

GAGTGTCACAGAGCAGGACAGCAAGGACAGCACCTACAGCCTCAGCAGCA

CCCTGACGCTGAGCAAAGCAGACTACGAGAAACACAAAGTCTACGCCTGC

GAAGTCACCCATCAGGGCCTGAGCTCGCCCGTCACAAAGAGCTTCAACAG

GGGAGAGTGTTAG.
```

In another embodiment of the invention, polynucleotides of the invention comprise, or alternatively consist of, the following polynucleotide sequence encoding the variable heavy chain polypeptide sequence of SEQ ID NO: 83:

(SEQ ID NO: 223)
CAGTCGCTGGAGGAGTCCGGGGGTCGCCTGGTCACGCCTGGGACACC

CCTGACACTCACCTGCACAGTCTCTGGAATCGGCCTCAGTAGCTACTACA

TGCAGTGGGTCCGCCAGTCTCCAGGGAGGGGGCTGGAATGGATCGGAGTC

ATTGGTAGTGATGGTAAGACATACTACGCGACCTGGGCGAAAGGCCGATT

CACCATCTCCAAGACCTCGTCGACCACGGTGGATCTGAGAATGGCCAGTC

TGACAACCGAGGACACGGCCACCTATTTCTGTACCAGAGGGGACATCTGG

GGCCCGGGGACCCTCGTCACCGTCTCGAGC.

In one embodiment of the invention, polynucleotides of the invention comprise, or alternatively consist of, the following polynucleotide sequence encoding the heavy chain polypeptide sequence or SEQ ID NO: 84:

(SEQ ID NO: 224)
CAGTCGCTGGAGGAGTCCGGGGGTCGCCTGGTCACGCCTGGGACACCCT

GACACTCACCTGCACAGTCTCTGGAATCGGCCTCAGTAGCTACTACATGC

AGTGGGTCCGCCAGTCTCCAGGGAGGGGGCTGGAATGGATCGGAGTCATT

GGTAGTGATGGTAAGACATACTACGCGACCTGGGCGAAAGGCCGATTCAC

CATCTCCAAGACCTCGTCGACCACGGTGGATCTGAGAATGGCCAGTCTGA

CAACCGAGGACACGGCCACCTATTTCTGTACCAGAGGGGACATCTGGGGC

CCGGGGACCCTCGTCACCGTCTCGAGCGCCTCCACCAAGGGCCCATCGGT

CTTCCCCCTGGCACCCTCCTCCAAGAGCACCTCTGGGGGCACAGCGGCCC

TGGGCTGCCTGGTCAAGGACTACTTCCCCGAACCGGTGACGGTGTCGTGG

AACTCAGGCGCCCTGACCAGCGGCGTGCACACCTTCCCGGCTGTCCTACA

GTCCTCAGGACTCTACTCCCTCAGCAGCGTGGTGACCGTGCCCTCCAGCA

GCTTGGGCACCCAGACCTACATCTGCAACGTGAATCACAAGCCCAGCAAC

ACCAAGGTGGACAAGAGAGTTGAGCCCAAATCTTGTGACAAAACTCACAC

ATGCCCACCGTGCCCAGCACCTGAACTCCTGGGGGGACCGTCAGTCTTCC

TCTTCCCCCCAAAACCCAAGGACACCCTCATGATCTCCCGGACCCCTGAG

GTCACATGCGTGGTGGTGGACGTGAGCCACGAAGACCCTGAGGTCAAGTT

CAACTGGTACGTGGACGGCGTGGAGGTGCATAATGCCAAGACAAAGCCGC

GGGAGGAGCAGTACGCCAGCACGTACCGTGTGGTCAGCGTCCTCACCGTC

CTGCACCAGGACTGGCTGAATGGCAAGGAGTACAAGTGCAAGGTCTCCAA

CAAAGCCCTCCCAGCCCCCATCGAGAAAACCATCTCCAAAGCCAAAGGGC

AGCCCCGAGAACCACAGGTGTACACCCTGCCCCCATCCCGGGAGGAGATG

ACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACA

AGACCACGCCTCCCGTGCTGGACTCCGACGGCTCCTTCTTCCTCTACAGC

AAGCTCACCGTGGACAAGAGCAGGTGGCAGCAGGGGAACGTCTTCTCATG

CTCCGTGATGCATGAGGCTCTGCACAACCACTACACGCAGAAGAGCCTCT

CCCTGTCTCCGGGTAAATGA.

In a further embodiment of the invention, polynucleotides encoding antibody fragments having binding specificity to CGRP comprise, or alternatively consist of, one or more of the polynucleotide sequences of SEQ ID NO: 225; SEQ ID NO: 226; and SEQ ID NO: 227 which correspond to polynucleotides encoding the complementarity-determining regions (CDRs, or hypervariable regions) of the light chain variable sequence of SEQ ID NO: 81 or the light chain sequence of SEQ ID NO: 82.

In a further embodiment of the invention, polynucleotides encoding antibody fragments having binding specificity to CGRP comprise, or alternatively consist of, one or more of the polynucleotide sequences of SEQ ID NO: 228; SEQ ID NO: 229; and SEQ ID NO: 230 which correspond to polynucleotides encoding the complementarity-determining regions (CDRs, or hypervariable regions) of the heavy chain variable sequence of SEQ ID NO: 83 or the heavy chain sequence of SEQ ID NO: 84.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 221 encoding the light chain variable sequence of SEQ ID NO: 81; the polynucleotide SEQ ID NO: 222 encoding the light chain sequence of SEQ ID NO: 82; the polynucleotide SEQ ID NO: 223 encoding the heavy chain variable sequence of SEQ ID NO: 83; the polynucleotide SEQ ID NO: 224 encoding the heavy chain sequence of SEQ ID NO: 84; polynucleotides encoding the complementarity-determining regions (SEQ ID NO: 225; SEQ ID NO: 226; and SEQ ID NO: 227) of the light chain variable sequence of SEQ ID NO: 81 or the light chain sequence of SEQ ID NO: 82; and polynucleotides encoding the complementarity-determining regions (SEQ ID NO: 228; SEQ ID NO: 229; and SEQ ID NO: 230) of the heavy chain variable sequence of SEQ ID NO: 83 or the heavy chain sequence of SEQ ID NO: 84.

In a preferred embodiment of the invention, polynucleotides of the invention comprise, or alternatively consist of, polynucleotides encoding Fab (fragment antigen binding) fragments having binding specificity for CGRP. With respect to antibody Ab9, the polynucleotides encoding the full length Ab9 antibody comprise, or alternatively consist of, the polynucleotide SEQ ID NO: 222 encoding the light chain sequence of SEQ ID NO: 82 and the polynucleotide SEQ ID NO: 224 encoding the heavy chain sequence of SEQ ID NO: 84.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab9 following expression of the full-length polynucleotides in a suitable host. In another embodiment of the invention, anti-CGRP antibodies such as Ab9 or Fab fragments thereof may be produced via expression of Ab9 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab10

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 91:

(SEQ ID NO: 231)
CAAGTGCTGACCCAGTCTCCATCCTCCCTGTCTGCATCTGTAGGAGAC

AGAGTCACCATCAATTGCCAGGCCAGTCAGAATGTTTACAATAACAACTA

CCTAGCCTGGTATCAGCAGAAACCAGGGAAAGTTCCTAAGCAACTGATCT

ATTCTACATCCACTCTGGCATCTGGGGTCCCATCTCGTTTCAGTGGCAGT

GGATCTGGGACAGATTTCACTCTCACCATCAGCAGCCTGCAGCCTGAAGA

TGTTGCAACTTATTACTGTCTGGGCAGTTATGATTGTAGTCGTGGTGATT

GTTTTGTTTTCGGCGGAGGAACCAAGGTGGAAATCAAACGT.

In one embodiment of the invention, polynucleotides of the invention comprise, or alternatively consist of, the following polynucleotide sequence encoding the light chain polypeptide sequence of SEQ ID NO: 92:

(SEQ ID NO: 232)
CAAGTGCTGACCCAGTCTCCATCCTCCCTGTCTGCATCTGTAGGAGAC

AGAGTCACCATCAATTGCCAGGCCAGTCAGAATGTTTACAATAACAACTA

CCTAGCCTGGTATCAGCAGAAACCAGGGAAAGTTCCTAAGCAACTGATCT

ATTCTACATCCACTCTGGCATCTGGGGTCCCATCTCGTTTCAGTGGCAGT

GGATCTGGGACAGATTTCACTCTCACCATCAGCAGCCTGCAGCCTGAAGA

TGTTGCAACTTATTACTGTCTGGGCAGTTATGATTGTAGTCGTGGTGATT

GTTTTGTTTTCGGCGGAGGAACCAAGGTGGAAATCAAACGTACGGTGGCT

GCACCATCTGTCTTCATCTTCCCGCCATCTGATGAGCAGTTGAAATCTGG

AACTGCCTCTGTTGTGTGCCTGCTGAATAACTTCTATCCCAGAGAGGCCA

AAGTACAGTGGAAGGTGGATAACGCCCTCCAATCGGGTAACTCCCAGGAG

AGTGTCACAGAGCAGGACAGCAAGGACAGCACCTACAGCCTCAGCAGCAC

CCTGACGCTGAGCAAAGCAGACTACGAGAAACACAAAGTCTACGCCTGCG

AAGTCACCCATCAGGGCCTGAGCTCGCCCGTCACAAAGAGCTTCAACAGG

GGAGAGTGTTAG.

In another embodiment of the invention, polynucleotides of the invention comprise, or alternatively consist of, the following polynucleotide sequence encoding the variable heavy chain polypeptide sequence of SEQ ID NO: 93:

(SEQ ID NO: 233)
GAGGTGCAGCTTGTGGAGTCTGGGGGAGGCTTGGTCCAGCCTGGGGG

GTCCCTGAGACTCTCCTGTGCAGTCTCTGGAATCGGCCTCAGTAGCTACT

ACATGCAATGGGTCCGTCAGGCTCCAGGGAAGGGGCTGGAGTGGGTCGGA

GTCATTGGTAGTGATGGTAAGACATACTACGCGACCTGGGCGAAAGGCCG

ATTCACCATCTCCAGAGACAATTCCAAGACCACGGTGTATCTTCAAATGA

ACAGCCTGAGAGCTGAGGACACTGCTGTGTATTTCTGTACCAGAGGGGAC

ATCTGGGGCCAAGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 94:

(SEQ ID NO: 234)
GAGGTGCAGCTTGTGGAGTCTGGGGGAGGCTTGGTCCAGCCTGGGGGGTC

CCTGAGACTCTCCTGTGCAGTCTCTGGAATCGGCCTCAGTAGCTACTACA

TGCAATGGGTCCGTCAGGCTCCAGGGAAGGGGCTGGAGTGGGTCGGAGTC

ATTGGTAGTGATGGTAAGACATACTACGCGACCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTACCAGAGGGGACATC

TGGGGCCAAGGGACCCTCGTCACCGTCTCGAGCGCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACAAGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.

In a further embodiment of the invention, polynucleotides encoding antibody fragments having binding specificity to CGRP comprise, or alternatively consist of, one or more of the polynucleotide sequences of SEQ ID NO: 235; SEQ ID NO: 236; and SEQ ID NO: 237 which correspond to polynucleotides encoding the complementarity-determining regions (CDRs, or hypervariable regions) of the light chain variable sequence of SEQ ID NO: 91 or the light chain sequence of SEQ ID NO: 92.

In a further embodiment of the invention, polynucleotides encoding antibody fragments having binding specificity to CGRP comprise, or alternatively consist of, one or more of the polynucleotide sequences of SEQ ID NO: 238; SEQ ID NO: 239; and SEQ ID NO:240 which correspond to polynucleotides encoding the complementarity-determining regions (CDRs, or hypervariable regions) of the heavy chain variable sequence of SEQ ID NO: 93 or the heavy chain sequence of SEQ ID NO: 94.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 231 encoding the light chain variable sequence of SEQ ID NO: 91; the polynucleotide SEQ ID NO: 232 encoding the light chain sequence of SEQ ID NO: 92; the polynucleotide SEQ ID NO: 233 encoding the heavy chain variable sequence of SEQ ID NO: 93; the polynucleotide SEQ ID NO: 234 encoding the heavy chain sequence of SEQ ID NO: 94; polynucleotides encoding the complementarity-determining regions (SEQ ID NO: 235; SEQ ID NO: 236; and SEQ ID NO: 237) of the light chain variable sequence of SEQ ID NO: 91 or the light chain sequence of SEQ ID NO: 92; and polynucleotides encoding the complementarity-determining regions (SEQ ID NO: 238; SEQ ID NO: 239; and SEQ ID NO: 240) of the heavy chain variable sequence of SEQ ID NO: 93 or the heavy chain sequence of SEQ ID NO: 94.

In a preferred embodiment of the invention, polynucleotides of the invention comprise, or alternatively consist of, polynucleotides encoding Fab (fragment antigen binding) fragments having binding specificity for CGRP. With respect to antibody Ab10, the polynucleotides encoding the full length Ab10 antibody comprise, or alternatively consist of, the polynucleotide SEQ ID NO: 232 encoding the light chain sequence of SEQ ID NO: 92 and the polynucleotide SEQ ID NO: 234 encoding the heavy chain sequence of SEQ ID NO: 94.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab10 following expression of the full-length polynucleotides in a suitable host. In another embodiment of the invention, anti-CGRP antibodies such as Ab10 or Fab fragments thereof may be produced via expression of Ab10 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab11

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 101:

(SEQ ID NO: 241)
CAGGTGCTGACCCAGACTGCATCCCCCGTGTCTCCAGCTGTGGGAAG

CACAGTCACCATCAATTGCCGGGCCAGTCAGAGTGTTTATTATAACAACT

-continued
ACCTAGCCTGGTATCAGCAGAAACCAGGGCAGCCTCCCAAGCAACTGATC

TATTCTACATCCACTCTGGCATCTGGGGTCTCATCGCGGTTCAAAGGCAG

TGGATCTGGGACACAGTTCACTCTCACCATCAGCGACGTGCAGTGTGACG

ATGCTGCCACTTACTACTGTCTAGGCAGTTATGATTGTAGTAATGGTGAT

TGTTTTGTTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 102:

(SEQ ID NO: 242)
CAGGTGCTGACCCAGACTGCATCCCCCGTGTCTCCAGCTGTGGGAAG

CACAGTCACCATCAATTGCCGGGCCAGTCAGAGTGTTTATTATAACAACT

ACCTAGCCTGGTATCAGCAGAAACCAGGGCAGCCTCCCAAGCAACTGATC

TATTCTACATCCACTCTGGCATCTGGGGTCTCATCGCGGTTCAAAGGCAG

TGGATCTGGGACACAGTTCACTCTCACCATCAGCGACGTGCAGTGTGACG

ATGCTGCCACTTACTACTGTCTAGGCAGTTATGATTGTAGTAATGGTGAT

TGTTTTGTTTTCGGCGGAGGGACCGAGGTGGTGGTCAAACGTACGGTGGC

TGCACCATCTGTCTTCATCTTCCCGCCATCTGATGAGCAGTTGAAATCTG

GAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGA

GAGTGTCACAGAGCAGGACAGCAAGGACAGCACCTACAGCCTCAGCAGCA

CCCTGACGCTGAGCAAAGCAGACTACGAGAAACACAAAGTCTACGCCTGC

GAAGTCACCCATCAGGGCCTGAGCTCGCCCGTCACAAAGAGCTTCAACAG

GGGAGAGTGTTAG.

In another embodiment of the invention, polynucleotides of the invention comprise, or alternatively consist of, the following polynucleotide sequence encoding the variable heavy chain polypeptide sequence of SEQ ID NO: 103:

(SEQ ID NO: 243)
CAGTCGCTGGAGGAGTCCGGGGGTCGCCTGGTCACGCCTGGAGGATC

CCTGACACTCACCTGCACAGTCTCTGGAATCGACGTCACTAACTACTATA

TGCAATGGGTCCGCCAGGCTCCAGGGAAGGGGCTGGAATGGATCGGAGTC

ATTGGTGTGAATGGTAAGAGATACTACGCGAGCTGGGCGAAAGGCCGATT

CACCATCTCCAAAACCTCGTCGACCACGGTGGATCTGAAAATGACCAGTC

TGACAACCGAGGACACGGCCACCTATTTCTGTGCCAGAGGCGACATCTGG

GGCCCGGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 104:

(SEQ ID NO: 244)
CAGTCGCTGGAGGAGTCCGGGGGTCGCCTGGTCACGCCTGGAGGATCCCT

GACACTCACCTGCACAGTCTCTGGAATCGACGTCACTAACTACTATATGC

-continued
```
AATGGGTCCGCCAGGCTCCAGGGAAGGGGCTGGAATGGATCGGAGTCATT

GGTGTGAATGGTAAGAGATACTACGCGAGCTGGGCGAAAGGCCGATTCAC

CATCTCCAAAACCTCGTCGACCACGGTGGATCTGAAAATGACCAGTCTGA

CAACCGAGGACACGGCCACCTATTTCTGTGCCAGAGGCGACATCTGGGGC

CCGGGGACCCTCGTCACCGTCTCGAGCG CCTCCACCAAGGGCCCATCGG

TCTTCCCCCTGGCACCCTCCTCCAAGAGCACCTCTGGGGGCACAGCGGCC

CTGGGCTGCCTGGTCAAGGACTACTTCCCCGAACC GGTGACGGTGTCGT

GGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAG

CAGCTTGGGCACCCAGACCTACATCTGCAACGTGAATCACAAGCCCAGCA

ACACCAAGGTGGACAAGAGAGTTGAGCCCAAATCTTGTGACAAAACTCAC

ACATGCCCACCGTGCCCAGCACCTGAACTCCTGGGGGACCGTCAGTCTT

CCTCTTCCCCCCAAAACCCAAGGACACCCTCATGATCTCCCGGACCCCTG

AGGTCACATGCGTGGTGGTGGACGTGAGCCACGAAGACCCTGAGGTCAAG

TTCAACTGGTACGTGGACGGCGTGGAGGTGCATAATGCCAAGACAAAGCC

GCGGGAGGAGCAGTACGCCAGCACGTACCGTGTGGTCAGCGTCCTCACCG

TCCTGCACCAGGACTGGCTGAATGGCAAGGAGTACAAGTGCAAGGTCTCC

AACAAAGCCCTCCCAGCCCCCATCGAGAAAACCATCTCCAAAGCCAAAGG

GCAGCCCCGAGAACCACAGGTGTACACCCTGCCCCCATCCCGGGAGGAGA

TGACCAAGAACCAGGTCAGCCTGACCTGCCTGGTCAAAGGCTTCTATCCC

AGCGACATCGCCGTGGAGTGGGAGAGCAATGGGCAGCCGGAGAACAACTA

CAAGACCACGCCTCCCGTGCTGGACTCCGACGGCTCCTTCTTCCTCTACA

GCAAGCTCACCGTGGACAAGAGCAGGTGGCAGCAGGGGAACGTCTTCTCA

TGCTCCGTGATGCATGAGGCTCTGCACAACCACTACACGCAGAAGAGCCT

CTCCCTGTCTCCGGGTAAATGA.
```

In a further embodiment of the invention, polynucleotides encoding antibody fragments having binding specificity to CGRP comprise, or alternatively consist of, one or more of the polynucleotide sequences of SEQ ID NO: 245; SEQ ID NO: 246; and SEQ ID NO: 247 which correspond to polynucleotides encoding the complementarity-determining regions (CDRs, or hypervariable regions) of the light chain variable sequence of SEQ ID NO: 101 or the light chain sequence of SEQ ID NO: 102.

In a further embodiment of the invention, polynucleotides encoding antibody fragments having binding specificity to CGRP comprise, or alternatively consist of, one or more of the polynucleotide sequences of SEQ ID NO: 248; SEQ ID NO: 249; and SEQ ID NO: 250 which correspond to polynucleotides encoding the complementarity-determining regions (CDRs, or hypervariable regions) of the heavy chain variable sequence of SEQ ID NO: 103 or the heavy chain sequence of SEQ ID NO: 104.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 241 encoding the light chain variable sequence of SEQ ID NO: 101; the polynucleotide SEQ ID NO: 242 encoding the light chain sequence of SEQ ID NO: 102; the polynucleotide SEQ ID NO: 243 encoding the heavy chain variable sequence of SEQ ID NO: 103; the polynucleotide SEQ ID NO: 244 encoding the heavy chain sequence of SEQ ID NO: 104; polynucleotides encoding the complementarity-determining regions (SEQ ID NO: 245; SEQ ID NO: 246; and SEQ ID NO: 247) of the light chain variable sequence of SEQ ID NO: 101 or the light chain sequence of SEQ ID NO: 102; and polynucleotides encoding the complementarity-determining regions (SEQ ID NO: 248; SEQ ID NO: 249; and SEQ ID NO: 250) of the heavy chain variable sequence of SEQ ID NO: 103 or the heavy chain sequence of SEQ ID NO: 104.

In a preferred embodiment of the invention, polynucleotides of the invention comprise, or alternatively consist of, polynucleotides encoding Fab (fragment antigen binding) fragments having binding specificity for CGRP. With respect to antibody Ab11, the polynucleotides encoding the full length Ab11 antibody comprise, or alternatively consist of, the polynucleotide SEQ ID NO: 242 encoding the light chain sequence of SEQ ID NO: 102 and the polynucleotide SEQ ID NO: 244 encoding the heavy chain sequence of SEQ ID NO: 104.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab11 following expression of the full-length polynucleotides in a suitable host. In another embodiment of the invention, anti-CGRP antibodies such as Ab1 or Fab fragments thereof may be produced via expression of Ab1 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab12

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 111:

```
                                          (SEQ ID NO: 251)
CAAGTGCTGACCCAGTCTCCATCCTCCCTGTCTGCATCTGTAGGAGAC

AGAGTCACCATCAATTGCCGGGCCAGTCAGAGTGTTTACTATAACAACTA

CCTAGCCTGGTATCAGCAGAAACCAGGGAAAGTTCCTAAGCAACTGATCT

ATTCTACATCCACTCTGGCATCTGGGGTCCCATCTCGTTTCAGTGGCAGT

GGATCTGGGACAGATTTCACTCTCACCATCAGCAGCCTGCAGCCTGAAGA

TGTTGCAACTTATTACTGTCTGGGCAGTTATGATTGTAGTAATGGTGATT

GTTTTGTTTTCGGCGGAGGAACCAAGGTGGAAATCAAACGT.
```

In one embodiment of the invention, polynucleotides of the invention comprise, or alternatively consist of, the following polynucleotide sequence encoding the light chain polypeptide sequence of SEQ ID NO: 112:

(SEQ ID NO: 252)
CAAGTGCTGACCCAGTCTCCATCCTCCCTGTCTGCATCTGTAGGAGAC

AGAGTCACCATCAATTGCCGGGCCAGTCAGAGTGTTTACTATAACAACTA

CCTAGCCTGGTATCAGCAGAAACCAGGGAAAGTTCCTAAGCAACTGATCT

ATTCTACATCCACTCTGGCATCTGGGGTCCCATCTCGTTTCAGTGGCAGT

GGATCTGGGACAGATTTCACTCTCACCATCAGCAGCCTGCAGCCTGAAGA

TGTTGCAACTTATTACTGTCTGGGCAGTTATGATTGTAGTAATGGTGATT

GTTTTGTTTTCGGCGGAGGAACCAAGGTGGAAATCAAACGTACGGTGGCT

GCACCATCTGTCTTCATCTTCCCGCCATCTGATGAGCAGTTGAAATCTGG

AACTGCCTCTGTTGTGTGCCTGCTGAATAACTTCTATCCCAGAGAGGCCA

AAGTACAGTGGAAGGTGGATAACGCCCTCCAATCGGGTAACTCCCAGGAG

AGTGTCACAGAGCAGGACAGCAAGGACAGCACCTACAGCCTCAGCAGCAC

CCTGACGCTGAGCAAAGCAGACTACGAGAAACACAAAGTCTACGCCTGCG

AAGTCACCCATCAGGGCCTGAGCTCGCCCGTCACAAAGAGCTTCAACAGG

GGAGAGTGTTAG.

In another embodiment of the invention, polynucleotides of the invention comprise, or alternatively consist of, the following polynucleotide sequence encoding the variable heavy chain polypeptide sequence or SEQ ID NO: 113:

(SEQ ID NO: 253)
GAGGTGCAGCTTGTGGAGTCTGGGGGAGGCTTGGTCCAGCCTGGGGG

GTCCCTGAGACTCTCCTGTGCAGTCTCTGGAATCGACGTCACTAACTACT

ACATGCAATGGGTCCGTCAGGCTCCAGGGAAGGGGCTGGAGTGGGTCGGA

GTCATTGGTGTGAATGGTAAGAGATACTACGCGAGCTGGGCGAAAGGCCG

ATTCACCATCTCCAGAGACAATTCCAAGACCACGGTGTATCTTCAAATGA

ACAGCCTGAGAGCTGAGGACACTGCTGTGTATTTCTGTGCCAGAGGGGAC

ATCTGGGGCCAAGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 114:

(SEQ ID NO: 254)
GAGGTGCAGCTTGTGGAGTCTGGGGGAGGCTTGGTCCAGCCTGGGGGTC

CCTGAGACTCTCCTGTGCAGTCTCTGGAATCGACGTCACTAACTACTACA

TGCAATGGGTCCGTCAGGCTCCAGGGAAGGGGCTGGAGTGGGTCGGAGTC

ATTGGTGTGAATGGTAAGAGATACTACGCGAGCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTGCCAGAGGGGACATC

TGGGGCCAAGGGACCCTCGTCACCGTCTCGAGCGCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACAAGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.

In a further embodiment of the invention, polynucleotides encoding antibody fragments having binding specificity to CGRP comprise, or alternatively consist of, one or more of the polynucleotide sequences of SEQ ID NO: 255; SEQ ID NO: 256; and SEQ ID NO: 257 which correspond to polynucleotides encoding the complementarity-determining regions (CDRs, or hypervariable regions) of the light chain variable sequence of SEQ ID NO: 111 or the light chain sequence of SEQ ID NO: 112.

In a further embodiment of the invention, polynucleotides encoding antibody fragments having binding specificity to CGRP comprise, or alternatively consist of, one or more of the polynucleotide sequences of SEQ ID NO: 258; SEQ ID NO: 259; and SEQ ID NO: 260 which correspond to polynucleotides encoding the complementarity-determining regions (CDRs, or hypervariable regions) of the heavy chain variable sequence of SEQ ID NO: 113 or the heavy chain sequence of SEQ ID NO: 114.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 251 encoding the light chain variable sequence of SEQ ID NO: 111; the polynucleotide SEQ ID NO: 252 encoding the light chain sequence of SEQ ID NO: 112; the polynucleotide SEQ ID NO: 253 encoding the heavy chain variable sequence of SEQ ID NO: 113; the polynucleotide SEQ ID NO: 254 encoding the heavy chain sequence of SEQ ID NO: 114; polynucleotides encoding the complementarity-determining regions (SEQ ID NO: 255; SEQ ID NO: 256; and SEQ ID NO: 257) of the light chain variable sequence of SEQ ID NO: 111 or the light chain sequence of SEQ ID NO: 112; and polynucleotides encoding the complementarity-determining regions (SEQ ID NO: 258; SEQ ID NO: 259; and SEQ ID NO: 260) of the heavy chain variable sequence of SEQ ID NO: 113 or the heavy chain sequence of SEQ ID NO: 114.

In a preferred embodiment of the invention, polynucleotides of the invention comprise, or alternatively consist of, polynucleotides encoding Fab (fragment antigen binding) fragments having binding specificity for CGRP. With respect to antibody Ab12, the polynucleotides encoding the full length Ab12 antibody comprise, or alternatively consist of, the polynucleotide SEQ ID NO: 252 encoding the light chain sequence of SEQ ID NO: 112 and the polynucleotide SEQ ID NO: 254 encoding the heavy chain sequence of SEQ ID NO: 114.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab12 following expression of the full-length polynucleotides in a suitable host. In another embodiment of the invention, anti-CGRP antibodies such as Ab12 or Fab fragments thereof may be produced via expression of Ab12 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab13

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 121:

(SEQ ID NO: 261)
GCCATCGTGATGACCCAGACTCCATCTTCCAAGTCTGTCCCTGTGGGA

GACACAGTCACCATCAATTGCCAGGCCAGTGAGAGTCTTTATAATAACAA

CGCCTTGGCCTGGTTTCAGCAGAAACCAGGGCAGCCTCCCAAGCGCCTGA

TCTATGATGCATCCAAACTGGCATCTGGGGTCCCATCGCGGTTCAGTGGC

GGTGGGTCTGGGACACAGTTCACTCTCACCATCAGTGGCGTGCAGTGTGA

CGATGCTGCCACTTACTACTGTGGAGGCTACAGAAGTGATAGTGTTGATG

GTGTTGCTTTCGCCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 122:

(SEQ ID NO: 262)
GCCATCGTGATGACCCAGACTCCATCTTCCAAGTCTGTCCCTGTGGGA

GACACAGTCACCATCAATTGCCAGGCCAGTGAGAGTCTTTATAATAACAA

CGCCTTGGCCTGGTTTCAGCAGAAACCAGGGCAGCCTCCCAAGCGCCTGA

TCTATGATGCATCCAAACTGGCATCTGGGGTCCCATCGCGGTTCAGTGGC

GGTGGGTCTGGGACACAGTTCACTCTCACCATCAGTGGCGTGCAGTGTGA

CGATGCTGCCACTTACTACTGTGGAGGCTACAGAAGTGATAGTGTTGATG

GTGTTGCTTTCGCCGGAGGGACCGAGGTGGTGGTCAAACGTACGGTGGCT

GCACCATCTGTCTTCATCTTCCCGCCATCTGATGAGCAGTTGAAATCTGG

AACTGCCTCTGTTGTGTGCCTGCTGAATAACTTCTATCCCAGAGAGGCCA

AAGTACAGTGGAAGGTGGATAACGCCCTCCAATCGGGTAACTCCCAGGAG

AGTGTCACAGAGCAGGACAGCAAGGACAGCACCTACAGCCTCAGCAGCAC

CCTGACGCTGAGCAAAGCAGACTACGAGAAACACAAAGTCTACGCCTGCG

AAGTCACCCATCAGGGCCTGAGCTCGCCCGTCACAAAGAGCTTCAACAGG

GGAGAGTGTTAG.

In another embodiment of the invention, polynucleotides of the invention comprise, or alternatively consist of, the following polynucleotide sequence encoding the variable heavy chain polypeptide sequence of SEQ ID NO: 123:

(SEQ ID NO: 263)
CAGTCGGTGGAGGAGTCCGGGGGAGGCCTGGTCCAGCCTGAGGGAT

CCCTGACACTCACCTGCACAGCCTCTGGATTCGACTTCAGTAGCAATGCA

ATGTGGTGGGTCCGCCAGGCTCCAGGGAAGGGGCTGGAGTGGATCGGATG

CATTTACAATGGTGATGGCAGCACATACTACGCGAGCTGGGTGAATGGCC

GATTCTCCATCTCCAAAACCTCGTCGACCACGGTGACTCTGCAACTGAAT

AGTCTGACAGTCGCGGACACGGCCACGTATTATTGTGCGAGAGATCTTGA

CTTGTGGGGCCCGGGCACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 124:

(SEQ ID NO: 264)
CAGTCGGTGGAGGAGTCCGGGGGAGGCCTGGTCCAGCCTGAGGGATCCCT

GACACTCACCTGCACAGCCTCTGGATTCGACTTCAGTAGCAATGCAATGT

GGTGGGTCCGCCAGGCTCCAGGGAAGGGGCTGGAGTGGATCGGATGCATT

TACAATGGTGATGGCAGCACATACTACGCGAGCTGGGTGAATGGCCGATT

CTCCATCTCCAAAACCTCGTCGACCACGGTGACTCTGCAACTGAATAGTC

TGACAGTCGCGGACACGGCCACGTATTATTGTGCGAGAGATCTTGACTTG

TGGGGCCCGGGCACCCTCGTCACCGTCTCGAGCGCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACAAGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

-continued
```
CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.
```

In a further embodiment of the invention, polynucleotides encoding antibody fragments having binding specificity to CGRP comprise, or alternatively consist of, one or more of the polynucleotide sequences of SEQ ID NO: 265; SEQ ID NO: 266; and SEQ ID NO: 267 which correspond to polynucleotides encoding the complementarity-determining regions (CDRs, or hypervariable regions) or the light chain variable sequence of SEQ ID NO: 121 or the light chain sequence of SEQ ID NO: 122.

In a further embodiment of the invention, polynucleotides encoding antibody fragments having binding specificity to CGRP comprise, or alternatively consist of, one or more of the polynucleotide sequences of SEQ ID NO: 268; SEQ ID NO: 269; and SEQ ID NO: 270 which correspond to polynucleotides encoding the complementarity-determining regions (CDRs, or hypervariable regions) of the heavy chain variable sequence of SEQ ID NO: 123 or the heavy chain sequence of SEQ ID NO: 124.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 261 encoding the light chain variable sequence of SEQ ID NO: 121; the polynucleotide SEQ ID NO: 262 encoding the light chain sequence of SEQ ID NO: 122; the polynucleotide SEQ ID NO: 263 encoding the heavy chain variable sequence of SEQ ID NO: 123; the polynucleotide SEQ ID NO: 264 encoding the heavy chain sequence of SEQ ID NO: 124; polynucleotides encoding the complementarity-determining regions (SEQ ID NO: 265; SEQ ID NO: 266; and SEQ ID NO: 267) of the light chain variable sequence of SEQ ID NO: 121 or the light chain sequence of SEQ ID NO: 122; and polynucleotides encoding the complementarity-determining regions (SEQ ID NO: 268; SEQ ID NO: 269; and SEQ ID NO: 270) of the heavy chain variable sequence of SEQ ID NO: 123 or the heavy chain sequence of SEQ ID NO: 124.

In a preferred embodiment of the invention, polynucleotides of the invention comprise, or alternatively consist of, polynucleotides encoding Fab (fragment antigen binding) fragments having binding specificity for CGRP. With respect to antibody Ab13, the polynucleotides encoding the full length Ab13 antibody comprise, or alternatively consist of, the polynucleotide SEQ ID NO: 262 encoding the light chain sequence of SEQ ID NO: 122 and the polynucleotide SEQ ID NO: 264 encoding the heavy chain sequence of SEQ ID NO: 124.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab13 following expression of the full-length polynucleotides in a suitable host. In another embodiment of the invention, anti-CGRP antibodies such as Ab13 or Fab fragments thereof may be produced via expression of Ab13 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia* pastoris.

Antibodies Ab14

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 131:

```
                                        (SEQ ID NO: 271)
CAAGTGCTGACCCAGTCTCCATCCTCCCTGTCTGCATCTGTAGGAGAC

AGAGTCACCATCAATTGCCAGGCCAGTCAGAATGTTTACAATAACAACTA

CCTAGCCTGGTATCAGCAGAAACCAGGGAAAGTTCCTAAGCAACTGATCT

ATTCTACATCCACTCTGGCATCTGGGGTCCCATCTCGTTTCAGTGGCAGT

GGATCTGGGACAGATTTCACTCTCACCATCAGCAGCCTGCAGCCTGAAGA

TGTTGCAACTTATTACTGTCTGGGCAGTTATGATTGTAGTCGTGGTGATT

GTTTTGTTTTCGGCGGAGGAACCAAGGTGGAAATCAAACGT.
```

In one embodiment of the invention, polynucleotides of the invention comprise, or alternatively consist of, the following polynucleotide sequence encoding the light chain polypeptide sequence of SEQ ID NO: 132:

```
                                        (SEQ ID NO: 272)
CAAGTGCTGACCCAGTCTCCATCCTCCCTGTCTGCATCTGTAGGAGAC

AGAGTCACCATCAATTGCCAGGCCAGTCAGAATGTTTACAATAACAACTA

CCTAGCCTGGTATCAGCAGAAACCAGGGAAAGTTCCTAAGCAACTGATCT

ATTCTACATCCACTCTGGCATCTGGGGTCCCATCTCGTTTCAGTGGCAGT

GGATCTGGGACAGATTTCACTCTCACCATCAGCAGCCTGCAGCCTGAAGA

TGTTGCAACTTATTACTGTCTGGGCAGTTATGATTGTAGTCGTGGTGATT

GTTTTGTTTTCGGCGGAGGAACCAAGGTGGAAATCAAACGTACGGTGGCT

GCACCATCTGTCTTCATCTTCCCGCCATCTGATGAGCAGTTGAAATCTGG

AACTGCCTCTGTTGTGCCTGCTGAATAACTTCTATCCCAGAGAGGCCA

AAGTACAGTGGAAGGTGGATAACGCCCTCCAATCGGGTAACTCCCAGGAG

AGTGTCACAGAGCAGGACAGCAAGGACAGCACCTACAGCCTCAGCAGCAC

CCTGACGCTGAGCAAAGCAGACTACGAGAAACACAAAGTCTACGCCTGCG
```

In another embodiment of the invention, polynucleotides of the invention comprise, or alternatively consist of, the following polynucleotide sequence encoding the variable heavy chain polypeptide sequence of SEQ ID NO: 133:

(SEQ ID NO: 273)
GAGGTGCAGCTTGTGGAGTCTGGGGGAGGCTTGGTCCAGCCTGGGGG

GTCCCTGAGACTCTCCTGTGCAGTCTCTGGAATCGGCCTCAGTAGCTACT

ACATGCAATGGGTCCGTCAGGCTCCAGGGAAGGGGCTGGAGTGGGTCGGA

GTCATTGGTAGTGATGGTAAGACATACTACGCGACCTGGGCGAAAGGCCG

ATTCACCATCTCCAGAGACAATTCCAAGACCACGGTGTATCTTCAAATGA

ACAGCCTGAGAGCTGAGGACACTGCTGTGTATTTCTGTACCAGAGGGGAC

ATCTGGGGCCAAGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 134:

(SEQ ID NO: 274)
GAGGTGCAGCTTGTGGAGTCTGGGGGAGGCTTGGTCCAGCCTGGGGGTC

CCTGAGACTCTCCTGTGCAGTCTCTGGAATCGGCCTCAGTAGCTACTACA

TGCAATGGGTCCGTCAGGCTCCAGGGAAGGGGCTGGAGTGGGTCGGAGTC

ATTGGTAGTGATGGTAAGACATACTACGCGACCTGGGCGAAAGGCCGATT

CACCATCTCCAGAGACAATTCCAAGACCACGGTGTATCTTCAAATGAACA

GCCTGAGAGCTGAGGACACTGCTGTGTATTTCTGTACCAGAGGGGACATC

TGGGGCCAAGGGACCCTCGTCACCGTCTCGAGCGCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACGCGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.

In a further embodiment of the invention, polynucleotides encoding antibody fragments having binding specificity to CGRP comprise, or alternatively consist of, one or more of the polynucleotide sequences of SEQ ID NO: 275; SEQ ID NO: 276; and SEQ ID NO: 277 which correspond to polynucleotides encoding the complementarity-determining regions (CDRs, or hypervariable regions) of the light chain variable sequence of SEQ ID NO: 131 or the light chain sequence of SEQ ID NO: 132.

In a further embodiment of the invention, polynucleotides encoding antibody fragments having binding specificity to CGRP comprise, or alternatively consist of, one or more of the polynucleotide sequences of SEQ ID NO: 278; SEQ ID NO: 279; and SEQ ID NO: 280 which correspond to polynucleotides encoding the complementarity-determining regions (CDRs, or hypervariable regions) of the heavy chain variable sequence of SEQ ID NO: 133 or the heavy chain sequence of SEQ ID NO: 134.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 271 encoding the light chain variable sequence of SEQ ID NO: 131; the polynucleotide SEQ ID NO: 272 encoding the light chain sequence of SEQ ID NO: 132; the polynucleotide SEQ ID NO: 273 encoding the heavy chain variable sequence of SEQ ID NO: 133; the polynucleotide SEQ ID NO: 274 encoding the heavy chain sequence of SEQ ID NO: 134; polynucleotides encoding the complementarity-determining regions (SEQ ID NO: 275; SEQ ID NO: 276; and SEQ ID NO: 277) of the light chain variable sequence of SEQ ID NO: 131 or the light chain sequence of SEQ ID NO: 132; and polynucleotides encoding the complementarity-determining regions (SEQ ID NO: 278; SEQ ID NO: 279; and SEQ ID NO: 280) of the heavy chain variable sequence of SEQ ID NO: 133 or the heavy chain sequence of SEQ ID NO: 134.

In a preferred embodiment of the invention, polynucleotides of the invention comprise, or alternatively consist of, polynucleotides encoding Fab (fragment antigen binding) fragments having binding specificity for CGRP. With respect to antibody Ab14, the polynucleotides encoding the full length Ab14 antibody comprise, or alternatively consist of, the polynucleotide SEQ ID NO: 272 encoding the light chain sequence of SEQ ID NO: 132 and the polynucleotide SEQ ID NO: 274 encoding the heavy chain sequence of SEQ ID NO: 134.

Another embodiment of the invention contemplates these polynucleotides incorporated into an expression vector for expression in mammalian cells such as CHO, NSO, HEK-293, or in fungal, insect, or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab14 following expression of the full-length polynucleotides in a suitable host. In another embodiment of the invention, anti-CGRP antibodies such as Ab14 or Fab fragments thereof may be produced via expression of Ab14 polynucleotides in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

In one embodiment, the invention is directed to an isolated polynucleotide comprising a polynucleotide encoding an anti-CGRP $V_H$ antibody amino acid sequence selected from SEQ ID NO: 3, 13, 23, 33, 43, 53, 63, 73, 83, 93, 103, 113, 123, or 133, or encoding a variant thereof wherein at least one framework residue (FR residue) has been substituted with an amino acid present at the corresponding position in a rabbit anti-CGRP antibody V polypeptide or a conservative amino acid substitution.

In another embodiment, the invention is directed to an isolated polynucleotide comprising the polynucleotide sequence encoding an anti-CGRP $V_L$ antibody amino acid sequence of 1, 11, 21, 31, 41, 51, 61, 71, 81, 91, 101, 111, 121, or 131, or encoding a variant thereof wherein at least one framework residue (FR residue) has been substituted with an amino acid present at the corresponding position in a rabbit anti-CGRP antibody $V_L$ polypeptide or a conservative amino acid substitution.

In yet another embodiment, the invention is directed to one or more heterologous polynucleotides comprising a sequence encoding the polypeptides contained in SEQ ID NO:1 and SEQ ID NO:3; SEQ ID NO: 11 and SEQ ID NO:13; SEQ ID NO:21 and SEQ ID NO:23; SEQ ID NO:31 and SEQ ID NO:33; SEQ ID NO: 41 and SEQ ID NO: 43; SEQ ID NO:51 and SEQ ID NO:53, SEQ ID NO: 61 and SEQ ID NO:63; SEQ ID NO: 71 and SEQ ID NO:73; SEQ ID NO: 81 and SEQ ID NO: 83; SEQ ID NO:91 and SEQ ID NO: 93; SEQ ID NO: 101 and SEQ ID NO: 103; SEQ ID NO:111 and SEQ ID NO:113; SEQ ID NO:121 and SEQ ID NO:123; or SEQ ID NO:131 and SEQ ID NO:133.

In another embodiment, the invention is directed to an isolated polynucleotide that expresses a polypeptide containing at least one CDR polypeptide derived from an anti-CGRP antibody wherein said expressed polypeptide alone specifically binds CGRP or specifically binds CGRP when expressed in association with another polynucleotide sequence that expresses a polypeptide containing at least one CDR polypeptide derived from an anti-CGRP antibody wherein said at least one CDR is selected from those contained in the $V_L$ or $V_H$ polypeptides of SEQ ID NO: 1, 3, 11, 13, 21, 23, 31, 33, 41, 43, 51, 53, 61, 63, 71, 73, 81, 83, 91, 93, 101, 103, 111, 113, 121, 123, 131, or SEQ ID NO:133.

Host cells and vectors comprising said polynucleotides are also contemplated.

The invention further contemplates vectors comprising the polynucleotide sequences encoding the variable heavy and light chain polypeptide sequences, as well as the individual complementarity-determining regions (CDRs, or hypervariable regions), as set forth herein, as well as host cells comprising said vector sequences. In one embodiment of the invention, the host cell is a yeast cell. In another embodiment of the invention, the yeast host cell belongs to the genus *Pichia*.

B-Cell Screening and Isolation

In one embodiment, the present invention contemplates the preparation and isolation of a clonal population of antigen-specific B cells that may be used for isolating at least one CGRP antigen-specific cell, which can be used to produce a monoclonal antibody against CGRP, which is specific to a desired CGRP antigen, or a nucleic acid sequence corresponding to such an antibody. Methods of preparing and isolating said clonal population of antigen-specific B cells are taught, for example, in U.S. patent publication no. US 2007/0269868 to Carvalho-Jensen et al., the disclosure of which is herein incorporated by reference in its entirety. Methods of preparing and isolating said clonal population of antigen-specific B cells are also taught herein in the examples. Methods of "enriching" a cell population by size or density are known in the art. See, e.g., U.S. Pat. No. 5,627,052. These steps can be used in addition to enriching the cell population by antigen-specificity.

Methods of Humanizing Antibodies

In another embodiment, the present invention contemplates methods for humanizing antibody heavy and light chains. Methods for humanizing antibody heavy and light chains which may be applied to anti-CGRP antibodies are taught, for example, in U.S. patent application publication no US 2009/0022659 to Olson et al., and in U.S. Pat. No. 7,935,340 to Garcia-Martinez et al., the disclosures of each of which are herein incorporated by reference in their entireties.

Methods of Producing Antibodies and Fragments Thereof

In another embodiment, the present invention contemplates methods for producing anti-CGRP antibodies and fragments thereof. Methods for producing anti-CGRP antibodies and fragments thereof secreted from polyploidal, preferably diploid or tetraploid strains of mating competent yeast are taught, for example, in U.S. patent application publication no. US 2009/0022659 to Olson et al., and in U.S. Pat. No. 7,935,340 to Garcia-Martinez et al., the disclosures of each of which are herein incorporated by reference in their entireties.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., P.N.A.S. USA, 81:8651-55 (1984); Neuberger, M. S. et al., Nature, 314:268-270 (1985); Boulianne, G. L. et al., Nature, 312:643-46 (1984), the disclosures of each of which are herein incorporated by reference in their entireties.

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al, Nature, 321:522-525 (1986); Reichmann, L., et al, Nature, 332:323-327 (1988); Verhoeyen, M, et al, Science, 239:1534-36 (1988), the disclosures of each of which are herein incorporated by reference in their entireties).

Antibody polypeptides of the invention having CGRP binding specificity may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibody polypeptides may be either a bacterial cell such as E. coli, or a eukaryotic cell such as P. pastoris. In one embodiment of the invention, a mammalian cell of a well-defined type for this purpose, such as a myeloma cell, a Chinese hamster ovary (CHO) cell line, a NSO cell line, or a HEK293 cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an E. coli-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography and the like.

The antibody polypeptides described herein may also be used for the design and synthesis of either peptide or non-peptide mimetics that would be useful for the same therapeutic applications as the antibody polypeptides of the invention. See, for example, Saragobi et al, Science, 253: 792-795 (1991), the contents of which is herein incorporated by reference in its entirety.

Screening Assays

The invention also includes screening assays designed to assist in the identification of diseases and disorders associated with CGRP in patients exhibiting symptoms of a CGRP associated disease or disorder.

In one embodiment of the invention, the anti-CGRP antibodies of the invention, or CGRP binding fragments thereof, are used to detect the presence of CGRP in a biological sample obtained from a patient exhibiting symptoms of a disease or disorder associated with CGRP. The presence of CGRP, or elevated levels thereof when compared to pre-disease levels of CGRP in a comparable biological sample, may be beneficial in diagnosing a disease or disorder associated with CGRP.

Another embodiment of the invention provides a diagnostic or screening assay to assist in diagnosis of diseases or disorders associated with CGRP in patients exhibiting symptoms of a CGRP associated disease or disorder identified herein, comprising assaying the level of CGRP expression in a biological sample from said patient using a post-translationally modified anti-CGRP antibody or binding fragment thereof. The anti-CGRP antibody or binding fragment thereof may be post-translationally modified to include a detectable moiety such as set forth previously in the disclosure.

The CGRP level in the biological sample is determined using a modified anti-CGRP antibody or binding fragment thereof as set forth herein, and comparing the level of CGRP in the biological sample against a standard level of CGRP (e.g., the level in normal biological samples). The skilled clinician would understand that some variability may exist between normal biological samples, and would take that into consideration when evaluating results. In one embodiment of the invention, the anti-CGRP antibodies of the invention may be used to correlate CGRP expression levels with a particular stage of cancerous development. One skilled in the art would be able to measure CGRP in numerous subjects in order to establish ranges of CGRP expression that correspond to clinically defined stages of cancerous development. These ranges will allow the skilled practitioner to measure CGRP in a subject diagnosed with a cancer and correlate the levels in each subject with a range that corresponds to a stage of said cancer. One skilled in the art would understand that by measuring CGRP in the patient at different intervals, the progression of the cancer can be determined.

The above-recited assay may also be useful in monitoring a disease or disorder, where the level of CGRP obtained in a biological sample from a patient believed to have a CGRP associated disease or disorder is compared with the level of CGRP in prior biological samples from the same patient, in order to ascertain whether the CGRP level in said patient has changed with, for example, a treatment regimen.

The invention is also directed to a method of in vivo imaging which detects the presence of cells which express CGRP comprising administering a diagnostically effective amount of a diagnostic composition. Said in vivo imaging is useful for the detection or imaging of CGRP expressing tumors or metastases, for example, and can be useful as part of a planning regimen for the design of an effective cancer treatment protocol. The treatment protocol may include, for example, one or more of radiation, chemotherapy, cytokine therapy, gene therapy, and antibody therapy, as well as an anti-CGRP antibody or fragment thereof.

The present invention further provides for a kit for detecting binding of an anti-CGRP antibody of the invention to CGRP. In particular, the kit may be used to detect the presence of a CGRP specifically reactive with an anti-CGRP antibody of the invention or an immunoreactive fragment thereof. The kit may also include an antibody bound to a substrate, a secondary antibody reactive with the antigen and a reagent for detecting a reaction of the secondary antibody with the antigen. Such a kit may be an ELISA kit and can comprise the substrate, primary and secondary antibodies when appropriate, and any other necessary reagents such as detectable moieties, enzyme substrates, and color reagents, for example as described herein. The diagnostic kit may also be in the form of an immunoblot kit. The diagnostic kit may also be in the form of a chemiluminescent kit (Meso Scale Discovery, Gaithersburg, Md.). The diagnostic kit may also be a lanthanide-based detection kit (PerkinElmer, San Jose, Calif.).

A skilled clinician would understand that a biological sample includes, but is not limited to, sera, plasma, urine, saliva, mucous, pleural fluid, synovial fluid and spinal fluid.

Methods of Ameliorating or Reducing Symptoms of, or Treating, or Preventing, Diseases and Disorders Associated with, CGRP In another embodiment of the invention, anti-CGRP antibodies described herein, or fragments thereof, are useful for ameliorating or reducing the symptoms of, or treating, or preventing, diseases and disorders associated with CGRP. Anti-CGRP antibodies described herein, or fragments thereof, as well as combinations, can also be administered in a therapeutically effective amount to patients in need of treatment of diseases and disorders associated with CGRP in the form of a pharmaceutical composition as described in greater detail below.

In another embodiment of the invention, anti-CGRP antibodies described herein, or fragments thereof, are useful for ameliorating or reducing the symptoms of, or treating, or preventing, migraines (with or without aura), weight loss, cancer or tumors, angiogenesis associated with cancer or tumor growth, angiogenesis associated with cancer or tumor survival, pain, hemiplagic migraines, cluster headaches, migrainous neuralgia, chronic headaches, tension headaches, general headaches, hot flushes, chronic paroxysomal hemicrania, secondary headaches due to an underlying structural problem in the head or neck, cranial neuralgia, sinus headaches (such as for example associated with sinusitis), and allergy-induced headaches or migraines.

In one embodiment of the invention, anti-CGRP antibodies described herein, or fragments thereof and/or with a second agent, are useful for ameliorating or reducing the symptoms of, or treating, or preventing, the following non-limiting listing of diseases and disorders: pain, inflammatory pain, post-operative incision pain, complex regional pain syndrome, cancer pain, primary or metastatic bone cancer pain, fracture pain, chronic pain, osteoporotic fracture pain, pain resulting from burn, osteoporosis, gout joint pain, abdominal pain, pain associated with sickle cell crises, and other nociceptic pain, as well as hepatocellular carcinoma, breast cancer, liver cirrhosis, neurogenic pain, neuropathic pain, nociceptic pain, trigeminal neuralgia, post-herpetic neuralgia phantom limb pain, fibromyalgia, menstrual pain, ovarialgia, reflex sympathetic dystrophy, neurogenic pain, osteoarthritis or rheumatoid arthritis pain, lower back pain, diabetic neuropathy, sciatica, or pain or visceral pain associated with: gastro-esophageal reflux, dyspepsia, irritable bowel syndrome, irritable colon, spastic colon, mucous colitis, inflammatory bowel disease, Crohn's disease, ileitis, ulcerative colitis, renal colic, dysmenorrhea cystitis, menstrual period, labor, menopause, prostatitis, pancreatitis, renal colic, dysmenorrhea cystitis, including interstitial cystitis (IC), surgery associated with the ileus, diverticulitis, peritonitis, pericarditis, hepatitis, appendicitis, colitis, cholecystitis, endometriosis, chronic and/or acute pancreatitis, myocardial infarction, kidney pain, pleural pain, prostatitis, pelvic pain, trauma to an organ, chronic nociceptive pain, chronic neuropathic pain, chronic inflammatory pain, fibromyalgia, breakthrough pain and persistent pain, and cancer pain arising from malignancy or from cancer preferably selected from one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia bladder cancer, bone cancer, brain cancer, breast cancer, carcinoid tumours, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumours, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukaemia, primary or secondary bone cancer, tumours that metastasize to the bone, tumours infiltrating the nerve and hollow viscus, tumours near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

In another embodiment of the invention, anti-CGRP antibodies described herein, or fragments thereof and/or with a second agent, are useful for ameliorating or reducing the symptoms of, or treating, or preventing, the following non-limiting listing of diseases and disorders cancer or tumors, angiogenesis associated with cancer or tumor growth, angiogenesis associated with cancer or tumor survival.

In another embodiment of the invention, anti-CGRP antibodies described herein, or fragments thereof and/or with a second agent, are useful for ameliorating or reducing the symptoms of, or treating, or preventing, the following non-limiting listing of diseases and disorders: neurogenic, neuropathic or nociceptic pain. Neuropathic pain may include, but is not limited to, trigeminal neuralgia, post-herpetic neuralgia, phantom limb pain, fibromyalgia, menstrual pain, ovarialgia, reflex sympathetic dystrophy and neurogenic pain. In other preferred embodiments, osteoarthritis or rheumatoid arthritis pain, lower back pain, diabetic neuropathy, sciatica, and other neuropathic pain.

In another embodiment of the invention, anti-CGRP antibodies described herein, or fragments thereof and/or with a second agent, are useful for ameliorating or reducing the symptoms of, or treating, or preventing, the following non-limiting listing of diseases and disorders: overactive bladder and other urinary conditions, gastro-esophageal reflux and visceral pain associated with gastro-esophageal reflux, dyspepsia, irritable bowel syndrome, inflammatory bowel disease, Crohn's disease, ileitis, ulcerative colitis, renal colic, dysmenorrhea, cystitis, menstrual period, labor, menopause, prostatitis, pruritis, or pancreatitis. Also, the subject CGRP antibodies and antibody fragments may be used alone or in conjunction with other active agents, e.g., opioids and non-opioid analgesics such as NSAIDs to elicit analgesia or to potentiate the efficacy or another analgesic or to prevent or alleviate tolerance to a specific analgesic such as morphine or related opioid analgesics. Evidence for role or CGRP in blocking/reversing development of morphine-induced analgesia is the fact that CGRP8-37 and CGRP Receptor antagonist (BIBN4096BS) reportedly prevent/reverse development of morphine tolerance—(Powell et al., 2000 J Brit J Pharmacol (131):875; Menard et al., 1996 J Neurosci (16):2342; Wang et al., 2009 FASEB J (23):2576; Wang et al., 2010 Pain (151):194)

The subject antibodies potentially may be combined with any opioid analgesic or NSAID or other analgesic, potentially another antibody, in order to increase or enhance pain management, or to reverse or suppress tolerance to an analgesic such as an opioid analgesic compound. This may allow for such analgesic compounds to be administered for longer duration or at reduced dosages thereby potentially alleviating adverse side effects associated therewith.

The term "opioid analgesic" herein refers to all drugs, natural or synthetic, with morphine-like actions. The synthetic and semi-synthetic opioid analgesics are derivatives or five chemical classes of compound: phenanthrenes; phenylheptylamines; phenylpiperidines; morphinans; and benzomorphans, all of which are within the scope or the term. Exemplary opioid analgesics include codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine or pharmaceutically acceptable salts thereof.

The term "NSAID" refers to a non-steroidal anti-inflammatory compound NSAIDs are categorized by virtue of their ability to inhibit cyclooxygenase. Cyclooxygenase 1 and cyclooxygenase 2 are two major isoforms or cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid, (4) biphenylcarboxylic acid derivatives, such as diflunisal and flufenisal; and (5) oxicams, such as piroxim, sudoxicam, and isoxicam. Another class of NSAID has been described which selectively inhibit cyclooxygenase 2. Cox-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

In some embodiments, aspirin and/or acetaminophen may be taken in conjunction with the subject CGRP antibody or fragment. Aspirin is another type of non-steroidal anti-inflammatory compound.

Exemplary, non-limiting diseases and disorders that can be treated and/or prevented by the administration of the CGRP antibodies of the present invention include, pain resulting from any condition associated with neurogenic, neuropathic, inflammatory, thermal or nociceptive pain. Preferably the disorder will be associated with increased CGRP at the pain site. In certain embodiments of neuropathic pain, referred trigeminal neuralgia, post-herpetic neuralgia, phantom limb pain, fibromyalgia, reflex sympathetic dystrophy and neurogenic pain conditions are preferably treated. In other embodiments, cancer pain, particularly, bone cancer pain, osteoarthritis or rheumatoid arthritis pain, lower back pain, post-operative incision pain, fracture pain, osteoporotic fracture pain, osteoporosis, gout joint pain, diabetic neuropathy, sciatica pains associated with sickle cell crises, migraine, and other neuropathic and/or nociceptive pain are preferably treated. Thus, the present invention includes methods of treating, preventing, and/or ameliorating any disease or disorder associated with CGRP activity or CGRP upregulation (including any of the above mentioned exemplary diseases, disorders and conditions) through use of the antibodies and antibody fragments of the invention. The therapeutic methods of the present invention comprise administering to a subject any formulation comprising an anti-CGRP antibody as disclosed herein alone or in association with another active agent.

The subject to which the pharmaceutical formulation is administered can be, e.g., any human or non-human animal that is in need of such treatment, prevention and/or amelioration, or who would otherwise benefit from the inhibition or attenuation of CGRP-mediated activity. For example, the subject can be an individual that is diagnosed with, or who is deemed to be at risk of being afflicted by any of the aforementioned diseases or disorders. The present invention further includes the use of any of the pharmaceutical formulations disclosed herein in the manufacture of a medicament for the treatment, prevention and/or amelioration of any disease or disorder associated with CGRP activity (including any of the above mentioned exemplary diseases, disorders and conditions).

Administration

In one embodiment of the invention, the anti-CGRP antibodies described herein, or CGRP binding fragments thereof, as well as combinations of said antibodies or antibody fragments, are administered to a subject at a concentration of between about 0.1 and 100.0 mg/kg of body weight of recipient subject. In a preferred embodiment of the invention, the anti-CGRP antibodies described herein, or CGRP binding fragments thereof, as well as combinations of said antibodies or antibody fragments, are administered to a subject at a concentration of about 0.4 mg/kg of body weight of recipient subject. In a preferred embodiment of the invention, the anti-CGRP antibodies described herein, or CGRP binding fragments thereof, as well as combinations of said antibodies or antibody fragments, are administered to a recipient subject with a frequency of once every twenty-six weeks or less, such as once every sixteen weeks or less, once every eight weeks or less, once every four weeks or less, once every two weeks or less, once every week or less, or once daily or less.

Fab fragments may be administered every two weeks or less, every week or less, once daily or less, multiple times per day, and/or every few hours. In one embodiment of the invention, a patient receives Fab fragments of 0.1 mg/kg to 40 mg/kg per day given in divided doses of 1 to 6 times a day, or in a sustained release form, effective to obtain desired results.

It is to be understood that the concentration of the antibody or Fab administered to a given patient may be greater or lower than the exemplary administration concentrations set forth above.

A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J. Harvey, R. A., Champe, P. C., & Mycek, M. J. (2006). Pharmacology. Lippincott's illustrated reviews. Philadelphia Lippincott Williams & Wilkins; and Golan, D. E. (2008). Principles of pharmacology the pathophysiologic basis of drug therapy. Philadelphia, Pa., [etc.]: Lippincott Williams & Wilkins.

In another embodiment of the invention, the anti-CGRP antibodies described herein, or CGRP binding fragments thereof, as well as combinations of said antibodies or antibody fragments, are administered to a subject in a pharmaceutical formulation.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-CGRP antibodies described herein, or CGRP binding fragments thereof, as well as combinations of said antibodies or antibody fragments, may be optionally administered in combination with one or more active agents. Such active agents include analgesic, anti-histamine, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VFGF, EPO, FGF, HRG, Hepatocyte Growth Factor (HGF), Hepcidin, including antibodies reactive against any of the foregoing, and antibodies reactive against any of their receptors. Active agents also include but are not limited to 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Nerve Growth Factor (NGF), Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Substance P, Sulfinpyrazone, Sulindac, Suprofen, Tenoxicam, Tiaprofenic acid, Tolfenamic acid, Tolmetin, and Valdecoxib.

An anti-histamine can be any compound that opposes the action of histamine or its release from cells (e.g., mast cells). Anti-histamines include but are not limited to acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast.

Antibiotics include but are not limited to Amikacin, Aminoglycosides, Amoxicillin, Ampicillin, Ansamycins, Arsphenamine, Arithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Celixime, Cefoperazone, Cefotaxime, Cefoxitin, Cerpodoxime, Cefprozil, Cefazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbitmycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithrolmycin, Tetracycline, Tetracyclines, Ticarcillin, Tinidazole, Tobramycin, Trimethoprim, Trimethoprim-Sulfamethoxazole, Troleandomycin, Trovafloxacin, and Vancomycin.

Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity t the formulation, though it may provide chemical and/or biological stability, and release characteristics. Exemplary formulations can be found, for example, in Remington's Pharmaceutical Sciences, 19th Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B cells were disclosed in U.S. Provisional patent application No. 60/801,412, filed May 19, 2006, the disclosure of which is herein incorporated by reference in its entirety.

Certain teachings related to humanization of rabbit-derived monoclonal antibodies and preferred sequence modifications to maintain antigen binding affinity were disclosed in International Application No. PCT/US2008/064421, corresponding to International Publication No. WO/2008/144757, entitled "Novel Rabbit Antibody Humanization Methods and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006, (U.S. Patent Application Publication No. US2006/0270045), the disclosure of which is herein incorporated by reference in its entirety.

Certain CGRP antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade, and pressure is at or near atmospheric.

EXAMPLES

Example 1 Preparation of Antibodies that Bind CGRP

By using the antibody selection protocol described herein, one can generate an extensive panel of antibodies.

Immunization Strategy

Rabbits were immunized with human CGRPα (American Peptides, Sunnyvale Calif. and Bachem, Torrance Calif.). Immunization consisted of a first subcutaneous (sc) injection of 100 µg of antigen mixed with 100 µg of KLII in complete Freund's adjuvant (CFA) (Sigma) followed by two boosts, two weeks apart each containing 50 µg antigen mixed with 50 µg in incomplete Freund's adjuvant (IFA) (Sigma). Animals were bled on day 55, and serum titers were determined by ELISA (antigen recognition) and by inhibition of CGRP driven cAMP increase in SK-N-MC.

Antibody Selection Titer Assessment

To identify and characterize antibodies that bind to human CGRPα, antibody-containing solutions were tested by ELISA. Briefly, neutravidin coated plates (Thermo Scientific), were coated with N-term biotinylated human CGRPα (50 µL per well, 1 µg/mL) diluted in ELISA buffer (0.5% fish skin gelatin in PBS pH 7.4) either for approximately 1 hr at room temperature or alternatively overnight at 4° C. The plates were then further blocked with ELISA buffer for one hour at room temperature and washed using wash buffer (PBS, 0.05% tween 20). Serum samples tested were serially diluted using ELISA buffer. Fifty microliters of diluted serum samples were transferred onto the wells and incubated for one hour at room temperature for one hour. After this incubation, the plate was washed with wash buffer. For development, an anti-rabbit specific Fc-HARP (1:5000 dilution in ELISA buffer) was added onto the wells and incubated for 45 min at RT. After a 3× wash step with wash solution, the plate was developed using TMB substrate for two minutes at room temperature and the reaction was quenched using 0.5M HCl. The well absorbance was read at 450 nm.

Titer Determination of Serum Samples by Functional Activity (Inhibition of CGRP Driven cAMP Levels)

To identify and characterize antibodies with functional activity, an inhibition of CGRP driven increase of cAMP levels assay was done using electrochemiluminescence (Meso Scale Discovery, MSD). Briefly, antibody preparations to be tested were serially diluted in MSD assay buffer (Hepes, MgCl2, pH 7.3, 1 mg/mL blocker A, Meso Scale Discovery) in a 96 well round bottom polystyrene plate (Costar). To this plate, human CGRPα was added (10 ng/mL final concentration) diluted in MSD assay buffer and incubated for one hour at 37 C. Appropriate controls were used as suggested by the assay-kit manufacturer. Human neuroepithelioma cells (SK-N-MC, ATCC) were detached using an EDTA solution (5 mM in PBS) and washed using growth media (MEM, 10% FBS, antibiotics) by centrifugation. The cell number was adjusted to 2 million cells per mL in assay buffer, and IBMX (3-Isobutyl-1Methylxanthine, Sigma) was added to a final concentration of 0.2 mM right before loading cells onto cAMP assay plate. After the antibody human CGRPα solution was incubated for one hour 20 microliters of solution containing cells were transferred to the cAMP assay plate. All tested samples were run in duplicates with appropriate controls. Ten microliters of cells were added to the wells and the plate was incubated for 30 minutes with shaking at room temperature. While cells were being incubated with the CGRP solution, the stop solution was prepared by making a 1:200 solution of TAG labeled cAMP (MSD) in lysis buffer (MSD). To stop the cells-CGRP incubation, 20 microliters of stop solution was added to the cells and the plate was incubated for one hour with shaking at room temperature. The read buffer (MSD) was diluted four times with water and 100 microliters were added to all wells on the plate. The plate was then read using a Sector Imager 2400 (MSD) and the Prism software was used for data fit and IC50 determination.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 µm (Fisher) with a plunger of a 20 cc syringe. Cells were collected in PBS. Cells were washed twice by centrifugation. After the last wash, cell density was determined by trypan blue. Cells were centrifuged at 1500 rpm for 10 minutes, the supernatant was discarded. Cells were resuspended in the appropriate volume of 10% dimethyl sulfoxide (DMSO, Sigma) in FBS (Hyclone) and dispensed at 1 ml/vial. Vials were stored at −70° C. in a slow freezing chamber for 24 hours and stored in liquid nitrogen.

Peripheral blood mononuclear cells (PBMCs) were isolated by mixing whole blood with equal parts of the low glucose medium described above without FBS. 35 ml of the whole blood mixture was carefully layered onto 8 ml of Lympholyte Rabbit (Cedarlane) into a 45 ml conical tube (Corning) and centrifuged 30 minutes at 2500 rpm at room temperature without brakes. After centrifugation, the PBMC layers were carefully removed using a glass Pasteur pipette (VWR), combined, and placed into a clean 50 ml vial. Cells were washed twice with the modified medium described above by centrifugation at 1500 rpm for 10 minutes at room temperature, and cell density was determined by trypan blue staining. After the last wash, cells were resuspended in an appropriate volume of 10% DMSO/FBS medium and frozen as described above.

B Cell Selection, Enrichment and Culture Conditions

On the day of setting up B cell culture, PBMC, splenocyte, or lymph node vials were thawed for use. Vials were removed from LN2 tank and placed in a 37° C. water bath until thawed. Contents of vials were transferred into 15 ml conical centrifuge tube (Corning) and 10 ml of modified RPMI described above was slowly added to the tube. Cells were centrifuged for 5 minutes at 2K RPM, and the supernatant was discarded. Cells were resuspended in 10 ml of fresh media. Cell density and viability was determined by trypan blue.

a) The Following Protocol was Used for Ab1 and Ab13

Cells were pre-mixed with the biotinylated human CGRPα as follows. Cells were washed again and resuspended at 1E07 cells/80 µL medium. Biotinylated human CGRPα was added to the cell suspension at the final concentration of 5 ug/mL and incubated for 30 minutes at 4° C. Unbound biotinylated human CGRPα was removed performing two 10 ml washes using PBF |Ca/Mg free PBS (Hyclone), 2 mM ethylenediamine tetraacetic acid (EDTA), 0.5% bovine serum albumin (BSA) (Sigma-biotin free)|. After the second wash, cells were resuspended at 1E07 cells/80 µl PBF and 20 µl of MACS® streptavidin beads (Miltenyi Biotech, Auburn Calif.) per 10E7 cells were added to the cell suspension. Cells and beads were incubated at 4° C. for 15 minutes and washed once with 2 ml of PBF per 10E7 cells.

b) The Following Protocol was Used for Ab4, Ab7, Ab9 and Ab11:

Biotinylated human CGRPα was pre-loaded onto the streptavidin beads as follows. Seventy five microliters of streptavidin beads (Milteny Biotec, Auburn Calif.) were mixed with N-terminally biotinylated huCGRPα (10 ug/ml final concentration) and 300 µl PBF. This mixture was incubated at 4° C. for 30 min and unbound biotinylated human CGRPα was removed using a MACS® separation column (Miltenyi Biotec, with a 1 ml rinse to remove unbound material. Then material was plunged out, then used to resuspend cells from above in 100 ul per 1E7 cells, the mixture was then incubated at 4° C. for 30 min and washed once with 10 ml of PBF.

For both a) and b) protocols the following applied: After washing, the cells were resuspended in 500 µl of PBF and set aside. A MACS® MS column (Miltenyi Biotec, Auburn Calif.) was pre-rinsed with 500 ml of PBF on a magnetic stand (Milteni). Cell suspension was applied to the column through a pre-filter, and unbound fraction was collected. The column was washed with 2.5 ml of PBF buffer. The column was removed from the magnet stand and placed onto a clean, sterile 1.5 ml eppendorf tube. 1 ml of PBF buffer was added to the top of the column, and positive selected cells were collected. The yield and viability of positive cell fraction was determined by trypan blue staining. Positive selection yielded an average of 1% of the starting cell concentration.

A pilot cell screen was established to provide information on seeding levels for the culture. Plates were seeded at 10, 25, 50, 100, or 200 enriched B cells/well. In addition, each well contained 50K cells/well or irradiated EL-4.B5 cells (5,000 Rads) and an appropriate level of activated rabbit T cell supernatant (See U.S. Patent Application Publication No. 20070269868) (ranging from 1-5% depending on preparation) in high glucose modified RPMI medium at a final volume of 250 μl/well. Cultures were incubated for 5 to 7 days at 37° C. in 4% $CO_2$.

B-Cell Culture Screening by Antigen-Recognition (ELISA)

To identify wells producing anti-human CGRPα antibodies, the same protocol as described for titer determination of serum samples by antigen-recognition (ELISA) was used with the following changes. Briefly, neutravidin coated plates were coated with a mixture of both N- and C-terminally biotinylated human CGRPα (50 μL per well, 1 μg/mL each). B-cell supernatant samples (50 μL) were tested without prior dilution.

Identification of Functional Activity in B-Cell Supernatants Using CGRP Driven cAMP Production To determine functional activity contained in B-cell supernatants, a similar procedure to that described for the determination of functional titer of serum samples was used with the following modifications. Briefly, B-cell supernatant (20 μL) were used in place of the diluted polyclonal scrum samples.

Isolation of Antigen-Specific B-Cells

Plates containing wells of interest were removed from −70° C., and the cells from each well were recovered using five washes of 200 microliters of medium (10% RPMI complete, 55 μM BME) per well. The recovered cells were pelleted by centrifugation and the supernatant was carefully removed. Pelleted cells were resuspended in 100 μl of medium. To identify antibody expressing cells, streptavidin coated magnetic beads (M280 dynabeads, Invitrogen) were coated with a combination of both N- and C-terminal biotinylated human CGRPα. Individual biotinylated human CGRPα lots were optimized by serial dilution. One hundred microliters containing approximately 4×10E7 coated beads were then mixed with the resuspended cells. To this mixture 15 microliters of goat anti-rabbit II&L IgG-FITC (Jackson Immunoresearch) diluted 1:100 in medium were added.

Twenty microliters of cell/beads/anti-rabbit H&L suspension were removed and 5 microliter droplets were dispensed on a one-well glass slide previously treated with Sigmacote (Sigma) totaling 35 to 40 droplets per slide. An impermeable barrier of paraffin oil (JT Baker) was used to submerge the droplets, and the slide was incubated for 90 minutes at 37° C. in a 4% CO2 incubator in the dark.

Specific B cells that produce antibody can be identified by the fluorescent ring around produced by the antibody secretion, recognition of the bead-associated biotinylated antigen, and subsequent detection by the fluorescent-IgG detection reagent. Once a cell of interest was identified it was recovered via a micromanipulator (Eppendorf). The single cell synthesizing and exporting the antibody was transferred into a microcentrifuge tube, frozen using dry ice and stored at −70° C.

Amplification and Sequence Determination of Antibody Sequences from Antigen-Specific B Cells Antibody sequences were recovered using a combined RT-PCR based method from a single isolated B-cell. Primers containing restriction enzymes were designed to anneal in conserved and constant regions of the target immunoglobulin genes (heavy and light), such as rabbit immunoglobulin sequences, and a two-step nested PCR recovery was used to amplify the antibody sequence. Amplicons from each well were analyzed for recovery and size integrity. The resulting fragments are then digested with AluI to fingerprint the sequence clonality. Identical sequences displayed a common fragmentation pattern in their electrophoretic analysis. The original heavy and light chain amplicon fragments were then digested using the restriction enzyme sites contained within the PCR primers and cloned into an expression vector. Vector containing subcloned DNA fragments were amplified and purified. Sequence of the subcloned heavy and light chains were verified prior to expression.

Recombinant Production of Monoclonal Antibody of Desired Antigen Specificity and/or Functional Properties To determine antigen specificity and functional properties of recovered antibodies from specific B-cells, vectors driving the expression of the desired paired heavy and light chain sequences were transfected into HEK-293 cells.

Antigen-Recognition of Recombinant Antibodies by ELISA

To characterize recombinant expressed antibodies for their ability to bind to human-CGRPα, antibody-containing solutions were tested by ELISA. All incubations were done at room temperature. Briefly, Immulon IV plagtes (Thermo Scientific) were coated with a CGRPα containing solution (1 ut/mL in PBS) for 2 hours CGRPα-coated plates were then washed three times in wash buffer (PBS, 0.05% Tween-20). The plates were then blocked using a blocking solution (PBS, 0.5% fish skin gelatin, 0.05% Tween-20) for approximately one hour. The blocking solution was then removed and the plates were then incubated with a dilution series of the antibody being tested for approximately one hour. At the end of this incubation, the plate was washed three times with wash buffer and further incubated with a secondary antibody containing solution (Peroxidase conjugated affinipure F(ab')2 fragment goat anti-human IgG, Fc fragment specific (Jackson Immunoresearch) for approximately 45 minutes and washed three times. At that point a substrate solution (TMB peroxidase substrate, BioFx) and incubated for 3 to 5 minutes in the dark. The reaction was stopped by addition of a HCl containing solution (0.5M) and the plate was read at 450 nm in a plate-reader.

Results: FIGS. 15-18 demonstrate that anti-CGRP antibodies Ab1-Ab14 bind to and recognize CGRPα.

Functional Characterization of Recombinant Antibodies by Modulation of CGRP Driven Intracellular cAMP Levels and Cross Reactivity to Rats To characterize recombinant expressed antibody for their ability to inhibit CGRPα mediated increased cellular levels of cAMP assay, an electrochemiluminescence assay-kit (Meso Scale Discovery, MSD) was used. Briefly, antibody preparations to be tested were serially diluted in MSD assay buffer (Hepes, $MgCl_2$, pH 7.3, 1 mg/mL blocker A, Meso Scale Discovery) in a 96 well round bottom polystyrene plate (Costar). To this plate, human CGRPα was added (25 ng/mL final concentration) diluted in MSD assay buffer and incubated for one hour at 37° C. Appropriate controls were used as suggested by the assay-kit manufacturer. Human neuroepithelioma cells (SK-N-MC, ATCC) were detached using an EDTA solution (5 mM) and washed using growth media (MEM, 10% FBS, antibiotics) by centrifugation. The cell number was adjusted to 2 million cells per mL in assay buffer, and IBMX (3-Isobutyl-1Methylxanthine, 50 mM Sigma) was added to a final concentration of 0.2 mM right before loading cells onto cAMP assay plate. The antibody human CGRPα solution was incubated for one hour after which 20 microliters of solution containing cells were transferred to the cAMP assay plate. All tested samples were run in duplicates with appropriate controls. Ten microliters of cells were added to the wells and the plate was incubated for 30 minutes with shaking. While cells were being incubated with the CGRP solution, the stop solution was prepared by making a 1:200 solution of TAG labeled cAMP (MSD) in lysis buffer (MSD). To stop the cells-CGRP incubation, 20 microliters of stop solution was added to the cells and the plate was incubated for one hour with shaking.

The read buffer (MSD) was diluted four times with water and 100 microliters were added to all wells on the plate. The plate was then read using a Sector Imager 2400 (MSD) and the Prism software was used for data fit and IC50 determination.

To test for the ability of recombinant antibodies to antagonize human CGRPβ a similar assay was performed with the substitution of the CGRP agonist (CGRPβ 10 ng/mL final concentration). Evaluation of the recombinant antibodies to recognize and inhibit rat CGRP-mediated cAMP generation was conducted using rat CGRP (5 ng/mL final concentration) and the rat L6 cell line (ATCC).

Results: FIGS. 19-37 demonstrate that anti-CGRP antibodies Ab1-Ab14 inhibit CGRPα, CGRPβ, and rat CGRP mediated increased cellular levels of cAMP.

Example 2: Enzymatic Production of Fab Fragments

Papain digestions were conducted using immobilized papain (Thermo/Pierce) as per manufacturer's instructions. Briefly, purified antibodies were incubated in a cystein/HCl-containing buffer with immobilized papain at 37° C. with gentle rocking. The digestion was monitored by taking an aliquot and analyzing using SDS-PAGE for cleavage of the heavy chain. To stop the reaction, the immobilized papain was spun out and washed using 50 mM Tris pH 7.5 and filtered. Undigested full length antibody and Fc fragments were removed by using a MabSelectSure (GE) column.

Example 3 Yeast Cell Expression

Construction of *Pichia pastoris* Expression Vectors for Heavy and Light Chain.

The humanized light and heavy chain fragments were commercially synthesized and subcloned into a pGAP expression vector. The pGAP expression vector uses the GAP promoter to drive expression of the immunoglobulin chain and the human serum albumin (HSA) leader sequence for export. In addition, this vector contains common elements such as a bacterial origin of replication, and a copy of the kanamycin resistance gene which confers resistance to the antibiotic G418 in *P. pastoris*. G418 provides a means of selection for strains that contain the desired expression vector integrated into their genome.

Transformation of Expression Vectors into Haploid Met1 and Lys3 Host Strains of *Pichia pastoris*

All methods used for transformation of haploid *P. pastoris* strains and manipulation of the *P. pastoris* sexual cycle were done as described in *Pichia* Protocols (Methods in Molecular Biology Higgings, D R, and Cregg, J M, Eds. 1998. Humana Press, Totowa, N.J.). Prior to transformation each vector was linearized within the GAP promoter sequences to direct the integration of the vector into the GAP promoter locus of the *P. pastoris* genome. Haploid strains were transfected using electroporation and successful transformants were selected on YPDS (yeast extract, peptone dextrose with sorbitol) G418 agar plates. Copy numbers of heavy and light chain genes were determined for haploid strains by Southern blot analysis. Haploid strains were then mated and selected for their ability to grow in the absence of the amino acid markers (i.e., Lys and Met). Resulting diploid clones were then subjected to a final Southern blot to confirm copy numbers of heavy and light chain genes. A clone expressing the antibody of interest was selected using biolayer interferometry Protein-A biosensors to monitor expression (Octet, ForteBio).

Example 4 Expression of Ab3, Ab6 and Ab14 in *Pichia pastoris*

Three *Pichia* strains for expression of full-length antibody were made. For all the full length antibody expressing strains, haploids strains were created and subsequently mated. One haploid strain expressed full-length light chain sequence and another haploid strain expressed the full-length heavy chain sequence. Each diploid strain was used to generate a research cell bank and used for expression in a bioreactor.

First an inoculum was expanded using the research cell bank using medium comprised of the following nutrients (% w/v) yeast extract 3%, anhydrous dextrose 4%, YNB 1.34%, Biotin 0.004% and 100 mM potassium phosphate. To generate the inoculum for the fermenters, the cell bank was expanded for approximately 24 hours in a shaking incubator at 30° C. and 300 rpm. A 10% inoculum was then added to Labfors 2.5 L working volume vessels containing 1 L sterile growth medium. The growth medium was comprised of the following nutrients: potassium sulfate 18.2 g/L, ammonium phosphate monobasic 36.4 g/L, potassium phosphate dibasic 12.8 g/L, magnesium sulfate heptahydrate 3.72 g/L, sodium citrate dihydrate 10 g/L, glycerol 40 g/L, yeast extract 30 g/L, PTM1 trace metals 4.35 mL/L, and antifoam 204 1.67 mL/L. The PTM1 trace metal solution was comprised of the following components: cupric sulfate pentahydrate 6 g/L, sodium iodide 0.08 g/L, manganese sulfate hydrate 3 g/L, sodium molybdate dihyrate 0.2 g/L, boric acid 0.02 g/L, cobalt chloride 0.5 g/L, zinc chloride 20 g/L, ferrous sulfate heptahydrate 65 g/L, biotin 0.2 g/L, and sulfuric acid 5 mL/L.

The bioreactor process control parameters were set as follows: Agitation 1000 rpm, airflow 1.35 standard liter per minute, temperature 28° C. and pH was controlled at six using ammonium hydroxide. No oxygen supplementation was provided.

Fermentation cultures were grown for approximately 12 to 16 hours until the initial glycerol was consumed as denoted by a dissolved oxygen spike. The cultures were starved for approximately three hours after the dissolved oxygen spike. After this starvation period, a bolus addition of ethanol was added to the reactor to reach 1% ethanol (w/v). The fermentation cultures were allowed to equilibrate for 15 to 30 minutes. Feed addition was initiated 30 minutes post-ethanol bolus and set at a constant rate of 1 mL/min for 40 minutes, then the feed pump was controlled by an ethanol sensor keeping the concentration of ethanol at 1% for the remainder of the run using an ethanol sensing probe (Raven Biotech). The feed was comprised of the following components: yeast extract 50 g/L, dextrose 500 g/L, magnesium sulfate heptahydrate 3 g/L, and PTM1 trace metals 12 mL/L. For fermentation of the full length Ab6 and Ab14, sodium citrate dihydrate (0.5 g/L) was also added to the feed. The total fermentation time was approximately 90 hours.

Example 5 Methods of Humanizing Antibodies

Methods of humanizing antibodies have been described previously in issued U.S. Pat. No. 7,935,340, the disclosure of which is incorporated herein by reference in its entirety. In some instances, a determination of whether additional rabbit framework residues are required to maintain activity is necessary. In some instances the humanized antibodies still requires some critical rabbit framework residues to be retained to minimize loss of affinity or activity. In these cases, it is necessary to change single or multiple framework amino acids from human germline sequences back to the original rabbit amino acids in order to have desired activity. These changes are determined experimentally to identify which rabbit residues are necessary to preserve affinity and activity. This is now the end of the variable heavy and light chain humanized amino acid sequence.

Example 6 Inhibition of CGRP Binding to its Cellular Receptor

To characterize recombinantly expressed antibodies for their ability to inhibit CGRP binding to its cellular receptor, a radioligand-binding assay was performed as previously described [Elshourbagy et al, Endocrinology 139:1678 (1998); Zimmerman et al, Peptides, 16:421 (1995)]. Membrane preparations of recombinant human CGRP receptors, calcitonin receptor-like receptor and RAMP (Chemiscreen, Millipore) were used. Antibody dilutions were preincubated with $^{125}$I radiolabeled human CGRPα (0.03 nM) for 30 minutes at room temperature. Non-specific binding was estimated in the presence of 0.1 M human CGRPα. Membranes were filtered and washed. The filters were then counted to determine $^{125}$I radiolabeled human CGRPα specifically bound.

Results: FIG. 38 demonstrates that anti-CGRP antibodies Ab1-Ab13 inhibit CGRP binding to its cellular receptor.

Example 7 Inhibition of Neurogenic Vasodilation by Anti-CGRP Antibodies in Rats

CGRP is a potent vasodilator (Nature 313: 54-56 (1985) and Br J. Clin. Pharmacol. 26(6):691-5 (1988)) A pharmacodynamic assay to measure CGRP receptor antagonist activity non-invasively was used to characterize anti-CGRP antibodies. The model relied on changes in dermal blood flow measured using a laser Doppler imaging following the topical application of a capsaicin solution. Capsaicin activates the transient receptor potential vanilloid type 1 receptor (TRPV-1), producing neurogenic inflammation and vasodilatation via the local release of vasoactive mediators including CGRP and substance P (Br. J. Pharmacol. 110: 772-776 (1993)).

On the day prior to the vasodilatation assay, animals were dosed with the test agent or control via IP (intraperitoneal). Following dosing, the animals were shaved and depilated in the lower back region of their dorsal side, in an area approximately 2×6 cm. The animals were then returned to their cages overnight. On the day of test, approximately 24 hours post dosing, animals were anesthetized with isoflurane gas and placed on a temperature controlled heating pad and fitted with a nose cone for continuous delivery of isoflurane. A laser Doppler imager was used for the observation of vasodilatation. A beam of coherent red light generated by a 633 nm helium-neon laser was directed to the shaved area, a rectangle (2×6 cm), and scanned at a medium resolution mode. A baseline Doppler scan was obtained first and the location of O-ring placement predetermined by identifying two similar low flux areas. Two rubber O-rings (~1 cm in diameter) were placed in the selected regions and a baseline scan was performed. Immediately after completion of the scan, 1 mg of capsaicin in 5 μL of an ethanol:acetone solution (1:1) was applied within each of the two O-rings Doppler scans were repeated at 2.5, 5, 7.5, 10, 12.5, 15, 17.5, 20, 22.5, 25, 27.5 and 30 minutes after the application of capsaicin. Percent change from baseline mean. Flux within each of the two O-rings, was plotted as the results of vasodilatation due to capsaicin.

In order to test recombinantly expressed antibodies for their ability to inhibit CGRP binding to its cellular receptor, a radioligand-binding assay was performed as previously described.

Figure 39:
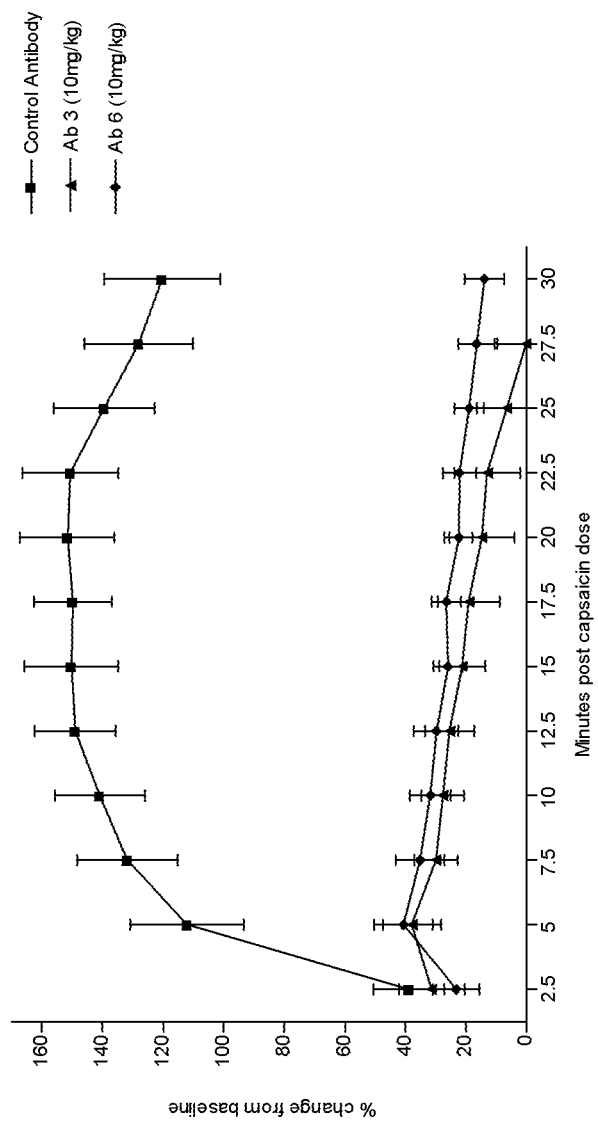
FIG. 39 demonstrates a reduction in vasodilation obtained by administering antibodies Ab3 and Ab6 following capsaicin administration in a rat model, relative to a control antibody, obtained following the protocol in Example 7 infra.
Figure 40:
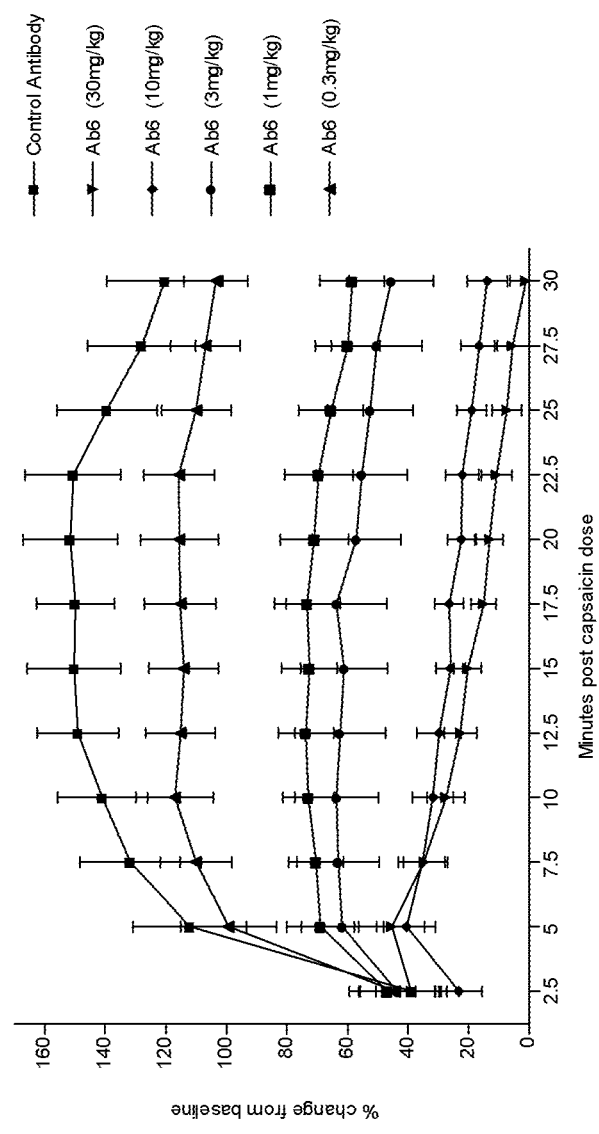
FIG. 40 demonstrates a reduction in vasodilation obtained by administering antibody Ab6 at differing concentrations following capsaicin administration in a rat model, relative to a control antibody, obtained following the protocol in Example 7 infra.

Results: FIGS. 39 and 40 demonstrates that anti-CGRP antibodies Ab3 and Ab6 reduced vasodilation in this model following capsaicin administration.

Example 8 Effect of CGRP Antibody Administration on Overactive Bladder

Experiments were conducted to assess the potential efficacy of an anti-CGRP antibody administration on bladder continence and overactive bladder. Bladder continence is a balance between urethral closure and detrusor muscle activity, and overactive bladder is a condition characterized by urgency, urinary incontinence, frequency and nocturia. Some anecdotal evidence reported in the literature suggests that CGRP may be involved with bladder continence and may correlate to and perhaps play a causal role in overactive bladder disease pathology. Accordingly, it was hoped that the inventive anti-CGRP antibodies, especially given their high affinity to CGRP, would potentially help prevent or alleviate this sometimes debilitating condition. (The evidence that that CGRP may play a role in overactive bladder includes the fact that CGRP is present in the urinary tract, DRG and spinal cord (Wharton et al., 1986 Neurosci (3): 727) Also, C-fiber afferents are critical for carrying impulses involved in micturition to spinal cord (Yoshida et al., 2011 J Pharmacol Sci (112):128) and these fibers are affected by CGRP. Further, it has been reported that intravesical administration of Botox suppresses CGRP and significantly reduces intercontraction interval in an acetic acid induced bladder pain model (Chuang et al., 2004 J Urol (172):1529; Chuang et al., 2009 J Urol (182):786)). Moreover, it has been recently reported that the administration of an anti-CGRP antibody purportedly reduces the number of bladder contractions in turpentine-oil-induced overactive bladder model (Pfizer PCT Patent Application WO 2011/024113)).

Materials and Methods

Animals:

Female Sprague-Dawley rats (247-299 g) (Charles River Laboratories, Saint Germain sur l'Arbresle, France) were delivered to the laboratory at least 5 days before the experiments in order to be acclimatized to laboratory conditions. They were housed 3 per cage (polypropylene type E cages size 1032 cm$^2$) and given food (Teklad 2016 global rodents, Harlan, 03800 Gannat, France) and water ad libitum. Sawdust (Souralit 2912 plus, Souralit, 17080 Girona, Spain) bedding for rodent cages was changed twice weekly. The animal room temperature (20=2° C.) was maintained with a 12/12 hour alternating light-dark cycle (light phase 7 am:7 pm) and relative humidity maintained at 40-70%.

Laboratory Equipment

Bladder catheters were connected via a T-tube to a strain gauge MX 860 Novatrans III Gold (Medex Medical SARL, Nantes-Carquerou, France) and a syringe pump (70-2208 Model II plus, Harvard Apparatus, Les Ullis, France and Razel R-99E, Fisher Bioblock, Illkirch, France). Intravesical pressure was recorded continuously using a PowerLab interface (ADInstruments Pty Ltd, Castle-Hill, Australia) and Chart® software running on a PC. Data were analyzed with Microsoft Excel® software.

Test Substances

Test Anti-CGRP antibody (Ab3)

Negative control antibody (Anti-digitoxin antibody).

Chemical Reagents

Physiological saline (NaCl 0.9%) (batch no 11043411, CAS no 7647-14-5) was purchased from B-Braun via Centravet (Lapalisse, France).

Anesthetic Substances

Urethane (batch no BCBC9294, CAS no 51-79-6) and sodium pentobarbital (batch no 150A1, CAS no 76-74-4) were supplied by Sigma-Aldrich (St Quentin Fallavier, France) and Centravet (Lapalisse, France), respectively.

Experimental Groups

Two experimental groups of 10 rats were used in the experiments. Each group was administered 10 mg/kg of either the control or the anti-CGRP antibody:

Study Design

Experimental Procedure

Female rats were administered test antibody or negative control antibody intravenously at a dose of 10 mg/kg, 18 hours prior to experiments using a tail vein injection. Fifteen (15) hours later, rats were anesthetized with urethane (1.2 g/kg, subcutaneous (s.c.). Three (3) hours after the s.c. administration of urethane, a polyethylene catheter (0.58 and 0.96 mm of internal and outer diameters, respectively) was inserted into the bladder through the dome and secured with a purse-string suture. Body temperature was maintained at 37=2° C. (TCAT-2LV controller, Physitemp, ADInstruments Pty Ltd., Casttle Hill, Australia) throughout the experiment.

Cystometric Experiment

Cystometric investigations were performed in anesthetized female rats after surgery. Physiological saline at room temperature was continuously infused into the bladder at a constant flow rate (2 mL/h) for a period of at least 30 min.

At the end of the cystometric experiments, animals were sacrificed by a lethal injection (1 mL) of sodium pentobarbital (54.7 mg/mL) (CAS no 76-74-4) followed by cervical dislocation.

Cystometric Parameters

The cystometric parameters measured were:

Amplitude of micturition (AM), i.e. pressure between threshold pressure and Maximal pressure of micturition (mmHg), Intercontraction interval (ICI), i.e. time between two subsequent micturitions (sec), Micturition frequency (MF), i.e. number of micturition contractions/15 min (peaks/15 min).

Exclusion Criteria

Two rats were excluded during the experiments: One was excluded as it presented with bladder hyperactivity during the saline intravesical infusion, and the other because the depth of anesthesia changed during the experiment inducing modifications of the cystometric profile.

Analysis of Results

For each rat, values for AM and ICI were calculated as the mean of the last four or live micturitions during saline infusion. Values for MF were calculated as the mean of micturitions obtained for two intervals of 15 minutes during saline infusion.

Results are presented as mean values±standard error of the mean (=scm). Figures and statistical analyses were performed using GraphPad Prism® (Version 4; GraphPad Software Inc., La Jolla, Calif., USA).

Statistical comparisons of values (saline infusion) in the anti-CGRP antibody group versus the control antibody group were performed using unpaired Student t-test.

A $p<0.05$ was accepted for statistical significance.

Figure 41:
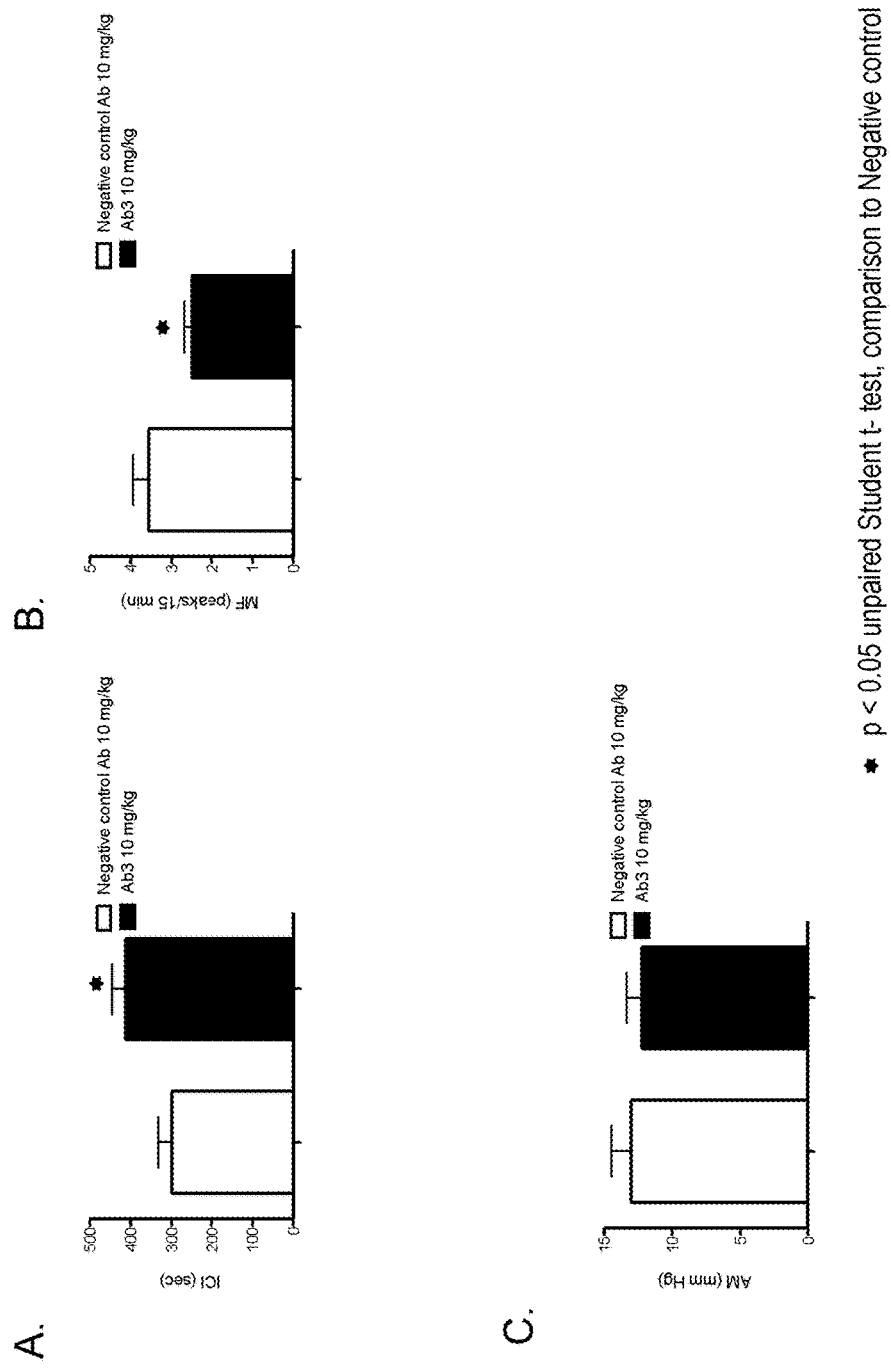
FIG. 41A-C shows the beneficial effect of Ab3 on bladder capacity during saline infusion. Animals were administered Ab3 or a negative control antibody, then monitored during infusion of saline into the bladder. ICI (panel A) was increased and MF (panel B) was decreased, indicating increased bladder capacity. Differences in AM (panel C) were within the standard deviation and not statistically significant. Asterisks indicate statistically significant improvement ($p<0.05$ unpaired Student's t-test, comparison to Negative control Ab). Legend: filled bars: Ab3 treated (10 mg/kg); open bars: negative control antibody (10 mg/kg). Error bars indicate the standard deviation. Abbreviations: ICI: Intercontraction Interval; MF: Micturition Frequency; AM: Amplitude of Micturition.

Results:

As shown in FIG. 41, ICI was significantly greater and MF was significantly lower in the anti-CGRP Ab-treated group (FIGS. 41A and B respectively, $p<0.05$, unpaired Student t-test). No significant difference was observed for AM between groups (FIG. 41C, $p>0.05$, unpaired Student t-test).

These results suggest that anti-CGRP antibodies may be useful in preventing or alleviating overactive bladder, improving urinary continency and treatment of related urinary conditions.

Example 9 Relief of Neuropathic Pain in Rats

Damage to the peripheral nerves often leads to chronic referred pain that is neuropathic in origin. This pain syndrome consists of sensitivity to external stimuli (e.g., mechanical and/or thermal) that are not normally noxious. Consequently, neuropathic pain is refractory to traditional analgesic approaches, making it difficult to treat. Experimentally, neuropathic pain can be modeled in animals via surgical trauma to peripheral nerves. The Chung model is one such system where neuropathic pain is induced by ligation of the spinal nerves of L5 and L6.

In this Example, a spinal nerve ligation was performed on male Sprague Dawley rats. They were tested for pain sensitivity on Day 13 (allodynia confirmation) and then again after each administration of Ab2 using the von Frey test of mechanical allodynia to assess possible anti-allodynic activity.

Methods

Male Sprague Dawley rats (Harlan Laboratories) weighing 200-225 g at arrival, were unpacked and placed in cages. A visual health inspection was performed on each animal to include evaluation of the coat, extremities and orifices. Each animal was also examined for any abnormal signs in posture or movement. All animals were found to be in good health and were placed on study.

The rats were acclimated for a minimum of two days prior to the commencement of the experimental procedures, with the exception of randomization body weights which were collected the day following arrival. The animals were housed individually in clear polycarbonate conventional cages or clear polycarbonate microisolator cages with certified irradiated contact bedding. Food and water were provided ad libitum. Environmental controls were set to maintain temperatures of 18° to 26° C. (64° to 79° F.) with a relative humidity of 30% to 70%. A 12:12 hour light dark cycle was maintained.

Rats were tested for baseline threshold using the von Frey filaments on Days −4 or −1 of acclimation.

On Day 0, animals underwent a spinal nerve ligation procedure. All surgeries were performed under aseptic conditions. Prior to surgeries, the rats were anesthetized. The back region was shaved and prepared for aseptic surgery. The rats were placed in ventral recumbence and an incision was made just left of midline at the L4-S2 region. The left paraspinal muscles were separated from the spinous processes (L4-S2). The L6-S1 facet joint were nipped and the transverse process gently trimmed to provide space to access the L4 & L5 spinal nerve. The left L5 and L6 spinal nerves were isolated and ligated with 6.0 silk sutures. The incision was then closed with appropriate suture material and skin wound clips. Post-operatively, Lactated Ringer's Solution (3.0 5.0 mL) was administered via subcutaneous injection to the animals.

All animals in Groups 1 and 2 received a von Frey test on Days −4 or −1, 13, 14, and 17. The measurement on Day 13 was taken pre-dose. The von Frey test for mechanical allodynia assesses anti-nociceptive properties of analgesic compounds. In this test, animals were first habituated to the testing chamber so they were calm enough for their pain threshold to be assessed. A technician blind to the treatment groups applied light pressure to the left hind paw of the rat using a series of graded nylon filaments (von Frey filaments) of increasing diameter. The filaments were pressed perpendicularly against the ventral surface of the paw until they bent. When considered painful, the rat responds by withdrawing its paw. Threshold allodynia was determined using the Chaplan up-down method (Chaplan et al., J Neurosci Methods, 53:55-63, 1994), which provides the precise force for withdrawal for each rat using a psychophysical scale of testing.

Animals were allocated into two treatment groups on Day 13, based on von Frey scores. Any animal that had a von Frey score greater than 6 g was excluded from the study. The mean von Frey scores for each group were reviewed to ensure that the mean values and standard deviation satisfied the assumption of homogeneity. Doses were administered by IP injection once on Day 13 (13 days after surgery) for Group 1 (Ab2) and Group 2 (negative control antibody) (11 animals in each group, Ab2 and negative control antibodies were administered at 10 mg/kg). Group 1 received an additional IV bolus (un-anesthetized) injection of Ab2 on Day 17 prior to behavioral testing.

Blood samples for plasma were taken on Day 17 for Group 1 and analyzed for Ab2 titer.

Outside of the expected surgical site observations and paw dragging associated with the Chung surgery, no abnormal observations were documented. Treatment appeared to have no adverse effect on overall animal health nor did it disrupt the normal weight gain expected in rats this age.

Results

Figure 42:
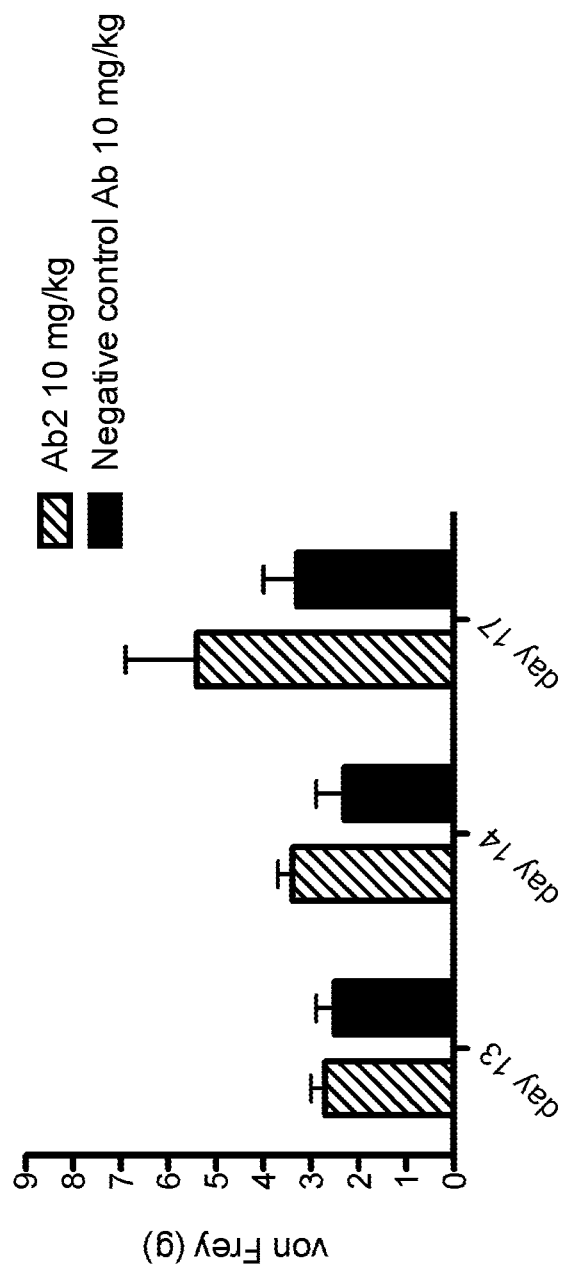
FIG. 42 shows the effect Ab2 in a model of neuropathic pain. Mechanical allodynia was induced by Chung surgery (1.5/1.6 spinal nerve ligation), and degree of sensitivity was compared between Ab2 treated animals (hashed bars) and control animals (filled bars). Higher values indicate less sensitivity. Average sensitivity was similar at day 13 (prior to Ab2 administration) but improved at days 14 and 17. Error bars indicate the standard error of the mean.

All animals that underwent baseline testing prior to surgery on Day 0 had a von Frey score of 15 (not shown) indicating normal sensitivity. On Day 13 (prior to antibody administration), all animals had von Frey scores lower than 6 g, indicating that sensitivity to external mechanical stimuli had developed, except for two animals which were removed from the study. Average von Frey scores at day 13 were less than 3 g (FIG. 42, left group of bars). Following testing on day 13, animals were administered Ab2 or a negative control antibody (10 mg/kg). On days 14 and 17, von Frey scores were again tested and were higher in the Ab2-treated animals than controls (FIG. 42, middle group of bars and right group of bars, respectively).

These results indicate that treatment with an anti-CGRP antibody such as Ab2 may help prevent or alleviate neuropathic pain.

Example 10 First Experiment Assessing Effect of Anti-CGRP Antibody Administration on Analgesia (Tail Flick Model)

Three different experiments (Examples 10-12) were conducted to assess the potential efficacy of an anti-CGRP antibody administration on analgesia or pain. In all of these experiments a rodent tail lick (also referred to as tail withdrawal) response model was used as the rodent tail lick response to radiant heat is a commonly used model to detect potentially useful analgesic agents. This assay is particularly useful to discriminate between centrally acting morphine-like analgesics (active) and non-opioid or peripherally acting anti-inflammatory agents (inactive). This animal model and methods and materials used therein are described below.

Materials and Methods

Animals:

Male Sprague Dawley derived male rats weighing 150-20 g.

Test CGRP Antibody:

Ab2

Vehicle:

15 mM Histidine 250 mM Sorbitol, pH 5.5

Analgesic Compound:

Morphine

Tail Flick Response Procedures:

The time (seconds) required to elicit a tail flick response induced by focused radiant heat was measured as the pain threshold in groups of 10 Sprague Dawley derived male rats weighing 150±20 g. Baseline testing for the tail flick response was done on Day 0. The rats that have a tail flick response of 3-5 seconds were included in the study and assigned to balanced treatment groups based on baseline tail flick responses. A 15 second cut was used to avoid tissue damage.

Development of Morphine Tolerance

Each of 3 groups of 10 Male Sprague Dawley rats were dosed 2× daily via i.p. administration with saline vehicle (2 ml/kg) in the morning and evening. One of the 3 groups was in addition administered i.p. analgesic (morphine) at a dosage of 5 mg/kg 2× daily for 7 consecutive days. A second of the 3 groups of rats was administered i.p. an anti-CGRP antibody according to the invention (Ab2) at a dosage of 10 mg/kg as a single bolus on day 0. The rats in the different groups were then each tested for tail flick response once per day 30 min after the morning dose.

A one-way ANOVA followed by Dunnett's t-test is applied for comparison between the vehicle control and test-compound treated groups P<0.05 is considered significant.

Figure 43:
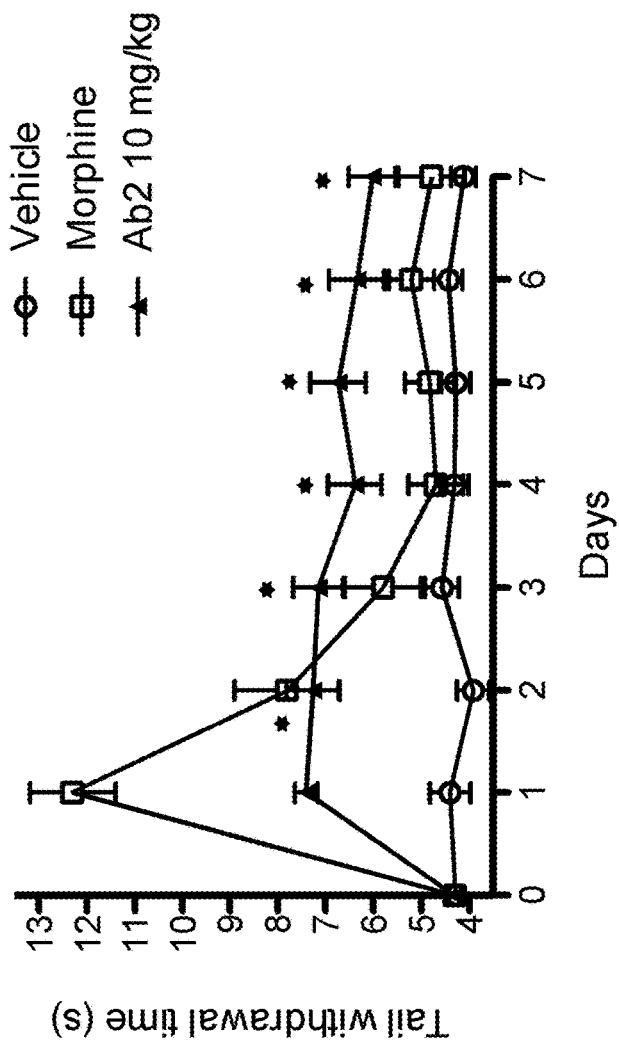
FIG. 43 shows the analgesic effect of Ab2 and morphine. Pain sensitivity was assessed by the tail withdrawal time (y-axis, seconds) for animals administered morphine (open squares), Ab2 (10 mg/kg, filled triangles), or vehicle (negative control, open circles). Animals developed morphine tolerance and exhibited tail withdrawal times similar to control animals by day 4. In contrast, Ab2-treated animals exhibited a sustained improvement in tail withdrawal time over the course of the experiment (to day 7). The improvement in Ab2-treated animals was statistically significant ($p<0.05$ one-way ANOVA followed by Dunnett's test comparison to vehicle, indicated by asterisks). Error bars indicate the standard error of the mean.

The results of these experiments are shown in FIG. 43. The results therein indicate that the test CGRP antibody when administered at 10 mg/kg elicited significant long-lasting analgesic effect to a thermal pain stimulus. Terminal blood samples were taken from all the tested rats via cardiac puncture and later analyzed for Ab2 titer.

Example 11: Second Tail Flick Experiment Assessing Effect of-CGRP Antibody on Analgesia) (Antibody Dose Titration)

A second set of tail flick experiments were conducted to assess the effects of different anti-CGRP antibody dosages on analgesia using an anti-CGRP antibody according to the invention (Ab2). The rats used in these experiments are the same type as in the previous experiment and the tail flick protocol substantially the same. In this experiment analgesia was compared in different groups of animals administered different anti-CGRP antibody dosages in order to assess whether the dosage has an effect on analgesia. In the second set of experiments, five groups of test animals were compared as follows. A first control group of animals were each administered the vehicle alone (15 mM Histidine 250 mM Sorbitol, pH 5.5), 3 groups of animals were each administered different dosages of the same anti-CGRP antibody contained in the vehicle (Ab2, respectively administered at dosages of 1 mg/kg, 3 mg/kg or 10 mg/kg on Day 0), and a fifth group of animals was administered 10 mg/kg of a negative control antibody (anti-digitoxin antibody) also on Day 0.

The tail flick protocols were otherwise substantially effected as above-described. The results were again assessed using one-way ANOVA followed by Dunnett's t-test for comparison between the vehicle control, negative control antibody and test-CGRP antibody treated groups. P<0.05 is considered significant.

Figure 44B:
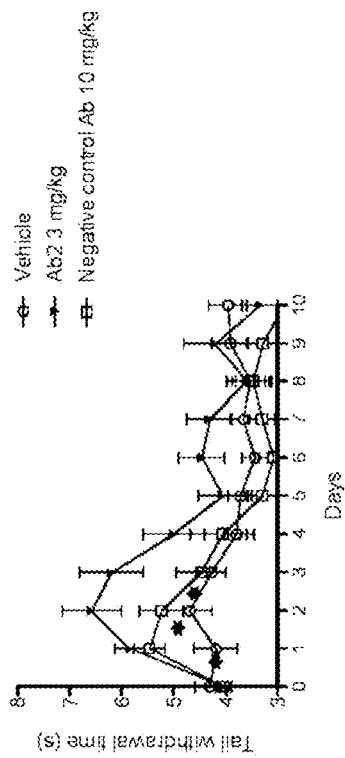
FIG. 44A-C shows the dosage-dependent analgesic effect of Ab2. On day 0 (subsequent to the first tail withdrawal time test), rats were administered antibody Ab2 at a dosage of 1 mg/kg (filled squares), 3 mg/kg (filled downward-pointing triangles), or 10 mg/kg (filled upward-pointing triangles), or a vehicle (open circles) or negative control antibody (open squares). The rats' tail withdrawal time in response to a painful thermal stimulus was assessed daily (higher times indicate relative insensitivity to pain). Tail withdrawal time was increased in a dosage-dependent manner by the administration of Ab2. Asterisks indicate statistically significant increases in tail withdrawal time ($p<0.05$ one-way ANOVA followed by Dunnett's test, comparison to vehicle). Error bars indicate the standard error of the mean.
Figure 44A:
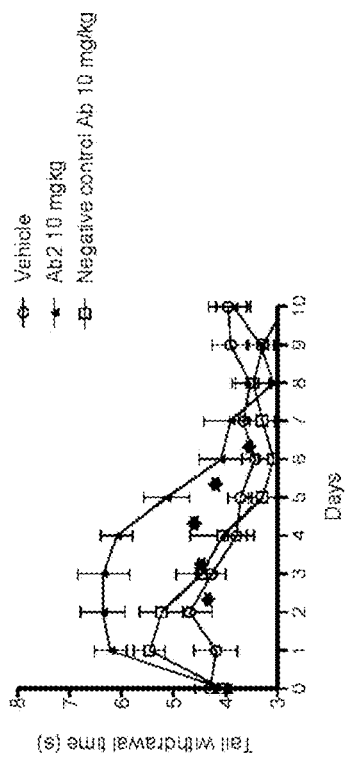
Figure 44C:
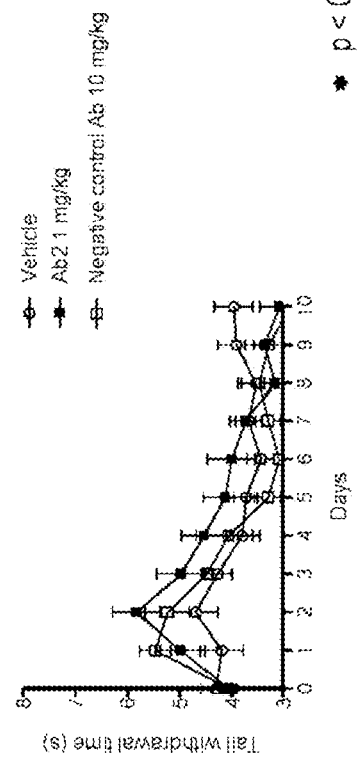

The results of these experiments are shown in FIG. 44. It can be seen therefrom that the higher antibody dosages of the test compound (inventive Ab2 anti-CGRP antibody) elicited better analgesic effects than the lower dosages. As anticipated the negative control antibody did not elicit a perceptible effect on analgesia relative to the control groups.

Example 12: Third Tail Flick Experiment Assessing Effect of Anti-CGRP Antibody/Morphine Co-Administration on Analgesia A third set of tail flick experiments were also conducted to assess the effects of anti-CGRP antibody/morphine co-administration on analgesia. In these experiments a first group of animals was administered the same vehicle alone at a dosage of 5 ml/kg. A second group of animals was administered morphine on days 1-10 at a dosage of 5 mg/kg, administered twice daily, wherein such animals were on Day 0 were also administered the anti-CGRP antibody Ab2 at a dosage of 10 mg/kg. A third group of animals was administered morphine on only days 1-4 again at a dosage concentration of 5 mg/kg, administered twice daily, and were further administered the Ab2 antibody on Day 0, at a dosage of 10 mg/kg. All administrations were i.p.

Tail flick experiments were effected in each of these groups of animals daily from Day 0-10. The results of these tail flick experiments were again assessed using one-way ANOVA followed by Dunnett's t-test for comparison between the vehicle control, negative control antibody and the test anti-CGRP antibody treated group. P<0.05 is considered significant.

Figure 45:
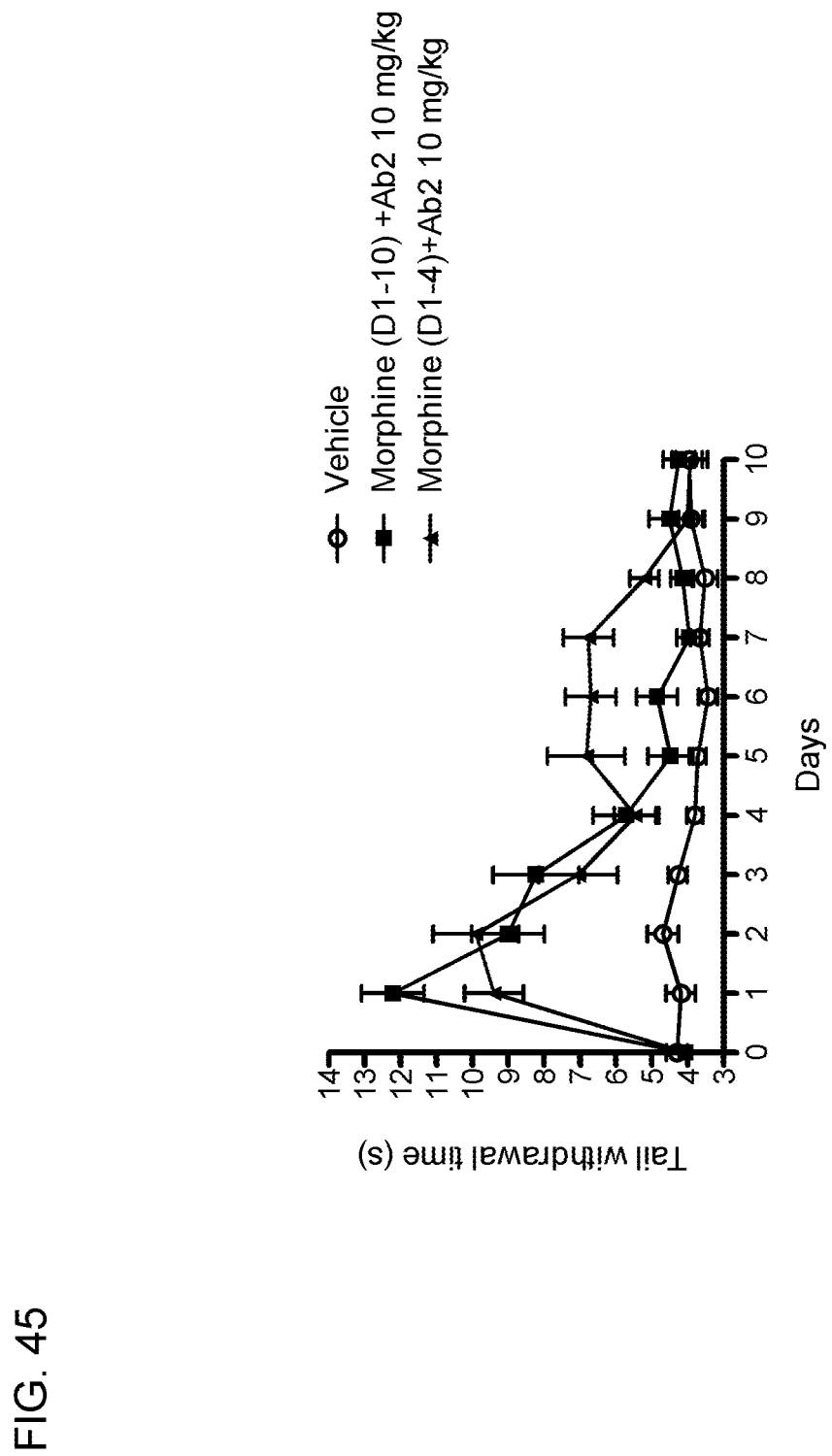
FIG. 45 shows the analgesic effect of Ab2 in combination with morphine, and when morphine is withdrawn after the onset of morphine tolerance. On day 0 (subsequent to the first tail withdrawal time test), rats were administered antibody Ab2 at a dosage of 10 mg/kg (filled squares and filled triangles) or vehicle (open circles). The rats were then daily administered morphine on days 1 to 10 (filled squares) or only on days 1 to 4 (filled triangles). The tail withdrawal time initially was greatly increased in the morphine-treated mice, but decreased on subsequent days indicating morphine tolerance. However, in the mice from which morphine was withdrawn after day 4, tail withdrawal time increased and remained elevated between days 5 and 8. Error bars indicate the standard error of the mean.

The results of these comparisons are summarized in FIG. 45. The Ab2-treated animals receiving a daily dose of morphine throughout the experiment exhibited morphine tolerance, and after day 5 the tail flick time had decreased almost to the level of vehicle-treated control animals. In contrast, in Ab2-treated animals receiving morphine only until day 4, the tail lick time improved on day 5 and remained improved until day 8. The results suggest that the administration of an anti-CGRP antibody may have analgesic effects even after onset of morphine tolerance, which may be more pronounced upon withdrawal of morphine.

Example 13 Relief of Visceral Pain in Rats

Patients suffering from irritable bowel syndrome (IBS) demonstrate a lower visceral sensory threshold to colorectal balloon distension (Ritchie, Gut, 1973, 14:125-32). It has been suggested in IBS that there is heightened pain sensitivity of the brain-gut axis, with a normal pattern of activation. It has previously been shown that injection of trinitrobenzene sulfonic acid (TNBS) into the proximal colon provoked chronic colonic hypersensitivity, measured in conscious rats by a decreased pain threshold in response to colonic distension (Diop et al., J. Pharmacol. Exp. Ther., 2002, 302:1013-22). This chronic hypersensitivity was found in the distal non-inflamed colon and persisted for 21 days. It mimicked certain characteristics of IBS and so it can be used as a model to experimentally explore the pathophysiological aspects of this disorder. This assay is used to determine the potential antihypersensitive effects of compounds for TNBS-induced colonic hypersensitivity.

Several studies have implicated CGRP in visceral pain (Friese et al., Regul Pept 1997; 70:1 7; Gschossmann et al., Neurogastroenterol Motil 2001; 13:229 36; Julia and Bueno, Am J Physiol 1997; 272:G141 6; Plourde et al., Am J Physiol 1997; 273:G191 6). CGRP is the most abundant peptide of capsaicin sensitive afferent fibers or gastrointestinal origin, accounting for up to 80% of overall peptide immunoreactivity (Clague et al., Neurosci Lett 1985; 56:63-8; Sternini et al., Gastroenterology 1987; 93:852-62). Additionally, injection of CGRP induces colonic hypersensitivity in a TNBS model (Delafoy et al., 2006, Gut 55:940-5), which is reversed by a CGRP antagonist peptide (CGRP 8-37).

This example describes testing of an anti-CGRP antibody in a model of visceral pain (TNBS-induced chronic colonic hypersensitivity) in rats.

Methods

Male Sprague-Dawley rats, weighing 390 to 450 g the day of surgery were included in this study. They were housed in a temperature (19.5° C.-24.5° C.) and relative humidity (45%-65%) controlled room with a 12 h-light/dark cycle. Animals were housed 2 or 3 per cage and an acclimation period (at least 5 days) was observed before testing. Each rat was identified by tail markings. The study was performed according to the guidelines or the Committee for Research and Ethical Issue or the I.A.S.P. (1983) and the European guidelines 2010/63/UE.

Colonic sensitivity was induced by surgical administration of Trinitrobenzene sulfonic acid (TNBS, 50 mg/kg) 7 days before behavioral testing. Fasted (24 hours) animals underwent surgery. Briefly, under anesthesia (Acepromazine 5 mg/kg/Ketamine 30 mg/kg), injection of TNBS (50 mg/kg, 1 ml/kg) was performed into the proximal part of the colon (1 cm from the caccum). After surgery, animals were returned to their cages in a regulated environment, and fed ad libitum until the testing day, 7 days later. "Naïve" animals (rats without surgery) were placed in the same housing conditions.

Animals were administered the anti-CGRP antibody Ab2 or a negative control antibody (both at 10 mg/kg) intravenously 24 hours prior to determination of colonic threshold. Three groups of rats were included in this study:

Group 1: A "Naïve" group composed of animals that did not undergo surgery or TNBS treatment on D-7 and were treated with the control antibody 24 hrs prior (i.e. D-1) to testing (i.e. measurements of the colonic distention threshold on D0) (n=7).

Group 2: A "TNBS" group composed of animals that underwent surgery on D-7 and were treated with control antibody (24 hrs prior (i.e. D-1) to testing (i.e. measurements or the colonic distention threshold on D0) (n 8).

Group 3: A "Treated" group composed of animals that underwent surgery on D-7 and were treated with Ab2 24 hrs prior (i.e. D-1) to testing day (i.e. measurements of the colonic distention threshold on D0) (n=8).

Seven days (D7) after TNBS injection, colonic sensitivity was assessed by measuring the intra-colonic pressure required to induce a behavioral response during colonic distension due to the inflation of a balloon introduced in the colon. The tests were conducted by a blinded experimenter. This response is characterized by an elevation of the hind part or the animal body and a clearly visible abdominal contraction corresponding to severe contractions (Al Chaer et al., Gastroenterology 2000, 119:1276-1285) and used as a pain marker (Bourdu et al., Gastroenterology. 2005:128, 1996-2008). The balloon (5 cm) was inserted intrarectally in a minimally invasive manner to 10 cm from the anus of fasted (24 h) vigil animals, and the catheter was taped to the base of the tail. Rats were then placed in the middle of a plexiglass box and the catheter was connected to an electronic barostat apparatus. After a 30 min-acclimation period with the inserted balloon, colonic pressure was gradually increased by 5 mmHg steps every 30 sec from 5 to 75 mmHg (cut off) until pain behavior is evidenced. Four determinations were performed, 30 min. 50 min. 70 min and 90 min after balloon insertion.

Using the data from each test, the percentage of activity on colonic hypersensitivity induced by the intracolonic administration of TNBS was calculated as follows $$(\text{Activity percentage})_{Treated}$$
$$\frac{Distentionthreshold_{Treated} - Distentionthreshold_{TNBS}}{Distentionthreshold_{Naive} - Distentionthreshold_{TNBS}} \times 100$$

Distention threshold$_{Treated}$ is the arithmetic mean of the values for the "Treated" group; Distention threshold$_{TNBS}$ is the arithmetic mean of the values for the "TNBS" group; and Distention threshold$_{Naive}$ is the arithmetic mean of the values for the "Naïve" group.

Results

Figure 46:
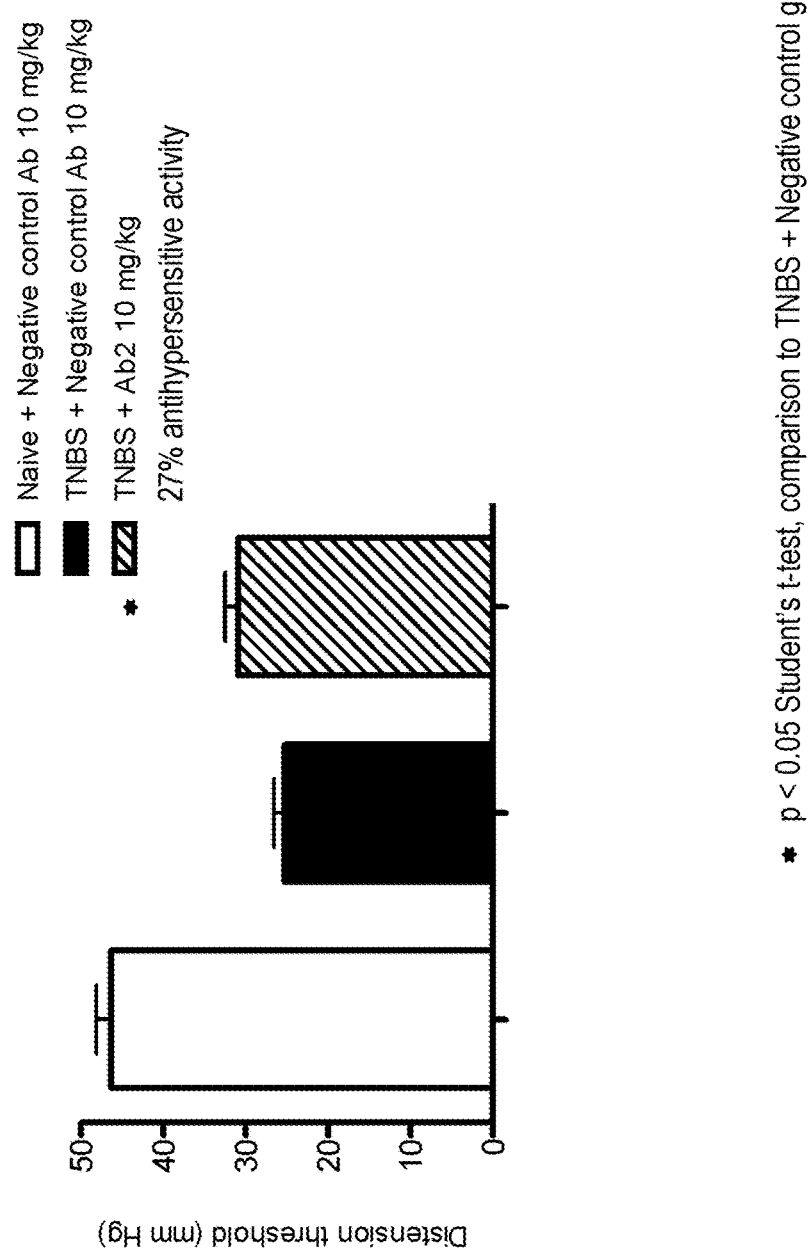
FIG. 46 shows the effect of Ab2 in a rat model of visceral pain. Visceral pain was quantified by measuring the colonic distension threshold (higher values indicate less sensitivity) for nave animals (open bar) or animals treated with TNBS to provoke chronic colonic hypersensitivity which either received a negative control antibody (filled bars) or Ab2 (hashed bars). Hypersensitivity was alleviated by 27% by the Ab2-treated animals, and distension threshold was significantly improved by administration of Ab2 ($p<0.05$ Student's t-test, comparison to TNBS+Negative control group). Error bars indicate the standard error of the mean.

The ability of an anti-CGRP antibody to alleviate visceral pain was tested in a rat model in which chronic colonic hypersensitivity was induced by administration of TNBS. Visceral pain was quantified by measuring the colonic distension threshold, i.e., the amount of abdominal pressure that the animals could tolerate before exhibiting a behavioral response (muscle contraction). Higher colonic distension threshold values indicate less sensitivity. As expected, TNBS treatment resulted in greatly decreased the colonic distension threshold compared to naïve animals (FIG. 46, compare middle bar (TNBS treated) and left bar (naïve)) Ab2 administration improved the colonic distension threshold compared to control animals (FIG. 46, compare right bar (Ab2 treated) and middle bar (control)). The improvement from Ab2 administration was statistically significant (p<0.05 Student's t-test, comparison to TNBS | Negative control group). The antihypersensitive activity of Ab2 was computed to be 27% (indicative of the degree of relief of the TNBS-induced hypersensitivity).

These results suggest that anti-CGRP antibodies may be useful in preventing or alleviating visceral pain.

---

What is claimed is:

1. A method of treatment comprising administering to a patient with a disease or condition associated with elevated CGRP a therapeutically effective amount of at least one anti-human CGRP antibody or fragment comprising a variable light chain comprising the complementarity-determining regions (CDRs, or hypervariable regions) of SEQ ID NO: 55; SEQ ID NO: 56; and SEQ ID NO: 57, and comprising a variable heavy chain comprising the complementarity-determining regions (CDRs, or hypervariable regions) of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 54.

2. The method of claim 1 wherein the anti-human CGRP antibody or antibody fragment contains an Fc region that has been modified to alter effector function, half-life, proteolysis, and/or glycosylation.

3. The method of claim 1 wherein the anti-human CGRP antibody or antibody fragment is a humanized, single chain or chimeric antibody.

4. The method of claim 1 wherein the disease is selected from migraine (with or without aura), weight loss, cancer or tumors, angiogenesis associated with cancer or tumor growth, angiogenesis associated with cancer or tumor survival, migraine, chronic migraine, frequent episodic migraines, or menstrual migraines hemiplegic migraines, cluster headaches, migrainous neuralgia, chronic headaches, tension headaches, general headaches, hot flushes, chronic paroxysomal hemicrania, secondary headaches due to an underlying structural problem in the head or neck, cranial neuralgia, sinus headaches (such as for example associated with sinusitis), allergy-induced headaches or migraines, pain, inflammatory pain, post-operative incision pain, complex regional pain syndrome, cancer pain, primary or metastatic bone cancer pain, fracture pain, osteoporotic fracture pain, pain resulting from burn, osteoporosis, gout joint pain, pain associated with sickle cell crises, and other nociceptive pain, as well as hepatocellular carcinoma, breast cancer, liver cirrhosis, neurogenic pain, neuropathic pain, nociceptive pain, trigeminal neuralgia, post-herpetic neuralgia, phantom limb pain, fibromyalgia, menstrual pain, ovarialgia, reflex sympathetic dystrophy, neurogenic pain, osteoarthritis or rheumatoid arthritis pain, lower back pain, diabetic neuropathy, sciatica, or visceral pain associated with gastro-esophageal reflux, dyspepsia, irritable bowel syndrome, inflammatory bowel disease, Crohn's disease, ileitis, ulcerative colitis, renal colic, dysmenorrhea, cystitis, menstrual period, labor, menopause, prostatitis, or pancreatitis or comprises overactive bladder; urinary incontinence; pain; chronic pain; neurogenic inflammation and inflammatory pain; neuropathic pain; eye pain; tooth pain; post-surgical pain, trauma related pain, diabetes; non-insulin dependent diabetes mellitus and other inflammatory autoimmune disorders, vascular disorders; inflammation; arthritis; bronchial hyperreactivity, asthma; shock; sepsis; opiate withdrawal syndrome: morphine tolerance; hot flashes in men and women; allergic dermatitis; psoriasis; encephalitis: brain trauma; epilepsy: neurodegenerative diseases; skin diseases including pruritus, neurogenic cutaneous redness, skin rosaceousness and erythema: inflammatory bowel disease, irritable bowel syndrome, cystitis; and dysmenorrhea.

5. The method of claim 4, wherein the antibody or antibody fragment comprises a $V_H$ polypeptide sequence of SEQ ID NO:53; and a $V_L$ polypeptide sequence of SEQ ID NO:51.

6. The method of claim 1, wherein the treatment further includes the administration of another therapeutic agent or regimen selected from anti-histamines, anti-inflammatory agents, analgesics or antibiotics.

7. The method of claim 1 wherein the antibody comprises a $V_H$ polypeptide comprising the sequence of SEQ ID NO:53; and a $V_L$ polypeptide comprising the sequence of SEQ ID NO:51.

8. The method of claim 7 which is used to treat or prevent headache.

9. The method of claim 8 wherein said headache is associated with a condition selected from migraine with aura, migraine without aura, chronic migraine, frequent episodic migraine, menstrual migraine, hemiplegic migraine, cluster headache, migrainous neuralgia, chronic headache, tension headache, general headache, hot flush, chronic paroxysmal hemicrania, secondary headache due to an underlying structural problem in the head or neck, cranial neuralgia, sinus headache, and allergy-induced headache or migraine.

10. The method of claim 9 wherein the antibody or antibody fragment is used to treat or prevent chronic migraine, or frequent episodic migraine.

11. The method of claim 7 which is used to treat or prevent migraine.

12. The method of claim 1 wherein the antibody comprises a heavy chain comprising the sequence of SEQ ID NO:54; and a light chain comprising the sequence of SEQ ID NO:52.

13. The method of claim 12 which is used to treat or prevent headache.

14. The method of claim 13 wherein said headache is associated with a condition selected from migraine with aura, migraine without aura, chronic migraine, frequent episodic migraine, menstrual migraine, hemiplegic migraine, cluster headache, migrainous neuralgia, chronic headache, tension headache, general headache, hot flush, chronic paroxysmal hemicrania, secondary headache due to an underlying structural problem in the head or neck, cranial neuralgia, sinus headache, and allergy-induced headache or migraine.

15. The method of claim 14 wherein the antibody or antibody fragment is used to treat or prevent chronic migraine, or frequent episodic migraine.

16. The method of claim 12 which is used to treat or prevent migraine.

17. The method of claim 1 which is used to treat or prevent headache.

18. The method of claim 17 wherein said headache is associated with a condition selected from migraine with aura, migraine without aura, chronic migraine, frequent episodic migraine, menstrual migraine, hemiplegic migraine, cluster headache, migrainous neuralgia, chronic headache, tension headache, general headache, hot flush, chronic paroxysmal hemicrania, secondary headache due to an underlying structural problem in the head or neck, cranial neuralgia, sinus headache, and allergy-induced headache or migraine.

19. The method of claim 18 wherein the antibody or antibody fragment is used to treat or prevent chronic migraine, or frequent episodic migraine.

20. The method of claim 1 is used to treat or prevent migraine.

21. A method of ameliorating or reducing symptoms of a disease or disorder associated with elevated CGRP comprising administering to an individual in need thereof a therapeutically effective amount of a CGRP antibody or antibody fragment comprising a variable light ($V_L$) chain comprising the complementarity-determining regions (CDRs, or hypervariable regions) of SEQ ID NO: 55; SEQ ID NO: 56; and SEQ ID NO: 57, and comprising a variable heavy ($V_H$) chain comprising the complementarity-determining regions (CDRs, or hypervariable regions) of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 54.

22. The method of claim 21, wherein said disease or disorder is selected from migraine (with or without aura), weight loss, cancer or tumors, angiogenesis associated with cancer or tumor growth, angiogenesis associated with cancer or tumor survival, hemiplegic migraines, cluster headaches, migrainous neuralgia, chronic headaches, tension headaches, general headaches, hot flushes, chronic paroxysomal hemicrania, secondary headaches due to an underlying structural problem in the head or neck, cranial neuralgia, sinus headaches (such as for example associated with sinusitis), allergy-induced headaches or migraines, pain, inflammatory pain, post-operative incision pain, complex regional pain syndrome, cancer pain, primary or metastatic bone cancer pain, fracture pain, osteoporotic fracture pain, pain resulting from burn, osteoporosis, gout joint pain, pain associated with sickle cell crises, and other nociceptic pain, as well as hepatocellular carcinoma, breast cancer, liver cirrhosis, neurogenic pain, neuropathic pain, nociceptic pain, trigeminal neuralgia, post-herpetic neuralgia, phantom limb pain, fibromyalgia, menstrual pain, ovarialgia, reflex sympathetic dystrophy, neurogenic pain, osteoarthritis or rheumatoid arthritis pain, lower back pain, diabetic neuropathy, sciatica, or visceral pain associated with gastro-esophageal reflux, dyspepsia, irritable bowel syndrome, inflammatory bowel disease, Crohn's disease, ileitis, ulcerative colitis, renal colic, dysmenorrhea, cystitis, menstrual period, labor, menopause, prostatitis, or pancreatitis.

23. The method of claim 22, wherein the antibody or antibody fragment is used to treat or prevent chronic migraine, or frequent episodic migraine.

24. The method of claim 21 wherein the disease or condition is pain, overactive bladder, headache, or migraine.

25. The method of claim 21 which is used to treat or prevent headache.

26. The method of claim 25 wherein said headache is associated with a condition selected from migraine with aura, migraine without aura, chronic migraine, frequent episodic migraine, menstrual migraine, hemiplegic migraine, cluster headache, migrainous neuralgia, chronic headache, tension headache, general headache, hot flush, chronic paroxysmal hemicrania, secondary headache due to an underlying structural problem in the head or neck, cranial neuralgia, sinus headache, and allergy-induced headache or migraine.

27. The method of claim 26 wherein the antibody or antibody fragment is used to treat or prevent chronic migraine, or frequent episodic migraine.

28. The method of claim 21 which is used to treat or prevent migraine.

29. The method of claim 21, wherein the antibody or antibody fragment comprises a $V_H$ polypeptide sequence that exhibits at least 90% sequence identity to SEQ ID NO:53; and a $V_L$ polypeptide that exhibits at least 90% sequence identity to SEQ ID NO:51.

30. The method of claim 21, wherein the antibody or antibody fragment comprises a $V_H$ polypeptide sequence that exhibits at least 95% sequence identity to SEQ ID NO:53; and a $V_L$ polypeptide that exhibits at least 95% sequence identity to SEQ ID NO:51.

\* \* \* \* \*